United States Patent
Christianson et al.

(10) Patent No.: US 11,331,186 B2
(45) Date of Patent: May 17, 2022

(54) SIDE-DELIVERABLE TRANSCATHETER PROSTHETIC VALVES AND METHODS FOR DELIVERING AND ANCHORING THE SAME

(71) Applicant: VDyne, Inc., Maple Grove, MN (US)

(72) Inventors: Mark Christianson, Plymouth, MN (US); Robert Vidlund, Forest Lake, MN (US); Neelakantan Saikrishnan, Plymouth, MN (US); Scott Kramer, Minneapolis, MN (US); Chad Perrin, Andover, MN (US); Lucas Harder, Minneapolis, MN (US)

(73) Assignee: VDyne, Inc., Maple Grove, MN (US)

( * ) Notice: Subject to any disclaimer, the term of this patent is extended or adjusted under 35 U.S.C. 154(b) by 0 days.

(21) Appl. No.: 17/167,988

(22) Filed: Feb. 4, 2021

(65) Prior Publication Data
US 2021/0220134 A1 Jul. 22, 2021

Related U.S. Application Data

(63) Continuation of application No. PCT/US2020/045195, filed on Aug. 6, 2020, which is
(Continued)

(51) Int. Cl.
*A61F 2/24* (2006.01)

(52) U.S. Cl.
CPC .......... *A61F 2/2436* (2013.01); *A61F 2/2418* (2013.01); *A61F 2220/0016* (2013.01); *A61F 2220/0075* (2013.01)

(58) Field of Classification Search
CPC .... A61F 2/2436; A61F 2/2418; A61F 2/2409; A61F 2/2451; A61F 2220/0016; A61F 2220/0075; A61F 2002/30841
See application file for complete search history.

(56) References Cited

U.S. PATENT DOCUMENTS

| | | |
|---|---|---|
| 3,744,060 A | 7/1973 | Bellhouse et al. |
| 4,079,468 A | 3/1978 | Liotta et al. |

(Continued)

FOREIGN PATENT DOCUMENTS

| | | |
|---|---|---|
| AU | 2006203686 B2 | 11/2008 |
| AU | 2009219415 A1 | 9/2009 |

(Continued)

OTHER PUBLICATIONS

Office Action for U.S. Appl. No. 16/448,108, dated Mar. 8, 2021, 8 pages.
(Continued)

*Primary Examiner* — Leslie Lopez
*Assistant Examiner* — Tiffany P Shipmon
(74) *Attorney, Agent, or Firm* — Cooley LLP

(57) ABSTRACT

A side-deliverable prosthetic heart valve includes an outer frame and a flow control component. The outer frame has a supra-annular region, a subannular region, and a transannular region therebetween. The flow control component is mounted to the outer frame such that at least a portion of the flow control component is disposed in the transannular region. The prosthetic valve has a delivery configuration for side-delivery via a delivery catheter and is expandable when the prosthetic valve is released from the delivery catheter. The subannular region of the outer frame is disposable in a first configuration as the prosthetic valve is seated in an annulus of a native heart valve and is transitionable to a second configuration after the prosthetic valve is seated in the annulus of the native heart valve.

34 Claims, 40 Drawing Sheets

Related U.S. Application Data a continuation-in-part of application No. PCT/US2019/067010, filed on Dec. 18, 2019, and a continuation-in-part of application No. PCT/US2020/015231, filed on Jan. 27, 2020, and a continuation-in-part of application No. PCT/US2020/031390, filed on May 4, 2020.

(60) Provisional application No. 62/891,956, filed on Aug. 26, 2019, provisional application No. 62/905,932, filed on Sep. 25, 2019, provisional application No. 63/014,059, filed on Apr. 22, 2020, provisional application No. 63/016,269, filed on Apr. 27, 2020, provisional application No. 63/027,345, filed on May 19, 2020.

(56) References Cited

U.S. PATENT DOCUMENTS

| | | | |
|---|---|---|---|
| 5,397,351 | A | 3/1995 | Pavcnik et al. |
| 5,509,428 | A | 4/1996 | Dunlop |
| 5,554,185 | A | 9/1996 | Block et al. |
| 6,006,134 | A | 12/1999 | Hill et al. |
| 6,197,013 | B1 | 3/2001 | Reed et al. |
| 6,290,719 | B1 | 9/2001 | Garberoglio |
| 6,449,507 | B1 | 9/2002 | Hill et al. |
| 6,458,153 | B1 | 10/2002 | Bailey et al. |
| 6,532,388 | B1 | 3/2003 | Hill et al. |
| 6,582,467 | B1 | 6/2003 | Teitelbaum et al. |
| 6,628,987 | B1 | 9/2003 | Hill et al. |
| 6,669,724 | B2 | 12/2003 | Park et al. |
| 6,718,208 | B2 | 4/2004 | Hill et al. |
| 6,769,434 | B2 | 8/2004 | Liddicoat et al. |
| 6,890,330 | B2 | 5/2005 | Streeter et al. |
| 6,896,690 | B1 | 5/2005 | Lambrecht et al. |
| 6,904,318 | B2 | 6/2005 | Hill et al. |
| 6,929,653 | B2 | 8/2005 | Streeter |
| 7,074,189 | B1 | 7/2006 | Montegrande |
| 7,125,418 | B2 | 10/2006 | Duran et al. |
| 7,175,660 | B2 | 2/2007 | Cartledge et al. |
| 7,201,761 | B2 | 4/2007 | Woolfson et al. |
| 7,225,019 | B2 | 5/2007 | Jahns et al. |
| 7,269,457 | B2 | 9/2007 | Shafer et al. |
| 7,331,991 | B2 | 2/2008 | Kheradvar et al. |
| 7,361,189 | B2 | 4/2008 | Case et al. |
| 7,374,571 | B2 | 5/2008 | Pease et al. |
| 7,442,204 | B2 | 10/2008 | Schwammenthal et al. |
| 7,449,027 | B2 | 11/2008 | Hunt et al. |
| 7,621,948 | B2 | 11/2009 | Herrmann et al. |
| 7,648,527 | B2 | 1/2010 | Agnew |
| 7,717,952 | B2 | 5/2010 | Case et al. |
| 7,749,245 | B2 | 7/2010 | Cohn et al. |
| 7,753,949 | B2 | 7/2010 | Lamphere et al. |
| 7,811,316 | B2 | 10/2010 | Kalmann et al. |
| 7,828,840 | B2 | 11/2010 | Biggs et al. |
| 7,846,199 | B2 | 12/2010 | Paul, Jr. et al. |
| 8,303,648 | B2 | 11/2012 | Grewe et al. |
| 8,366,768 | B2 | 2/2013 | Zhang |
| 8,491,650 | B2 | 7/2013 | Wiemeyer et al. |
| 8,568,474 | B2 | 10/2013 | Yeung et al. |
| 8,628,571 | B1 | 1/2014 | Hacohen et al. |
| 8,641,752 | B1 | 2/2014 | Holm et al. |
| 8,696,743 | B2 | 4/2014 | Holecek et al. |
| 8,728,153 | B2 | 5/2014 | Bishop et al. |
| 8,758,395 | B2 | 6/2014 | Kleshinski et al. |
| 8,846,390 | B2 | 9/2014 | Dove et al. |
| 8,876,892 | B2 | 11/2014 | Tran et al. |
| 8,900,295 | B2 | 12/2014 | Migliazza et al. |
| 8,915,958 | B2 | 12/2014 | Braido |
| 8,926,690 | B2 | 1/2015 | Kovalsky |
| 8,926,692 | B2 | 1/2015 | Dwork |
| 8,926,694 | B2 | 1/2015 | Costello |
| 8,940,044 | B2 | 1/2015 | Hammer et al. |
| 8,956,404 | B2 | 2/2015 | Bortlein et al. |
| 8,986,370 | B2 | 3/2015 | Annest et al. |
| 9,011,524 | B2 | 4/2015 | Eberhardt |
| 9,017,399 | B2 | 4/2015 | Gross et al. |
| 9,050,188 | B2 | 6/2015 | Schweich, Jr. et al. |
| 9,072,604 | B1 | 7/2015 | Melnick et al. |
| 9,119,714 | B2 | 9/2015 | Shandas et al. |
| 9,216,076 | B2 | 12/2015 | Mitra et al. |
| 9,232,995 | B2 | 1/2016 | Kovalsky et al. |
| 9,241,792 | B2 | 1/2016 | Benichou et al. |
| 9,248,016 | B2 | 2/2016 | Oba et al. |
| 9,259,215 | B2 | 2/2016 | Chou et al. |
| 9,277,990 | B2 | 3/2016 | Klima et al. |
| 9,289,282 | B2 | 3/2016 | Olson et al. |
| 9,289,296 | B2 | 3/2016 | Braido et al. |
| 9,295,547 | B2 | 3/2016 | Costello et al. |
| 9,301,839 | B2 | 4/2016 | Stante et al. |
| 9,308,086 | B2 | 4/2016 | Ho |
| 9,339,367 | B2 | 5/2016 | Carpenter et al. |
| 9,370,418 | B2 | 6/2016 | Pintor et al. |
| 9,381,083 | B2 | 7/2016 | Costello |
| 9,387,075 | B2 | 7/2016 | Bortlein et al. |
| 9,393,111 | B2 | 7/2016 | Ma et al. |
| 9,414,915 | B2 | 8/2016 | Lombardi et al. |
| 9,433,500 | B2 | 9/2016 | Chau et al. |
| 9,440,054 | B2 | 9/2016 | Bishop et al. |
| 9,456,899 | B2 | 10/2016 | Yeung et al. |
| 9,468,525 | B2 | 10/2016 | Kovalsky et al. |
| 9,474,604 | B2 | 10/2016 | Centola et al. |
| 9,486,306 | B2 | 11/2016 | Tegels et al. |
| 9,510,941 | B2 | 12/2016 | Bishop et al. |
| 9,554,902 | B2 | 1/2017 | Braido et al. |
| 9,579,196 | B2 | 2/2017 | Morriss et al. |
| 9,579,200 | B2 | 2/2017 | Lederman et al. |
| 9,597,181 | B2 | 3/2017 | Christianson et al. |
| 9,610,159 | B2 | 4/2017 | Christianson et al. |
| 9,615,925 | B2 | 4/2017 | Subramanian et al. |
| 9,629,719 | B2 | 4/2017 | Rothstein |
| 9,636,222 | B2 | 5/2017 | Oslund |
| 9,649,191 | B2 | 5/2017 | Savage et al. |
| 9,662,202 | B2 | 5/2017 | Quill et al. |
| 9,662,203 | B2 | 5/2017 | Sheahan et al. |
| 9,662,209 | B2 | 5/2017 | Gross et al. |
| 9,675,454 | B2 | 6/2017 | Vidlund et al. |
| 9,675,485 | B2 | 6/2017 | Essinger et al. |
| 9,687,343 | B2 | 6/2017 | Bortlein et al. |
| 9,707,076 | B2 | 7/2017 | Stack et al. |
| 9,713,530 | B2 | 7/2017 | Cabiri et al. |
| 9,750,607 | B2 | 9/2017 | Ganesan et al. |
| 9,763,778 | B2 | 9/2017 | Eidenschink et al. |
| 9,763,779 | B2 | 9/2017 | Bortlein et al. |
| 9,788,946 | B2 | 10/2017 | Bobo, Jr. et al. |
| 9,839,511 | B2 | 12/2017 | Ma et al. |
| 9,849,011 | B2 | 12/2017 | Zimmerman et al. |
| 9,855,384 | B2 | 1/2018 | Cohen et al. |
| 9,861,464 | B2 | 1/2018 | Azimpour et al. |
| 9,895,219 | B2 | 2/2018 | Costello et al. |
| 9,901,330 | B2 | 2/2018 | Akpinar |
| 9,918,838 | B2 | 3/2018 | Ring |
| 9,943,409 | B2 | 4/2018 | Kim et al. |
| 9,949,825 | B2 | 4/2018 | Braido et al. |
| 9,968,444 | B2 | 5/2018 | Millwee et al. |
| 9,968,445 | B2 | 5/2018 | Kheradvar |
| 9,980,815 | B2 | 5/2018 | Nitzan et al. |
| 9,987,121 | B2 | 6/2018 | Blanzy |
| 10,010,411 | B2 | 7/2018 | Peter |
| 10,010,412 | B2 | 7/2018 | Taft et al. |
| 10,022,054 | B2 | 7/2018 | Najafi et al. |
| 10,022,222 | B2 | 7/2018 | Groothuis et al. |
| 10,022,223 | B2 | 7/2018 | Bruchman |
| 10,028,821 | B2 | 7/2018 | Centola et al. |
| 10,028,831 | B2 | 7/2018 | Morin et al. |
| 10,034,667 | B2 | 7/2018 | Morris et al. |
| 10,034,747 | B2 | 7/2018 | Harewood |
| 10,039,638 | B2 | 8/2018 | Bruchman et al. |
| 10,058,315 | B2 | 8/2018 | Rafiee et al. |
| 10,058,411 | B2 | 8/2018 | Fifer et al. |
| 10,058,421 | B2 | 8/2018 | Eberhardt et al. |
| 10,058,426 | B2 | 8/2018 | Barbarino |
| 10,064,405 | B2 | 9/2018 | Dale et al. |
| 10,080,653 | B2 | 9/2018 | Conklin et al. |

(56) References Cited

U.S. PATENT DOCUMENTS

| | | |
|---|---|---|
| 10,085,835 B2 | 10/2018 | Thambar et al. |
| 10,105,224 B2 | 10/2018 | Buchbinder et al. |
| 10,117,741 B2 | 11/2018 | Schweich, Jr. et al. |
| 10,123,874 B2 | 11/2018 | Khairkhahan et al. |
| 10,130,331 B2 | 11/2018 | Stigall et al. |
| 10,130,467 B2 | 11/2018 | Braido et al. |
| 10,149,685 B2 | 12/2018 | Kizuka |
| 10,154,905 B2 | 12/2018 | Duffy |
| 10,179,043 B2 | 1/2019 | Cohen-Tzemach et al. |
| 10,182,908 B2 | 1/2019 | Tubishevitz et al. |
| 10,182,911 B2 | 1/2019 | Hillukka |
| 10,206,775 B2 | 2/2019 | Kovalsky et al. |
| 10,219,895 B2 | 3/2019 | Wagner et al. |
| 10,219,896 B2 | 3/2019 | Sandstrom et al. |
| 10,220,192 B2 | 3/2019 | Drasler et al. |
| 10,226,178 B2 | 3/2019 | Cohen et al. |
| 10,226,335 B2 | 3/2019 | Cartledge et al. |
| 10,245,142 B2 | 4/2019 | Bonhoeffer |
| 10,258,467 B2 | 4/2019 | Hou et al. |
| 10,265,173 B2 | 4/2019 | Griffin et al. |
| 10,321,987 B2 | 6/2019 | Wang et al. |
| 10,321,995 B1 | 6/2019 | Christianson et al. |
| 10,327,895 B2 | 6/2019 | Lozonschi et al. |
| 10,327,899 B2 | 6/2019 | Sandstrom et al. |
| 10,329,066 B2 | 6/2019 | Kruetzfeldt et al. |
| 10,350,047 B2 | 7/2019 | Rajpara et al. |
| 10,357,361 B2 | 7/2019 | Rafi et al. |
| 10,368,989 B2 | 8/2019 | Duffy et al. |
| 10,398,550 B2 | 9/2019 | Chalekian et al. |
| 10,426,611 B2 | 10/2019 | Hariton et al. |
| 10,433,957 B2 | 10/2019 | Khouengboua et al. |
| 10,433,960 B1 | 10/2019 | Sutherland et al. |
| 10,463,489 B2 | 11/2019 | Christianson et al. |
| 10,485,976 B2 | 11/2019 | Streeter et al. |
| 10,595,994 B1 | 3/2020 | Christianson et al. |
| 10,631,983 B1 | 4/2020 | Christianson et al. |
| 10,653,522 B1 | 5/2020 | Vidlund et al. |
| 10,758,346 B1 | 9/2020 | Christianson et al. |
| 10,761,511 B2 | 9/2020 | Chen et al. |
| 10,779,937 B2 | 9/2020 | Vidlund et al. |
| 11,071,627 B2 | 7/2021 | Saikrishnan et al. |
| 11,076,956 B2 | 8/2021 | Christianson et al. |
| 11,109,969 B2 | 9/2021 | Vidlund et al. |
| 11,166,814 B2 | 11/2021 | Vidlund |
| 11,173,027 B2 | 11/2021 | Christianson et al. |
| 11,179,239 B2 | 11/2021 | Vidlund et al. |
| 11,185,409 B2 | 11/2021 | Christianson et al. |
| 11,202,706 B2 | 12/2021 | Christianson et al. |
| 2003/0040772 A1 | 2/2003 | Hyodoh et al. |
| 2003/0040808 A1 | 2/2003 | Stack et al. |
| 2003/0153901 A1 | 8/2003 | Herweck et al. |
| 2003/0166990 A1 | 9/2003 | Trauthen et al. |
| 2003/0171801 A1 | 9/2003 | Bates |
| 2004/0049207 A1 | 3/2004 | Goldfarb et al. |
| 2004/0088047 A1 | 5/2004 | Spence et al. |
| 2004/0093060 A1 | 5/2004 | Seguin et al. |
| 2004/0116996 A1 | 6/2004 | Freitag |
| 2004/0199209 A1 | 10/2004 | Hill et al. |
| 2004/0225352 A1 | 11/2004 | Osborne et al. |
| 2005/0010246 A1 | 1/2005 | Streeter et al. |
| 2005/0075659 A1 | 4/2005 | Realyvasquez et al. |
| 2005/0075725 A1 | 4/2005 | Rowe |
| 2005/0107811 A1 | 5/2005 | Starksen et al. |
| 2005/0137686 A1 | 6/2005 | Salahieh et al. |
| 2005/0228495 A1 | 10/2005 | Macoviak |
| 2006/0015167 A1 | 1/2006 | Armstrong et al. |
| 2006/0190075 A1 | 8/2006 | Jordan et al. |
| 2006/0195180 A1 | 8/2006 | Kheradvar et al. |
| 2006/0229708 A1 | 10/2006 | Powell et al. |
| 2006/0241745 A1 | 10/2006 | Solem |
| 2006/0271098 A1 | 11/2006 | Peacock, III |
| 2006/0276887 A1 | 12/2006 | Brady et al. |
| 2007/0016286 A1 | 1/2007 | Herrmann et al. |
| 2007/0027535 A1 | 2/2007 | Purdy, Jr. et al. |
| 2007/0032850 A1 | 2/2007 | Ruiz et al. |
| 2007/0038295 A1 | 2/2007 | Case et al. |
| 2007/0100427 A1 | 5/2007 | Perouse |
| 2007/0162102 A1 | 7/2007 | Ryan et al. |
| 2007/0208417 A1 | 9/2007 | Agnew |
| 2007/0213805 A1 | 9/2007 | Schaeffer et al. |
| 2007/0233176 A1 | 10/2007 | Gilson et al. |
| 2007/0233228 A1 | 10/2007 | Eberhardt et al. |
| 2007/0239271 A1 | 10/2007 | Nguyen |
| 2007/0288087 A1 | 12/2007 | Fearnot et al. |
| 2008/0004686 A1 | 1/2008 | Hunt et al. |
| 2008/0020013 A1 | 1/2008 | Reyes et al. |
| 2008/0065204 A1 | 3/2008 | Macoviak et al. |
| 2008/0071287 A1 | 3/2008 | Goto |
| 2008/0132999 A1 | 6/2008 | Mericle et al. |
| 2008/0140181 A1 | 6/2008 | Reynolds et al. |
| 2008/0154355 A1 | 6/2008 | Benichou et al. |
| 2008/0183279 A1 | 7/2008 | Bailey et al. |
| 2008/0200977 A1 | 8/2008 | Paul et al. |
| 2008/0200980 A1 | 8/2008 | Robin et al. |
| 2008/0208332 A1 | 8/2008 | Lamphere et al. |
| 2008/0221672 A1* | 9/2008 | Lamphere ............ A61F 2/2439 623/2.12 |
| 2008/0262592 A1 | 10/2008 | Jordan et al. |
| 2008/0262609 A1 | 10/2008 | Gross et al. |
| 2008/0275550 A1 | 11/2008 | Kheradvar et al. |
| 2009/0005863 A1 | 1/2009 | Goetz et al. |
| 2009/0054976 A1 | 2/2009 | Tuval et al. |
| 2009/0094189 A1 | 4/2009 | Stephens |
| 2009/0192586 A1 | 7/2009 | Tabor et al. |
| 2009/0254174 A1 | 10/2009 | Case et al. |
| 2009/0264991 A1 | 10/2009 | Paul, Jr. et al. |
| 2009/0287290 A1 | 11/2009 | Macaulay et al. |
| 2010/0049294 A1 | 2/2010 | Zukowski et al. |
| 2010/0049313 A1 | 2/2010 | Alon et al. |
| 2010/0121434 A1 | 5/2010 | Paul et al. |
| 2010/0160773 A1 | 6/2010 | Cohen et al. |
| 2010/0161043 A1 | 6/2010 | Maisano et al. |
| 2010/0168844 A1 | 7/2010 | Toomes et al. |
| 2010/0174363 A1 | 7/2010 | Castro |
| 2010/0179583 A1 | 7/2010 | Carpenter et al. |
| 2010/0179584 A1 | 7/2010 | Carpenter et al. |
| 2010/0179647 A1 | 7/2010 | Carpenter et al. |
| 2010/0280591 A1 | 11/2010 | Shin et al. |
| 2010/0298929 A1 | 11/2010 | Thornton et al. |
| 2010/0305685 A1 | 12/2010 | Millwee et al. |
| 2011/0004237 A1 | 1/2011 | Schneider et al. |
| 2011/0029071 A1 | 2/2011 | Zlotnick et al. |
| 2011/0029072 A1 | 2/2011 | Gabbay |
| 2011/0066233 A1 | 3/2011 | Thornton et al. |
| 2011/0071613 A1 | 3/2011 | Wood et al. |
| 2011/0098804 A1 | 4/2011 | Yeung et al. |
| 2011/0125145 A1 | 5/2011 | Mody et al. |
| 2011/0137397 A1* | 6/2011 | Chau ............... A61F 2/246 623/1.11 |
| 2011/0160836 A1 | 6/2011 | Behan |
| 2011/0172764 A1 | 7/2011 | Badhwar |
| 2011/0224785 A1 | 9/2011 | Hacohen et al. |
| 2011/0245911 A1* | 10/2011 | Quill ............... A61F 2/2418 623/1.26 |
| 2011/0245917 A1 | 10/2011 | Savage et al. |
| 2011/0251675 A1 | 10/2011 | Dwork |
| 2011/0257721 A1 | 10/2011 | Tabor |
| 2011/0264191 A1 | 10/2011 | Rothstein |
| 2012/0022605 A1 | 1/2012 | Jahns et al. |
| 2012/0022633 A1 | 1/2012 | Olson et al. |
| 2012/0022639 A1 | 1/2012 | Hacohen et al. |
| 2012/0022640 A1 | 1/2012 | Gross et al. |
| 2012/0022644 A1 | 1/2012 | Reich et al. |
| 2012/0035701 A1 | 2/2012 | To |
| 2012/0065723 A1 | 3/2012 | Drasler et al. |
| 2012/0083874 A1 | 4/2012 | Dale et al. |
| 2012/0123531 A1 | 5/2012 | Tsukashima et al. |
| 2012/0137521 A1 | 6/2012 | Millwee et al. |
| 2012/0165928 A1 | 6/2012 | Nitzan et al. |
| 2012/0172981 A1 | 7/2012 | DuMontelle |
| 2012/0203336 A1 | 8/2012 | Annest |
| 2012/0209375 A1 | 8/2012 | Madrid et al. |
| 2012/0232574 A1 | 9/2012 | Kim et al. |
| 2012/0277853 A1 | 11/2012 | Rothstein |

(56) References Cited

U.S. PATENT DOCUMENTS

| | | |
|---|---|---|
| 2012/0310327 A1 | 12/2012 | McHugo |
| 2012/0310328 A1 | 12/2012 | Olson et al. |
| 2013/0035759 A1* | 2/2013 | Gross ............... A61F 2/2418 623/2.38 |
| 2013/0055941 A1 | 3/2013 | Holecek et al. |
| 2013/0131714 A1 | 5/2013 | Wang et al. |
| 2013/0131792 A1 | 5/2013 | Miller et al. |
| 2013/0166017 A1 | 6/2013 | Cartledge et al. |
| 2013/0184742 A1 | 7/2013 | Ganesan et al. |
| 2013/0190857 A1 | 7/2013 | Mitra et al. |
| 2013/0190861 A1 | 7/2013 | Chau et al. |
| 2013/0197621 A1 | 8/2013 | Ryan et al. |
| 2013/0226289 A1 | 8/2013 | Shaolian et al. |
| 2013/0238010 A1 | 9/2013 | Johnson et al. |
| 2013/0238089 A1 | 9/2013 | Lichtenstein et al. |
| 2013/0253570 A1 | 9/2013 | Bates |
| 2013/0274618 A1 | 10/2013 | Hou et al. |
| 2013/0274855 A1 | 10/2013 | Stante et al. |
| 2013/0282110 A1 | 10/2013 | Schweich, Jr. et al. |
| 2013/0297010 A1 | 11/2013 | Bishop et al. |
| 2013/0304197 A1 | 11/2013 | Buchbinder et al. |
| 2013/0304200 A1* | 11/2013 | McLean ............... A61F 2/2436 623/2.18 |
| 2013/0331929 A1 | 12/2013 | Mitra et al. |
| 2013/0338764 A1 | 12/2013 | Thornton et al. |
| 2014/0000112 A1 | 1/2014 | Braido et al. |
| 2014/0005540 A1 | 1/2014 | Merhi |
| 2014/0005768 A1 | 1/2014 | Thomas et al. |
| 2014/0005778 A1 | 1/2014 | Buchbinder et al. |
| 2014/0012372 A1 | 1/2014 | Chau et al. |
| 2014/0018915 A1 | 1/2014 | Baidillah et al. |
| 2014/0039511 A1 | 2/2014 | Morris et al. |
| 2014/0039611 A1 | 2/2014 | Lane et al. |
| 2014/0052237 A1 | 2/2014 | Lane et al. |
| 2014/0081383 A1 | 3/2014 | Eberhardt et al. |
| 2014/0088680 A1 | 3/2014 | Costello et al. |
| 2014/0107758 A1 | 4/2014 | Glazier |
| 2014/0110279 A1 | 4/2014 | Kruetzfeldt et al. |
| 2014/0114403 A1 | 4/2014 | Dale et al. |
| 2014/0121763 A1 | 5/2014 | Duffy et al. |
| 2014/0135895 A1 | 5/2014 | Andress et al. |
| 2014/0135908 A1 | 5/2014 | Glozman et al. |
| 2014/0142695 A1 | 5/2014 | Gross et al. |
| 2014/0172070 A1 | 6/2014 | Seguin |
| 2014/0180069 A1 | 6/2014 | Millett |
| 2014/0180070 A1 | 6/2014 | Millett et al. |
| 2014/0194704 A1 | 7/2014 | Millett et al. |
| 2014/0194983 A1 | 7/2014 | Kovalsky et al. |
| 2014/0207231 A1 | 7/2014 | Hacohen et al. |
| 2014/0214069 A1 | 7/2014 | Franklin |
| 2014/0214159 A1 | 7/2014 | Vidlund et al. |
| 2014/0222136 A1 | 8/2014 | Geist et al. |
| 2014/0222137 A1 | 8/2014 | Miller et al. |
| 2014/0222142 A1 | 8/2014 | Kovalsky et al. |
| 2014/0249566 A1 | 9/2014 | Quinn et al. |
| 2014/0257466 A1 | 9/2014 | Board et al. |
| 2014/0257467 A1 | 9/2014 | Lane et al. |
| 2014/0276616 A1 | 9/2014 | Smith et al. |
| 2014/0276971 A1 | 9/2014 | Kovach |
| 2014/0277342 A1 | 9/2014 | Roeder et al. |
| 2014/0277388 A1 | 9/2014 | Skemp |
| 2014/0277408 A1 | 9/2014 | Folan |
| 2014/0296962 A1 | 10/2014 | Cartledge et al. |
| 2014/0296969 A1 | 10/2014 | Tegels et al. |
| 2014/0296975 A1 | 10/2014 | Tegels et al. |
| 2014/0303718 A1 | 10/2014 | Tegels et al. |
| 2014/0303724 A1 | 10/2014 | Bluestein et al. |
| 2014/0309732 A1 | 10/2014 | Solem |
| 2014/0324161 A1 | 10/2014 | Tegels et al. |
| 2014/0350662 A1 | 11/2014 | Vaturi |
| 2014/0358224 A1 | 12/2014 | Tegels et al. |
| 2014/0371789 A1 | 12/2014 | Hariton et al. |
| 2014/0379076 A1 | 12/2014 | Vidlund et al. |
| 2015/0005808 A1 | 1/2015 | Chouinard et al. |
| 2015/0005874 A1 | 1/2015 | Vidlund et al. |
| 2015/0039081 A1 | 2/2015 | Costello |
| 2015/0045880 A1 | 2/2015 | Hacohen |
| 2015/0051687 A1 | 2/2015 | Dickerhoff et al. |
| 2015/0094802 A1 | 4/2015 | Buchbinder et al. |
| 2015/0112188 A1 | 4/2015 | Stigall et al. |
| 2015/0119982 A1 | 4/2015 | Quill et al. |
| 2015/0127093 A1 | 5/2015 | Hosmer et al. |
| 2015/0142103 A1* | 5/2015 | Vidlund ............... A61F 2/2439 623/2.17 |
| 2015/0157457 A1 | 6/2015 | Hacohen |
| 2015/0173898 A1 | 6/2015 | Drasler et al. |
| 2015/0196390 A1 | 7/2015 | Ma et al. |
| 2015/0196391 A1 | 7/2015 | Dwork |
| 2015/0202044 A1 | 7/2015 | Chau et al. |
| 2015/0216661 A1* | 8/2015 | Hacohen ............ A61B 17/0401 623/2.37 |
| 2015/0230919 A1 | 8/2015 | Chau et al. |
| 2015/0245934 A1 | 9/2015 | Lombardi et al. |
| 2015/0257878 A1 | 9/2015 | Lane et al. |
| 2015/0257880 A1 | 9/2015 | Bortlein et al. |
| 2015/0257882 A1 | 9/2015 | Bortlein et al. |
| 2015/0265400 A1 | 9/2015 | Eidenschink et al. |
| 2015/0272731 A1 | 10/2015 | Racchini et al. |
| 2015/0282922 A1 | 10/2015 | Hingston et al. |
| 2015/0282931 A1 | 10/2015 | Brunnett et al. |
| 2015/0289971 A1 | 10/2015 | Costello et al. |
| 2015/0289975 A1 | 10/2015 | Costello |
| 2015/0297241 A1 | 10/2015 | Yodfat et al. |
| 2015/0305867 A1 | 10/2015 | Liu et al. |
| 2015/0313701 A1 | 11/2015 | Krahbichler |
| 2015/0335424 A1 | 11/2015 | McLean et al. |
| 2015/0342717 A1 | 12/2015 | O'Donnell et al. |
| 2015/0351904 A1 | 12/2015 | Cooper et al. |
| 2015/0351906 A1 | 12/2015 | Hammer et al. |
| 2015/0351910 A1 | 12/2015 | Gilmore et al. |
| 2015/0359629 A1 | 12/2015 | Ganesan et al. |
| 2016/0008130 A1 | 1/2016 | Hasin |
| 2016/0008131 A1 | 1/2016 | Christianson et al. |
| 2016/0022417 A1 | 1/2016 | Karapetian et al. |
| 2016/0030165 A1 | 2/2016 | Mitra et al. |
| 2016/0030167 A1 | 2/2016 | Delaloye et al. |
| 2016/0038280 A1* | 2/2016 | Morriss ............... A61F 2/2436 623/2.18 |
| 2016/0038283 A1 | 2/2016 | Divekar et al. |
| 2016/0045165 A1 | 2/2016 | Braido et al. |
| 2016/0045306 A1 | 2/2016 | Agrawal et al. |
| 2016/0045309 A1 | 2/2016 | Valdez et al. |
| 2016/0067031 A1 | 3/2016 | Kassab et al. |
| 2016/0081799 A1 | 3/2016 | Leo et al. |
| 2016/0095703 A1 | 4/2016 | Thomas et al. |
| 2016/0095704 A1 | 4/2016 | Whitman |
| 2016/0113764 A1 | 4/2016 | Sheahan et al. |
| 2016/0113766 A1 | 4/2016 | Ganesan et al. |
| 2016/0113768 A1 | 4/2016 | Ganesan et al. |
| 2016/0143721 A1 | 5/2016 | Rosenbluth et al. |
| 2016/0143730 A1 | 5/2016 | Kheradvar |
| 2016/0143735 A1 | 5/2016 | Subramanian et al. |
| 2016/0143739 A1 | 5/2016 | Horgan et al. |
| 2016/0158004 A1 | 6/2016 | Kumar et al. |
| 2016/0158007 A1 | 6/2016 | Centola et al. |
| 2016/0158008 A1 | 6/2016 | Miller et al. |
| 2016/0166382 A1 | 6/2016 | Nguyen |
| 2016/0184488 A1 | 6/2016 | Toyoda et al. |
| 2016/0194425 A1 | 7/2016 | Mitra et al. |
| 2016/0213470 A1 | 7/2016 | Ahlberg et al. |
| 2016/0213473 A1 | 7/2016 | Hacohen et al. |
| 2016/0220367 A1 | 8/2016 | Barrett |
| 2016/0220372 A1 | 8/2016 | Medema et al. |
| 2016/0220734 A1 | 8/2016 | Dyamenahalli et al. |
| 2016/0228250 A1 | 8/2016 | Casley et al. |
| 2016/0235530 A1 | 8/2016 | Thomas et al. |
| 2016/0256269 A1 | 9/2016 | Cahalane et al. |
| 2016/0256270 A1 | 9/2016 | Folan et al. |
| 2016/0270911 A1 | 9/2016 | Ganesan et al. |
| 2016/0303804 A1 | 10/2016 | Grbic et al. |
| 2016/0310274 A1* | 10/2016 | Gross ............... A61B 17/122 |
| 2016/0317301 A1 | 11/2016 | Quadri et al. |
| 2016/0324633 A1* | 11/2016 | Gross ............... A61F 2/2409 |
| 2016/0324639 A1 | 11/2016 | Nguyen et al. |

(56) References Cited

U.S. PATENT DOCUMENTS

| | | |
|---|---|---|
| 2016/0331534 A1 | 11/2016 | Buchbinder et al. |
| 2016/0354201 A1 | 12/2016 | Keogh |
| 2016/0361169 A1 | 12/2016 | Gross et al. |
| 2016/0361184 A1 | 12/2016 | Tabor et al. |
| 2016/0367360 A1 | 12/2016 | Cartledge et al. |
| 2016/0367364 A1 | 12/2016 | Torrianni et al. |
| 2017/0000603 A1 | 1/2017 | Conklin et al. |
| 2017/0000604 A1 | 1/2017 | Conklin et al. |
| 2017/0020670 A1 | 1/2017 | Murray et al. |
| 2017/0035562 A1 | 2/2017 | Quadri et al. |
| 2017/0035568 A1 | 2/2017 | Lombardi et al. |
| 2017/0056166 A1 | 3/2017 | Ratz et al. |
| 2017/0056171 A1 | 3/2017 | Cooper et al. |
| 2017/0071733 A1 | 3/2017 | Ghione et al. |
| 2017/0071736 A1 | 3/2017 | Zhu et al. |
| 2017/0076014 A1 | 3/2017 | Bressloff |
| 2017/0079786 A1 | 3/2017 | Li et al. |
| 2017/0079795 A1 | 3/2017 | Morrissey |
| 2017/0100246 A1 | 4/2017 | Rust et al. |
| 2017/0112620 A1 | 4/2017 | Curley et al. |
| 2017/0128208 A1* | 5/2017 | Christianson ...... A61B 17/1227 |
| 2017/0143488 A1 | 5/2017 | Lashinski |
| 2017/0143489 A1 | 5/2017 | Lashinski |
| 2017/0165065 A1 | 6/2017 | Rothstein et al. |
| 2017/0172737 A1 | 6/2017 | Kuetting et al. |
| 2017/0172738 A1 | 6/2017 | Kassas |
| 2017/0181851 A1 | 6/2017 | Annest |
| 2017/0181852 A1 | 6/2017 | Kassas |
| 2017/0189177 A1 | 7/2017 | Schweich, Jr. et al. |
| 2017/0196690 A1 | 7/2017 | Racchini et al. |
| 2017/0209266 A1 | 7/2017 | Lane et al. |
| 2017/0209268 A1 | 7/2017 | Cunningham et al. |
| 2017/0216023 A1 | 8/2017 | Lane et al. |
| 2017/0216026 A1 | 8/2017 | Quill et al. |
| 2017/0216030 A1 | 8/2017 | Jonsson |
| 2017/0224480 A1 | 8/2017 | Garde et al. |
| 2017/0224486 A1 | 8/2017 | Delaloye et al. |
| 2017/0231755 A1 | 8/2017 | Gloss et al. |
| 2017/0231760 A1 | 8/2017 | Lane et al. |
| 2017/0239047 A1 | 8/2017 | Quill et al. |
| 2017/0245993 A1 | 8/2017 | Gross et al. |
| 2017/0245994 A1 | 8/2017 | Khairkhahan et al. |
| 2017/0252163 A1 | 9/2017 | Kheradvar |
| 2017/0258584 A1 | 9/2017 | Chang et al. |
| 2017/0258585 A1 | 9/2017 | Marquez et al. |
| 2017/0273784 A1 | 9/2017 | Racchini et al. |
| 2017/0281337 A1 | 10/2017 | Campbell |
| 2017/0281341 A1* | 10/2017 | Lim ...................... A61F 2/2418 |
| 2017/0296340 A1 | 10/2017 | Gross et al. |
| 2017/0325948 A1 | 11/2017 | Wallace et al. |
| 2017/0325976 A1 | 11/2017 | Nguyen et al. |
| 2017/0333184 A1 | 11/2017 | Ryan |
| 2017/0333240 A1 | 11/2017 | Stangenes et al. |
| 2017/0348099 A1 | 12/2017 | Mendelson et al. |
| 2017/0348100 A1 | 12/2017 | Lane et al. |
| 2017/0360557 A1 | 12/2017 | Kheradvar et al. |
| 2017/0360558 A1 | 12/2017 | Ma |
| 2017/0360561 A1 | 12/2017 | Bell et al. |
| 2018/0014932 A1* | 1/2018 | Hammer ............... A61F 2/2418 |
| 2018/0021130 A1 | 1/2018 | Danino |
| 2018/0035971 A1 | 2/2018 | Brenner et al. |
| 2018/0042549 A1 | 2/2018 | Ho et al. |
| 2018/0042723 A1 | 2/2018 | Yellin et al. |
| 2018/0043133 A1 | 2/2018 | Wong |
| 2018/0049875 A1 | 2/2018 | Iflah et al. |
| 2018/0049876 A1 | 2/2018 | Miraki |
| 2018/0055628 A1 | 3/2018 | Patel et al. |
| 2018/0055633 A1 | 3/2018 | Costello et al. |
| 2018/0056045 A1 | 3/2018 | Donoghue et al. |
| 2018/0056046 A1 | 3/2018 | Kiersey et al. |
| 2018/0071088 A1 | 3/2018 | Badhwar et al. |
| 2018/0078367 A1 | 3/2018 | Saar et al. |
| 2018/0078368 A1 | 3/2018 | Vidlund et al. |
| 2018/0078370 A1 | 3/2018 | Kovalsky et al. |
| 2018/0085219 A1 | 3/2018 | Krivoruchko |
| 2018/0098837 A1 | 4/2018 | Shahriari |
| 2018/0099124 A1 | 4/2018 | McLoughlin et al. |
| 2018/0116793 A1 | 5/2018 | Salahieh et al. |
| 2018/0116843 A1 | 5/2018 | Schreck et al. |
| 2018/0125642 A1 | 5/2018 | White et al. |
| 2018/0125654 A1 | 5/2018 | Duffy |
| 2018/0126127 A1 | 5/2018 | Devereux et al. |
| 2018/0133000 A1 | 5/2018 | Scheinblum et al. |
| 2018/0133006 A1 | 5/2018 | Jones et al. |
| 2018/0133011 A1 | 5/2018 | Perouse |
| 2018/0140417 A1 | 5/2018 | Sciscio et al. |
| 2018/0147041 A1 | 5/2018 | Chouinard et al. |
| 2018/0147055 A1 | 5/2018 | Vidlund et al. |
| 2018/0153689 A1 | 6/2018 | Maimon et al. |
| 2018/0161158 A1 | 6/2018 | Kovalsky et al. |
| 2018/0161161 A1 | 6/2018 | Yellin et al. |
| 2018/0168793 A1 | 6/2018 | Lees et al. |
| 2018/0177580 A9 | 6/2018 | Shemesh et al. |
| 2018/0177594 A1 | 6/2018 | Patel et al. |
| 2018/0185153 A1 | 7/2018 | Bishop et al. |
| 2018/0193138 A1 | 7/2018 | Vidlund |
| 2018/0200049 A1* | 7/2018 | Chambers ............. A61F 2/2436 |
| 2018/0206983 A1 | 7/2018 | Noe et al. |
| 2018/0214141 A1 | 8/2018 | Mendez |
| 2018/0221016 A1 | 8/2018 | Conklin et al. |
| 2018/0243071 A1 | 8/2018 | Eigler et al. |
| 2018/0243532 A1 | 8/2018 | Willard et al. |
| 2018/0256322 A1 | 9/2018 | Zhang et al. |
| 2018/0256327 A1 | 9/2018 | Perszyk et al. |
| 2018/0256329 A1 | 9/2018 | Chambers et al. |
| 2018/0263767 A1 | 9/2018 | Chau et al. |
| 2018/0263773 A1 | 9/2018 | Poppe et al. |
| 2018/0280174 A1 | 10/2018 | Dwork |
| 2018/0289474 A1 | 10/2018 | Rajagopal et al. |
| 2018/0289475 A1 | 10/2018 | Chung et al. |
| 2018/0289485 A1 | 10/2018 | Rajagopal et al. |
| 2018/0296325 A1* | 10/2018 | McLean ................ A61F 2/2433 |
| 2018/0296335 A1 | 10/2018 | Miyashiro |
| 2018/0296337 A1 | 10/2018 | Duhay et al. |
| 2018/0296341 A1 | 10/2018 | Noe et al. |
| 2018/0303488 A1 | 10/2018 | Hill |
| 2018/0303612 A1 | 10/2018 | Pasquino et al. |
| 2018/0311037 A1 | 11/2018 | Morriss et al. |
| 2018/0311474 A1 | 11/2018 | Tyler, II et al. |
| 2018/0318073 A1 | 11/2018 | Tseng et al. |
| 2018/0318078 A1 | 11/2018 | Willard |
| 2018/0325665 A1 | 11/2018 | Gurovich et al. |
| 2018/0325671 A1 | 11/2018 | Abunassar et al. |
| 2018/0338832 A1 | 11/2018 | Ganesan et al. |
| 2018/0344456 A1 | 12/2018 | Barash et al. |
| 2018/0353293 A1 | 12/2018 | Colavito et al. |
| 2018/0353295 A1 | 12/2018 | Cooper et al. |
| 2018/0360439 A1 | 12/2018 | Niland et al. |
| 2018/0360599 A1 | 12/2018 | Drasler et al. |
| 2019/0000619 A1 | 1/2019 | Quijano et al. |
| 2019/0008640 A1 | 1/2019 | Cooper et al. |
| 2019/0015188 A1 | 1/2019 | Eigler et al. |
| 2019/0021834 A1 | 1/2019 | Nir et al. |
| 2019/0029819 A1 | 1/2019 | Huber |
| 2019/0029823 A1 | 1/2019 | Nguyen et al. |
| 2019/0038404 A1 | 2/2019 | Iamberger et al. |
| 2019/0038405 A1 | 2/2019 | Iamberger et al. |
| 2019/0053894 A1 | 2/2019 | Levi et al. |
| 2019/0053895 A1 | 2/2019 | Levi |
| 2019/0053897 A1 | 2/2019 | Levi et al. |
| 2019/0053898 A1 | 2/2019 | Maimon et al. |
| 2019/0053899 A1 | 2/2019 | Levi |
| 2019/0060051 A1 | 2/2019 | Scheeff et al. |
| 2019/0060057 A1 | 2/2019 | Cohen et al. |
| 2019/0060059 A1 | 2/2019 | Delgado et al. |
| 2019/0060069 A1 | 2/2019 | Maimon et al. |
| 2019/0060071 A1 | 2/2019 | Lane et al. |
| 2019/0069995 A1* | 3/2019 | Levi ...................... A61F 2/2418 |
| 2019/0070003 A1 | 3/2019 | Siegel et al. |
| 2019/0076233 A1 | 3/2019 | Fish |
| 2019/0076249 A1 | 3/2019 | Khairkhahan et al. |
| 2019/0083085 A1 | 3/2019 | Gilmore et al. |
| 2019/0091005 A1 | 3/2019 | Fifer et al. |
| 2019/0091015 A1 | 3/2019 | Dienno et al. |

(56) References Cited

U.S. PATENT DOCUMENTS

| | | |
|---|---|---|
| 2019/0091018 A1 | 3/2019 | Hariton et al. |
| 2019/0091022 A1 | 3/2019 | Yellin et al. |
| 2019/0099265 A1 | 4/2019 | Braido et al. |
| 2019/0099270 A1 | 4/2019 | Morrissey et al. |
| 2019/0105153 A1 | 4/2019 | Barash et al. |
| 2019/0117223 A1 | 4/2019 | Abunassar et al. |
| 2019/0117387 A1 | 4/2019 | Li et al. |
| 2019/0117391 A1 | 4/2019 | Humair |
| 2019/0117400 A1 | 4/2019 | Medema et al. |
| 2019/0117401 A1 | 4/2019 | Cortez, Jr. et al. |
| 2019/0125287 A1 | 5/2019 | Itou et al. |
| 2019/0125536 A1 | 5/2019 | Prabhu et al. |
| 2019/0133528 A1 | 5/2019 | Kassab et al. |
| 2019/0133756 A1 | 5/2019 | Zhang et al. |
| 2019/0133757 A1 | 5/2019 | Zhang et al. |
| 2019/0133765 A1 | 5/2019 | Yellin et al. |
| 2019/0142566 A1 | 5/2019 | Lansky et al. |
| 2019/0142582 A1 | 5/2019 | Drasler et al. |
| 2019/0150867 A1 | 5/2019 | Itou et al. |
| 2019/0151509 A1 | 5/2019 | Kheradvar et al. |
| 2019/0167423 A1 | 6/2019 | Hariton et al. |
| 2019/0167429 A1 | 6/2019 | Stearns et al. |
| 2019/0175338 A1 | 6/2019 | White et al. |
| 2019/0175339 A1 | 6/2019 | Vidlund |
| 2019/0175344 A1 | 6/2019 | Khairkhahan |
| 2019/0183639 A1 | 6/2019 | Moore |
| 2019/0183644 A1 | 6/2019 | Hacohen |
| 2019/0183648 A1 | 6/2019 | Trapp et al. |
| 2019/0192287 A1 | 6/2019 | Sandstrom et al. |
| 2019/0192296 A1 | 6/2019 | Schwartz et al. |
| 2019/0209317 A1 | 7/2019 | Zhang et al. |
| 2019/0209320 A1 | 7/2019 | Drasler et al. |
| 2019/0231523 A1 | 8/2019 | Lombardi et al. |
| 2019/0240020 A1 | 8/2019 | Rafiee et al. |
| 2019/0240022 A1 | 8/2019 | Rafiee et al. |
| 2019/0247050 A1 | 8/2019 | Goldsmith |
| 2019/0254815 A1 | 8/2019 | Bruchman et al. |
| 2019/0254816 A1 | 8/2019 | Anderson et al. |
| 2019/0262118 A1 | 8/2019 | Eigler et al. |
| 2019/0262129 A1 | 8/2019 | Cooper et al. |
| 2019/0269413 A1 | 9/2019 | Yodfat et al. |
| 2019/0269504 A1 | 9/2019 | Wang et al. |
| 2019/0269839 A1 | 9/2019 | Wilson et al. |
| 2019/0282360 A1 | 9/2019 | Colavito et al. |
| 2019/0290426 A1 | 9/2019 | Maimon et al. |
| 2019/0290427 A1 | 9/2019 | Mantanus et al. |
| 2019/0307563 A1 | 10/2019 | Sandstrom et al. |
| 2019/0307589 A1 | 10/2019 | Goldberg et al. |
| 2019/0365538 A1 | 12/2019 | Chambers et al. |
| 2019/0388219 A1 | 12/2019 | Lane et al. |
| 2020/0121452 A1 | 4/2020 | Saikrishnan et al. |
| 2020/0121458 A1 | 4/2020 | Vidlund et al. |
| 2020/0179146 A1 | 6/2020 | Christianson et al. |
| 2020/0188097 A1 | 6/2020 | Perrin et al. |
| 2020/0237506 A1 | 7/2020 | Christianson et al. |
| 2020/0289259 A1 | 9/2020 | Christianson et al. |
| 2021/0000592 A1 | 1/2021 | Christianson et al. |
| 2021/0137677 A1 | 5/2021 | Christianson et al. |
| 2021/0154011 A1 | 5/2021 | Christianson et al. |
| 2021/0186693 A1 | 6/2021 | Vidlund et al. |
| 2021/0220126 A1 | 7/2021 | Perrin |
| 2021/0220127 A1 | 7/2021 | Vidlund et al. |
| 2021/0228349 A1 | 7/2021 | Vidlund et al. |
| 2021/0236280 A1 | 8/2021 | Christianson et al. |
| 2021/0244533 A1 | 8/2021 | Vidlund et al. |
| 2021/0244535 A1 | 8/2021 | Iyer et al. |
| 2021/0244536 A1 | 8/2021 | Christianson et al. |
| 2021/0290381 A1 | 9/2021 | Vidlund et al. |
| 2021/0290385 A1 | 9/2021 | Christianson et al. |
| 2021/0315694 A1 | 10/2021 | Vidlund et al. |
| 2021/0330459 A1 | 10/2021 | Christianson et al. |
| 2021/0353412 A1 | 11/2021 | Christianson et al. |

FOREIGN PATENT DOCUMENTS

| | | |
|---|---|---|
| AU | 2011238752 A1 | 10/2012 |
| AU | 2011240940 A1 | 10/2012 |
| AU | 2012272855 A1 | 1/2014 |
| AU | 2011236036 B2 | 6/2014 |
| AU | 2011248657 B2 | 12/2014 |
| AU | 2016228261 A1 | 4/2017 |
| AU | 2017210659 A1 | 8/2017 |
| AU | 2013245201 B2 | 10/2017 |
| AU | 2014360294 B2 | 10/2017 |
| AU | 2016249819 A1 | 11/2017 |
| AU | 2016371525 A1 | 5/2018 |
| AU | 2016366783 A1 | 6/2018 |
| AU | 2017214672 B2 | 10/2018 |
| AU | 2017285993 A1 | 1/2019 |
| AU | 2014201920 B2 | 2/2019 |
| AU | 2015411406 B2 | 2/2019 |
| AU | 2019202290 A1 | 4/2019 |
| AU | 2017388857 A1 | 8/2019 |
| BR | PI0909379 B1 | 9/2019 |
| CA | 2531528 A1 | 1/2005 |
| CA | 2609800 A1 | 1/2007 |
| CA | 2822636 A1 | 10/2008 |
| CA | 2398948 C | 8/2009 |
| CA | 2813419 A1 | 4/2012 |
| CA | 2856088 A1 | 5/2013 |
| CA | 2866315 A1 | 9/2013 |
| CA | 2922123 A1 | 4/2015 |
| CA | 2504258 C | 6/2015 |
| CA | 2677648 C | 10/2015 |
| CA | 2815331 C | 10/2015 |
| CA | 2986584 A1 | 11/2015 |
| CA | 2975294 A1 | 8/2016 |
| CA | 2995603 A1 | 2/2017 |
| CA | 2753853 C | 4/2017 |
| CA | 2702615 C | 6/2017 |
| CA | 2744395 C | 8/2017 |
| CA | 3020238 A1 | 11/2017 |
| CA | 3033666 A1 | 2/2018 |
| CA | 3031572 A1 | 3/2018 |
| CA | 3022641 A1 | 5/2018 |
| CA | 3044062 A1 | 6/2018 |
| CA | 3048893 A1 | 7/2018 |
| CA | 3049792 A1 | 7/2018 |
| CA | 3046693 A1 | 8/2018 |
| CA | 2778944 C | 8/2019 |
| CN | 2855366 Y | 1/2007 |
| CN | 100584292 C | 1/2010 |
| CN | 101677820 A | 3/2010 |
| CN | 101677851 A | 3/2010 |
| CN | 102858272 A | 1/2013 |
| CN | 102869320 A | 1/2013 |
| CN | 102892384 A | 1/2013 |
| CN | 103118630 A | 5/2013 |
| CN | 103189015 A | 7/2013 |
| CN | 103228231 A | 7/2013 |
| CN | 103298426 A | 9/2013 |
| CN | 103370035 A | 10/2013 |
| CN | 103391756 A | 11/2013 |
| CN | 102245120 B | 8/2014 |
| CN | 104220027 A | 12/2014 |
| CN | 102917668 B | 1/2015 |
| CN | 104394803 A | 3/2015 |
| CN | 104582637 A | 4/2015 |
| CN | 102905647 B | 7/2015 |
| CN | 103648570 B | 9/2015 |
| CN | 104884000 A | 9/2015 |
| CN | 104160076 B | 12/2015 |
| CN | 105380730 A | 3/2016 |
| CN | 105451687 A | 3/2016 |
| CN | 105520792 A | 4/2016 |
| CN | 105530893 A | 4/2016 |
| CN | 102458309 B | 5/2016 |
| CN | 103200900 B | 5/2016 |
| CN | 105555232 A | 5/2016 |
| CN | 105578992 A | 5/2016 |
| CN | 103338709 B | 6/2016 |
| CN | 105658178 A | 6/2016 |

(56) References Cited

FOREIGN PATENT DOCUMENTS

| | | |
|---|---|---|
| CN | 105792780 A | 7/2016 |
| CN | 103347467 B | 8/2016 |
| CN | 103648439 B | 8/2016 |
| CN | 103889472 B | 8/2016 |
| CN | 105899150 A | 8/2016 |
| CN | 103153232 B | 9/2016 |
| CN | 106061437 A | 10/2016 |
| CN | 106068109 A | 11/2016 |
| CN | 106073946 A | 11/2016 |
| CN | 106255475 A | 12/2016 |
| CN | 103917194 B | 2/2017 |
| CN | 106456324 A | 2/2017 |
| CN | 106456325 A | 2/2017 |
| CN | 105073068 B | 3/2017 |
| CN | 106470641 A | 3/2017 |
| CN | 105451684 B | 4/2017 |
| CN | 106573129 A | 4/2017 |
| CN | 103945792 B | 5/2017 |
| CN | 106659394 A | 5/2017 |
| CN | 106716098 A | 5/2017 |
| CN | 106794063 A | 5/2017 |
| CN | 106890035 A | 6/2017 |
| CN | 106943207 A | 7/2017 |
| CN | 106999054 A | 8/2017 |
| CN | 106999281 A | 8/2017 |
| CN | 104114127 B | 9/2017 |
| CN | 107115161 A | 9/2017 |
| CN | 107249482 A | 10/2017 |
| CN | 107260366 A | 10/2017 |
| CN | 104918582 B | 11/2017 |
| CN | 107374783 A | 11/2017 |
| CN | 107427364 A | 12/2017 |
| CN | 106255476 B | 1/2018 |
| CN | 107530157 A | 1/2018 |
| CN | 107530167 A | 1/2018 |
| CN | 107530177 A | 1/2018 |
| CN | 107613908 A | 1/2018 |
| CN | 104869948 B | 2/2018 |
| CN | 107714240 A | 2/2018 |
| CN | 107920897 A | 4/2018 |
| CN | 104853696 B | 6/2018 |
| CN | 108135696 A | 6/2018 |
| CN | 108430392 A | 8/2018 |
| CN | 108472142 A | 8/2018 |
| CN | 106726007 B | 11/2018 |
| CN | 109124829 A | 1/2019 |
| CN | 109199641 A | 1/2019 |
| CN | 109561962 A | 4/2019 |
| CN | 109567991 A | 4/2019 |
| CN | 109862835 A | 6/2019 |
| CN | 109906063 A | 6/2019 |
| CN | 109996581 A | 7/2019 |
| CN | 110013358 A | 7/2019 |
| CN | 110290764 A | 9/2019 |
| DE | 102014102648 A1 | 9/2015 |
| DE | 102014102650 A1 | 9/2015 |
| DE | 102014102718 A1 | 9/2015 |
| DE | 102014102722 A1 | 9/2015 |
| DE | 202017104793 U1 | 11/2018 |
| DE | 202016008737 U1 | 4/2019 |
| DK | 2549953 T3 | 2/2017 |
| DK | 2254514 T3 | 12/2018 |
| EA | 027348 B1 | 7/2017 |
| EP | 0902704 A4 | 3/1999 |
| EP | 1301225 A2 | 4/2003 |
| EP | 1684666 A2 | 8/2006 |
| EP | 1996246 A2 | 12/2008 |
| EP | 2211779 A1 | 8/2010 |
| EP | 2254513 A1 | 12/2010 |
| EP | 2263605 A1 | 12/2010 |
| EP | 2273947 A1 | 1/2011 |
| EP | 2296744 A1 | 3/2011 |
| EP | 2379008 A2 | 10/2011 |
| EP | 2400926 A2 | 1/2012 |
| EP | 2427145 A2 | 3/2012 |
| EP | 1582178 B1 | 9/2012 |
| EP | 2542186 A2 | 1/2013 |
| EP | 2558030 A1 | 2/2013 |
| EP | 2560579 A1 | 2/2013 |
| EP | 2575681 A1 | 4/2013 |
| EP | 2603172 A2 | 6/2013 |
| EP | 2637607 A1 | 9/2013 |
| EP | 2651337 A2 | 10/2013 |
| EP | 2658476 A1 | 11/2013 |
| EP | 2699201 A1 | 2/2014 |
| EP | 2405966 B1 | 4/2014 |
| EP | 2055263 B1 | 6/2014 |
| EP | 2741711 A2 | 6/2014 |
| EP | 2793763 A1 | 10/2014 |
| EP | 2822503 A2 | 1/2015 |
| EP | 2538879 B1 | 4/2015 |
| EP | 2444031 B1 | 7/2015 |
| EP | 1702247 B1 | 8/2015 |
| EP | 2772228 B1 | 11/2015 |
| EP | 2943160 A2 | 11/2015 |
| EP | 2470098 B1 | 12/2015 |
| EP | 1991168 B1 | 1/2016 |
| EP | 2254512 B1 | 1/2016 |
| EP | 2964152 A1 | 1/2016 |
| EP | 2967853 A1 | 1/2016 |
| EP | 2967860 A1 | 1/2016 |
| EP | 2994073 A1 | 3/2016 |
| EP | 3001978 A1 | 4/2016 |
| EP | 3003187 A1 | 4/2016 |
| EP | 3007649 A1 | 4/2016 |
| EP | 3010447 A1 | 4/2016 |
| EP | 3017792 A1 | 5/2016 |
| EP | 3019092 A1 | 5/2016 |
| EP | 2563236 B1 | 6/2016 |
| EP | 3027143 A1 | 6/2016 |
| EP | 3037064 A1 | 6/2016 |
| EP | 2211758 B1 | 7/2016 |
| EP | 3052053 A1 | 8/2016 |
| EP | 3060140 A1 | 8/2016 |
| EP | 3062745 A1 | 9/2016 |
| EP | 3071149 A1 | 9/2016 |
| EP | 2282700 B1 | 11/2016 |
| EP | 2967854 B1 | 11/2016 |
| EP | 1998713 B1 | 12/2016 |
| EP | 3099271 A1 | 12/2016 |
| EP | 3100701 A1 | 12/2016 |
| EP | 3141219 A1 | 3/2017 |
| EP | 3157469 A1 | 4/2017 |
| EP | 2538880 B1 | 5/2017 |
| EP | 2967852 B1 | 6/2017 |
| EP | 3174503 A1 | 6/2017 |
| EP | 3182931 A1 | 6/2017 |
| EP | 2830536 B1 | 8/2017 |
| EP | 2830537 B1 | 9/2017 |
| EP | 2720642 B1 | 10/2017 |
| EP | 3232941 A1 | 10/2017 |
| EP | 3256076 A1 | 12/2017 |
| EP | 3281608 A1 | 2/2018 |
| EP | 2608815 B1 | 3/2018 |
| EP | 3310302 A1 | 4/2018 |
| EP | 3311778 A1 | 4/2018 |
| EP | 3337412 A1 | 6/2018 |
| EP | 3340931 A1 | 7/2018 |
| EP | 3344188 A1 | 7/2018 |
| EP | 3344197 A1 | 7/2018 |
| EP | 3345573 A1 | 7/2018 |
| EP | 2822473 B1 | 8/2018 |
| EP | 3354208 A1 | 8/2018 |
| EP | 3370649 A1 | 9/2018 |
| EP | 3372198 A1 | 9/2018 |
| EP | 3372199 A1 | 9/2018 |
| EP | 3375411 A1 | 9/2018 |
| EP | 2928538 B1 | 11/2018 |
| EP | 3399947 A1 | 11/2018 |
| EP | 3400913 A1 | 11/2018 |
| EP | 3406224 A1 | 11/2018 |
| EP | 2555709 B1 | 12/2018 |
| EP | 3417813 A1 | 12/2018 |
| EP | 3426188 A1 | 1/2019 |

(56) References Cited

FOREIGN PATENT DOCUMENTS

| | | |
|---|---|---|
| EP | 3429507 A1 | 1/2019 |
| EP | 3431040 A1 | 1/2019 |
| EP | 3432825 A1 | 1/2019 |
| EP | 3432834 A1 | 1/2019 |
| EP | 3437669 A1 | 2/2019 |
| EP | 3448312 A1 | 3/2019 |
| EP | 3454787 A1 | 3/2019 |
| EP | 2663259 B1 | 5/2019 |
| EP | 3302364 B1 | 5/2019 |
| EP | 3478224 A1 | 5/2019 |
| EP | 3484411 A1 | 5/2019 |
| EP | 3487420 A1 | 5/2019 |
| EP | 2560580 B1 | 6/2019 |
| EP | 3508113 A1 | 7/2019 |
| EP | 3518748 A1 | 8/2019 |
| EP | 3522830 A1 | 8/2019 |
| EP | 3528749 A1 | 8/2019 |
| EP | 3288495 B1 | 9/2019 |
| EP | 3538024 A1 | 9/2019 |
| EP | 3538025 A1 | 9/2019 |
| EP | 3019123 B1 | 10/2019 |
| EP | 3552584 A1 | 10/2019 |
| EP | 3552655 A1 | 10/2019 |
| ES | 2369241 T3 | 11/2011 |
| ES | 2647777 T3 | 12/2017 |
| ES | 2664243 T3 | 4/2018 |
| ES | 2675726 T3 | 7/2018 |
| GB | 2539444 A | 12/2016 |
| JP | 2003530956 A | 10/2003 |
| JP | 2005521513 A | 7/2005 |
| JP | 2008506459 A | 3/2008 |
| JP | 2008512211 A | 4/2008 |
| JP | 2009148579 A | 7/2009 |
| JP | 2009525138 A | 7/2009 |
| JP | 2009527316 A | 7/2009 |
| JP | 2009254864 A | 11/2009 |
| JP | 4426182 B2 | 3/2010 |
| JP | 2010518947 A | 6/2010 |
| JP | 2010537680 A | 12/2010 |
| JP | 2011510797 A | 4/2011 |
| JP | 2013503009 A | 1/2013 |
| JP | 2013505082 A | 2/2013 |
| JP | 2013508027 A | 3/2013 |
| JP | 2013512765 A | 4/2013 |
| JP | 2013523261 A | 6/2013 |
| JP | 2013527010 A | 6/2013 |
| JP | 2013543399 A | 12/2013 |
| JP | 2014501563 A | 1/2014 |
| JP | 2014505537 A | 3/2014 |
| JP | 5527850 B2 | 6/2014 |
| JP | 2014518697 A | 8/2014 |
| JP | 2014522678 A | 9/2014 |
| JP | 2015503948 A | 2/2015 |
| JP | 2015510819 A | 4/2015 |
| JP | 2015517854 A | 6/2015 |
| JP | 5767764 B2 | 8/2015 |
| JP | 5803010 B2 | 11/2015 |
| JP | 2015531283 A | 11/2015 |
| JP | 2015534887 A | 12/2015 |
| JP | 2016503710 A | 2/2016 |
| JP | 2016506794 A | 3/2016 |
| JP | 2016508858 A | 3/2016 |
| JP | 2016517748 A | 6/2016 |
| JP | 2016520391 A | 7/2016 |
| JP | 2016526438 A | 9/2016 |
| JP | 2016530046 A | 9/2016 |
| JP | 2016533787 A | 11/2016 |
| JP | 2016540617 A | 12/2016 |
| JP | 2017000729 A | 1/2017 |
| JP | 2017504410 A | 2/2017 |
| JP | 2017515609 A | 6/2017 |
| JP | 2017516536 A | 6/2017 |
| JP | 2017516609 A | 6/2017 |
| JP | 2017131738 A | 8/2017 |
| JP | 2017159055 A | 9/2017 |
| JP | 2017529908 A | 10/2017 |
| JP | 2018501001 A | 1/2018 |
| JP | 2018501901 A | 1/2018 |
| JP | 2018506412 A | 3/2018 |
| JP | 6329570 B2 | 5/2018 |
| JP | 2018515306 A | 6/2018 |
| JP | 2018118136 A | 8/2018 |
| JP | 2018532556 A | 11/2018 |
| JP | 2018535074 A | 11/2018 |
| JP | 2019500952 A | 1/2019 |
| JP | 2019501696 A | 1/2019 |
| JP | 2019501712 A | 1/2019 |
| JP | 6466853 B2 | 2/2019 |
| JP | 6480343 B2 | 3/2019 |
| JP | 2019507664 A | 3/2019 |
| JP | 6506813 B2 | 4/2019 |
| JP | 6526043 B2 | 6/2019 |
| JP | 2019103821 A | 6/2019 |
| JP | 2019514490 A | 6/2019 |
| JP | 2019516527 A | 6/2019 |
| JP | 2019517346 A | 6/2019 |
| JP | 6568213 B2 | 8/2019 |
| JP | 2019134972 A | 8/2019 |
| JP | 2019523090 A | 8/2019 |
| JP | 2019155178 A | 9/2019 |
| JP | 2019526303 A | 9/2019 |
| KR | 20010013991 A | 2/2001 |
| KR | 20120101625 A | 9/2012 |
| KR | 101223313 B1 | 1/2013 |
| KR | 101354189 B1 | 1/2014 |
| KR | 20140139060 A | 12/2014 |
| KR | 20150097757 A | 8/2015 |
| KR | 20160024992 A | 3/2016 |
| RU | 177405 U1 | 2/2018 |
| WO | WO-0044308 A2 | 8/2000 |
| WO | WO-03072287 A1 | 9/2003 |
| WO | WO-2004093728 A2 | 11/2004 |
| WO | WO-2006029062 A1 | 3/2006 |
| WO | WO-2006066150 A2 | 6/2006 |
| WO | WO-2007047945 A2 | 4/2007 |
| WO | WO-2007054015 A1 | 5/2007 |
| WO | WO-2007095233 A2 | 8/2007 |
| WO | WO-2007129220 A2 | 11/2007 |
| WO | WO-2008013915 A2 | 1/2008 |
| WO | WO-2008091925 A2 | 7/2008 |
| WO | WO-2008103280 A2 | 8/2008 |
| WO | WO-2009081396 A2 | 7/2009 |
| WO | WO-2009094188 A2 | 7/2009 |
| WO | WO-2009094189 A1 | 7/2009 |
| WO | WO-2009094197 A1 | 7/2009 |
| WO | WO-2009094501 A1 | 7/2009 |
| WO | WO-2009100242 A2 | 8/2009 |
| WO | WO-2010029190 A1 | 3/2010 |
| WO | WO-2010119110 A1 | 10/2010 |
| WO | WO-2011112706 A2 | 9/2011 |
| WO | WO-2011137531 A1 | 11/2011 |
| WO | WO-2012009558 A2 | 1/2012 |
| WO | WO 2012/035279 | 3/2012 |
| WO | WO-2012063228 A1 | 5/2012 |
| WO | WO-2012063242 A1 | 5/2012 |
| WO | WO-2012112469 A2 | 8/2012 |
| WO | WO-2012145545 A1 | 10/2012 |
| WO | WO-2012161786 A1 | 11/2012 |
| WO | WO-2012175483 A1 | 12/2012 |
| WO | WO-2012178115 A2 | 12/2012 |
| WO | WO-2013021375 A2 | 2/2013 |
| WO | WO-2013085719 A1 | 6/2013 |
| WO | WO-2013103612 A1 | 7/2013 |
| WO | WO-2013116785 A1 | 8/2013 |
| WO | WO-2013128436 A1 | 9/2013 |
| WO | WO-2013148019 A1 | 10/2013 |
| WO | WO-2013166356 A1 | 11/2013 |
| WO | WO-2013177684 A1 | 12/2013 |
| WO | WO-2013184945 A1 | 12/2013 |
| WO | WO-2014011330 A1 | 1/2014 |
| WO | WO-2014064695 A2 | 5/2014 |
| WO | WO-2014121042 A1 | 8/2014 |
| WO | WO-2014133667 A1 | 9/2014 |
| WO | WO-2014137805 A1 | 9/2014 |

(56) References Cited

FOREIGN PATENT DOCUMENTS

| | | |
|---|---|---|
| WO | WO-2014140230 A1 | 9/2014 |
| WO | WO-2014162306 A2 | 10/2014 |
| WO | WO-2014164151 A1 | 10/2014 |
| WO | WO-2014168655 A1 | 10/2014 |
| WO | WO-2015004173 A1 | 1/2015 |
| WO | WO-2015014960 A1 | 2/2015 |
| WO | WO-2015017075 A1 | 2/2015 |
| WO | WO-2015055605 A1 | 4/2015 |
| WO | WO-2015057735 A1 | 4/2015 |
| WO | WO-2015058039 A1 | 4/2015 |
| WO | WO-2015061021 A1 | 4/2015 |
| WO | WO-2015117025 A1 | 8/2015 |
| WO | WO-2015120122 A2 | 8/2015 |
| WO | WO-2015123607 A2 | 8/2015 |
| WO | WO-2015127264 A1 | 8/2015 |
| WO | WO-2015142834 A1 | 9/2015 |
| WO | WO-2015153755 A2 | 10/2015 |
| WO | WO-2016011267 A1 | 1/2016 |
| WO | WO-2016025733 A1 | 2/2016 |
| WO | WO-2016083351 A1 | 6/2016 |
| WO | WO-2016097337 A1 | 6/2016 |
| WO | WO-2016100799 A1 | 6/2016 |
| WO | WO-2016118851 A1 | 7/2016 |
| WO | WO-2016130913 A1 | 8/2016 |
| WO | WO-2016148777 A1 | 9/2016 |
| WO | WO-2016149083 A1 | 9/2016 |
| WO | WO-2016150806 A1 | 9/2016 |
| WO | WO-2016189391 A2 | 12/2016 |
| WO | WO-2017040684 A1 | 3/2017 |
| WO | WO-2017096157 A1 | 6/2017 |
| WO | WO-2017114928 A1 | 7/2017 |
| WO | WO-2017120404 A1 | 7/2017 |
| WO | WO-2017121193 A1 | 7/2017 |
| WO | WO-2017121194 A1 | 7/2017 |
| WO | WO-2017121195 A1 | 7/2017 |
| WO | WO-2017136596 A1 | 8/2017 |
| WO | WO-2017151292 A1 | 9/2017 |
| WO | WO-2017155892 A1 | 9/2017 |
| WO | WO-2017156352 A1 | 9/2017 |
| WO | WO-2017161204 A1 | 9/2017 |
| WO | WO-2017165842 A1 | 9/2017 |
| WO | WO-2017196511 A1 | 11/2017 |
| WO | WO-2017201082 A1 | 11/2017 |
| WO | WO-2017202042 A1 | 11/2017 |
| WO | WO-2017210356 A1 | 12/2017 |
| WO | WO-2017218375 A1 | 12/2017 |
| WO | WO-2018008019 A2 | 1/2018 |
| WO | WO-2018026445 A1 | 2/2018 |
| WO | WO-2018026904 A1 | 2/2018 |
| WO | WO-2018035105 A1 | 2/2018 |
| WO | WO-2018040244 A1 | 3/2018 |
| WO | WO-2018042439 A1 | 3/2018 |
| WO | WO-2018045156 A2 | 3/2018 |
| WO | WO-2018071115 A1 | 4/2018 |
| WO | WO-2018077143 A1 | 5/2018 |
| WO | WO-2018077146 A1 | 5/2018 |
| WO | WO-2018080328 A1 | 5/2018 |
| WO | WO-2018083493 A1 | 5/2018 |
| WO | WO-2018090576 A1 | 5/2018 |
| WO | WO-2018098032 A1 | 5/2018 |
| WO | WO-2018106460 A1 | 6/2018 |
| WO | WO-2018119304 A1 | 6/2018 |
| WO | WO-2018138658 A1 | 8/2018 |
| WO | WO-2018145055 A1 | 8/2018 |
| WO | WO-2018156767 A1 | 8/2018 |
| WO | WO-2018156922 A1 | 8/2018 |
| WO | WO-2018158747 A1 | 9/2018 |
| WO | WO-2018160790 A1 | 9/2018 |
| WO | WO-2018165358 A1 | 9/2018 |
| WO | WO-2018170149 A1 | 9/2018 |
| WO | WO-2018175220 A1 | 9/2018 |
| WO | WO-2018175619 A1 | 9/2018 |
| WO | WO-2018178208 A1 | 10/2018 |
| WO | WO-2018178977 A1 | 10/2018 |
| WO | WO-2018183832 A1 | 10/2018 |
| WO | WO-2018184225 A1 | 10/2018 |
| WO | WO-2018184226 A1 | 10/2018 |
| WO | WO-2018187495 A1 | 10/2018 |
| WO | WO-2018187753 A1 | 10/2018 |
| WO | WO-2018191681 A1 | 10/2018 |
| WO | WO-2018200531 A1 | 11/2018 |
| WO | WO-2018200942 A2 | 11/2018 |
| WO | WO-2018201111 A2 | 11/2018 |
| WO | WO-2018201212 A1 | 11/2018 |
| WO | WO-2018204106 A1 | 11/2018 |
| WO | WO-2018209302 A1 | 11/2018 |
| WO | WO-2018213209 A1 | 11/2018 |
| WO | WO-2018217525 A1 | 11/2018 |
| WO | WO-2018222799 A1 | 12/2018 |
| WO | WO-2018226628 A1 | 12/2018 |
| WO | WO-2019003221 A1 | 1/2019 |
| WO | WO-2019006383 A2 | 1/2019 |
| WO | WO-2019010458 A1 | 1/2019 |
| WO | WO-2019014473 A1 | 1/2019 |
| WO | WO-2019018319 A1 | 1/2019 |
| WO | WO-2019023385 A1 | 1/2019 |
| WO | WO-2019026059 A1 | 2/2019 |
| WO | WO-2019032992 A2 | 2/2019 |
| WO | WO-2019037579 A1 | 2/2019 |
| WO | WO-2019040357 A1 | 2/2019 |
| WO | WO-2019042472 A1 | 3/2019 |
| WO | WO-2019046099 A1 | 3/2019 |
| WO | WO-2019046205 A1 | 3/2019 |
| WO | WO-2019051168 A2 | 3/2019 |
| WO | WO-2019051180 A2 | 3/2019 |
| WO | WO-2019051587 A1 | 3/2019 |
| WO | WO-2019055577 A1 | 3/2019 |
| WO | WO-2019058178 A1 | 3/2019 |
| WO | WO-2019067219 A1 | 4/2019 |
| WO | WO-2019081689 A1 | 5/2019 |
| WO | WO-2019081985 A2 | 5/2019 |
| WO | WO-2019086958 A1 | 5/2019 |
| WO | WO-2019089136 A1 | 5/2019 |
| WO | WO-2019089821 A1 | 5/2019 |
| WO | WO-2019093387 A1 | 5/2019 |
| WO | WO-2019095049 A1 | 5/2019 |
| WO | WO-2019096033 A1 | 5/2019 |
| WO | WO-2019099722 A2 | 5/2019 |
| WO | WO-2019116322 A1 | 6/2019 |
| WO | WO-2019119674 A1 | 6/2019 |
| WO | WO-2019126518 A1 | 6/2019 |
| WO | WO-2019131148 A1 | 7/2019 |
| WO | WO-2019136162 A1 | 7/2019 |
| WO | WO-2019140293 A1 | 7/2019 |
| WO | WO-2019143775 A1 | 7/2019 |
| WO | WO-2019144036 A1 | 7/2019 |
| WO | WO-2019147585 A1 | 8/2019 |
| WO | WO-2019165213 A1 | 8/2019 |
| WO | WO-2019173475 A1 | 9/2019 |
| WO | WO 2019/195860 | 10/2019 |
| WO | WO-2019190800 A1 | 10/2019 |
| WO | WO-2019191102 A1 | 10/2019 |

OTHER PUBLICATIONS

Office Action for U.S. Appl. No. 16/163,577, dated Mar. 8, 2021, 10 pages.
Office Action for U.S. Appl. No. 17/154,227, dated Mar. 29, 2021, 6 pages.
International Search Report and Written Opinion for International Application No. PCT/US2021/013570, dated Apr. 1, 2021, 9 pages.
Office Action for U.S. Appl. No. 17/167,983, dated Apr. 13, 2021, 20 pages.
International Search Report and Written Opinion for International Application No. PCT/US2019/028822, dated Oct. 24, 2019, 14 pages.
Office Action for U.S. Appl. No. 17/154,438, dated May 3, 2021, 16 pages.
Office Action for U.S. Appl. No. 17/193,936, dated May 27, 2021, 6 pages.
Office Action for U.S. Appl. No. 17/154,227, dated Jun. 18, 2021, 8 pages.

(56) References Cited

OTHER PUBLICATIONS

Office Action for U.S. Appl. No. 16/435,687, dated Aug. 7, 2019, 19 pages.
International Search Report and Written Opinion for International Application No. PCT/US2019/051615, dated Mar. 2, 2020, 14 pages.
International Search Report and Written Opinion for International Application No. PCT/US2019/051957, dated Apr. 30, 2020, 16 pages.
Office Action for U.S. Appl. No. 16/155,890, dated Feb. 8, 2019, 13 pages.
Office Action for U.S. Appl. No. 16/448,108, dated Jan. 21, 2020, 14 pages.
Office Action for U.S. Appl. No. 16/448,108, dated Sep. 1, 2020, 14 pages.
Office Action for U.S. Appl. No. 16/455,417, dated Sep. 23, 2019, 11 pages.
International Search Report and Written Opinion for International Application No. PCT/US2019/067010, dated Mar. 10, 2020, 17 pages.
Office Action for U.S. Appl. No. 16/455,740, dated Jul. 24, 2020, 7 pages.
International Search Report and Written Opinion for International Application No. PCT/US2020/015231, dated Apr. 23, 2020, 10 pages.
International Search Report and Written Opinion for International Application No. PCT/US2020/021300, dated Oct. 7, 2020, 6 pages.
International Search Report and Written Opinion for International Application No. PCT/US2020/031390, dated Aug. 3, 2020, 10 pages.
International Search Report and Written Opinion for International Application No. PCT/US2020/013240, dated Jun. 3, 2020, 7 pages.
International Search Report and Written Opinion for International Application No. PCT/US2020/022828, dated May 19, 2020, 12 pages.
Office Action for U.S. Appl. No. 16/442,504, dated Jan. 14, 2020, 11 pages.
Office Action for U.S. Appl. No. 16/445,210, dated Jan. 28, 2021, 7 pages.
International Search Report and Written Opinion for International Application No. PCT/US2020/045195, dated Jan. 8, 2021, 18 pages.
International Search Report and Written Opinion for International Application No. PCT/US2020/047162, dated Dec. 30, 2020, 9 pages.
Office Action for U.S. Appl. No. 16/449,420, dated Sep. 1, 2021, 16 pages.
Office Action for U.S. Appl. No. 17/221,547, dated Aug. 4, 2021, 11 pages.
Office Action for U.S. Appl. No. 17/222,182, dated Sep. 2, 2021, 23 pages.
Office Action for U.S. Appl. No. 17/236,219, dated Aug. 4, 2021, 17 pages.
Office Action for U.S. Appl. No. 16/443,862, dated Nov. 12, 2021, 9 pages.
Office Action for U.S. Appl. No. 17/221,547, dated Oct. 21, 2021, 9 pages.
Office Action for U.S. Appl. No. 17/222,430, dated Oct. 7, 2021, 17 pages.

\* cited by examiner

FIG. 55A
FIG. 55B
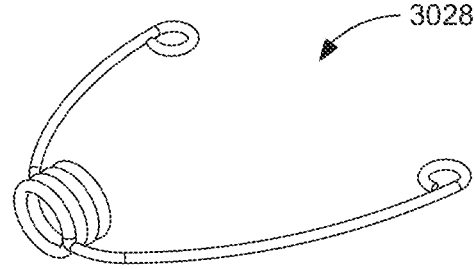
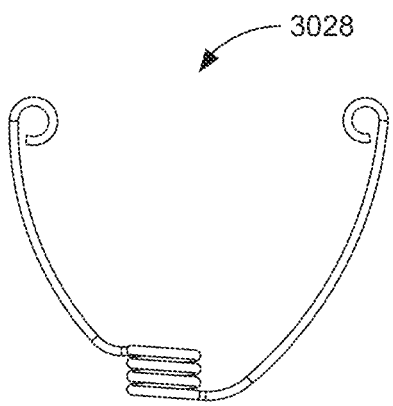
FIG. 56A
FIG. 56B
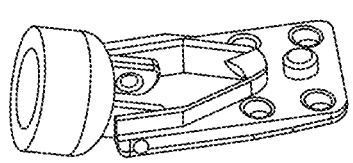
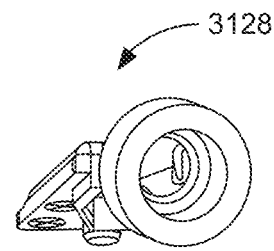
FIG. 56C
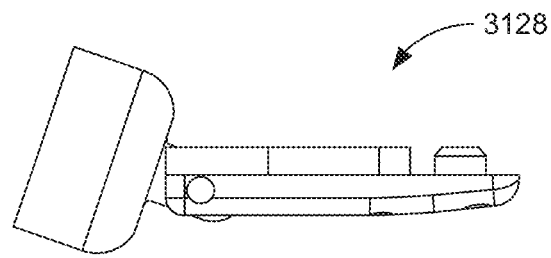

20

```
┌─────────────────────────────────────────────────────────┐
│ Form, from a single workpiece, a supra-annular member   │
│ of a valve frame having an outer loop, an inner loop,   │
│ and a spline suspending the inner loop from the outer   │
│ loop                                                    │
│ 21                                                      │
└─────────────────────────────────────────────────────────┘
                            ▼
┌─────────────────────────────────────────────────────────┐
│ Form, from a single workpiece, a subannular member of   │
│ the valve frame having a distal anchoring element and   │
│ a proximal anchoring element                            │
│ 22                                                      │
└─────────────────────────────────────────────────────────┘
                            ▼
┌─────────────────────────────────────────────────────────┐
│ Form, from a single workpiece, each of a first sidewall │
│ and a second sidewall                                   │
│ 23                                                      │
└─────────────────────────────────────────────────────────┘
                            ▼
┌─────────────────────────────────────────────────────────┐
│ Couple the first sidewall and the second sidewall to    │
│ form a transannular member of the valve frame           │
│ 24                                                      │
└─────────────────────────────────────────────────────────┘
                            ▼
┌─────────────────────────────────────────────────────────┐
│ Couple the supra-annular member to a supra-annular      │
│ portion of the transannular member                      │
│ 25                                                      │
└─────────────────────────────────────────────────────────┘
                            ▼
┌─────────────────────────────────────────────────────────┐
│ Couple the subannular member to a subannular portion    │
│ of the transannular member                              │
│ 26                                                      │
└─────────────────────────────────────────────────────────┘
```

FIG. 71

SIDE-DELIVERABLE TRANSCATHETER PROSTHETIC VALVES AND METHODS FOR DELIVERING AND ANCHORING THE SAME

CROSS-REFERENCE TO RELATED APPLICATIONS

This application is a continuation of International Patent Application No. PCT/US2020/045195, filed Aug. 6, 2020, entitled "Side-Deliverable Transcatheter Prosthetic Valves and Methods for Delivering and Anchoring the Same," the disclosure of which is incorporated herein by reference in its entirety.

International Patent Application No. PCT/US2020/045195 claims priority to and is a continuation-in-part of International Patent Application No. PCT/US2019/067010, filed Dec. 18, 2019, entitled "Transcatheter Deliverable Prosthetic Heart Valves and Methods of Delivery," the disclosure of which is incorporated herein by reference in its entirety.

International Patent Application No. PCT/US2020/045195 also claims priority to and is a continuation-in-part of International Patent Application No. PCT/US2020/015231, filed Jan. 27, 2020, entitled "Collapsible Inner Flow Control Component for Side-Deliverable Transcatheter Heart Valve Prosthesis," the disclosure of which is incorporated herein by reference in its entirety.

International Patent Application No. PCT/US2020/045195 also claims priority to and is a continuation-in-part of International Patent Application No. PCT/US2020/031390, filed May 4, 2020, entitled "Cinch Device and Method for Deployment of a Side-Delivered Prosthetic Heart Valve in a Native Annulus," the disclosure of which is incorporated herein by reference in its entirety.

International Patent Application No. PCT/US2020/045195 also claims priority to and the benefit of U.S. Provisional Patent Application No. 62/891,956, filed Aug. 26, 2019, entitled "Methods and Apparatus for Temporary Compression of a Proximal Sidewall for Side-Delivered Transcatheter Heart Valve Prosthesis;" U.S. Provisional Patent Application No. 62/905,932, filed Sep. 25, 2019, entitled "Methods and Apparatus for Temporary Compression of a Proximal Sidewall for Side-Delivered Transcatheter Heart Valve Prosthesis;" U.S. Provisional patent Application No. 63/014,059, filed Apr. 22, 2020, entitled "Subannular Proximal Tab Projections for Side-Deliverable Transcatheter Prosthetic Valves;" U.S. Provisional Patent Application No. 63/016,269, filed Apr. 27, 2020 entitled "Freewall Support Flare and Posterio-Septal Commissure Flare as Subannular Anchor Elements for Side-Deliverable Transcatheter Prosthetic Valves;" and U.S. Provisional Patent Application No. 63/027,345, filed May 19, 2020 entitled "Side-Deliverable Transcatheter Prosthetic Valves and Method for Delivering and Anchoring the Same," the disclosure of each of which is incorporated herein by reference in its entirety.

BACKGROUND

The embodiments described herein relate generally to transcatheter prosthetic valves and more particularly, to side-deliverable transcatheter prosthetic valves having one or more anchoring elements for securing the prosthetic valves in an annulus of a native valve and methods for delivering the same.

Prosthetic heart valves can pose challenges for delivery and deployment within a heart, particularly for delivery by catheters through the patient's vasculature rather than through a surgical approach. Delivery of traditional transcatheter prosthetic valves generally includes compressing the valve in a radial direction and loading the valve into a delivery catheter such that a central annular axis of the valve is parallel to a lengthwise axis of the delivery catheter. The valves are deployed from the end of the delivery catheter and expanded outwardly in a radial direction from the central annular axis. The expanded size (e.g., diameter) of traditional valves, however, can be limited by the internal diameter of the delivery catheter. The competing interest of minimizing delivery catheter size presents challenges to increasing the expanded diameter of traditional valves (e.g., trying to compress too much material and structure into too little space). Moreover, the orientation of the traditional valves during deployment can create additional challenges when trying to align the valves with the native valve annulus.

Some transcatheter prosthetic valves can be configured for side and/or orthogonal delivery, which can have an increased expanded diameter relative to traditional valves. For example, in side and/or orthogonal delivery, the valve is compressed and loaded into a delivery catheter such that a central annular axis of the valve is substantially orthogonal to the lengthwise axis of the delivery catheter, which can allow the valve to be compressed laterally and extended longitudinally (e.g., in a direction parallel to the lengthwise axis of the delivery catheter). In some such implementations, it is further desirable to provide an outer portion or valve frame that has a size and/or shape that corresponds to a size and/or shape of the annulus of the native valve (e.g., a mitral and/or a tricuspid valve of a human heart) while providing an inner flow control component that (i) is compatible with the lateral compression and/or longitudinal extension experienced during delivery and (ii) has a substantially cylindrical shape that allows for optimal function of the prosthetic valve leaflets included therein. With traditional and/or orthogonally delivered transcatheter prosthetic valves, it is also desirable to provide one or more ways of anchoring the valve in the native annuls without substantially increasing a compressed size of the valve.

Accordingly, a need exists for side-deliverable transcatheter prosthetic valves having one or more anchoring elements for securing the prosthetic valves in an annulus of a native valve and methods of delivering such prosthetic valves.

SUMMARY

The embodiments described herein are directed to side-deliverable transcatheter prosthetic valves having one or more anchoring elements for securing the prosthetic valves in an annulus of a native valve and methods for delivering the same. In some embodiments, a side-deliverable prosthetic heart valve includes an outer frame having a supra-annular region, a subannular region, and a transannular region coupled therebetween. A flow control component is mounted to the outer frame such that at least a portion of the flow control component is disposed in the transannular region. The prosthetic valve has a delivery configuration for side-delivery of the prosthetic valve via a delivery catheter and is expandable when the prosthetic valve is released from the delivery catheter. The subannular region of the outer frame is disposable in a first configuration as the prosthetic valve is seated in an annulus of a native heart valve and is transitionable to a second configuration after the prosthetic valve is seated in the annulus of the native heart valve.

BRIEF DESCRIPTION OF THE DRAWINGS

FIGS. 55A and 55B illustrate various views of a delivery-valve attachment point (e.g., a waypoint) of a prosthetic valve, according to an embodiment, and shown having a yoke design for removably coupling the prosthetic valve to a portion of the delivery system.

FIGS. 56A-56C illustrate various views of a delivery-valve attachment point (e.g., a waypoint) of a prosthetic valve, according to an embodiment, and shown having a hinged design for removably coupling the prosthetic valve to a portion of the delivery system.

FIG. 71 is a flowchart illustrating a method of manufacturing at least a portion of a side-deliverable transcatheter prosthetic valve according to an embodiment.

DETAILED DESCRIPTION

Figure 1A:
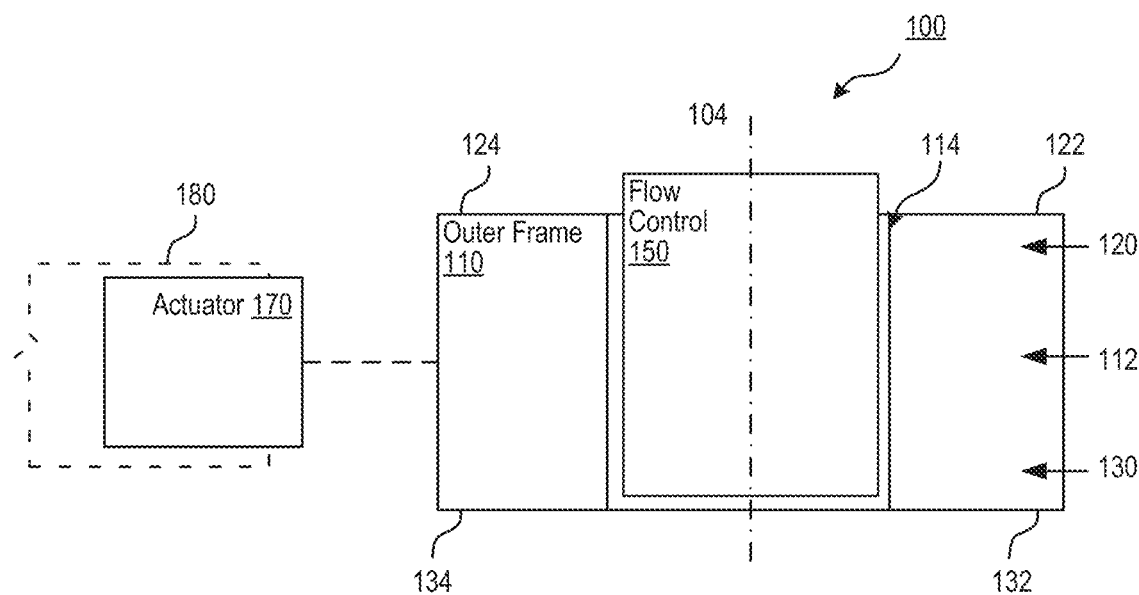
FIGS. 1A and 1B are front view schematic illustrations of a side-delivered transcatheter prosthetic heart valve (also referred to herein as "prosthetic valve"), according to an embodiment, and shown in an expanded configuration and a compressed configuration, respectively.

Disclosed embodiments are directed to transcatheter prosthetic heart valves and/or components thereof, and methods of manufacturing, loading, delivering, and/or deploying the transcatheter prosthetic valves and/or components thereof. In some embodiments, a side-deliverable prosthetic heart valve includes an outer frame having a supra-annular region, a subannular region, and a transannular region coupled therebetween. A flow control component is mounted to the outer frame such that at least a portion of the flow control component is disposed in the transannular region. The prosthetic valve has a delivery configuration for side-delivery of the prosthetic valve via a delivery catheter and is expandable when the prosthetic valve is released from the delivery catheter. The subannular region of the outer frame is disposable in a first configuration as the prosthetic valve is seated in an annulus of a native heart valve and is transitionable to a second configuration after the prosthetic valve is seated in the annulus of the native heart valve.

In some embodiments, a side-deliverable prosthetic heart valve includes an outer frame and a flow control component. The outer frame has a supra-annular member, a subannular member, and a transannular member coupled therebetween. The flow control component has an inner frame and a plurality of leaflets mounted within the inner frame. The flow control component is mounted to the outer frame such that a portion of the flow control component is disposed in the transannular member.

In some embodiments, a side-deliverable prosthetic heart valve has a delivery configuration for side-delivery via a delivery catheter and is expandable when the prosthetic valve is released from the delivery catheter. The prosthetic valve includes an outer frame having a supra-annular member that forms an outer loop, an inner loop, and a spline coupled to the outer loop and the inner loop, and a flow control component having an inner frame and a plurality of leaflets mounted within the inner frame. The flow control component is mounted to the inner loop of the supra-annular member. The spline suspends the inner loop from the outer loop to limit an amount of stress transferred to the flow control component when the prosthetic valve is seated into an annulus of the native heart valve.

In some embodiments, a side-deliverable prosthetic heart valve is compressible for side-delivery via a delivery catheter of a delivery system and expandable when released from the delivery catheter. The prosthetic valve includes an outer frame having a supra-annular member, a subannular member, and a transannular member coupling the supra-annular member to the subannular member. The supra-annular member forms an outer loop, an inner loop, and a spline coupled to the outer loop and the inner loop. The supra-annular member is removably coupleable to the delivery system. A flow control component having an inner frame and a plurality of leaflets mounted within the inner frame is mounted to the outer frame such that a portion of the flow control component is disposed in the transannular member.

In some embodiments, an outer frame for a prosthetic heart valve includes a supra-annular member, a subannular member, and a transannular member. The supra-annular member forms an outer loop, an inner loop, and a spline at least partially suspending the inner loop from the outer loop. The outer loop forms a distal supra-annular anchoring element and a proximal supra-annular anchoring element. The inner loop is coupleable to a flow control component having an inner frame and a plurality of leaflets mounted within the inner frame. The subannular member forms a distal subannular anchoring element and a proximal subannular anchoring element. The transannular member couples the supra-annular member to the subannular member.

Any of the prosthetic heart valves described herein can be a relatively low profile, side-deliverable implantable prosthetic heart valve (also referred to herein as "prosthetic valve" or simply, "valve"). Any of the prosthetic valves can be transcatheter prosthetic valves configured to be delivered into a heart via a delivery catheter. The prosthetic valves can have at least an annular outer valve frame and an inner flow control component (e.g., a 2-leaflet or 3-leaflet valve, sleeve, and/or the like) mounted within and/or extending through a central lumen or aperture of the valve frame. The flow control component can be configured to permit blood flow in a first direction through an inflow end of the valve and block blood flow in a second direction, opposite the first direction, through an outflow end of the valve. In addition, the prosthetic valves can include a single anchoring element or multiple anchoring elements configured to anchor the valve in the annulus of a native valve.

Any of the prosthetic valves described herein can be configured to transition between a compressed or delivery configuration for introduction into the body using the delivery catheter, and an expanded or deployed configuration for implanting at a desired location in the body. For example, any of the embodiments described herein can be a balloon-inflated prosthetic valve, a self-expanding prosthetic valve, and/or the like.

Any of the prosthetic valves described herein can be compressible—into the compressed or delivery configuration—in a lengthwise or orthogonal direction relative to the central axis of the flow control component (e.g., along a longitudinal axis) that can allow a large diameter valve (e.g., having a height of about 5-60 mm and a diameter of about 20-80 mm) to be delivered and deployed from the inferior vena cava directly into the annulus of a native mitral or tricuspid valve using, for example, a 24-36 Fr delivery catheter. The longitudinal axis can be substantially parallel to a lengthwise cylindrical axis of the delivery catheter, which can allow deployment of the prosthetic valves without an acute angle of approach common in traditional transcatheter delivery.

Any of the prosthetic valves described herein can have a central axis that is co-axial or at least substantially parallel with blood flow direction through the valve. In some embodiments, the compressed or delivery configuration of the valve is orthogonal to the blood flow direction. In some embodiments, the compressed or delivery configuration of the valve is parallel to or aligned with the blood flow direction. In some embodiment, the valve can be compressed to the compressed or delivery configuration in two directions—orthogonal to the blood flow direction (e.g., laterally) and parallel to the blood flow (e.g., axially). In some embodiments, a long-axis or longitudinal axis is oriented at an intersecting angle of between 45-135 degrees to the first direction when in the compressed or delivery configuration and/or the expanded or deployed configuration.

Any of the prosthetic valves described herein can include an outer support frame that includes a set of compressible wire cells having an orientation and cell geometry substantially orthogonal to the central axis to minimize wire cell strain when the outer support frame is in a delivery configuration (e.g., a compressed configuration, a rolled and compressed configuration, or a folded and compressed configuration).

Any of the outer support frames described herein can have a supra-annular region, a subannular region, and a transannular region coupled therebetween. The supra-annular region can form, for example, an upper collar portion of the outer support frame and can include any number of features configured to engage native tissue, an inner flow control component of the prosthetic valve, and/or a delivery, actuator, and/or retrieval mechanism. The subannular region can form, for example, a distal anchoring element and a proximal anchoring element configured to engage subannular (ventricle) tissue when the prosthetic valve is seated in the native annulus. The transannular region can be coupled between the supra-annular region and the subannular region. The transannular region can form a shape such as a funnel, cylinder, flat cone, or circular hyperboloid when the outer support frame is in an expanded configuration. In some embodiments, the outer support frame is formed from a wire, a braided wire, or a laser-cut wire frame, and is covered with a biocompatible material. The biocompatible material can cover the outer support frame such that an inner surface is covered with pericardial tissue, an outer surface is covered with a woven synthetic polyester material, and/or both the inner surface is covered with pericardial tissue and the outer surface is covered with a woven synthetic polyester material.

Any of the outer support frames described herein can have a side profile of a flat cone shape having an outer diameter R of 40-80 mm, an inner diameter r of 20-60 mm, and a height of 5-60 mm. In some embodiments, an annular support frame has a side profile of an hourglass shape having a top diameter R1 of 40-80 mm, a bottom diameter R2 of 50-70 mm, an internal diameter r of 20-60 mm, and a height of 5-60 mm.

Any of the prosthetic valves described herein can include one or more anchoring elements extending from, coupled to, and/or otherwise integral with a portion of a valve frame. For example, any of the prosthetic valves can include a distal anchoring element, which can be used, for example, as a Right Ventricular Outflow Tract ("RVOT") tab, a Left Ventricular Outflow Tract ("LVOT") tab, and/or any other suitable tab or the like. Any of the valves described herein can also include an anchoring element extending from a proximal sided of the valve frame, which can be used, for example, to anchor the valve to proximal subannular tissue of the ventricle. The anchoring elements can include and/or can be formed from a wire loop or wire frame, an integrated frame section, and/or a stent, extending from about 10-40 mm away from the tubular frame. For example, any of the prosthetic valves described herein can include a valve frame having a wire or laser cut subannular region or member that forms a distal and proximal anchoring element.

Any of the prosthetic valves described herein can also include (i) a distal upper (supra-annular) anchoring element extending from, attached to, and/or otherwise integral with a distal upper edge of the valve frame and (ii) a proximal upper (supra-annular) anchoring element extending from, attached to, and/or otherwise integral with a proximal upper edge of the valve frame. The distal and proximal upper anchoring elements can include or be formed from a wire loop or wire frame extending from about 2-20 mm away from the valve frame. In some embodiments, the prosthetic valves described herein can include a wire or laser cut supra-annular region or member that forms the distal and proximal upper anchoring elements. The distal and proximal upper anchoring elements are configured to be positioned into a supra-annular position in contact with and/or adjacent to supra-annular tissue of the atrium. In some implementations, the prosthetic valves described herein can be cinched or at least partially compressed after being seated in a native annulus such that the proximal and distal upper anchoring elements exert a force on supra-annular tissue and the proximal and distal lower anchoring elements exert a force in an opposite direction on subannular tissue, thereby securing the prosthetic valve in the native annulus. Any of the valves described herein can also include an anterior or posterior anchoring element extending from and/or attached to an anterior or posterior side of the valve frame, respectively. Any of the valves described herein can include one or more anchoring elements that is/are movable, transitionable, and/or otherwise reconfigurable, which can facilitate, delivery, deployment, and/or securement of the valve.

Any of the prosthetic valves described herein can include an inner flow control component (also referred to herein as "flow control component") that has a leaflet frame with 2-4 flexible leaflets mounted thereon. The 2-4 leaflets are configured to permit blood flow in a first direction through an inflow end of the flow control component and block blood flow in a second direction, opposite the first direction, through an outflow end of the flow control component. The leaflet frame can include two or more panels of diamond-shaped or eye-shaped wire cells made from heat-set shape memory alloy material such as, for example, Nitinol. The leaflet frame can be configured to be foldable along a z-axis (e.g., a longitudinal axis) from a rounded or cylindrical configuration to a flattened cylinder configuration, and compressible along a vertical y-axis (e.g., a central axis) to a compressed configuration. In some implementations, the leaflet frame can include a pair of hinge areas, fold areas, connection points, etc. that can allow the leaflet frame to be folded flat along the z-axis prior to the leaflet frame being compressed along the vertical y-axis. The leaflet frame can be, for example, a single-piece structure with two or more living hinges (e.g., stress concentration riser and/or any suitable structure configured to allow for elastic/nonpermanent deformation of the leaflet frame) or a two-piece structure where the hinge areas are formed using a secondary attachment method (e.g. sutures, fabrics, molded polymer components, etc.)

In some embodiments, the flow control component in an expanded configuration forms a shape such as a funnel, cylinder, flat cone, or circular hyperboloid. In some embodiments, the flow control component has a leaflet frame with a side profile of a flat cone shape having an outer diameter R of 20-60 mm, an inner diameter r of 10-50 mm, where diameter R is great than diameter r, and a height of 5-60 mm. In some embodiments, the leaflet frame is comprised of a wire, a braided wire, or a laser-cut wire frame. In some embodiments, the leaflet frame can have one or more longitudinal supports integrated into or mounted thereon and selected from rigid or semi-rigid posts, rigid or semi-rigid ribs, rigid or semi-rigid batons, rigid or semi-rigid panels, and combinations thereof.

Any of the prosthetic valves and/or components thereof may be fabricated from any suitable biocompatible material or combination of materials. For example, an outer valve frame, an inner valve frame (e.g., of an inner flow control component), and/or components thereof may be fabricated from biocompatible metals, metal alloys, polymer coated metals, and/or the like. Suitable biocompatible metals and/or metal alloys can include stainless steel (e.g., 316 L stainless steel), cobalt chromium (Co—Cr) alloys, nickel-titanium alloys (e.g., Nitinol®), and/or the like. Moreover, any of the outer or inner frames described herein can be formed from superelastic or shape-memory alloys such as nickel-titanium alloys (e.g., Nitinol®). Suitable polymer coatings can include polyethylene vinyl acetate (PEVA), poly-butyl methacrylate (PBMA), translute Styrene Isoprene Butadiene (SIBS) copolymer, polylactic acid, polyester, polylactide, D-lactic polylactic acid (DLPLA), polylactic-co-glycolic acid (PLGA), and/or the like. Some such polymer coatings may form a suitable carrier matrix for drugs such as, for example, Sirolimus, Zotarolimus, Biolimus, Novolimus, Tacrolimus, Paclitaxel, Probucol, and/or the like.

Some biocompatible synthetic material(s) can include, for example, polyesters, polyurethanes, polytetrafluoroethylene (PTFE) (e.g., Teflon), and/or the like. Where a thin, durable synthetic material is contemplated (e.g., for a covering), synthetic polymer materials such expanded PTFE or polyester may optionally be used. Other suitable materials may optionally include elastomers, thermoplastics, polyurethanes, thermoplastic polycarbonate urethane, polyether urethane, segmented polyether urethane, silicone polyether urethane, polyetheretherketone (PEEK), silicone-polycarbonate urethane, polypropylene, polyethylene, low-density polyethylene (LDPE), high-density polyethylene (HDPE), ultra-high density polyethylene (UHDPE), polyolefins, polyethylene-glycols, polyethersulphones, polysulphones, polyvinylpyrrolidones, polyvinylchlorides, other fluoropolymers, polyesters, polyethylene-terephthalate (PET) (e.g., Dacron), Poly-L-lactic acids (PLLA), polyglycolic acid (PGA), poly(D, L-lactide/glycolide) copolymer (PDLA), silicone polyesters, polyamides (Nylon), PTFE, elongated PTFE, expanded PTFE, siloxane polymers and/or oligomers, and/or polylactones, and block co-polymers using the same.

Any of the outer valve frames, inner valve frames (e.g., of the flow control components), and/or portions or components thereof can be internally or externally covered, partially or completely, with a biocompatible material such as pericardium. A valve frame may also be optionally externally covered, partially or completely, with a second biocompatible material such as polyester or Dacron®. Disclosed embodiments may use tissue, such as a biological tissue that is a chemically stabilized pericardial tissue of an animal, such as a cow (bovine pericardium), sheep (ovine pericardium), pig (porcine pericardium), or horse (equine pericardium). Preferably, the tissue is bovine pericardial tissue. Examples of suitable tissue include that used in the products Duraguard®, Peri-Guard®, and Vascu-Guard®, all products currently used in surgical procedures, and which are marketed as being harvested generally from cattle less than 30 months old.

Any of the prosthetic valves described herein and/or any component, feature, and/or aspect thereof can be similar to and/or substantially the same as the prosthetic valves (or components, features, and/or aspects thereof) described in International Patent Application No. PCT/US2019/051957 (referred to herein as "the '957 PCT"); International Patent Application No. PCT/US2019/067010 (referred to herein as "the '010 PCT"); International Patent Application No. PCT/US2020/015231 (referred to herein as "the '231 PCT"); International Patent Application No. PCT/US2020/031390 (referred to herein as "the '390 PCT"); U.S. Provisional Patent Application No. 62/891,956 (referred to herein as "the '956 Provisional"); U.S. Provisional Patent Application No. 62/905,932 (referred to herein as "the '932 Provisional"); U.S. Provisional Patent Application No. 63/014,059 (referred to herein as "the '059 Provisional"); U.S. provisional Patent Application No. 63/016,269 (referred to herein as "the '269 Provisional"); and/or U.S. Provisional patent Application Ser. No. 63/027,345 (referred to herein as "the '345 Provisional"), the disclosure of each of which was incorporated above by reference in its entirety.

Any of the delivery systems described herein can include a delivery system that has a delivery catheter for side-delivery of a side-deliverable prosthetic valve. The delivery catheter can include an outer shaft having an outer proximal end, an outer distal end, and an outer shaft lumen, wherein the outer distal end is closed with an atraumatic ball mounted thereon. The outer shaft lumen has an inner diameter of 8-10 mm sized for passage of a side delivered transcatheter prosthetic valve (e.g., a prosthetic tricuspid valve and/or a prosthetic mitral valve) therethrough.

In some embodiments, a method of manufacturing a side-deliverable prosthetic heart valve includes forming, from a single workpiece, a supra-annular member of a valve frame having an outer loop, an inner loop, and a spline suspending the inner loop from the outer loop. A subannular member is formed from a single workpiece and has a distal anchoring element and a proximal anchoring element. Each of a first sidewall and a second sidewall is formed from a single workpiece and are coupled to form a transannular member of the valve frame. The supra-annular member is coupled to a supra-annular portion of the transannular member and the subannular member is coupled to a subannular portion of the transannular member.

Any method for manufacturing prosthetic valves described herein can include using additive or subtractive metal or metal-alloy manufacturing to produce, for example, a compressible/expandable outer support frame and/or a compressible/expandable inner leaflet frame. Additive metal or metal-alloy manufacturing can include but is not limited to 3D printing, direct metal laser sintering (powder melt), and/or the like. Subtractive metal or metal-alloy manufacturing can include but is not limited to photolithography, etching, laser sintering/cutting, CNC machining, electrical discharge machining, and/or the like. Moreover, any of the manufacturing processes described herein can include forming and/or setting (e.g., heat setting) a cut or machined workpiece into any suitable shape, size, and/or configuration. For example, any of the outer support frames and/or inner leaflet frames described herein can be laser cut from one or more workpieces and heat set into a desired shape, size, and/or configuration. Moreover, any of the frames described herein can include multiple independent components that are formed into desired shapes and coupled together to form the frames.

In some embodiments, a process of manufacturing can further include mounting 2-4 flexible leaflets to the inner leaflet frame to collectively form a flow control component, mounting the flow control component within the outer support frame, and/or covering at least a portion of the outer support frame with a pericardium material or similar biocompatible material.

In some embodiments, a side-deliverable prosthetic heart valve has an outer frame with a supra-annular member, a subannular member, and a transannular member coupled therebetween and a flow control component mounted to the outer frame and at least partially disposed in the transannular member. In some implementations, a method of deploying the prosthetic valve in an annulus of a native heart valve includes removably coupling the outer frame to a portion of a delivery system. The prosthetic valve in a delivery configuration is advanced through a lumen of a delivery catheter included in the delivery system. The delivery catheter has a distal end that is disposed in an atrium of the heart as the prosthetic valve is advanced. The prosthetic valve is released from the distal end of the delivery catheter. After releasing the prosthetic valve, a proximal anchoring element of the subannular member of the outer frame is placed in a first configuration and the prosthetic valve is seated in the annulus of the native heart valve while the proximal anchoring element is in the first configuration. The proximal anchoring element is transitioned from the first configuration to a second configuration after seating the prosthetic valve in the annulus.

Any method for delivering and/or deploying prosthetic heart valves described herein can include orthogonal delivery of the prosthetic heart valve to a native annulus of a human heart that includes at least one of (i) advancing a delivery catheter to the tricuspid valve or pulmonary artery of the heart through the inferior vena cava (IVC) via the femoral vein, (ii) advancing to the tricuspid valve or pulmonary artery of the heart through the superior vena cava (SVC) via the jugular vein, or (iii) advancing to the mitral valve of the heart through a trans-atrial approach (e.g., fossa ovalis or lower), via the IVC-femoral or the SVC jugular approach; and (iv) delivering and/or deploying the prosthetic heart valve to the native annulus by releasing the valve from the delivery catheter.

Any method for delivering prosthetic valves described herein can include placing the prosthetic valves in a delivery configuration. The delivery configuration can include at least one of (i) compressing the valve along a central vertical axis to reduce a vertical dimension of the valve from top to bottom to place the valve in the delivery configuration, (ii) unilaterally rolling the valve from one side of the annular support frame to place the valve in the delivery configuration, (iii) bilaterally rolling the valve from two opposing sides of the annular support frame to place the valve in the delivery configuration, (iv) flattening the valve into two parallel panels that are substantially parallel to the long-axis to place the valve in the delivery configuration, (v) flattening the valve into two parallel panels that are substantially parallel to the long-axis and then rolling the flattened valve to place the valve in the delivery configuration, or (vi)

flattening the valve into two parallel panels that are substantially parallel to the long-axis and then compressing the valve along a central vertical axis to reduce a vertical dimension of the valve from top to bottom to place the valve in the delivery configuration.

Any method for delivering prosthetic valves described herein can include orthogonal delivery of the prosthetic valve to a desired location in the body that includes (i) advancing a delivery catheter to the desired location in the body and (ii) delivering the prosthetic valve to the desired location in the body by releasing the valve from the delivery catheter. The valve is in a compressed or delivery configuration when in the delivery catheter and transitions to an expanded or released configuration when released from the delivery catheter.

Any method for delivering prosthetic valves described herein can include releasing the valve from the delivery catheter by (i) pulling the valve out of the delivery catheter using a pulling member (e.g., a wire or rod) that is releasably connected to a sidewall, a drum or collar, and/or an anchoring element (e.g., a distal anchoring element), wherein advancing the pulling member away from the delivery catheter pulls the valve out of the delivery catheter, or (ii) pushing the valve out of the delivery catheter using a pushing member (e.g., a wire, rod, catheter, delivery member, yoke, etc.) that is releasably connected to a sidewall, a drum or collar, and/or an anchoring element (e.g., a proximal and/or distal anchoring element), wherein advancing the pushing member out of a distal end of the delivery catheter pushes the valve out of the delivery catheter. Moreover, releasing the valve from the delivery catheter allows the valve to transition and/or expand from its delivery configuration to an expanded and/or deployment configuration.

Any method for delivering and/or deploying prosthetic valves described herein can include releasing the valve from a delivery catheter while increasing blood flow during deployment of the valve by (i) partially releasing the valve from the delivery catheter to establish blood flow around the partially released valve and blood flow through the flow control component; (ii) completely releasing the valve from the delivery catheter while maintaining attachment to the valve to transition to a state with increased blood flow through the flow control component and decreased blood flow around the valve; (iii) deploying the valve into a final mounted or seated position in a native annulus to transition to a state with complete blood flow through the flow control component and minimal or no blood flow around the valve; and (iv) disconnecting and withdrawing a positioning catheter, pulling or pushing wire or rod, delivery catheter, actuator, and/or other suitable portion of a delivery system. In some implementations, prior to the disconnecting and withdrawing, any of the methods described herein optionally can include transitioning the valve to a secured or cinched state via an actuator or portion of a delivery system such that the valve contacts annular tissue to secure the valve in the native annulus.

Any method for delivering and/or deploying prosthetic valves described herein can include positioning the valve or a portion thereof in a desired position relative to the native tissue. For example, the method can include positioning a distal anchoring tab of the heart valve prosthesis into a ventricular outflow tract of the left or right ventricle. In some embodiments, the method can further include positioning an upper distal anchoring tab into a supra-annular position, where the upper distal anchoring tab provides a supra-annular downward force in the direction of the ventricle and the distal anchoring tab (e.g., the lower distal anchoring tab) provides a subannular upward force in the direction of the atrium. In some implementations, the method can include partially inserting the prosthetic valve into the annulus such that a distal portion thereof contact native annular tissue while a proximal portion of the prosthetic valve is at least partially compressed and disposed in the delivery catheter. In some embodiments, the method can include rotating the heart valve prosthesis, using a steerable catheter, a yoke, a set of tethers, an actuator, and/or any other portion of a delivery system (or combinations thereof), along an axis parallel to the plane of the valve annulus. In some embodiments, the method can include transitioning one or more anchoring elements into a desired position and/or state to engage native tissue surrounding at least a portion of the annulus. In some implementations, one or more tissue anchors may be attached to the valve and to native tissue to secure the valve in a desired position.

Any method for delivering and/or deploying prosthetic valves described herein and/or any portion thereof can be similar to and/or substantially the same as one or more methods for delivering and/or deploying prosthetic valves (or portion(s) thereof) described in the '957 PCT, the '010 PCT, the '231 PCT, the '390 PCT, the '956 Provisional, the '932 Provisional, the '059 Provisional, the '269 Provisional, and/or the '345 Provisional.

The terminology used herein is for the purpose of describing particular embodiments only and is not intended to limit the full scope of the claims. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

As used herein, the singular forms "a," "an," and "the" are intended to include the plural forms as well, unless the context clearly indicates otherwise. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In general, terms used herein, and especially in the appended claims (e.g., bodies of the appended claims) are generally intended as "open" terms (e.g., the term "including" should be interpreted as "including but not limited to," the term "having" should be interpreted as "having at least," etc.). Similarly, the terms "comprises" and/or "comprising," when used in this specification, specify the presence of stated features, integers (or fractions thereof), steps, operations, elements, and/or components, but do not preclude the presence or addition of one or more other features, integers (or fractions thereof), steps, operations, elements, components, and/or groups thereof. As used in this document, the term "comprising" means "including, but not limited to."

As used herein the term "and/or" includes any and all combinations of one or more of the associated listed items. It should be understood that any suitable disjunctive word and/or phrase presenting two or more alternative terms, whether in the description, claims, or drawings, contemplate the possibilities of including one of the terms, either of the terms, or both terms. For example, the phrase "A or B" will be understood to include the possibilities of "A" or "B" or "A and B."

All ranges disclosed herein also encompass any and all possible subranges and combinations of subranges thereof unless expressly stated otherwise. Any listed range should be recognized as sufficiently describing and enabling the same range being broken down into at least equal subparts unless expressly stated otherwise. As will be understood by one skilled in the art, a range includes each individual member.

The term "valve prosthesis," "prosthetic heart valve," and/or "prosthetic valve" can refer to a combination of a frame and a leaflet or flow control structure or component, and can encompass both complete replacement of an anatomical part (e.g., a new mechanical valve replaces a native valve), as well as medical devices that take the place of and/or assist, repair, or improve existing anatomical parts (e.g., the native valve is left in place).

Prosthetic valves disclosed herein can include a member (e.g., a frame) that can be seated within a native valve annulus and can be used as a mounting element for a leaflet structure, a flow control component, or a flexible reciprocating sleeve or sleeve-valve. It may or may not include such a leaflet structure or flow control component, depending on the embodiment. Such members can be referred to herein as an "annular support frame," "tubular frame," "wire frame," "valve frame," "flange," "collar," and/or any other similar terms.

The term "flow control component" can refer in a non-limiting sense to a leaflet structure having 2-, 3-, 4-leaflets of flexible biocompatible material such a treated or untreated pericardium that is sewn or joined to an annular support frame, to function as a prosthetic heart valve. Such a valve can be a heart valve, such as a tricuspid, mitral, aortic, or pulmonary, that is open to blood flowing during diastole from atrium to ventricle, and that closes from systolic ventricular pressure applied to the outer surface. Repeated opening and closing in sequence can be described as "reciprocating." The flow control component is contemplated to include a wide variety of (bio)prosthetic artificial heart valves. Bioprosthetic pericardial valves can include bioprosthetic aortic valves, bioprosthetic mitral valves, bioprosthetic tricuspid valves, and bioprosthetic pulmonary valves.

Any of the disclosed valve embodiments may be delivered by a transcatheter approach. The term "transcatheter" is used to define the process of accessing, controlling, and/or delivering a medical device or instrument within the lumen of a catheter that is deployed into a heart chamber (or other desired location in the body), as well as an item that has been delivered or controlled by such as process. Transcatheter access is known to include cardiac access via the lumen of the femoral artery and/or vein, via the lumen of the brachial artery and/or vein, via lumen of the carotid artery, via the lumen of the jugular vein, via the intercostal (rib) and/or sub-xiphoid space, and/or the like. Moreover, transcatheter cardiac access can be via the inferior vena cava (IVC), superior vena cava (SVC), and/or via a trans-atrial (e.g., fossa ovalis or lower). Transcatheter can be synonymous with transluminal and is functionally related to the term "percutaneous" as it relates to delivery of heart valves. As used herein, the term "lumen" can refer to the inside of a cylinder or tube. The term "bore" can refer to the inner diameter of the lumen.

The mode of cardiac access can be based at least in part on a "body channel," used to define a blood conduit or vessel within the body, and the particular application of the disclosed embodiments of prosthetic valves can determine the body channel at issue. An aortic valve replacement, for example, would be implanted in, or adjacent to, the aortic annulus. Likewise, a tricuspid or mitral valve replacement would be implanted at the tricuspid or mitral annulus, respectively. While certain features described herein may be particularly advantageous for a given implantation site, unless the combination of features is structurally impossible or excluded by claim language, any of the valve embodiments described herein could be implanted in any body channel.

The term "expandable" as used herein may refer to a prosthetic heart valve or a component of the prosthetic heart valve capable of expanding from a first, delivery size or configuration to a second, implantation size or configuration. An expandable structure, therefore, is not intended to refer to a structure that might undergo slight expansion, for example, from a rise in temperature or other such incidental cause, unless the context clearly indicates otherwise. Conversely, "non-expandable" should not be interpreted to mean completely rigid or a dimensionally stable, as some slight expansion of conventional "non-expandable" heart valves, for example, may be observed.

The prosthetic valves disclosed herein and/or components thereof are generally capable of transitioning between two or more configurations, states, shapes, and/or arrangements. For example, prosthetic valves described herein can be "compressible" and/or "expandable" between any suitable number of configurations. Various terms can be used to describe or refer to these configurations and are not intended to be limiting unless the context clearly states otherwise. For example, a prosthetic valve can be described as being placed in a "delivery configuration," which may be any suitable configuration that allows or enables delivery of the prosthetic valve. Examples of delivery configurations can include a compressed configuration, a folded configuration, a rolled configuration, and/or similar configuration or any suitable combinations thereof. Similarly, a prosthetic valve can be described as being placed in an "expanded configuration," which may be any suitable configuration that is not expressly intended for delivery of the prosthetic valve. Examples of expanded configuration can include a released configuration, a relaxed configuration, a deployed configuration, a non-delivery configuration, and/or similar configurations or any suitable combinations thereof. Some prosthetic valves described herein and/or components or features thereof can have a number of additional configurations that can be associated with various modes, levels, states, and/or portions of actuation, deployment, engagement, etc. Examples of such configurations can include an actuated configuration, a seated configuration, a secured configuration, an engaged configuration, and/or similar configurations or any suitable combinations thereof. While specific examples are provided above, it should be understood that they are not intended to be an exhaustive list of configurations. Other configurations may be possible. Moreover, various terms can be used to describe the same or substantially similar configurations and thus, the use of particular terms are not intended to be limiting and/or to the exclusion of other terms unless the terms and/or configurations are mutually exclusive, or the context clearly states otherwise.

In general, traditional delivery of prosthetic valves can be such that a central cylinder axis of the valve is substantially parallel to a length-wise axis of a delivery catheter used to deliver the valve. Typically, the valves are compressed in a radial direction relative to the central cylinder axis and advanced through the lumen of the delivery catheter. The valves are deployed from the end of the delivery catheter and expanded outwardly in a radial direction from the central cylinder axis. The delivery orientation of the valve generally means that the valve is completely released from the delivery catheter while in the atrium of the heart and reoriented relative to the annulus, which in some instances, can limit a size of the valve.

The prosthetic valves described herein are configured to be delivered via side or orthogonal delivery techniques, unless clearly stated otherwise. As used herein the terms "side-delivered," "side-delivery," "orthogonal delivery," "orthogonally delivered," and/or so forth can be used interchangeably to describe such a delivery method and/or a valve delivered using such a method. Orthogonal delivery of prosthetic valves can be such that the central cylinder axis of the valve is substantially orthogonal to the length-wise axis of the delivery catheter. With orthogonal delivery, the valves are compressed (or otherwise reduced in size) in a direction substantially parallel to the central cylinder axis and/or in a lateral direction relative to the central cylinder axis. As such, a length-wise axis (e.g., a longitudinal axis) of an orthogonally delivered valve is substantially parallel to the length-wise axis of the delivery catheter. In other words, an orthogonally delivered prosthetic valve is compressed and/or delivered at a roughly 90-degree angle compared to traditional processes of compressing and delivering transcatheter prosthetic valves. Moreover, in some instances, the orientation of orthogonally delivered valves relative to the annulus can allow a distal portion of the valve to be at least partially inserted into the annulus of the native heart valve while the proximal portion of the valve, at least in part, remains in the delivery catheter, thereby avoiding at least some of the size constraints faced with some know traditional delivery techniques. Examples of prosthetic valves configured to be orthogonally delivered and processes of delivering such valves are described in detail in the '957 PCT and/or the '010 PCT incorporated by reference hereinabove.

Mathematically, the term "orthogonal" refers to an intersecting angle of 90 degrees between two lines or planes. As used herein, the term "substantially orthogonal" refers to an intersecting angle of 90 degrees plus or minus a suitable tolerance. For example, "substantially orthogonal" can refer to an intersecting angle ranging from 75 to 105 degrees.

As used herein, the term "tissue anchor" generally refers to a fastening device that connects a portion of an outer frame of a prosthetic to native annular tissue, usually at or near a periphery of a collar of the prosthetic valve. The tissue anchor may be positioned to avoid piercing tissue and just rely on the compressive force of two plate-like collars or anchoring elements on the captured tissue, or a tissue anchor (with or without an integrated securement wire) may pierce through native tissue to provide anchoring, or a combination of both. Embodiments including anchoring elements such as plate-like collars or the like can include one or more movable, reconfigurable, and/or actuatable elements, protrusions, tabs, skirts, plates, arms, levers, etc., that can be manipulated to engage native tissue. Moreover, such anchoring elements can include any suitable surface finish(es), feature(s), and/or the like that can facilitate engagement of the native tissue. Embodiments including, for example, tissues anchor(s) can include a tissue anchor with a securement mechanism, such as a pointed tip, a groove, a flanged shoulder, a lock, one or more apertures, and/or the like. In some embodiments, a securement mechanism can be attached or anchored to a portion of an outer frame by any attachment or anchoring mechanisms, including a knot, a suture, a wire crimp, a wire lock, a cam mechanism, or combinations.

The embodiments herein, and/or the various features or advantageous details thereof, are explained more fully with reference to the non-limiting embodiments that are illustrated in the accompanying drawings and detailed in the following description. Descriptions of well-known components and processing techniques are omitted so as to not unnecessarily obscure the embodiments herein. Like numbers refer to like elements throughout.

The examples and/or embodiments described herein are intended to facilitate an understanding of structures, functions, and/or aspects of the embodiments, ways in which the embodiments may be practiced, and/or to further enable those skilled in the art to practice the embodiments herein. Similarly, methods and/or ways of using the embodiments described herein are provided by way of example only and not limitation. Specific uses described herein are not provided to the exclusion of other uses unless the context expressly states otherwise. For example, any of the prosthetic valves described herein can be used to replace a native valve of a human heart including, for example, a mitral valve, a tricuspid valve, an aortic valve, and/or a pulmonary valve. While some prosthetic valves are described herein in the context of replacing a native mitral valve or a native tricuspid valve, it should be understood that such a prosthetic valve can be used to replace any native valve unless expressly stated otherwise or unless one skilled in the art would clearly recognize that one or more components and/or features would otherwise make the prosthetic valve incompatible for such use. Accordingly, specific examples, embodiments, methods, and/or uses described herein should not be construed as limiting the scope of the inventions or inventive concepts herein. Rather, examples and embodiments are provided so that this disclosure will be thorough and complete, and will fully convey the scope of the inventive concepts to those skilled in the art.

FIGS. 1A-1E are various schematic illustrations of a transcatheter prosthetic valve 100 according to an embodiment. The transcatheter prosthetic valve 100 is configured to be deployed in a desired location within a body (e.g., of a human patient) and to permit blood flow in a first direction through an inflow end of the transcatheter prosthetic valve 100 and to block blood flow in a second direction, opposite the first direction, through an outflow end of the transcatheter prosthetic valve 100. For example, the transcatheter prosthetic valve 100 can be a transcatheter prosthetic heart valve configured to be deployed within the annulus of a native tricuspid valve or native mitral valve of a human heart to supplement and/or replace the functioning of the native valve.

The transcatheter prosthetic valve 100 (also referred to herein as "prosthetic valve" or simply "valve") is compressible and expandable in at least one direction relative to a long-axis 102 of the valve 100 (also referred to herein as "horizontal axis," "longitudinal axis," or "lengthwise axis"). The valve 100 is compressible and expandable between an expanded configuration (FIGS. 1A, 1C, and 1E) for implanting at a desired location in a body (e.g., a human heart) and a compressed or delivery configuration (FIGS. 1B and 1D) for introduction into the body using a delivery catheter.

In some embodiments, the valve 100 (and/or at least a portion thereof) may start in a roughly tubular configuration and may be heat-shaped and/or otherwise formed into any desired shape. In some embodiments, the valve 100 can include an upper atrial cuff or flange for atrial sealing, a lower ventricle cuff or flange for ventricular sealing, and a transannular section or region (e.g., a body section, a tubular section, a cylindrical section, etc.) disposed therebetween. The transannular region can have an hourglass cross-section for about 60-80% of the circumference to conform to the native annulus along the posterior and anterior annular segments while remaining substantially vertically flat along 20-40% of the annular circumference to conform to the septal annular segment. While the valve 100 is shown in FIGS. 1A-1E as having a given shape, it should be understood that the size and/or shape of the valve 100 (and/or at least a portion thereof) can be based on a size and/or shape of the anatomical structures of the native tissue.

For example, the valve 100 can be centric (e.g., radially symmetrical relative to a central y-axis 104), or can be eccentric (e.g., radially asymmetrical relative to the central y-axis axis 104). In some eccentric embodiments, the valve 100, or an outer frame thereof, may have a complex shape determined by the anatomical structures where the valve 100 is being mounted. For example, in some instances, the valve 100 may be deployed in the tricuspid annulus having a circumference in the shape of a rounded ellipse with a substantially vertical septal wall, and which is known to enlarge in disease states along an anterior-posterior line. In some instances, the valve 100 may be deployed in the mitral annulus (e.g., near the anterior leaflet) having a circumference in the shape of a rounded ellipse with a substantially vertical septal wall, and which is known to enlarge in disease states. As such, the valve 100 can have a complex shape that determined, at least in part, by the native annulus and/or a disease state of the native valve. For example, in some such embodiments, the valve 100 or the outer frame thereof may have a D-shape (viewed from the top) so the flat portion can be matched to the anatomy in which the valve 100 will be deployed.

As shown, the valve 100 generally includes an annular support frame 110 and a flow control component 150. In addition, the valve 100 and/or at least the annular support frame 110 of the valve 100 can include and/or can couple to an actuator 170 and/or a delivery system interface 180. In some implementations, the valve 100 and/or aspects or portions thereof can be similar to and/or substantially the same as the valves (and/or the corresponding aspects or portions thereof) described in detail in the '957 PCT, the '010 PCT, the '231 PCT, the '390 PCT, the '932 Provisional, the '059 Provisional, and/or the '269 Provisional incorporated by reference hereinabove. Accordingly, certain aspects, portions, and/or details of the valve 100 may not be described in further detail herein.

The annular support frame 110 (also referred to herein as "tubular frame," "valve frame," "wire frame," "outer frame," or "frame") can have a supra-annular region 120, a subannular region 130, and a transannular region 112, disposed and/or coupled therebetween. In some embodiments, the supra-annular region 120, the subannular region 130, and the transannular region 112 can be separate, independent, and/or modular components that are coupled to collectively form the frame 110. In some implementations, such a modular configuration can allow the frame 110 to be adapted to a given size and/or shape of the anatomical structures where the valve 100 is being mounted. For example, one or more of the supra-annular region(s) 120, the subannular region 130, and/or the transannular region 112 can be designed and/or adapted so that that the support frame has any desirable height, outer diameter, and/or inner diameter such as any of those described above. Moreover, such a modular configuration can allow the frame 110 to bend, flex, compress, fold, roll, and/or otherwise reconfigure without plastic or permanent deformation thereof. For example, the frame 110 is compressible to a compressed or delivery configuration for delivery and when released it is configured to return to its original shape (uncompressed, expanded, or released configuration).

The support frame 110 and/or the supra-annular region 120, subannular region 130, and/or transannular region 112 can be formed from or of any suitable material. In some embodiments, the supra-annular region 120, the subannular region 130, and the transannular region 112 can be formed from or of a shape-memory or superelastic metal, metal alloy, plastic, and/or the like. For example, the supra-annular region 120, the subannular region 130, and the transannular region 112 can be formed from or of Nitinol or the like. In some embodiments, the support frame 110 (and/or any of the regions thereof) can be laser cut from a Nitinol sheet or tube. In other embodiments, the support frame 110 (and/or any of the regions thereof) can be formed of or from a Nitinol wire that is bent, kink, formed, and/or manipulated into a desired shape. In still other embodiments, the support frame 110 (and/or any of the regions thereof) can be formed of or from a desired material using any suitable additive or subtractive manufacturing process such as those described above. Moreover, the supra-annular region 120, the subannular region 130, and the transannular region 112 can be coupled to from a frame portion (e.g., a metal or other structural frame portion) of the support frame 110, which in turn, is covered by a biocompatible material such as, for example, pericardium tissue (e.g., Duraguard®, Peri-Guard®, Vascu-Guard®, etc.), polymers (e.g., polyester, Dacron®, etc.), and/or the like, as described above.

The supra-annular region 120 of the frame 110 can be and/or can form, for example, a cuff or collar that can be attached or coupled to an upper edge or upper portion of the transannular region 112, as described in further detail herein. When the valve 100 is deployed within a human heart, the supra-annular region 120 can be an atrial collar that is shaped to conform to the native deployment location. In a tricuspid and/or mitral valve replacement, for example, the supra-annular region 120 collar can have various portions configured to conform to the native valve and/or a portion of the atrial floor surrounding the tricuspid and/or mitral valve, respectively. In some implementations, the supra-annular region 120 can be deployed on the atrial floor to direct blood from the atrium into the flow control component 150 of the valve 100 and to seal against blood leakage (perivalvular leakage) around the frame 110.

In some embodiments, the supra-annular region 120 can be a wire frame that is laser cut out of any suitable material. In some embodiments, the supra-annular region 120 can be formed from a shape-memory or superelastic material such as, for example, Nitinol. In some embodiments, the supra-annular region 120 can be laser cut from a sheet or tube of a shape-memory metal alloy such as Nitinol and, for example, heat-set into a desired shape and/or configuration. In some embodiments, forming the supra-annular region 120 in such a manner can allow the supra-annular region 120 to bend, flex, fold, compress, and/or otherwise reconfigure substantially without plastically deforming and/or without fatigue that may result in failure or breaking of one or more portions thereof. Moreover, the wire frame of the supra-annular region 120 can be covered by any suitable biocompatible material such as any of those described above.

As shown in FIG. 1A, the supra-annular region 120 includes a distal portion 122 and a proximal portion 124. In some embodiments, the distal portion 122 can be and/or can include a distal supra-annular anchoring element and/or the like that can engage native tissue on a distal side of the annulus as the prosthetic valve 100 is seated into the annulus. In some embodiments, the proximal portion 124 can be and/or can include a proximal supra-annular anchoring element and/or the like that can engage native tissue on a proximal side of the annulus as the prosthetic valve 100 is seated in the annulus. In some embodiments, the distal portion 122 and/or the distal supra-annular anchoring element can be sized and/or shaped to correspond to a size and/or shape of the distal portion of the atrial floor of the heart in which the prosthetic valve 100 is disposed. Similarly, the proximal portion 124 and/or the proximal supra-annular anchoring element can be sized and/or shaped to correspond to a size and/or shape of a proximal portion of the atrial floor of the heart.

Although not shown in FIGS. 1A-1E, the supra-annular region 120 can be shaped and/or formed to include any number of features configured to engage native tissue and/or one or more other portions of the valve 100, the actuator 170, and/or the delivery system interface 180. For example, in some embodiments, the supra-annular region 120 can include and/or can form an outer portion, an inner portion, and one or more splines disposed between the outer portion and the inner portion. In some implementations, the outer portion can be sized and/or shaped to engage native tissue, the inner portion can provide structure for mounting the flow control component 150 to the support frame 110, and the one or more splines can receive, couple to, and/or otherwise engage the actuator 170 and/or the delivery system interface 180, as described in further detail herein with reference to specific embodiments.

The subannular region 130 of the frame 110 can be and/or can form, for example, a cuff or collar that can be attached or coupled to a lower edge or upper portion of the transannular region 112, as described in further detail herein. When the valve 100 is deployed within a human heart, the subannular region 130 can be a ventricular collar that is shaped to conform to the native deployment location. In a tricuspid and/or mitral valve replacement, for example, the subannular region 130 collar can have various portions configured to conform to the native valve and/or a portion of the ventricular ceiling surrounding the tricuspid and/or mitral valve, respectively. In some implementations, the subannular region 130 or at least a portion thereof can engage the ventricular ceiling surrounding the native annulus to secure the valve 100 in the native annulus, to prevent dislodging of the valve 100, to sandwich or compress the native annulus or adjacent tissue between the supra-annular region 120 and the subannular region 130, and/or a to seal against blood leakage (perivalvular leakage and/or regurgitation during systole) around the frame 110.

In some embodiments, the subannular region 130 can be a wire frame that is laser cut out of any suitable material. In some embodiments, the subannular region 130 can be formed from a shape-memory or superelastic material such as, for example, Nitinol. In some embodiments, the subannular region 130 can be laser cut from a sheet of a shape-memory metal alloy such as Nitinol and, for example, heat-set into a desired shape and/or configuration. In some embodiments, forming the subannular region 130 in such a manner can allow the subannular region 130 to bend, flex, fold, compress, and/or otherwise reconfigure substantially without plastically deforming and/or without fatigue that may result in failure or breaking of one or more portions thereof. Moreover, the wire frame of the subannular region 130 can be covered by any suitable biocompatible material such as any of those described above.

The subannular region 130 can be shaped and/or formed to include any number of features configured to engage native tissue, one or more other portions of the valve 100, and/or the actuator 170. For example, in some embodiments, the subannular region 130 can include and/or can form a distal portion having a distal anchoring element 132 and a proximal portion having a proximal anchoring element 134. In some embodiments, the subannular region 130 can include and/or can form any other suitable anchoring element (not shown in FIGS. 1A-1E). In some embodiments, the anchoring elements 132 and 134 are integrally and/or monolithically formed with the subannular region 130. The distal anchoring element 132 and the proximal anchoring element 134 of the subannular region 130 can be any suitable shape, size, and/or configuration such as any of those described in detail in the '957 PCT, the '010 PCT, the '231 PCT, the '390 PCT, the '932 Provisional, the '059 Provisional, any of those described herein with respect to specific embodiments. For example, the anchoring elements 132 and 134 can extend from a portion of the subannular region 130 by about 10-40 mm.

In some embodiments, the distal anchoring element 132 can optionally include a guidewire coupler configured to selectively engage and/or receive a portion of a guidewire or a portion of a guidewire assembly. The guidewire coupler is configured to allow a portion of the guidewire to extend through an aperture of the guidewire coupler, thereby allowing the valve 100 to be advanced over or along the guidewire during delivery and deployment. In some embodiments, the guidewire coupler can selectively allow the guidewire to be advanced therethrough while blocking or preventing other elements and/or components such as a pusher or the like.

The anchoring elements 132 and/or 134 of the subannular region 130 can be configured to engage a desired portion of the native tissue to mount the valve 100 and/or the support frame 110 to the annulus of the native valve in which it is deployed. For example, in some implementations, the distal anchoring element 132 can be a projection or protrusion extending from the subannular region 130 and into a RVOT and/or any other suitable tract or portion of the ventricle. In such implementations, the distal anchoring element 132 can be shaped and/or biased such that the distal anchoring element 132 exerts a force on the subannular tissue operable to at least partially secure the distal end portion of the valve 100 in the native annulus. In some implementations, the proximal anchoring element 134 can be configured to engage subannular tissue on a proximal side of the native annulus to aid in the securement of the valve 100 in the annulus.

In some implementations, at least the proximal anchoring element 134 can be configured to transition, move, and/or otherwise reconfigure between a first configuration in which the proximal anchoring element 134 extends from the subannular region 130 a first amount or distance and a second configuration in which the proximal anchoring element 134 extends from the subannular region 130 a second amount or distance. For example, in some embodiments, the proximal anchoring element 134 can have a first configuration in which the proximal anchoring element 134 is in a compressed, contracted, retracted, undeployed, folded, and/or restrained state (e.g., a position that is near, adjacent to, and/or in contact with the transannular region 112 and/or the supra-annular region 120 of the support frame 110), and a second configuration in which the proximal anchoring element 134 is in an expanded, extended, deployed, unfolded, and/or unrestrained state (e.g., extending away from the transannular region 112). Moreover, in some implementations, the proximal anchoring element 134 can be transitioned in response to actuation of the actuator 170, as described in further detail herein.

In some implementations, the proximal anchoring element 134 can be transitioned from the first configuration to the second configuration during deployment to selectively engage native tissue, chordae, trabeculae, annular tissue, leaflet tissue, and/or any other anatomic structures to aid in the securement of the valve 100 in the native annulus. The proximal anchoring element 134 (and/or the distal anchoring element 132) can include any suitable feature, surface, member, etc. configured to facilitate the engagement between the proximal anchoring element 134 (and/or the distal anchoring element 132) and the native tissue. For example, in some embodiments, the proximal anchoring element 134 can include one or more features configured to engage and/or become entangled in the native tissue, chordae, trabeculae, annular tissue, leaflet tissue, and/or any other anatomic structures when in the second configuration, as described in further detail herein with reference to specific embodiments.

The transannular region 112 of the support frame 110 is disposed between the supra-annular region 120 and the subannular region 130. In some embodiments, the transannular region 112 can be coupled to each of the supra-annular region 120 and the subannular region 130 such that a desired amount of movement and/or flex is allowed therebetween (e.g., welded, bonded, sewn, bound, and/or the like). For example, in some implementations, the transannular region 112 and/or portions thereof can be sewn to each of the supra-annular region 120 and the subannular region 130 (and/or portions thereof).

The transannular region 112 can be shaped and/or formed into a ring, a cylindrical tube, a conical tube, D-shaped tube, and/or any other suitable annular shape. In some embodiments, the transannular region 112 may have a side profile of a flat-cone shape, an inverted flat-cone shape (narrower at top, wider at bottom), a concave cylinder (walls bent in), a convex cylinder (walls bulging out), an angular hourglass, a curved, graduated hourglass, a ring or cylinder having a flared top, flared bottom, or both. Moreover, the transannular region 112 can form and/or define an aperture or central channel 114 that extends along the central axis 104 (e.g., the y-axis). The central channel 114 (e.g., a central axial lumen or channel) can be sized and configured to receive the flow control component 150 across a portion of a diameter of the central channel 114. In some embodiments, the transannular region 112 can have a shape and/or size that is at least partially based on a size, shape, and/or configuration of the supra-annular region 120 and/or subannular region 130 of the support frame 110, and/or the native annulus in which it is configured to be deployed. For example, the transannular region 112 can have an outer circumference surface for engaging native annular tissue that may be tensioned against an inner aspect of the native annulus to provide structural patency to a weakened native annular ring.

In some embodiments, the transannular region 112 can be a wire frame that is laser cut out of any suitable material. In some embodiments, the transannular region 112 can be formed from a shape-memory or superelastic material such as, for example, Nitinol. In some embodiments, the transannular region 112 can be laser cut from a sheet of a shape-memory metal alloy such as Nitinol and, for example, heat-set into a desired shape and/or configuration. Although not shown in FIGS. 1A-1E, in some embodiments, the transannular region 112 can include and/or can be formed with two laser cut halves that can be formed into a desired shape and/or configuration and coupled together to form the transannular region 112. The transannular region 112 can be formed to include a set of compressible wire cells having an orientation and/or cell geometry substantially orthogonal to the central axis 104 (FIG. 1A) to minimize wire cell strain when the transannular region 112 is in a vertical compressed configuration, a rolled and compressed configuration, or a folded and compressed configuration. In some embodiments, forming the transannular region 112 in such a manner can allow the transannular region 112 to bend, flex, fold, deform, and/or otherwise reconfigure (substantially without plastic deformation and/or undue fatigue) in response to lateral folding along or in a direction of a lateral axis 106 (FIG. 1C) and/or vertical compression along or in a direction of the central axis 104 (FIG. 1D), as described in further detail herein.

As described above with reference to the supra-annular region 120 and the subannular region 130, the wire frame of the transannular region 112 can be covered by any suitable biocompatible material such as any of those described above. In some implementations, the wire frames of the supra-annular region 120, transannular region 112, and subannular region 130 can be flexibly coupled (e.g., sewn) to form a wire frame portion of the support frame 110, which in turn, is covered in the biocompatible material. Said another way, the supra-annular region 120, the transannular region 112, and the subannular region 130 can be covered with the biocompatible material prior to being coupled or after being coupled. In embodiments in which the wire frames are covered after being coupled, the biocompatible material can facilitate and/or support the coupling therebetween.

Although not shown in FIGS. 1A-1E, the frame 110 may also have and/or form additional functional elements (e.g., loops, anchors, etc.) for attaching accessory components such as biocompatible covers, tissue anchors, releasable deployment and retrieval controls (e.g., the actuator 170, the delivery system interface 180, and/or other suitable guides, knobs, attachments, rigging, etc.) and so forth. In some implementations, the frame 110 (or aspects and/or portions thereof) can be structurally and/or functionally similar to the frames (or corresponding aspects and/or portions thereof) described in detail in the '957 PCT, the '010 PCT, the '231 PCT, the '390 PCT, the '932 Provisional, the '059 Provisional.

The flow control component 150 can refer in a non-limiting sense to a device for controlling fluid flow therethrough. In some embodiments, the flow control component 150 can be a leaflet structure having 2-leaflets, 3-leaflets, 4-leaflets, or more, made of flexible biocompatible material such a treated or untreated pericardium. The leaflets can be sewn or joined to a support structure such as an inner frame, which in turn, can be sewn or joined to the outer frame 110. The leaflets can be configured to move between an open and a closed or substantially sealed state to allow blood to flow through the flow control component 150 in a first direction through an inflow end of the valve 100 and block blood flow in a second direction, opposite to the first direction, through an outflow end of the valve 100. For example, the flow control component 150 can be configured such that the valve 100 functions, for example, as a heart valve, such as a tricuspid valve, mitral valve, aortic valve, or pulmonary valve, that can open to blood flowing during diastole from atrium to ventricle, and that can close from systolic ventricular pressure applied to the outer surface. Repeated opening and closing in sequence can be described as "reciprocating."

The inner frame and/or portions or aspects thereof can be similar in at least form and/or function to the outer frame 110 and/or portions or aspects thereof. For example, the inner frame can be a laser cut frame formed from or of a shape-memory material such as Nitinol. Moreover, the inner frame can be compressible for delivery and configured to return to its original (uncompressed) shape when released (e.g., after delivery). In some embodiments, the inner frame can include and/or can form any suitable number of compressible, elastically deformable diamond-shaped or eye-shaped wire cells, and/or the like. The wire cells can have an orientation and cell geometry substantially orthogonal to an axis of the flow control component 150 to minimize wire cell strain when the inner frame is in a compressed configuration.

Figure 1B:
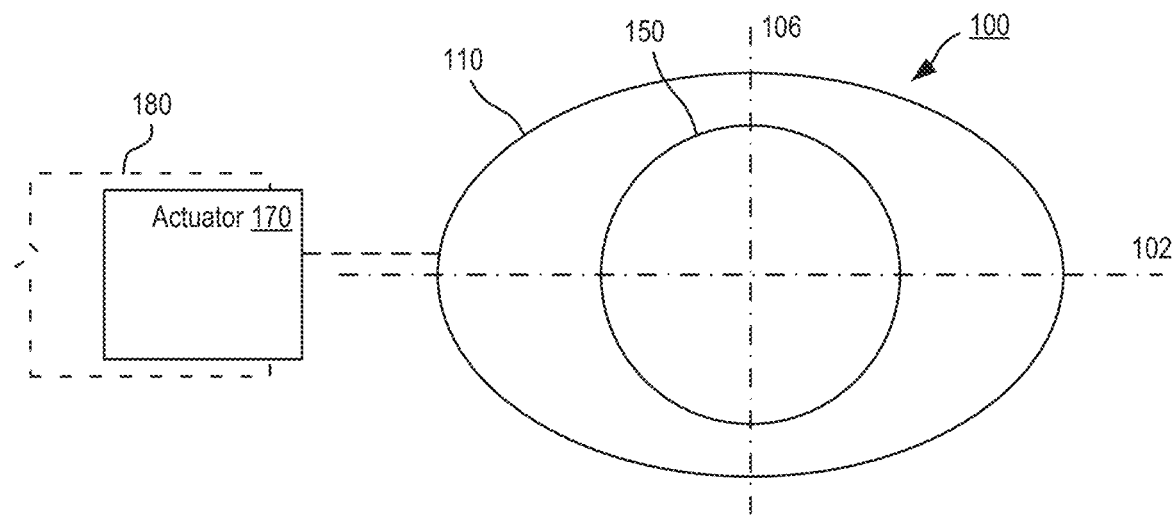
Figure 1C:
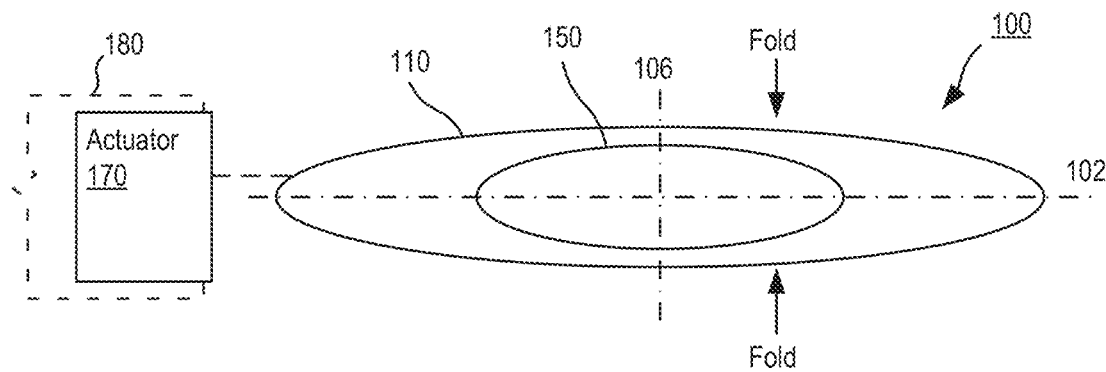
FIGS. 1C and 1D are top view schematic illustrations of the prosthetic valve of FIGS. 1A and 1B and shown in the expanded configuration and the compressed configuration, respectively.
Figure 1D:
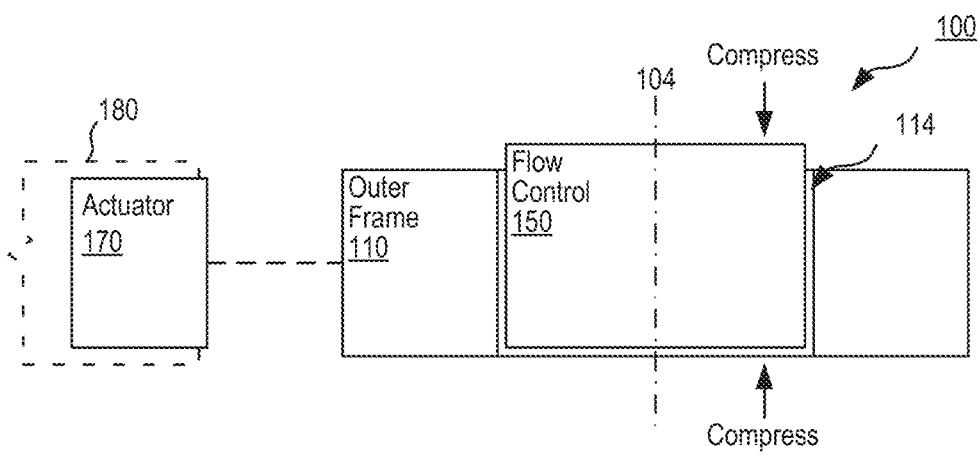

In some embodiments, the flow control component 150 and/or the inner frame thereof can have a substantially cylindrical or tubular shape when the valve 100 is in the expanded configuration (see e.g., FIG. 1C) and can be configured to elastically deform when the valve 100 is placed in the compressed configuration (see e.g., FIGS. 1B and 1D). Although not shown in FIGS. 1A-1E, in some embodiments, the inner frame of the flow control component 150 can include and/or can be formed with two halves that can be coupled together to allow the inner frame to elastically deform in response to lateral compression or folding along or in a direction of the lateral axis 106 (FIG. 1C), as described in further detail herein.

As shown in FIGS. 1A-1D, the flow control component 150 is mounted within the central channel 114 of the frame 110. More specifically, the flow control component 150 is mounted and/or coupled to the supra-annular region 120 (e.g., an inner portion thereof) and is configured to extended into and/or through the central channel 114 formed and/or defined by the transannular region 112. In some embodiments, the flow control component 150 can be coupled to the supra-annular region 120 via tissue, a biocompatible mesh, one or more woven or knitted fabrics, one or more super-elastic or shape-memory alloy structures, which is sewn, sutured, and/or otherwise secured to a portion supra-annular region 120. In some embodiments, the flow control component 150 can be coupled to the supra-annular region 120 such that a portion of the flow control component 150 is disposed above and/or otherwise extends beyond the supra-annular region 120 (e.g., extends away from the annulus in the direction of the atrium). In some embodiments, the portion of the flow control component 150 extending above and/or beyond the supra-annular region 120 can form a ridge, ledge, wall, step-up, and/or the like. In some implementations, such an arrangement can facilitate ingrowth of native tissue over the supra-annular region 120 without occluding the flow control component 150.

The flow control component 150 can be at least partially disposed in the central channel 114 such that the axis of the flow control component 150 that extends in the direction of blood flow through the flow control component 150 is substantially parallel to the central axis 104 of the frame 110. In some embodiments, the arrangement of the support frame 110 can be such that the flow control component 150 is centered within the central channel 114. In other embodiments, the arrangement of the support frame 110 can be such that the flow control component 150 is off-centered within the central channel 114. In some embodiments, the central channel 114 can have a diameter and/or perimeter that is larger than a diameter and/or perimeter of the flow control component 150. Although not shown in FIGS. 1A-1E, in some embodiments, the valve 100 can include a spacer or the like that can be disposed within the central channel 114 adjacent to the flow control component 150. In other embodiments, a spacer can be a cover, or the like coupled to a portion of the frame 110 and configured to cover a portion of the central channel 114. In some instances, the spacer can be used to facilitate the coupling of the flow control component 150 to the frame 110.

In some embodiments, the flow control component 150 (or portions and/or aspects thereof) can be similar to, for example, any of the flow control components described in the '231 PCT. Thus, the flow control component 150 and/or aspects or portions thereof are not described in further detail herein.

Referring back to FIG. 1A, the valve 100 includes and/or is coupled to the actuator 170 and the delivery interface 180. The actuator 170 can be any suitable member, mechanism, and/or device configured to actuate at least a portion of the valve 100. For example, in some embodiments, the actuator 170 and/or a portion of the actuator 170 can be configured to at least temporarily couple to the supra-annular region 120 of the support frame 110 (e.g., a spline and/or other portion thereof) and can be configured to actuate one or more portions of the valve 100. More specifically, the actuator 170 can be configured to actuate at least the proximal anchoring element 134 of the subannular region 120 of the support frame 110 to transition the proximal anchoring element 134 between its first and second configurations. In some implementations, the actuator 170 can include one or more cables, tethers, linkages, joints, connections etc., that can exert a force (or can remove an exerted force) on a portion of the proximal anchoring element 134 operable to transition the proximal anchoring element 134 between the first and second configuration. For example, the subannular region 130 of the support frame 110 can be formed with the proximal anchoring element 134 biased in the uncompressed and/or expanded configuration and the actuator 170 can be actuated to exert a force, via the one or more cables, tethers, etc., operable to transition the proximal anchoring element 134 to the compressed and/or retracted configuration.

In some implementations, the actuator 170 can be secured and/or locked when the proximal anchoring element 134 is compressed and/or retracted (e.g., a first configuration) to at least temporarily maintain the proximal anchoring element 134 in the first configuration. As described above, in some implementations, the proximal anchoring element 134 can be in the first configuration for delivery and deployment prior to seating the valve 100 in the native annulus. Once the valve 100 is seated in the native annulus, a user can manipulate a portion of the delivery system to actuate the actuator 170. In this example, actuating the actuator 170 can cause the actuator 170 to release and/or remove the force exerted on the proximal anchoring element 134 (e.g., via the cable(s), tether(s), etc.), thereby allowing the proximal anchoring element 134 to return to its original or biased configuration (e.g., a second configuration), as described above.

The delivery system interface 180, shown in FIG. 1A, can include any number of components having any suitable shape, size, and/or configuration. In some implementations, the delivery system interface 180 can be and/or can include, for example, a distal end portion of the delivery system used to deliver the valve 100 to a desired location in the body of a patient (e.g., the annulus of a native heart valve). In some embodiments, the delivery system interface can include a delivery catheter such as, for example, a 12-34 Fr delivery catheter with any suitable corresponding internal lumen diameter sufficient to receive the prosthetic valve 100 in the compressed configuration, as described, for example, in the '957 PCT. Moreover, the delivery system can include a secondary catheter that can be, for example, a multi-lumen catheter configured to engage the valve 100 to advance the valve 100 through the delivery catheter. In some embodiments, each lumen of the multi-lumen secondary catheter can include, for example, a cable, tether, and/or any other suitable component associated with and/or included in the actuator 170. Each cable, tether, and/or component can, in turn, be coupled to a portion of the valve 100 or support frame 110 and configured to actuate a portion thereof, as described in further detail herein with reference to specific embodiments.

Furthermore, a lumen of the multi-lumen secondary catheter (e.g., a central lumen) can include and/or can receive a torque cable and a guidewire. The guidewire extends though the secondary catheter and into a desired position relative to the native tissue (e.g., the RVOT) to provide a path along which the valve 100 travels during delivery and/or deployment, as described in the '957 PCT. The torque cable can be any suitable cable, or the like configured to removably couple to the supra-annular region 120 of the frame 110 (e.g., a waypoint coupled to and/or formed by the supra-annular region 120). The torque cable can be a relatively stiff cable that can be configured to facilitate delivery and/or deployment of the valve 100 as well as retraction of the valve 100 if desirable. In this manner, the delivery system interface 180 shown in FIG. 1A, can be a distal end portion of the delivery system including any of the components described above. Thus, the delivery system interface 180 can be used in and/or otherwise can facilitate the delivery of the valve 100, deployment and/or actuation of the valve 100 or a portion thereof (e.g., the proximal anchoring element 134), and/or retraction of the valve 100. Moreover, the delivery system interface 180 can be configured to decouple, disengage, and/or otherwise release the valve 100 after the valve 100 is deployed in a native annulus, as described in further detail herein with reference to specific embodiments.

As described above, the valve 100 is compressible and expandable between the expanded configuration and the compressed configuration. The valve 100 can have a first height or size along the central axis 104 when in the expanded configuration and can have a second height or size, less than the first height or size, along the central axis 104 when in the compressed configuration. The valve 100 can also be compressed in additional directions. For example, the valve 100 can be compressed along the lateral axis 106 that is perpendicular to both the longitudinal axis 102 and the central axis 104 (see e.g., FIGS. 1B and 1C).

The valve 100 is compressed during delivery of the valve 100 and is configured to expand once released from the delivery catheter. More specifically, the valve 100 is configured for transcatheter orthogonal delivery to the desired location in the body (e.g., the annulus of a native valve), in which the valve 100 is compressed in an orthogonal or lateral direction relative to the dimensions of the valve 100 in the expanded configuration (e.g., along the central axis 104 and/or the lateral axis 106). During delivery, the longitudinal axis 102 of the valve 100 is substantially parallel to a longitudinal axis of the delivery catheter, as described in the '957 PCT.

The valve 100 is in the expanded configuration prior to being loaded into the delivery system and after being released from the delivery catheter and deployed or implanted (or ready to be deployed or implanted) at the desired location in the body. When in the expanded configuration shown in FIGS. 1A, 1B, and 1E, the valve 100 has an extent in any direction orthogonal or lateral to the longitudinal axis 102 (e.g., along the central axis 104 and/or the lateral axis 106) that is larger than a diameter of the lumen of the delivery catheter used to deliver the valve 100. For example, in some embodiments, the valve 100 can have an expanded height (e.g., along the central axis 104) of 5-60 mm. In some embodiments, the valve 100 can have an expanded diameter length (e.g., along the longitudinal axis 102) and width (e.g., along the lateral axis 106) of about 20-80 mm, or about 40-80 mm.

When in the compressed configuration shown in FIGS. 1C and 1D, the valve 100 has an extent in any direction orthogonal or lateral to the longitudinal axis 102 (e.g., along the central axis 104 and/or the lateral axis 106) that is smaller than the diameter of the lumen of the delivery catheter, allowing the valve 100 to be delivered therethrough. For example, in some embodiments, the valve 100 can have a compressed height (e.g., along the central axis 104) and a compressed width (e.g., along the lateral axis 106) of about 6-15 mm, about 8-12 mm, or about 9-10 mm. The valve 100 can be compressed by compressing, rolling, folding, and/or any other suitable manner, or combinations thereof, as described in detail in the '957 PCT, the '010 PCT, the '231 PCT, the '390 PCT, the '932 Provisional, the '059 Provisional. It is contemplated in some embodiments that the length of the valve 100 (e.g., along the longitudinal axis 102) is not compressed for delivery. Rather, in some embodiments, the length of the valve 100 can be increased in response to compression of the valve 100 along the central axis 104 and/or the lateral axis 106.

Figure 1E:
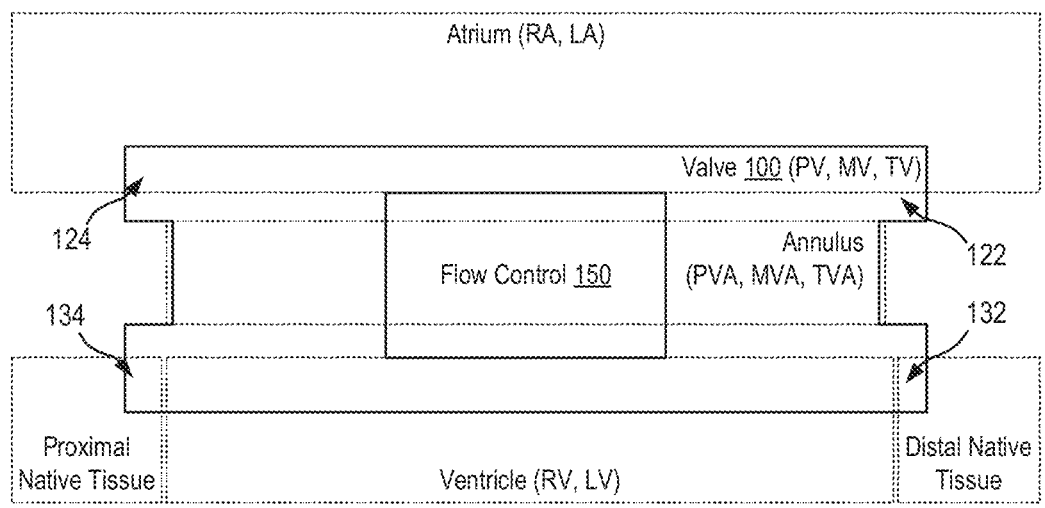
FIG. 1E is a schematic illustration of the prosthetic valve of FIGS. 1A-1D deployed within an annulus of a native heart valve.

As shown in FIG. 1E, the valve 100 can be delivered, for example, to an atrium of the human heart (or any other space or chamber of the human heart) and disposed within an annulus of a native valve such as, for example, the pulmonary valve (PV), the mitral valve (MV), the aortic valve (AV), and/or the tricuspid valve (TV). As described above, the valve 100 can be in the compressed configuration and delivered to the annulus via the delivery system and can be released from the delivery system and allowed to expand to the expanded configuration. For example, the valve 100 can be delivered to the atrium of the human heart and released from the delivery catheter (not shown) via any of the delivery systems, devices, and/or methods described in detail in the '957 PCT, the '010 PCT, the '231 PCT, the '390 PCT, the '932 Provisional, the '059 Provisional.

In some implementations, the delivery of the valve 100 can include advancing a guidewire into the atrium of the human heart, through the native valve, and to a desired position within the ventricle (e.g., the RVOT). After positioning the guidewire, the delivery catheter can be advanced along and/or over the guidewire and into the atrium (e.g., via the IVC, the SVC, and/or a trans-septal access). In some embodiments, a guidewire coupler of the valve 100 (e.g., included in or on the distal anchoring element 132) can be coupled to a proximal end portion of the guidewire and the valve 100 can be placed in the compressed configuration, allowing the valve 100 to be advanced along the guidewire and through a lumen of the delivery catheter, and into the atrium.

The deployment of the valve 100 can include placing the distal anchoring element 132 of the subannular region 130 in the ventricle (RV, LV) below the annulus while the remaining portions of the valve 100 are in the atrium (RA, LA). In some instances, the distal anchoring element 132 can be advanced over and/or along the guidewire to a desired position within the ventricle such as, for example, an outflow tract of the ventricle. For example, in some implementations, the valve 100 can be delivered to the annulus of the native tricuspid valve (TV) and at least a portion of the distal anchoring element 132 can be positioned in the RVOT. In other implementations, the valve 100 can be delivered to the annulus of the native mitral valve (MV) and at least a portion of the distal anchoring element 132 can be positioned in the LVOT and/or in any other suitable position in which the distal anchoring element 132 can engage native tissue, leaflets, chordae, etc.

In some implementations, the prosthetic valve 100 can be temporarily maintained in a partially deployed state. For example, the valve 100 can be partially inserted into the annulus and held at an angle relative to the annulus to allow blood to flow from the atrium to the ventricle partially through the native valve annulus around the valve 100, and partially through the valve 100, which can allow for assessment of the valve function.

The valve 100 can be placed or seated in the annulus (PVA, MVA, AVA, and/or TVA) of the native valve (PV, MV, AV, and/or TV) such that the subannular region 130 (e.g., a ventricular collar) is disposed in a subannular position, the transannular region 112 of the valve frame 110 extends through the annulus, and the supra-annular region 120 (e.g., a atrial collar) remains in a supra-annular position. For example, in some embodiments, the delivery system, the delivery system interface 180, the actuator 170, and/or any other suitable member, tool, etc. can be used to push at least the proximal end portion of the valve 100 into the annulus. In some implementations, the proximal anchoring element 134 can be maintained in its first configuration as the valve 100 is seated in the annulus. For example, as described above, the proximal anchoring element 134 can be in a compressed, contracted, and/or retracted configuration in which the proximal anchoring element 134 is in contact with, adjacent to, and/or near the transannular region 112 and/or the supra-annular region 120 of the frame 110, which in turn, can limit an overall circumference of the subannular region 130 of the frame 110, thereby allowing the subannular region 130 and the transannular region 112 of the frame 110 to be inserted into and/or through the annulus.

Once seated, the proximal anchoring element 134 can be transitioned from its first configuration to its second configuration, as described in detail in the '010 PCT. For example, in some implementations, a user can manipulate a portion of the delivery system to actuate the actuator 170. In some implementations, actuating the actuator 170 can release and/or reduce an amount of tension within or more tethers, cables, connections, and/or portions of the actuator 170, thereby allowing the proximal anchoring element 134 to transition Accordingly, once the valve 100 is seated in the annulus, the proximal anchoring element 134 can be placed in its second configuration in which the proximal anchoring element 134 contacts, engages, and/or is otherwise disposed adjacent to subannular tissue. In some implementations, the proximal anchoring element 134 can be configured to engage and/or capture native tissue, chordae, trabeculae, annular tissue, leaflet tissue, and/or the like when the proximal anchoring element 134 is disposed in the ventricle. For example, in some implementations, after seating the valve 100 in the annulus, the proximal anchoring element 134 can be transitioned from the first (compressed) configuration to the second (extended) configuration such that the proximal anchoring element 134 extends around and/or through one or more portions of native tissue, chordae, etc. The proximal anchoring element 134 can then be returned to the first configuration to capture and/or secure the one or more portions of native tissue, chordae, trabeculae, annular tissue, leaflet tissue, etc. between the proximal anchoring element 134 and, for example, the transannular section of the outer frame 110. In other implementations, the proximal anchoring element 134 can be maintained in the second (extended) configuration after the valve 100 is seated in the native annulus. In such implementations, the proximal anchoring element 134, for example, can contact and/or engage subannular tissue on a proximal side of the annulus such that the proximal anchoring element and a proximal portion of the atrial collar exert a compressive force on a proximal portion of the annular tissue.

In this manner, the distal anchoring element 132 can be configured to engage native tissue on a distal side of the annulus and the proximal anchoring element 134 can be configured to engage native tissue on a proximal side of the annulus (e.g., when in the second or expanded configuration), thereby securely seating the valve 100 in the native annulus, as shown in FIG. 1E. In some implementations, any other or additional portions of the valve can similarly engage native tissue to securely seat the valve 100 in the native annulus and/or to form a seal between the support frame 110 and the tissue forming the native annulus (e.g., the distal portion 122 and/or the proximal portion 124 of the supra-annular region 120, the transannular region 112, and/or one or more other or additional anchoring elements (not shown in FIGS. 1A-1E).

While not shown in FIGS. 1A-1E, in some implementations, the valve 100 and/or the delivery system can include one or more tissue anchors that can be used to anchor one or more portions of the valve 100 to the annular tissue, as described in detail in the '957 PCT. In some embodiments, the tissue anchors can be configured to puncture, pierce, and/or otherwise secure the anchoring elements 132 and/or 134, and/or the atrial collar to the annular tissue. In other embodiments, the tissue anchors can be, for example, atraumatic anchors configured to secure the anchoring elements 132 and/or 134, and/or the atrial collar to the annular tissue without puncturing, piercing, and/or otherwise causing trauma to the native tissue.

FIGS. 2A-2D are schematic illustrations of an annular support frame 210 according to an embodiment. The annular support frame 210 (also referred to herein as "tubular frame," "valve frame," "wire frame," "outer frame," "support frame," or "frame") can include and/or can be coupled to an actuator 270 configured to actuate one or more portions of the support frame 210. In some embodiments, the support frame 210 and/or the actuator 270 can be substantially similar in at least form and/or function to the support frame 110 and/or the actuator 170, respectively, described above with reference to FIGS. 1A-1E. Thus, portions and/or aspects of the support frame 210 and/or the actuator 270 are not described in further detail herein.

As shown, the annular support frame 210 has a supra-annular member and/or region 220, a subannular member and/or region 230, and a transannular member and/or region 212, disposed and/or coupled therebetween. In the embodiment shown in FIGS. 2A-2D, the supra-annular member and/or region 220, the subannular member and/or region 230, and the transannular member and/or region 212 are separate, independent, and/or modular components that are coupled to collectively form the frame 210. Each of the supra-annular member and/or region 220, the subannular member and/or region 230, and the transannular member and/or region 212 (referred to herein as the supra-annular, subannular, and transannular "member") are a wire frame that is laser cut out of any suitable material such as a shape-memory or superelastic material like Nitinol. In some implementations, each of the supra-annular member 220, the subannular member 230, and the transannular member 212 can be laser cut from a sheet of Nitinol and, for example, heat-set into a desired shape and/or configuration. As described above, forming the supra-annular member 220, the subannular member 230, and the transannular member 212 in such a manner can provide a desired amount of flexibility and/or resistance to plastic or permanent deformation that can allow the frame 210 to be folded and/or compressed for delivery. Moreover, the wire frame portions of the supra-annular member 220, the subannular member 230, and the transannular member 212 can be covered by any suitable biocompatible material such as any of those described above.

In some embodiments, the supra-annular member 220 of the frame 210 can be similar in at least form and/or function to the supra-annular member 120 described above with reference to FIGS. 1A-1E. For example, the supra-annular member 220 can be and/or can form, for example, a cuff or collar that can be attached or coupled to an upper edge or upper portion of the transannular member 212, as described in further detail herein. In some implementations, the supra-annular member 220 can be deployed on the atrial floor to direct blood from the atrium into a flow control component mounted to the frame 210, as described in detail above. The supra-annular member 220 can be shaped and/or formed to include any number of features configured to engage native tissue and/or one or more other portions of the frame 210 and/or the actuator 270. For example, in some embodiments, the supra-annular member 220 can include and/or can form an outer portion or loop, an inner portion or loop, and one or more splines disposed between the outer and inner portions or loops.

In some embodiments, the outer portion or loop (referred to herein as "outer loop") can be shaped and/or sized to engage native tissue. More specifically, the supra-annular member 220 (or an outer loop thereof) can have a distal portion 222 configured to engage distal supra-annular tissue and a proximal portion 224 configured to engage proximal supra-annular tissue. In some embodiments, the distal and proximal portions 222 and 224 can have a rounded and/or curved shape, wherein a radius of curvature of the proximal portion 224 is larger than a radius of curvature of the distal portion 222. In some implementations, the distal portion 222 can form, for example, a distal upper anchoring element that can engage distal supra-annular tissue to at least partially stabilize and/or secure the frame 210 in the native annulus. Similarly, the proximal portion 224 can form, for example, a proximal upper anchoring element that can engage proximal supra-annular tissue to at least partially stabilize and/or secure the frame 210 in the native annulus.

The inner portion or loop (referred to herein as "inner loop") of the supra-annular member 220 can be substantially circular and can be coupled to and/or suspended from the outer loop by the one or more splines. As described in further detail herein with reference to specific embodiments, the inner loop can be coupled to an inner frame of the flow control component to at least partially mount the flow control component to the support frame 210. In some implementations, suspending the inner loop from the outer loop (via the one or more splines) can, for example, at least partially isolate the inner loop from at least a portion of the force associated with transitioning the frame 210 between the expanded configuration and the compressed configuration, as described in further detail herein. Moreover, mounting the flow control component to the inner loop of the supra-annular member 220 similarly at least partially isolates and/or reduces an amount of force transferred to the flow control component when the frame 210 is transitioned between its expanded configuration and its compressed configuration.

The one or more splines of the supra-annular member 220 can be any suitable shape, size, and/or configuration. For example, in some embodiments, the supra-annular member 220 can include a distal spline and a proximal spline. As described above, the splines can be configured to support the inner loop and/or otherwise couple the inner loop to the outer loop. In some embodiments, the supra-annular member 220 can include a spline (e.g., a proximal spline) configured to receive, couple to, and/or otherwise engage the actuator 270 and/or delivery system interface. For example, in some embodiments, a proximal spline can form a connection point, attachment point, waypoint, and/or any other suitable feature that can temporarily and/or removably couple to the actuator 270, as described in further detail herein with reference to specific embodiments.

In some embodiments, the subannular member 230 of the frame 210 can be similar in at least form and/or function to the subannular region 130 described above with reference to FIGS. 1A-1E. For example, the subannular member 230 of the frame 210 can be and/or can form, for example, a cuff or collar that can be attached or coupled to a lower edge or upper portion of the transannular member 212, as described in further detail herein. When the frame 210 is deployed within a human heart, the subannular member 230 can be a ventricular collar that is shaped to conform to the native deployment location. In a tricuspid and/or mitral valve replacement, for example, the subannular member 230 collar can have various portions configured to conform to the native valve and/or a portion of the ventricular ceiling surrounding the tricuspid and/or mitral valve, respectively. In some implementations, the subannular member 230 or at least a portion thereof can engage the ventricular ceiling surrounding the native annulus to secure the frame 210 in the native annulus, to prevent dislodging of the frame 210, to sandwich or compress the native annulus or adjacent tissue between the supra-annular member 220 and the subannular member 230, and/or to seal against blood leakage (perivalvular leakage and/or regurgitation during systole) around the frame 210.

The subannular member 230 can be shaped and/or formed to include any number of features configured to engage native tissue, one or more other portions of the frame 210, and/or the actuator 270. For example, in some embodiments, the subannular member 230 can include and/or can form a distal portion having a distal anchoring element 232 and a proximal portion having a proximal anchoring element 234. In some embodiments, the subannular member 230 can include and/or can form any other suitable anchoring element (not shown in FIGS. 2A-2D). In some embodiments, the anchoring elements 232 and 234 are integrally and/or monolithically formed with the subannular member 230. The distal anchoring element 232 and the proximal anchoring element 234 of the subannular member 230 can be any suitable shape, size, and/or configuration such as any of those described in detail in the '957 PCT, the '010 PCT, the '231 PCT, the '390 PCT, the '932 Provisional, the '059 Provisional, any of those described above with reference to the valve 100, and/or any of those described herein with respect to specific embodiments.

In some embodiments, the distal anchoring element 232 can optionally include a guidewire coupler configured to selectively engage and/or receive a portion of a guidewire or a portion of a guidewire assembly. The guidewire coupler is configured to allow a portion of the guidewire to extend through an aperture of the guidewire coupler, thereby allowing the frame 210 to be advanced over or along the guidewire during delivery and deployment. In some embodiments, the guidewire coupler can selectively allow the guidewire to be advanced therethrough while blocking or preventing other elements and/or components such as a pusher or the like.

The anchoring elements 232 and/or 234 of the subannular member 230 can be configured to engage a desired portion of the native tissue to mount the frame 210 to the annulus of the native valve in which it is deployed. For example, in some implementations, the distal anchoring element 232 can be a projection or protrusion extending from the subannular member 230 and into, for example, a RVOT. In such implementations, the distal anchoring element 232 can be shaped and/or biased such that the distal anchoring element 232 exerts a force on the subannular tissue operable to at least partially secure the distal end portion of the frame 210 in the native annulus. In some implementations, the proximal anchoring element 234 can be configured to engage subannular tissue on a proximal side of the native annulus to aid in the securement of the frame 210 in the annulus.

In some implementations, at least the proximal anchoring element 234 can be configured to transition, move, and/or otherwise reconfigure between a first configuration in which the proximal anchoring element 234 extends from the subannular member 230 a first amount or distance and a second configuration in which the proximal anchoring element 234 extends from the subannular member 230 a second amount or distance. As described above, the subannular member 230 of the frame 210 can be and/or can include, for example, a laser cut frame formed of a shape-memory material such as Nitinol, which is heat-set into a desired shape. In some embodiments, heat-setting the subannular member 230 can include forming one or more twists in a portion of the laser cut wire, which in turn, can allow one or more portions of the subannular member 230 to be biased in different directions and/or orientations. For example, in general, the subannular member 230 of the frame 210 can be formed to provide a high amount of flexibility in a direction that allows the subannular member 230 to be folded and/or compressed (e.g., relative to a longitudinal axis of the subannular member 230). In some embodiments, however, a portion of the subannular member 230 can be twisted and/or otherwise oriented to provide a high amount of flexibility in a direction that allows the proximal anchoring element 234 to be actuated and/or to otherwise transition between its first and second configurations (e.g., in a direction orthogonal to the longitudinal axis of the subannular member 230 and orthogonal to a fold and/or compression direction.

In some embodiments, the proximal anchoring element 234 can be in a compressed, contracted, retracted, undeployed, folded, and/or restrained state (e.g., a position that is near, adjacent to, and/or in contact with the transannular member 212 and/or the supra-annular member 220 of the support frame 210) when in the first configuration, and can be in an expanded, extended, deployed, unfolded, and/or unrestrained state (e.g., extending away from the transannular member 212) when in the second state. In some embodiments, the proximal anchoring element 234 can be biased and/or heat-set in the second configuration. Moreover, in some implementations, the proximal anchoring element 234 can be transitioned in response to actuation of the actuator 270, as described in further detail herein.

In some implementations, the proximal anchoring element 234 can be transitioned from the first configuration to the second configuration during deployment to selectively engage native tissue, chordae, trabeculae, annular tissue, leaflet tissue, and/or any other anatomic structures to aid in the securement of the frame 210 in the native annulus. The proximal anchoring element 234 (and/or the distal anchoring element 232) can include any suitable feature, surface, member, etc. configured to facilitate the engagement between the proximal anchoring element 234 (and/or the distal anchoring element 232) and the native tissue. For example, in some embodiments, the proximal anchoring element 234 can include one or more features configured to engage and/or become entangled in the native tissue, chordae, trabeculae, annular tissue, leaflet tissue, and/or any other anatomic structures when in the second configuration, as described in further detail herein with reference to specific embodiments.

In some embodiments, the transannular member 212 of the frame 210 can be similar in at least form and/or function to the transannular region 112 described above with reference to FIGS. 1A-1E. For example, the transannular member 212 is disposed between the supra-annular member 220 and the subannular member 230. In some embodiments, the transannular member 212 can be coupled to each of the supra-annular member 220 and the subannular member 230 such that a desired amount of movement and/or flex is allowed therebetween (e.g., welded, bonded, sewn, bound, and/or the like). For example, in some implementations, the transannular member 212 and/or portions thereof can be sewn to each of the supra-annular member 220 and the subannular member 230 (and/or portions thereof). The transannular member 212 can be shaped and/or formed into a ring, a cylindrical tube, a conical tube, D-shaped tube, and/or any other suitable annular shape, as described above with reference to the transannular member 112. In some embodiments, the transannular member 212 can have a shape and/or size that is at least partially based on a size, shape, and/or configuration of the supra-annular member 220 and/or subannular member 230 of the support frame 210, the flow control component configured to be coupled to the support frame 210, and/or the native annulus in which it is configured to be deployed. For example, the transannular member 212 can have an outer circumference surface for engaging native annular tissue that may be tensioned against an inner aspect of the native annulus to provide structural patency to a weakened native annular ring.

As described above, the supra-annular member 220, the subannular member 230, and the transannular member 212 can be independent and/or modular components that are coupled to collectively form the frame 210. In some embodiments, the supra-annular member 220 is configured to engage supra-annular tissue of the native valve and can be shaped and/or biased to form a substantially fluid tight seal with the atrial floor to limit and/or substantially prevent leakage around the frame (e.g., perivalvular leaks). Similarly, the subannular member 220 is configured to engage subannular tissue of the native valve and can be shaped and/or biased to form a substantially fluid tight seal with the ventricular ceiling to limit and/or substantially prevent leakage around the frame. Moreover, in some implementations, the transannular member 212 can have a slightly oversized circumference relative to the native annular tissue and can, for example, form at least a partial seal between the transannular member 212 of the frame 210 and the native tissue forming the walls of the annulus. In such implementations, forming a seal against the atrial floor, the ventricular ceiling, and the walls of the annulus can provide redundancy in the event of an imperfect or partial seal formed by one or more of the supra-annular member(s) 220, the subannular member 230, and/or the transannular member 212.

In other implementations, the distal and proximal anchoring elements 232 and 234 can exert a force on the subannular tissue that is operable in pulling the supra-annular member 220 of the frame 210 toward the atrial floor, thereby facilitating the formation of a seal. In such implementations, for example, the subannular member 230 and/or the transannular member 212 need not form a seal or can form a partially seal with the native tissue because of the seal formed by the supra-annular member 220.

In some implementations, the arrangement of the frame 210 can be such that structural support and/or stiffness is provided by the supra-annular member 220 and the subannular member 230, while the transannular member 212 need not provide substantial support and/or stiffness. In some such implementations, the transannular member 212 can be configured to couple the supra-annular member 220 to the subannular member 230 and to easily deform (elastically) for delivery rather than provide substantial support and/or stiffness. Moreover, while the transannular member 212 is described above as being formed by a laser cut frame that is covered by biocompatible material, in other embodiments, the transannular member 212 can be formed from any suitable flexible material such as pericardial tissue, fabric, polyester, and/or the like. In some such embodiments, forming the flexible material without the laser cut frame can, for example, reduce a size of the frame 210 when in the compressed configuration, thereby allowing a valve to be delivered using a smaller delivery catheter. In some embodiments, the frame 210 need not include a separate transannular member 212. For example, in such embodiments, a flow control component can be coupled between the supra-annular member 220 and the subannular member 230, thereby allowing a further reduction in a size of a valve in the compressed configuration.

As shown in FIGS. 2A-2D, the actuator 270 can be at least temporarily coupled to the supra-annular member 220 and the subannular member 230. In some embodiments, the actuator 270 or a portion thereof can also at least temporarily couple to a portion of the transannular member 212. The actuator 270 can be any suitable member, mechanism, and/or device configured to actuate at least a portion of the frame 210. Moreover, a portion of the actuator 270 can extend through a portion of a delivery system used to deliver the frame 210 and/or a valve including the frame 210. In this manner, a user can manipulate a proximal end portion of the actuator 270 to actuate the actuator 270.

In some embodiments, the actuator 270 and/or a portion of the actuator 270 can be configured to at least temporarily couple to the spline of the supra-annular member 220 (e.g., an attachment point, waypoint, connector, threaded coupler, etc.) and can be configured to actuate one or more portions of the frame 210. The actuator 270 can be configured to actuate at least the proximal anchoring element 234 of the subannular member 220 of the support frame 210 to transition the proximal anchoring element 234 between its first and second configurations (described above).

In some implementations, the actuator 270 can include one or more cables, tethers, linkages, joints, connections etc., that can exert a force (or can remove an exerted force) on a portion of the proximal anchoring element 234 operable to transition the proximal anchoring element 234 between the first and second configuration. For example, the actuator 270 can couple to a waypoint or the like of the supra-annular member 220 and can include one or more tethers, cables, and/or members that extend through the waypoint and/or one or more openings or apertures and couple to the proximal anchoring element 234. In some implementations, the one or more tethers, cables, and/or members can be removably and/or temporarily coupled to the proximal anchoring element 234, as described, for example, in the '010 PCT.

Figure 2A:
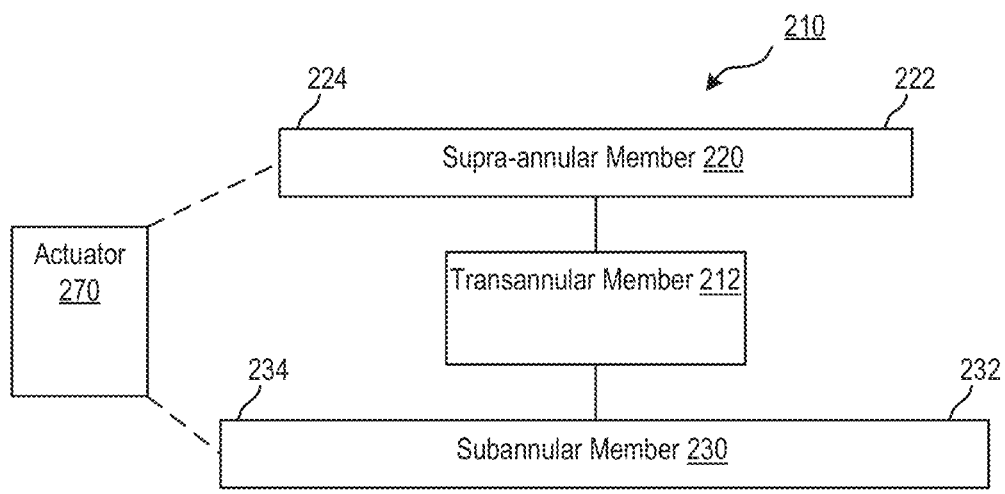
FIGS. 2A and 2B are side-view schematic illustrations of a prosthetic valve in a first configuration and a second configuration, respectively, according to an embodiment.
Figure 2B:
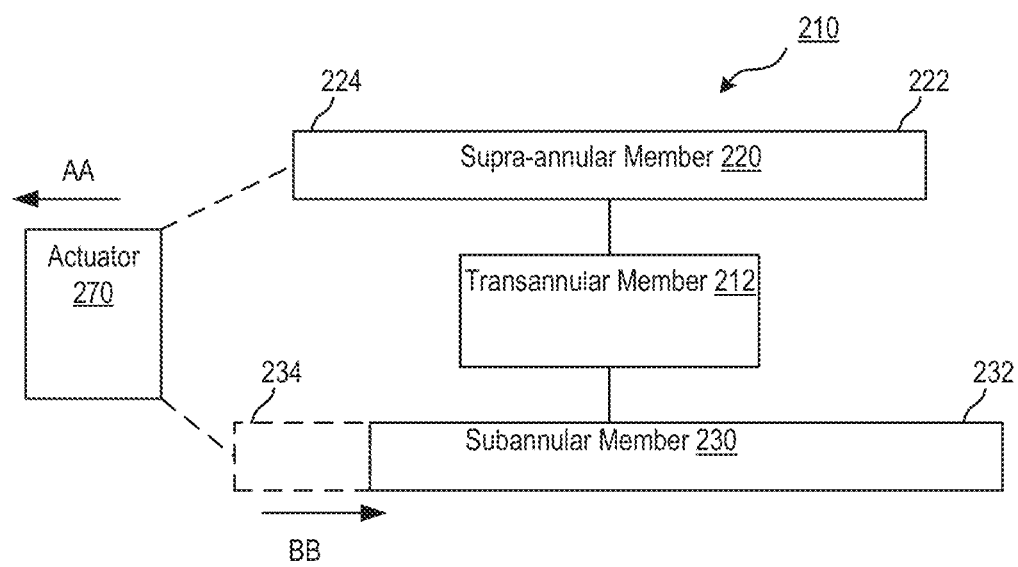

As described above, the subannular member 230 can be formed with the proximal anchoring element 234 biased in the uncompressed and/or expanded configuration. In this manner, the actuator 270 can be actuated to exert a force, via the one or more cables, tethers, etc., operable to transition the proximal anchoring element 234 to the compressed and/or retracted configuration. More specifically, the user can manipulate the proximal end portion of the actuator 270 to actuate a distal end portion of the actuator 270 that is coupled to the frame 210. For example, actuating the actuator 270 can be such that the one or more cables, tethers, and/or members are pulled in a proximal direction (e.g., away from the frame 210 and/or in a manner that increases a tension therein), as indicated by the arrow AA in FIG. 2B. The coupling of the distal end portion of the actuator 270 to the frame 210 can be such that the proximal movement of the cables, tethers, etc., pull the proximal anchoring element 234 toward a central axis of the frame 210, as indicated by the arrow BB in FIG. 2B. As such, actuating the actuator 270 can exert a force on the proximal anchoring element 234 operable to place the proximal anchoring element 234 in a compressed, retracted, restrained, and/or actuated configuration, as shown in FIG. 2B.

Figure 2C:
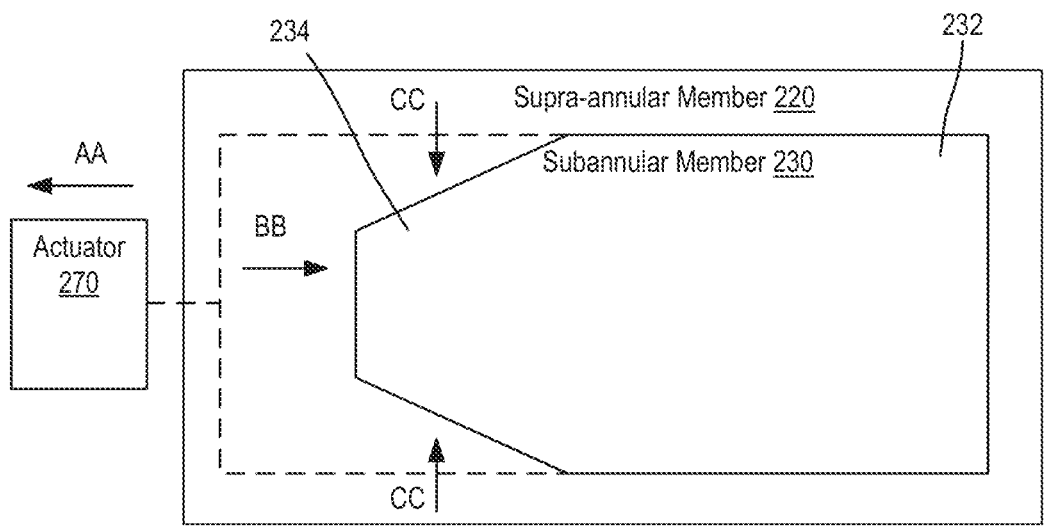
FIGS. 2C and 2D are a bottom-view schematic illustration and a side-view schematic illustration of the prosthetic valve of FIGS. 2A-2B and shown in the second configuration and a third configuration, respectively.

In some implementations, actuating the actuator 270 also can be operable to pull a proximal-anterior portion of the subannular member and/or transannular wall and a proximal-posterior portion of the subannular member and/or transannular wall to or toward the longitudinal axis of the valve 200. For example, FIG. 2C shows that the actuation of the actuator 270 (e.g., moving the actuator 270 or tethers in the AA direction) compresses and/or moves the proximal anchoring element 234 toward a central portion of the valve frame 210, as indicated by the arrow BB, and compresses the posterior and anterior sidewalls toward a central portion of the valve frame 210, as indicated by the arrows CC. As such, actuating the actuator 270 can reduce a perimeter of at least the subannular member 230 allowing a desired portion of the valve frame 210 to be inserted into the annulus of the native valve.

In some implementations, the actuator 270 can be secured and/or locked when the proximal anchoring element 234 is compressed and/or retracted (e.g., a first configuration) to at least temporarily maintain the proximal anchoring element 234 in the first configuration. As described above, in some implementations, the proximal anchoring element 234 can be in the first configuration for delivery and deployment prior to seating the frame 210 (or valve) in the native annulus. Once the frame 210 is seated in the native annulus, a user can manipulate the proximal portion of the actuator 270 to actuate and/or release the actuator 270. In this example, the actuation can cause the actuator 270 to release and/or remove at least a portion of the force exerted on the proximal anchoring element 234 (e.g., via the cable(s), tether(s), etc.), thereby allowing the proximal anchoring element 234 (and/or one or more portions of the anterior and/or posterior walls) to return to its biased configuration or a second configuration (see e.g., FIG. 2A), as described above.

In some implementations, the actuator 270 can be configured to further actuate the frame 210 after the frame 210 (or valve) is seated in the native annulus. For example, in some implementations, the user can manipulate the proximal end portion of the actuator 270 (e.g., in the same way as just described or in a different manner) to move one or more cables, tethers, and/or members of the actuator 270 in the proximal direction (e.g., away from the frame 210 and/or in a manner that increases a tension therein), as indicated by the arrow DD in FIG. 2D. In this example, the proximal anchoring element 234 is in its uncompressed or unactuated state after seating the frame 210 in the native annulus. The actuator 270 can be coupled to the supra-annular member 220, the subannular member 230, and/or the proximal anchoring element 234 such that the actuation of the actuator 270 results in a force operable to pull the proximal anchoring element 234 toward the proximal portion 224 of the supra-annular member 220, as indicated by the arrow EE in FIG. 2D. For example, the actuator 270 can exert a compressive force or the like that is operable in cinching at least portion of the frame 210.

Figure 2D:
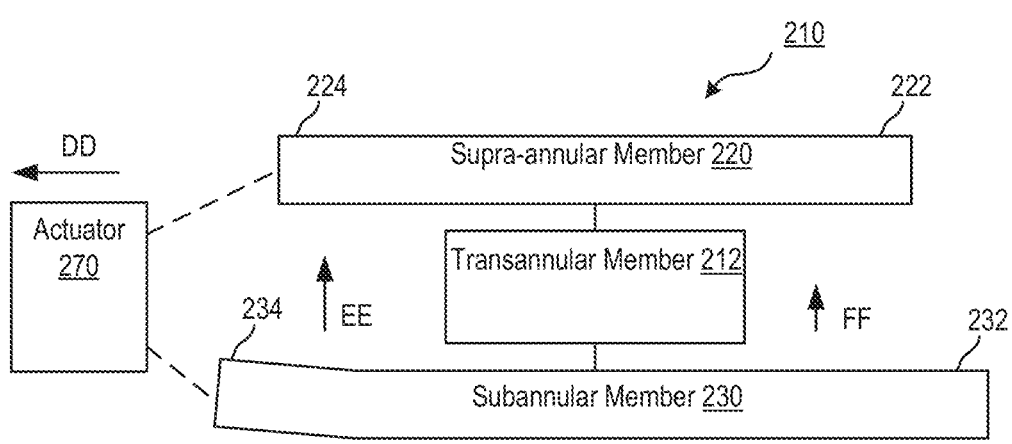

As shown in FIG. 2D, in some instances, the proximal anchoring element 234 can flex in the direction of the native annulus (e.g., beyond its biased position), which can facilitate an engagement between the proximal anchoring element 234 and the native tissue and/or chordae on the proximal side of the native annulus. In some implementations, the force resulting from the actuation of the actuator 270 can be operable to pull, move, compress, and/or cinch other portions of the subannular member 230 toward the supra-annular member 220, as indicated by the arrow FF in FIG. 2D. In some such implementations, an amount of cinching can be varied across the frame 210. For example, an amount of cinching at or near a proximal portion of the frame 210 can be greater than an amount of cinching at or near a distal portion of the frame 210. In other implementations, the amount of cinching can be substantially consistent across the frame 210. Moreover, at least some tissue surrounding the native annulus can be disposed between the supra-annular member 220 and the subannular member 230 when the frame 210 is seated in the native annulus and thus, the cinching of the supra-annular member 220 and the subannular member 230 can be operable to squeeze and/or sandwich the native tissue between the members 220 and 230. In this manner, the cinching can enhance a securement of the frame 210 in the native annulus.

Although not shown in FIGS. 2A-2D, in some embodiments, the proximal anchoring element 234 can be sized and/or shaped to engage native tissue, chordae, trabeculae, annular tissue, leaflet tissue, and/or the like when the frame 210 is cinched against or relative to the native annulus. In some embodiments, the proximal anchoring element 234 can include one or more protrusions, features, ridges, ribs, knobs, knots, beads, loops, etc. that can engage and/or that can facilitate the engagement of the native tissue when the frame 210 is cinched against or relative to the native annulus.

While the frame 210 and/or one or more portions of the subannular member 230 are described above as being compressed to move inward toward a central axis of the frame 210 in response to actuation of the actuator 270, in other embodiments, the actuator 270 can be removably coupled to one or more portions of the frame 210 and configured to move such portions in any suitable manner. For example, in some implementations, the actuator 270 (e.g., one or more tethers or the like, as described above) can be coupled to the proximal anchoring element 234 such that actuation of the actuator 270 results in the proximal anchoring element 234 folding or wrapping around the transannular member 212 of the frame 210 in either an anterior direction or a posterior direction, or both directions depending on the mode of actuation. As described above, the folding and/or wrapping of the proximal anchoring element 234 around the transannular member 212 can reduce a circumference or diameter of at least the subannular member 230 allowing the frame 210 to be inserted into and/or at least partially through the annulus of the native heart valve.

Figure 3A:
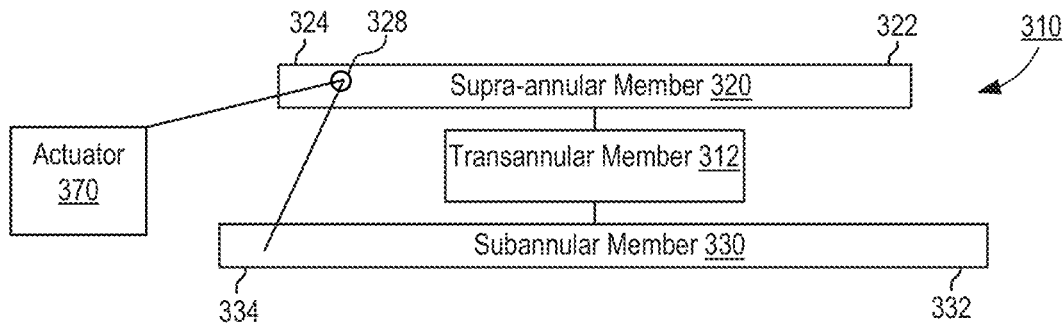
FIGS. 3A-3C are schematic illustrations of an outer frame of a side-delivered transcatheter prosthetic heart valve, according to an embodiment, and shown in a delivery configuration, a seating configuration, and a deployed configuration, respectively.
Figure 3B:
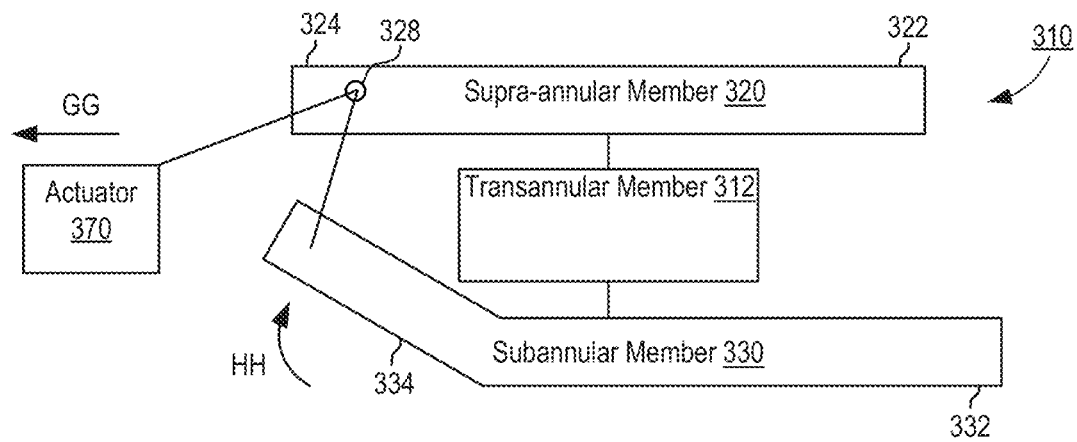
Figure 3C:
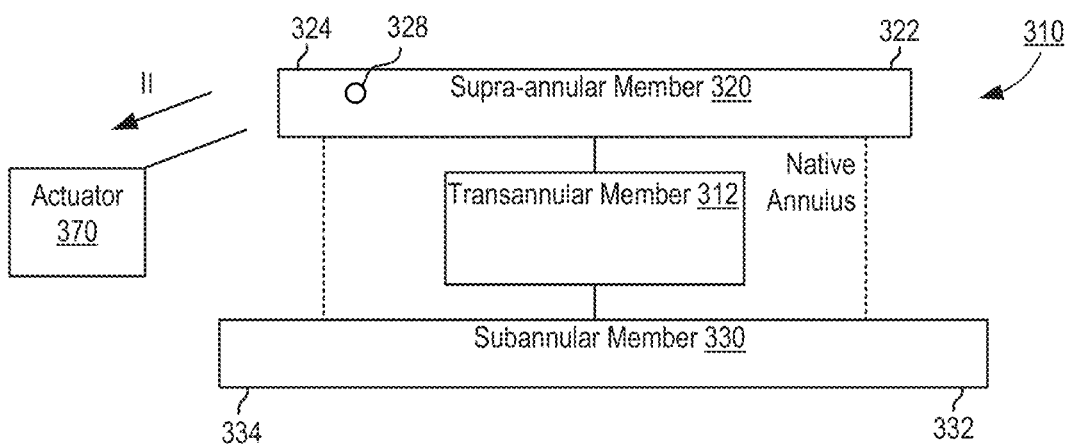

FIGS. 3A-3C are schematic illustrations of an annular support frame 310 according to an embodiment. The annular support frame 310 (also referred to herein as "tubular frame," "valve frame," "wire frame," "outer frame," "support frame," or "frame") can include and/or can be coupled to an actuator 370 configured to actuate one or more portions of the support frame 310. In some embodiments, the support frame 310 and/or the actuator 370 can be substantially similar in at least form and/or function to the support frames 110, 210 and/or the actuators 170, 270, respectively. Thus, portions and/or aspects of the support frame 310 and/or the actuator 370 are not described in further detail herein.

As shown, the annular support frame 310 has a supra-annular member and/or region 320, a subannular member and/or region 330, and a transannular member and/or region 312, disposed and/or coupled therebetween. In the embodiment shown in FIGS. 3A-3C, the supra-annular member and/or region 320, the subannular member and/or region 330, and the transannular member and/or region 312 are separate, independent, and/or modular components that are coupled to collectively form the frame 310. Each of the supra-annular member and/or region 320, the subannular member and/or region 330, and the transannular member and/or region 312 (referred to herein as the supra-annular, subannular, and transannular "member") are a wire frame that is laser cut out of any suitable material such as a shape-memory or superelastic material like Nitinol. In some implementations, each of the supra-annular member 320, the subannular member 330, and the transannular member 312 can be laser cut from a sheet of Nitinol and, for example, heat-set into a desired shape and/or configuration. As described above, forming the supra-annular member 320, the subannular member 330, and the transannular member 312 in such a manner can provide a desired amount of flexibility and/or resistance to plastic or permanent deformation that can allow the frame 310 to be folded and/or compressed for delivery. Moreover, the wire frame portions of the supra-annular member 320, the subannular member 330, and the transannular member 312 can be covered by any suitable biocompatible material such as any of those described above.

In some embodiments, the supra-annular member 320 of the frame 310 can be similar in at least form and/or function to the supra-annular members 120, 220 described above. For example, the supra-annular member 320 can be and/or can form, for example, a cuff or collar that can be attached or coupled to an upper edge or upper portion of the transannular member 312. The supra-annular member 320 can be shaped and/or formed to include any number of features configured to engage native tissue and/or one or more other portions of the frame 310 and/or the actuator 370. For example, the supra-annular member 320 (or an outer loop thereof) can have a distal portion 322 configured to engage distal supra-annular tissue and a proximal portion 324 configured to engage proximal supra-annular tissue.

As described above, the supra-annular member 320 can include and/or can form an outer portion or loop, an inner portion or loop, and one or more splines disposed between the outer and inner portions or loops. The outer portion or loop (referred to herein as "outer loop") can be shaped and/or sized to engage native tissue. In some implementations, the outer loop can form, for example, one or more upper or supra-annular anchoring elements that can engage supra-annular tissue to at least partially stabilize and/or secure the frame 310 in the native annulus. The inner portion or loop (referred to herein as "inner loop") of the supra-annular member 320 is coupled to and/or suspended from the outer loop by the one or more splines and is coupleable to an inner frame of the flow control component to at least partially mount the flow control component to the support frame 310, as described above with reference to the supra-annular member 220. The one or more splines of the supra-annular member 320 can be any suitable shape, size, and/or configuration. For example, in some embodiments, the supra-annular member 320 can include a distal spline and a proximal spline. In some embodiments, the supra-annular member 320 can include a spline (e.g., a proximal spline) configured to receive, couple to, and/or otherwise engage the actuator 370 and/or delivery system interface. For example, in the embodiment shown in FIGS. 3A-3C, the supra-annular member 330 (e.g., a spline thereof) can form a waypoint and/or the like that can temporarily and/or removably couple to and/or receive the actuator 370 and any other suitable portion of the delivery system, as described in further detail herein with reference to specific embodiments.

The subannular member 330 of the frame 310 can be similar in at least form and/or function to the subannular regions and/or members 130, 230 described above. For example, the subannular member 330 of the frame 310 can be and/or can form, for example, a cuff or collar that can be attached or coupled to a lower edge or upper portion of the transannular member 312. When the frame 310 is deployed within a human heart, the subannular member 330 can be a ventricular collar that is shaped to conform to the native deployment location. In some implementations, the subannular member 330 or at least a portion thereof can engage the ventricular ceiling surrounding the native annulus to secure the frame 310 in the native annulus, to prevent dislodging of the frame 310 and/or to seal against blood leakage (perivlvular leakage and/or regurgitation during systole) around the frame 310.

The subannular member 330 included in the frame 310 shown in FIGS. 3A-3C can include and/or can form a distal portion having a distal anchoring element 332 and a proximal portion having a proximal anchoring element 334. In some embodiments, the subannular member 330 can include and/or can form any other suitable anchoring element (not shown in FIGS. 3A-3C). The anchoring elements 332 and 334 can be integrally and/or monolithically formed with the subannular member 330. The distal anchoring element 332 and the proximal anchoring element 334 of the subannular member 330 can be any suitable shape, size, and/or configuration such as any of those described in detail in the '957 PCT, the '010 PCT, the '231 PCT, the '390 PCT, the '932 Provisional, the '059 Provisional, any of those described above with reference to the valve 100, and/or any of those described herein with respect to specific embodiments. The distal anchoring element 332 can be substantially similar to the distal anchoring elements 132, 232 and therefore, is not described in further detail herein.

The proximal anchoring element 334 can be configured to transition, move, and/or otherwise reconfigure between a first configuration in which the proximal anchoring element 334 extends from the subannular member 330 a first amount, distance, and/or direction and a second configuration in which the proximal anchoring element 334 extends from the subannular member 330 a second amount, distance, and/or direction. In some embodiments, the proximal anchoring element 334 can be substantially similar in at least form and/or function to the proximal anchoring element 234 described above with reference to FIGS. 2A-2D. Accordingly, such similarities are not described in further detail herein.

In some embodiments, the proximal anchoring element 334 can be in a compressed, contracted, retracted, undeployed, folded, and/or restrained state (e.g., a position that is near, adjacent to, and/or in contact with the transannular member 312 and/or the supra-annular member 320 of the support frame 310) when in the first configuration, and can be in an expanded, extended, deployed, unfolded, and/or unrestrained state (e.g., extending away from the transannular member 312) when in the second state. In some embodiments, the proximal anchoring element 334 can be biased and/or heat-set in the second configuration. Moreover, in some implementations, the proximal anchoring element 334 can be transitioned in response to actuation of the actuator 370, as described in further detail herein.

The transannular member 312 is disposed between the supra-annular member 320 and the sub annular member 330. In some embodiments, the transannular member 312 can be coupled to each of the supra-annular member 320 and the subannular member 330 such that a desired amount of movement and/or flex is allowed therebetween (e.g., welded, bonded, sewn, bound, and/or the like). In some embodiments, the transannular member 312 of the frame 310 can be similar in at least form and/or function to the transannular regions 112, 212 described above and thus, is not described in further detail herein.

While the frame 310 is described above as being substantially similar to the frame 210 described above with reference to FIGS. 2A-2D, the frame 310 can differ from the frame 210 in the engagement with the actuator and the movement of the proximal anchoring element 334. As shown in FIGS. 3A-3C, the actuator 370 can at least temporarily engage with the supra-annular member 320 and the subannular member 330. The actuator 370 can be any suitable member, mechanism, and/or device configured to actuate at least a portion of the frame 310. Moreover, a portion of the actuator 370 can extend through a portion of a delivery system used to deliver the frame 310 and/or a valve including the frame 310. In this manner, a user can manipulate a proximal end portion of the actuator 370 to actuate the actuator 370.

FIG. 3A shows the actuator 370 engaged with the frame 310 while the frame 310 is in a compressed or delivery configuration. As described above with reference to the valve 100, the frame 310 can be compressed, folded, and/or otherwise placed into a delivery configuration for side-delivery via a delivery catheter. Prior to placing the frame 310 in the delivery system, the actuator 370 can be removably coupled to the frame 310 such that the frame 310 (or valve) and the actuator 370 are advanced through the delivery catheter together. In this embodiment, the actuator 370 can be a tether that extends through the waypoint 328 defined by the supra-annular member 320, looped through one or more attachment points of the subannular member 330 (e.g., one or more attachment points on or near the proximal anchoring element 334, and then looped back through the waypoint 328. As such, both ends of the tether are proximal to the frame 310 and can be maintained proximal to and/or at a proximal end of the delivery system, allowing an operator to manipulate the actuator 370 (tether) to actuate the proximal anchoring element 334. FIG. 3A shows that the proximal anchoring element 334 is in an extended or unactuated configuration when the frame 310 is in the delivery configuration for side-delivery through the delivery catheter.

FIG. 3B shows the actuator 370 being actuated to move the proximal anchoring element 334 from the first position or configuration to the second position or configuration. More specifically, the frame 310 (and/or valve) can advanced through the delivery catheter and allowed to at least partially expand as the frame 310 is released from the delivery catheter. In some implementations, the frame 310 is at least partially inserted into the annulus while the proximal end portion of the frame 310 remains in the delivery catheter. After fully releasing the frame 310 from the delivery catheter, the operator can manipulate the proximal end portion of the actuator 370 to actuate a distal end portion of the actuator 370 that is coupled to the proximal anchoring element 334.

For example, actuating the actuator 370 can be such that the one or more tethers are pulled in a proximal direction (e.g., away from the frame 310 and/or in a manner that increases a tension therein), as indicated by the arrow GG in FIG. 3B. With the actuator 370 passing through the waypoint 328 of the supra-annular member 320, which in this embodiment is not actuated by the actuator 370), the proximal movement of the cables, tethers, etc., pull the proximal anchoring element 334 toward the waypoint 328, as indicated by the arrow HH in FIG. 3B. As such, actuating the actuator 370 can exert a force on the proximal anchoring element 334 operable to place the proximal anchoring element 334 in a compressed, retracted, restrained, and/or actuated configuration, as shown in FIG. 3B. As described above, placing the proximal anchoring element 334 in the compressed and/or actuated configuration reduces a perimeter of at least the subannular member 330 allowing the subannular member 330 to be passed through the annulus of the native valve. While the proximal anchoring element 334 is shown in moving and/or pivoting in a supra-annular direction toward the waypoint 328, in some implementations, the proximal anchoring element 334 and/or one or more portions to the subannular member 330 and/or transannular member 312 can similarly be moved or pivoted toward the waypoint 328, which in turn, can reduce a perimeter of the subannular member 330, as described in detail above with reference to the frame 210 shown in FIGS. 2A-2D.

After the frame 310 (or valve) is seated in the annulus, the actuator 370 can be actuated again and/or otherwise returned to an unactuated state or configuration. As such, the proximal anchoring element 334 is allowed to return to the extended and/or unactuated configuration. In the embodiment shown in FIGS. 3A-3C, the proximal anchoring element 334 can be biased such that in the extended and/or unactuated configuration, the proximal anchoring element 334 engages native subannular tissue to at least partially secure the frame 310 in the annulus. FIG. 3C shows that once the frame 310 is seated in the annulus, the operator can manipulate the actuator 370 to remove the actuator 370 from the frame 310. For example, the operator can pull on one end of the tether (e.g., actuator 370) such that the tether is withdrawn from the attachment points of the subannular member 330 and the waypoint 328 of the supra-annular member 320. As such, the actuator 370 and/or a delivery system of which the actuator 370 is a part can be withdrawn from a patient while the frame 310 remains in the annulus of the native heart valve.

Provided below is a discussion of certain aspects or embodiments of side deliverable transcatheter prosthetic valves (e.g., prosthetic valves). The transcatheter prosthetic valves (or aspects or portions thereof) described below with respect to specific embodiments can be substantially similar in at least form and/or function to the valves 100 and/or 200 (or corresponding aspects or portions thereof). Similarly, the valves described below (or aspects or portions thereof) can be similar in at least form and/or function to the valves described in detail in the '957 PCT, the '010 PCT, the '231 PCT, the '390 PCT, the '932 Provisional, the '059 Provisional. Thus, certain aspects and/or portions of the specific embodiments may not be described in further detail herein.

Figure 4:
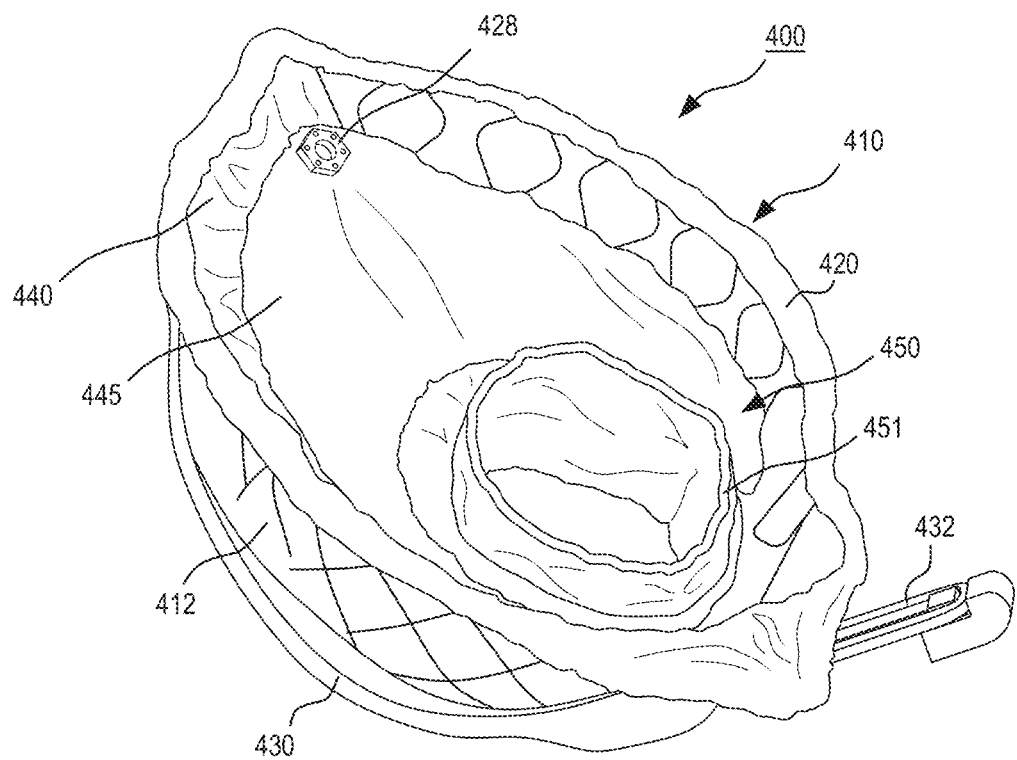
FIG. 4 is a perspective view illustration of a prosthetic valve according to an embodiment.

FIGS. 4-24 illustrate a side-deliverable (orthogonally deliverable) transcatheter prosthetic heart valve 400 (also referred to herein as "prosthetic valve" or "valve"), according to an embodiment. FIG. 4 is an illustration of a top perspective view of the valve 400. In some implementations, the valve 400 can be deployed in, for example, an annulus of a native tricuspid and/or mitral valve. The valve 400 is configured to permit blood flow in a first direction through an inflow end of the valve 400 and to block blood flow in a second direction, opposite the first direction, through an outflow end of the valve 400. For example, the prosthetic valve 400 can be a side deliverable transcatheter prosthetic heart valve configured to be deployed within the annulus of a native tricuspid valve or native mitral valve of a human heart to supplement and/or replace the functioning of the native valve.

The valve 400 is compressible and expandable in at least one direction relative to an x-axis of the valve 400 (also referred to herein as "horizontal axis," "longitudinal axis," "long axis," and/or "lengthwise axis"). The valve 400 is compressible and expandable between an expanded configuration for implanting at a desired location in a body (e.g., a human heart) and a compressed configuration for introduction into the body using a delivery catheter (not shown in FIG. 4). In some embodiments, the horizontal x-axis of the valve 400 is orthogonal to (90 degrees), or substantially orthogonal to (75-105 degrees), or substantially oblique to (45-135 degrees) to a central (vertical) y-axis when in the expanded and/or compressed configuration. Moreover, the horizontal x-axis of the valve 400 in the compressed configuration is substantially parallel to a lengthwise cylindrical axis of the delivery catheter in which the valve 400 is disposed.

In some embodiments, the valve 400 has an expanded or deployed height of about 5-60 mm, about 5-30 mm, about 5-20 mm, about 8-12 mm, or about 8-10 mm, and an expanded or deployed diameter (e.g., length and/or width) of about 25-80 mm, or about 40-80 mm. In some embodiments, the valve 400 has a compressed height (y-axis) and width (z-axis) of about 6-15 mm, about 8-12 mm, or about 9-10 mm. It is contemplated in some implementations that the length of the valve 400 (e.g., along the x-axis) is not compressed or otherwise reduced since it can extend along the length of the central cylindrical axis of the delivery catheter.

In certain embodiments, the valve 400 is centric, or radially symmetrical. In other embodiments, the valve 400 is eccentric, or radially asymmetrical (e.g., along or relative to the y-axis). In some eccentric embodiments, the frame 410 may have a D-shape in cross-section, with a flat portion or surface configured to substantially match an annulus of a native mitral valve at or near the anterior leaflet. In the example shown in FIGS. 4-24, the valve 400 is eccentric with one or more components being offset or asymmetrical region to the y-axis.

The valve 400 includes an annular outer support frame 410 and a collapsible inner flow control component 450 mounted within the annular outer support frame 410. The annular outer support frame 410 (also referred to herein as "outer frame") is made from a shape-memory material such as Nickel-Titanium alloy (Nitinol) and is therefore a self-expanding structure from a compressed configuration to an expanded configuration. As shown in FIG. 4, at least the outer support frame 410 of the valve 400 is covered, wrapped, and/or surrounded by a biocompatible cover 440. The biocompatible cover 440 can be a mesh material, a pericardial tissue, a woven synthetic polyester material, and/or any other suitable biocompatible material such as those described above.

The outer frame 410 has a transannular member 412 and/or body that circumscribes, forms, and/or defines a central (interior) channel about and/or along the vertical or central axis (y-axis). The outer frame 410 has a supra-annular member 420 attached circumferentially at a top edge of the transannular member 412 and a subannular member 410 attached circumferentially at a bottom edge of the transannular member 412. The supra-annular member 420 is shaped to conform to the native deployment location. In a tricuspid replacement, for example, the supra-annular member 420 or atrial collar can have a tall back wall portion to conform to the septal area of the native valve and can have a distal and proximal portion. The distal portion can be larger than the proximal portion to account for the larger flat space above (atrial) the distal subannular area (e.g., a right ventricular outflow tract (RVOT) subannular area). In a mitral replacement, for example, the supra-annular member 420 of the outer frame 410 may be D-shaped or shaped like a hyperbolic paraboloid to mimic the native structure.

The collapsible inner flow control component 450 (also referred to herein as "collapsible flow control component," "inner flow control component," and/or "flow control component") is mounted within the outer frame 410. The flow control component 450 has a foldable and compressible inner wire frame 35 (also referred to as "inner leaflet frame" or "inner frame") with two or more fold areas, hinge areas, coupling areas, elastically deformable regions, etc. A set of 2-4 flexible leaflets 461 are mounted in or on the inner frame 451 (not shown in FIG. 4). In some embodiments, the flow control component 450 has three leaflets 461 cusps or pockets mounted within the inner frame 451, as described in further detail herein.

The flow control component 450, like the outer frame 410, is foldable and compressible. For example, the inner frame 451 is foldable along or in the direction of a z-axis (e.g., foldable at the fold areas or the like) from a cylindrical configuration to a flattened cylinder configuration (or a two-layer band), where the fold areas are located on a distal side and on a proximal side of the inner frame 451. The flow control component 450, like the outer frame 410, is also vertically (y-axis) compressible to a shortened or compressed configuration. By folding (compressing) in the direction of the z-axis and vertically compressing in the y-axis, the valve 400 is permitted to maintain a relatively large dimension along the horizontal (x-axis). In some implementations, the outer frame 410 and the flow control component 450 are reduced along z-axis until the side walls are in contact or nearly so. This also allows the outer frame 410 and the flow control component 450 to maintain the radius along the horizontal axis (x-axis), to minimize the number of wire cells, which make up the outer and the inner frames, that can be damaged by forces applied during folding and/or compression necessary for loading into the delivery catheter.

The flow control component 450 has a diameter and/or perimeter that is smaller than a diameter and/or perimeter of the central channel of the outer frame 410. The flow control component 450 is mounted to or within the outer frame 410 such that a central or vertical axis (y-axis) of the inner frame 451 is parallel to the central or vertical axis (y-axis) of the outer frame 410. In some embodiments, the y-axis defined by the inner frame 451 is parallel to but offset from the y-axis defined by the outer frame 410 (FIG. 4). In some implementations, a spacer element 445 is disposed within and/or across the central channel and can facilitate the mounting of a portion of the flow control component 450 (e.g., an otherwise unsupported portion) to the outer support frame 410 and/or an ingrowth of native tissue over at least a portion of the supra-annular member 420 of the valve 400, in some embodiments, the spacer element 445 can be similar to any of those described in the '231 PCT.

In certain embodiments, the inner frame 451 can have a diameter of about 20-60 mm, the outer frame 410 (or the transannular member 412 thereof) can have a diameter of about 40-80 mm, and the supra-annular member 420 (or atrial collar) extend beyond the top edge of the transannular member 412 by about 10-30 mm to provide a seal on the atrial floor against perivalvular leaks (PVLs). The flow control component 450 and the outer frame 410 can be foldable (e.g., in the direction of the z-axis) and/or compressible (e.g., in the direction of the y-axis) to reduce a size of the entire valve 400 to fit within the inner diameter of a 24-36 Fr (8-12 mm inner diameter) delivery catheter (not shown in this FIG. 4).

Figure 5:
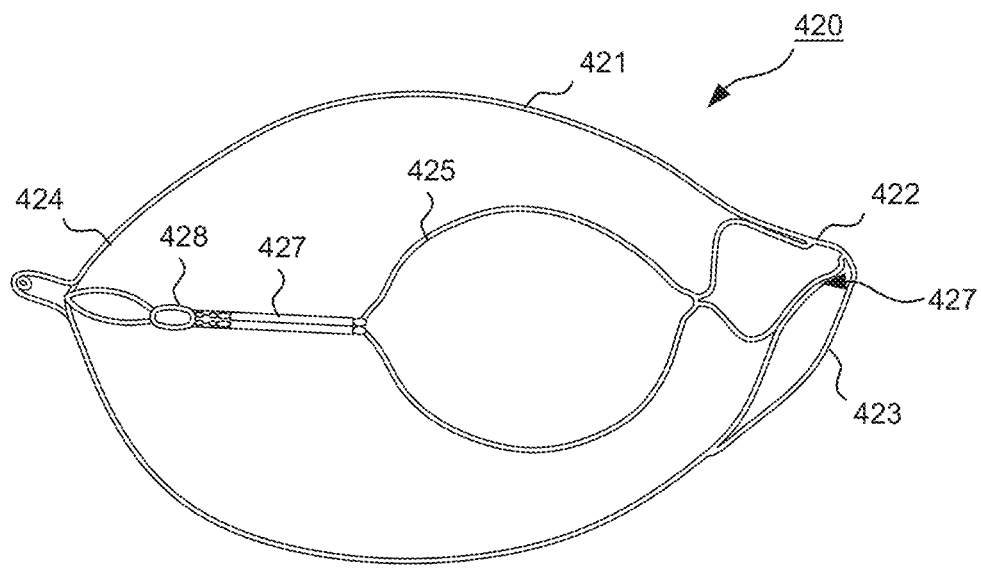
FIGS. 5 and 6 are various views illustrating a supra-annular region of an outer support frame of the prosthetic valve shown in FIG. 4.
Figure 6:
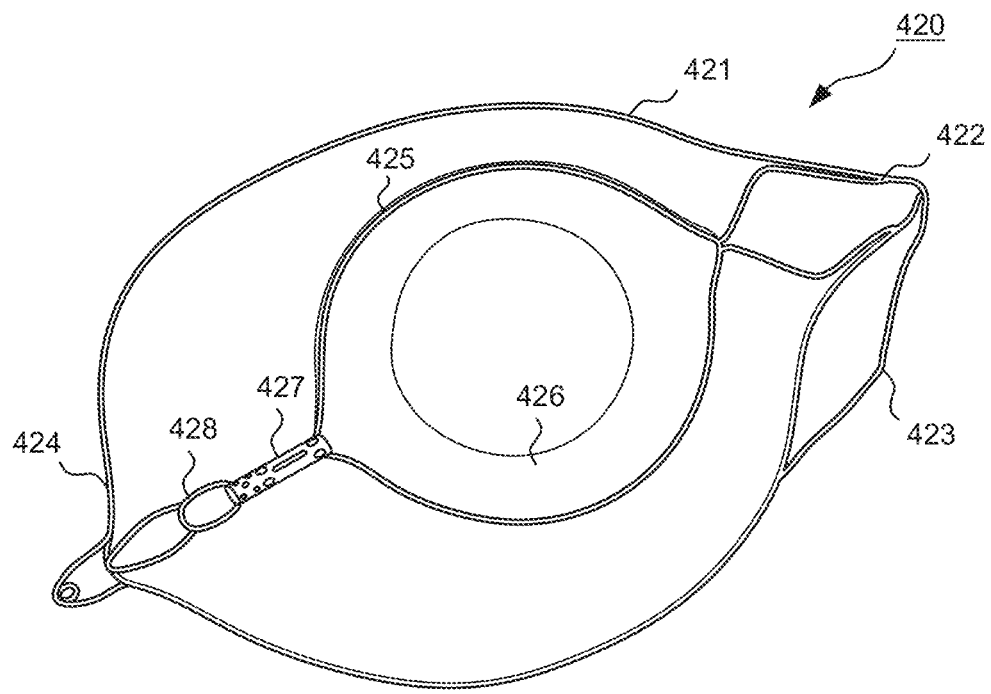
Figure 7:
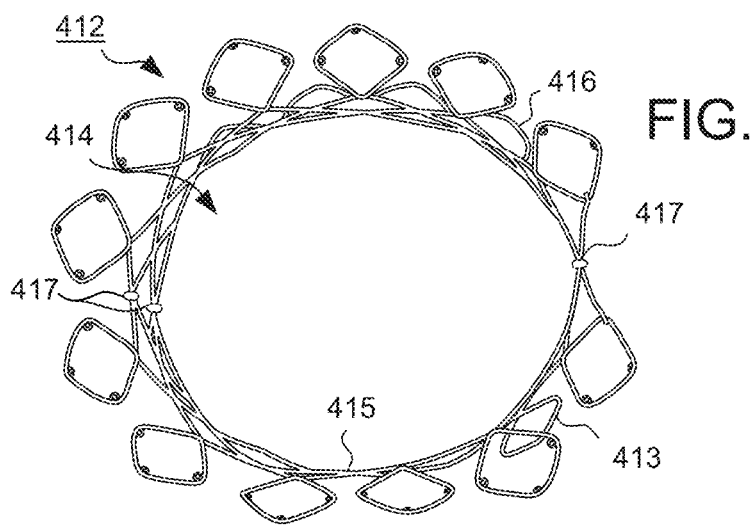
FIGS. 7-11 are various views illustrating a transannular region of the outer support frame of the prosthetic valve shown in FIG. 4.
Figure 8:
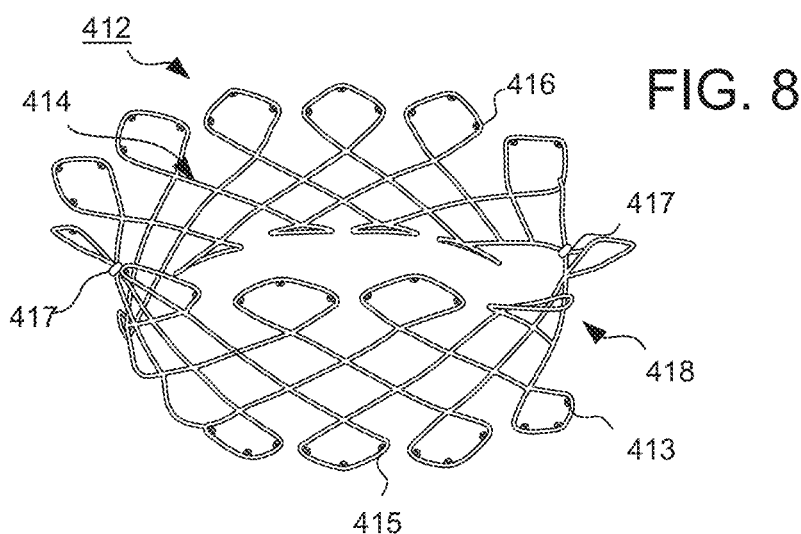
Figure 9:
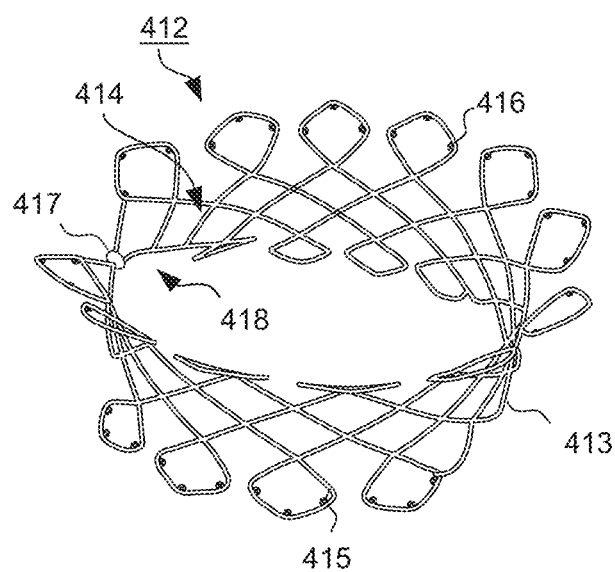
Figure 10:
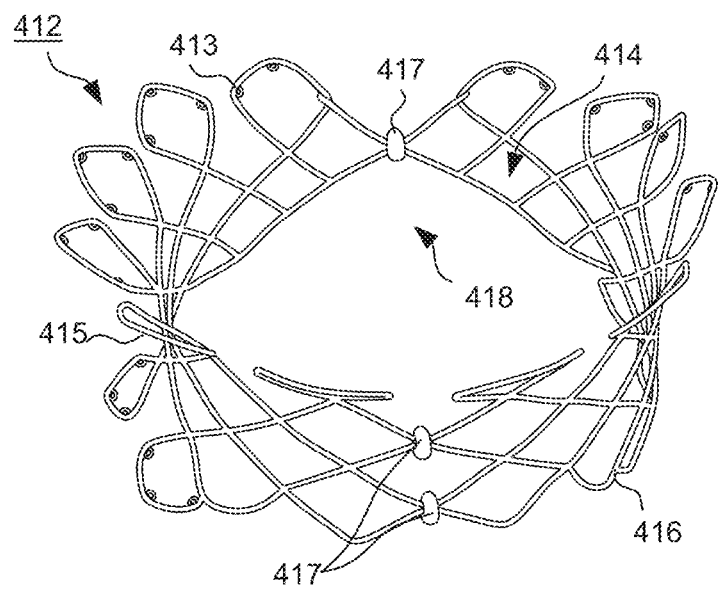
Figure 11:
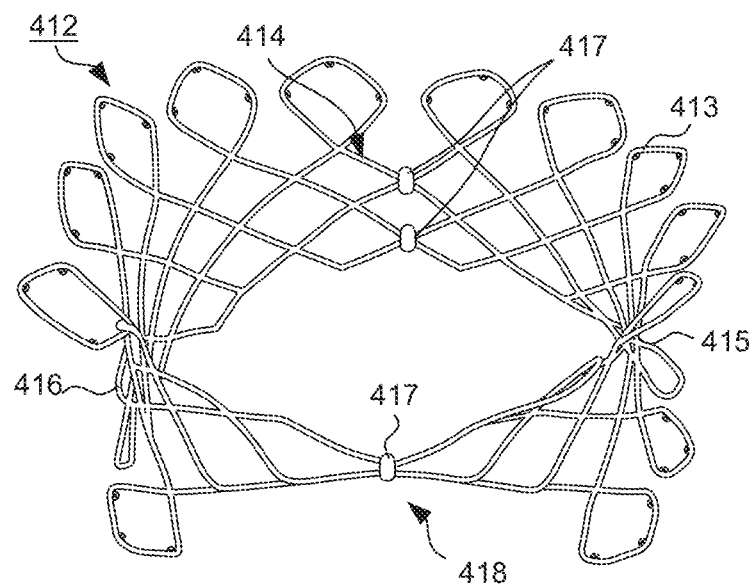

FIGS. 5 and 6 are top perspective views illustrating the supra-annular member 420 of the outer support frame 410 of the valve 400 shown in FIG. 4. FIG. 5 shows a laser cut frame of the supra-annular member 420. FIG. 6 shows the laser cut frame of the supra-annular member 420 with a biocompatible material 426 coupled thereto to facilitate the mounting of the flow control component 450 to the outer frame 410. In some embodiments, the supra-annular member 420 of the outer frame 410 can be substantially similar in at least form and/or function to the supra-annular members 120 and/or 220 described above. Thus, portions and/or aspects of the supra-annular member 420 may not be described in further detail herein.

As shown, the supra-annular member 420 includes a distal portion 422, a proximal portion 424, an outer loop 421, an inner loop 425, and at least one spline 427. In some embodiments, the outer loop 421 can be shaped and/or sized to engage native tissue. For example, the distal portion 422 of the supra-annular member 420 (formed at least in part by the outer loop 421) is configured to engage distal supra-annular tissue and the proximal portion 424 (formed at least in part by the outer loop 421) is configured to engage proximal supra-annular tissue. The distal and proximal portions 422 and 424 can have a rounded and/or curved shape, wherein a radius of curvature of the proximal portion 424 is larger than a radius of curvature of the distal portion 422. The distal portion 422 can form, for example, a distal anchoring loop 423 that can engage distal supra-annular tissue to at least partially stabilize and/or secure the frame 410 in the native annulus. Although not shown in FIGS. 5 and 6, the proximal portion 424 similarly can form a proximal upper anchoring element that can engage proximal supra-annular tissue to at least partially stabilize and/or secure the frame 410 in the native annulus.

The inner loop 425 of the supra-annular member 420 can be substantially circular and can be coupled to and/or suspended from the outer loop by the one or more splines 427. As shown in FIG. 6, the inner loop 425 can be coupled to biocompatible material 426, which can be used to couple the inner frame 451 of the flow control component 450 to the inner loop 425 of the support frame 410. In some implementations, suspending the inner loop 425 from the outer loop 421 can, for example, at least partially isolate the inner loop 425 (and the flow control component 450 coupled to the inner loop 425) from at least a portion of the force associated with transitioning the frame 410 between the expanded configuration and the compressed configuration, as described above with reference to the frame 210.

The one or more splines 427 of the supra-annular member 420 can be any suitable shape, size, and/or configuration. For example, in some embodiments, the supra-annular member 420 can include a proximal spline 427 and one or more distal splines 427. The distal splines 427 can couple a distal portion of the inner loop 425 to a distal portion of the outer loop 421. Similarly, the proximal spline 427 can couple a proximal portion of the inner loop 425 to a proximal portion of the outer loop 421. In some embodiments, the proximal spline 427 can be configured to receive, couple to, and/or otherwise engage an actuator and/or a portion of a delivery system. For example, the proximal spline 427 includes, forms, and/or can be coupled to a waypoint 428 that can be used to couple to one or more portions of the actuator and/or delivery system, as described above with reference to the frames 110 and 210.

FIGS. 7-11 are a top view, a posterior perspective view, an anterior perspective view, a distal perspective view, and a proximal perspective view, respectively, illustrating the transannular member 412 of the outer frame 410 of the valve 400 shown in FIG. 4. In some embodiments, the transannular member 420 of the outer frame 410 can be substantially similar in at least form and/or function to the transannular regions and/or members 112 and/or 212 described above. Thus, portions and/or aspects of the transannular member 412 may not be described in further detail herein.

The transannular member 412 can be shaped and/or formed into a ring, a cylindrical tube, a conical tube, and/or any other suitable annular shape. In some embodiments, the transannular member 412 may have a side profile of a concave cylinder (walls bent in), an angular hourglass, a curved, graduated hourglass, a ring or cylinder having a flared top, flared bottom, or both. Moreover, the transannular member 412 can form and/or define an aperture or central channel 414 that extends along the central axis 404 (e.g., the y-axis). The central channel 414 (e.g., a central axial lumen or channel) can be sized and configured to receive the flow control component 450 across a portion of a diameter of the central channel 414. In some embodiments, the transannular member 412 can have a shape and/or size that is at least partially based on a size, shape, and/or configuration of the supra-annular member 420 and/or subannular member 430 of the support frame 410, and/or the native annulus in which it is configured to be deployed, as described above.

The transannular member 412 can be and/or can include a wire frame that is laser cut out of Nitinol or the like and, for example, heat-set into a desired shape and/or configuration. The transannular member 412 can be formed to include a set of compressible wire cells 413 having an orientation and/or cell geometry substantially orthogonal to the central axis extending through the central channel 414 to minimize wire cell strain when the transannular member 412 is in a vertical compressed configuration, a rolled and compressed configuration, or a folded and compressed configuration. As shown in FIGS. 7-11, the transannular member 412 includes a first laser cut half 415 (e.g., an anterior side) and a second laser cut half 416 (e.g., a posterior side) that can be formed into a desired shape and coupled together to form the transannular member 412. The anterior side 415 and the posterior side 416 can be coupled at one or more hinge points 417 along a distal portion and a proximal portion of the transannular member 412. More specifically, the anterior side 415 and the posterior side 416 can be coupled along the distal side of the transannular member 412 via two sutures forming two hinge or coupling points 417 and can be coupled along the proximal side of the transannular member 412 via one suture forming a single hinge or coupling point 417.

In some embodiments, forming the transannular member 412 in such a manner can allow the transannular member 412 to bend, flex, fold, deform, and/or otherwise reconfigure (substantially without plastic deformation and/or undue fatigue) in response to lateral folding along or in a direction of a lateral or z-axis and/or vertical compression along or in a direction of the central or y-axis. Moreover, coupling at the hinge points 417 using sutures can allow for a desired amount of slippage between the sutures and the anterior/posterior sides 415/416, which in turn, can limit and/or substantially prevent binding, sticking, and/or failure in response to folding along the lateral or z-axis.

As shown in FIGS. 7-11, the proximal portion of the transannular member 412 includes a single hinge or coupling point 417. In some embodiments, the transannular member 412 can define a gap or space 418 below the proximal hinge or coupling point 417 that can provide space to allow a proximal anchoring element of the subannular member 430 to transition between a first configuration and a second configuration, as described in further detail herein.

Figure 12:
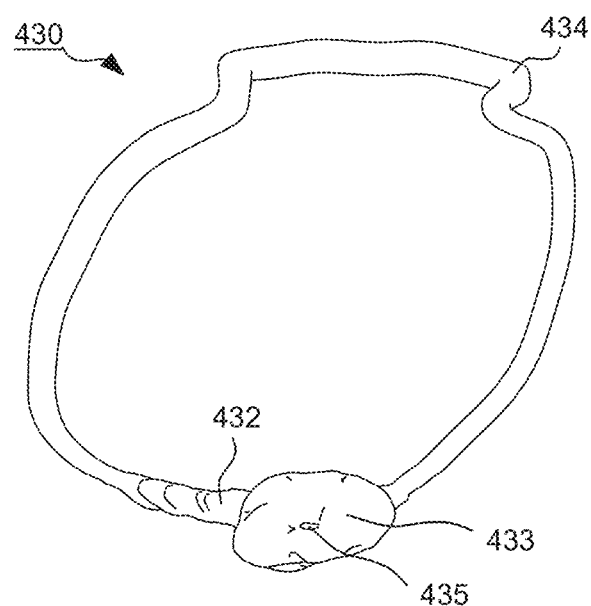
FIGS. 12 and 13 are various views illustrating a subannular region of the outer support frame of the prosthetic valve shown in FIG. 4.
Figure 13:
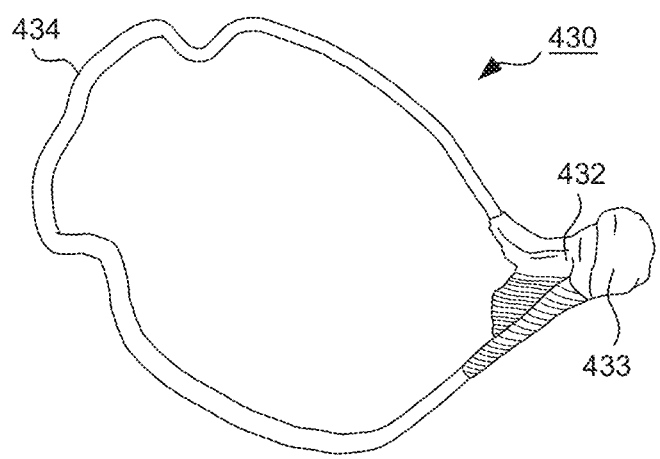

FIGS. 12 and 13 are a distal perspective view and a top view, respectively, illustrating the subannular member 430 of the outer frame 410 of the valve 400 shown in FIG. 4. In some embodiments, the subannular member 430 of the frame 410 can be similar in at least form and/or function to the subannular regions and/or members 130 and/or 230 described above. Thus, portions and/or aspects of the transannular member 412 may not be described in further detail herein.

As shown, the subannular member 430 of the frame 410 includes and/or forms a distal portion having a distal anchoring element 432 and a proximal portion having a proximal anchoring element 434. The anchoring elements 432 and 434 are integrally and/or monolithically formed with the subannular member 430. The distal anchoring element 432 and the proximal anchoring element 434 of the subannular member 430 can be any suitable shape, size, and/or configuration such as any of those described in detail in the '957 PCT, the '010 PCT, the '231 PCT, the '490 PCT, the '932 Provisional, the '059 Provisional, any of those described above with reference to the frames 110 and/or 210, and/or any of those described herein with respect to specific embodiments.

The distal anchoring element 432 is shown as including an atraumatic end that forms a guidewire coupler 433 configured to selectively engage and/or receive a portion of a guidewire or a portion of a guidewire assembly. The guidewire coupler 433, for example, is configured to allow a portion of the guidewire to extend through an opening and/or aperture 435 of the guidewire coupler 433, thereby allowing the frame 410 to be advanced over or along the guidewire during delivery and deployment. In some embodiments, the guidewire coupler 433 can selectively allow the guidewire to be advanced therethrough while blocking or preventing other elements and/or components such as a pusher or the like.

The anchoring elements 432 and/or 434 are configured to engage a desired portion of the native tissue to mount the frame 410 to the annulus of the native valve in which it is deployed. For example, the distal anchoring element 432 can extend (e.g., about 10-40 mm) from the subannular member 430 and into, for example, a RVOT. The distal anchoring element 432 can be shaped and/or biased such that the distal anchoring element 432 exerts a force on the subannular tissue operable to at least partially secure the distal end portion of the frame 410 in the native annulus.

The proximal anchoring element 434 can be configured to engage subannular tissue on a proximal side of the native annulus to aid in the securement of the frame 410 in the annulus. More specifically, the proximal anchoring element 434 is configured to transition, move, and/or otherwise reconfigure between a first configuration in which the proximal anchoring element 434 extends from the subannular member 430 a first amount or distance and a second configuration in which the proximal anchoring element 434 extends from the subannular member 430 a second amount or distance. As described above, the subannular member 430 of the frame 410 can be and/or can include, for example, a laser cut frame formed of a shape-memory material such as Nitinol, which is heat-set into a desired shape and wrapped in a biocompatible material (e.g., a fabric as shown in FIGS. 12 and 13).

As described above, the proximal anchoring element 434 can be in a compressed, contracted, retracted, undeployed, folded, and/or restrained state (e.g., a position that is near, adjacent to, and/or in contact with the transannular member 412 and/or the supra-annular member 420 of the support frame 410) when in the first configuration, and can be in an expanded, extended, deployed, unfolded, and/or unrestrained state (e.g., extending away from the transannular member 412) when in the second state. In some embodiments, the proximal anchoring element 434 can be biased and/or heat-set in the second configuration. Moreover, in some implementations, the space 418 defined by the transannular member 412 of the outer frame 410 is configured to provide sufficient room to allow the proximal anchoring element 434 to transition between the first and second configurations.

Figure 14:
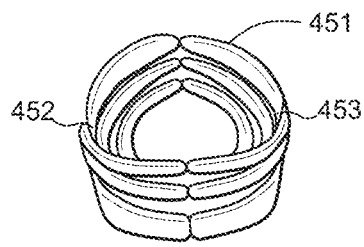
FIG. 14 is an illustration of a top perspective view of an inner frame of a flow control component included in the prosthetic valve shown in FIG. 4.

FIGS. 14-19 illustrate an inner leaflet frame 451 of the flow control component 450 included in the valve 400 shown in FIG. 4. FIG. 14 is an illustration of a top perspective view of the inner leaflet frame 451. In some embodiments, the inner leaflet frame 451 is formed of two separate wireframe sheets or members that are coupled at lateral connection points 451 and 453 (e.g., fold areas, elastically deformable regions, coupled edged portions, etc.). The inner leaflet frame 451 is shown in an expanded or cylindrical configuration (e.g., prior to being folded and/or compressed).

Figure 15:
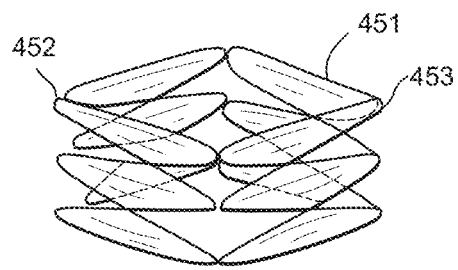
FIGS. 15-17 illustrate of various views of the inner frame of FIG. 14 and shown in a partially folded configuration, a folded configuration, and a folded and compressed configuration, respectively.
Figure 16:
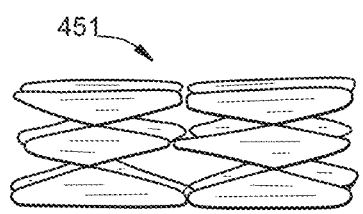

FIG. 15 shows the inner leaflet frame 451 in a partially folded configuration. The inner leaflet frame 451 is shown with wireframe sidewalls that allow for rotating or hinging at least at the lateral connection points 451 and 453. The inner leaflet frame 451 can be configured to fold as shown in response to the valve being folded and/or compressed for delivery. FIG. 16 shows the inner leaflet frame 451 in a completely folded configuration. The wireframe sidewalls have been rotated, hinged, and/or folded at their lateral connection points 451 and 453.

Figure 17:

FIG. 17 shows the inner leaflet frame 451 in a folded and vertically compressed into a compressed configuration. The wireframe sidewalls can form cells (e.g., diamond-shaped cells or the like) that can be oriented in a direction of compression to allow for elastic compression of the inner frame 451. In some embodiments, the inner frame 451 can be vertically compressed into a pleated or accordion (compressed) configuration.

Figure 18:
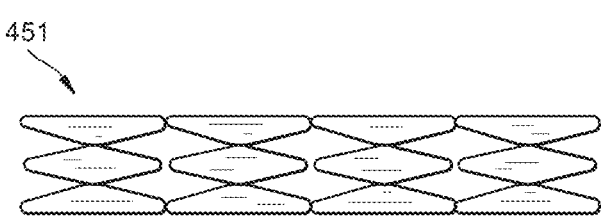
FIG. 18 is an illustration of a side view of the inner frame of FIG. 14 and shown as a linear wireframe sheet prior to being formed into a cylindrical configuration.
Figure 19:
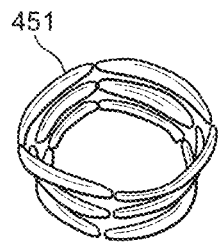
FIG. 19 is an illustration of a side perspective view of the inner frame of FIG. 14 and shown in the cylindrical configuration.

FIG. 18 is an illustration of a side view of the inner leaflet frame 451 of the flow control component 450 and is shown as and/or forming a linear wireframe or laser cut sheet prior to being further assembled into a cylinder structure. FIG. 19 shows the inner leaflet frame 451 in the cylinder structure or configuration (or a conical structure or configuration) with edge portions of the linear wireframe sheet being connected or coupled at the lateral connection points 451 and 453 (e.g., hinge areas, fold areas, etc.). Moreover, the inner leaflet frame 451 can be expanded (e.g., driven, formed, bent, etc.) from the linear sheet configuration into the cylinder structure or configuration.

While FIGS. 14-19 illustrate the inner leaflet frame 451 as including two wireframe sheets, members, and/or halves that are coupled at and/or coupled to form two hinge points, in some embodiments, an inner leaflet frame can be formed from a single component or more than two components that are heat-set, worked, and/or otherwise coupled to form and/or define one or more hinge points. For example, an inner leaflet frame can be formed from a single Nitinol tube and can have hinge points that are formed by heat-setting the material in a desired manner. As another example, an inner leaflet frame can be made from a sheet of material (e.g., Nitinol) and formed into a substantially cylindrical shape with free ends of the material being coupled (e.g., via sutures) to form a single hinge point. In such examples, a second hinge point can be formed opposite the sutured hinge point by heat-setting or working the material in a desired manner. As still another example, an inner leaflet frame can be made from more than two sheets or members, which are coupled together (e.g., via sutures) to form a corresponding number of hinge points.

Figure 20:
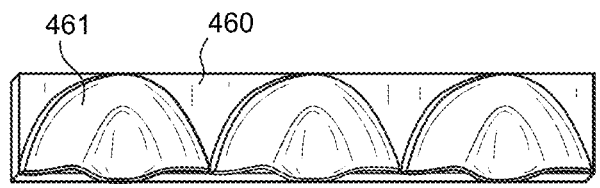
FIGS. 20 and 21 are illustrations of a side view and a bottom view, respectively, of a leaflet band of the flow control component having leaflet pockets sewn into a structural band of pericardial tissue and shown in a linear configuration.
Figure 21:
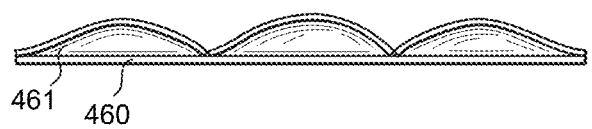

FIGS. 20-24 illustrate a structural band 460 of pericardial tissue with leaflet pockets 461 sewn into the structural band 460. FIGS. 20 and 21 are a side view and a bottom view, respectively, illustrating the structural band 460 and leaflet pockets 461 before assembly into a cylindrical leaflet component and before mounting on and/or into the inner frame 451 to form the collapsible (foldable, compressible) flow control component 450.

Figure 22:
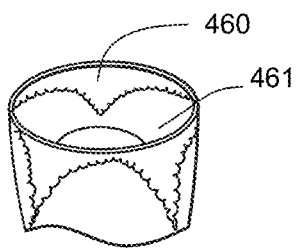
FIG. 22 is an illustration of a side perspective view of the leaflet band of FIG. 20 and shown in a cylindrical configuration suitable for coupling to the inner frame of FIG. 19.

FIG. 22 is an illustration of a side perspective view of the structural band 460 formed of pericardial tissue with the leaflet pockets 461 sewn into the structural band 460, after assembly into the cylindrical leaflet configuration, the leaflet pockets 461 being disposed on an inner surface of the structural band 460.

Figure 23:
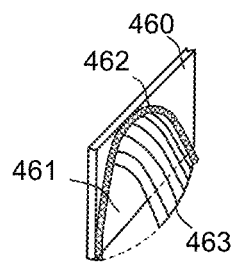
FIG. 23 is an illustration of a side perspective view of a portion of the leaflet band of FIG. 20 showing a single leaflet pocket sewn into the structural band.

FIG. 23 is an illustration of a side perspective view of part of the structural band 460 of pericardial tissue showing a single leaflet pocket 461 sewn into the structural band 460. The leaflet pocket 461 is shown with partial coaptation of the leaflet pocket 461 to the structural band 460 such that an open edge 463 extends outward and a sewn edge 462 forms a closed top parabolic edge providing attachment.

Figure 24:
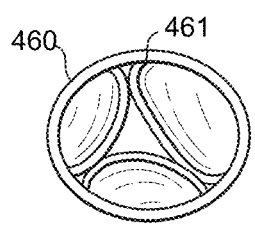
FIG. 24 is an illustration of a bottom view of the leaflet band of FIG. 20 in the cylindrical configuration and showing partial coaptation of the leaflets to form a partially closed fluid-seal.

FIG. 24 is an illustration of a bottom view of the flow control component 450. The cylindrical structural band 460 and leaflet components 461 are shown with partial coaptation towards forming a closed fluid-seal.

As described above, any of the prosthetic valves described herein can include a proximal anchoring element or tab that can be activated and/or actuated in any suitable manner. In some implementations, a proximal anchoring element and/or tab can be activated in a manner similar to those described in the '390 PCT, the '932 Provisional, and/or the '269 Provisional incorporated by reference hereinabove.

Figure 25:
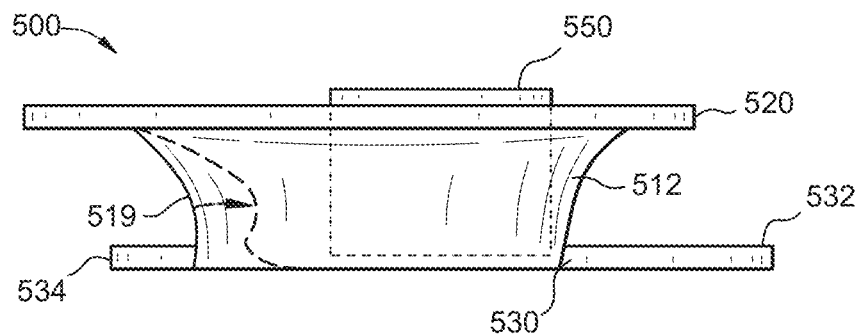
FIGS. 25 and 26 are a schematic cross-sectional side view and a bottom view, respectively, of a prosthetic valve according to an embodiment.
Figure 26:
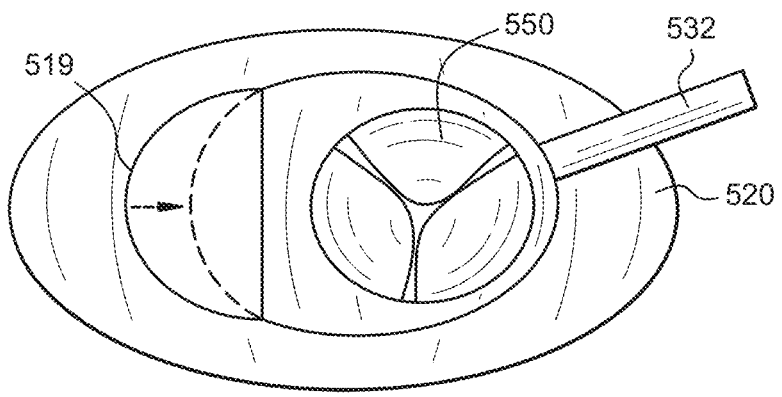
Figure 27:
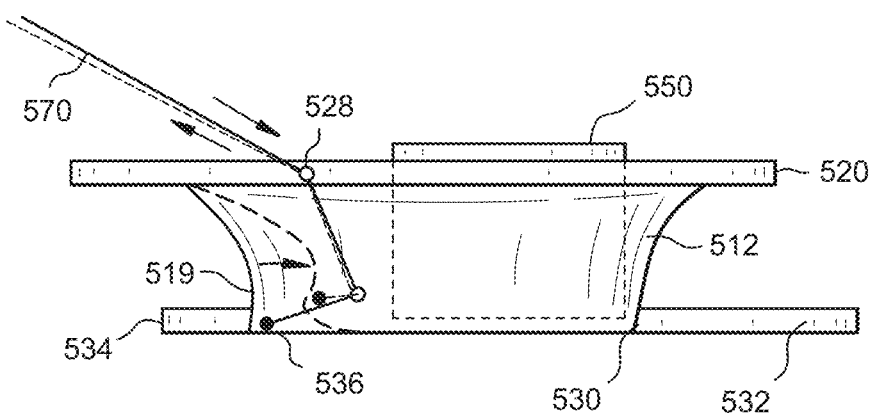
FIG. 27 is a schematic cross-sectional side view of the prosthetic valve of FIG. 25 and shown with an actuator and/or cinching assembly attached to the prosthetic valve.

For example, FIGS. 25-27 illustrate a prosthetic valve 500 according to an embodiment. The valve 500 includes an outer support frame 510 and a flow control component 550 mounted therein. The outer support frame includes a supra-annular member 520, a subannular member 530, and a transannular member, portion, and/or region 512 coupled therebetween. The subannular member 530 includes a distal anchoring element 532 and a proximal anchoring element 534.

FIG. 25 is a schematic cross-sectional side view and shows how the perimeter (circumference) of the transannular region 512 of the valve 500 can be cinched inward. This allows the valve 500 to be designed with an over-sized transannular circumference, e.g. 5-20%, often 10-15%, to promote a tight fit of the valve within the native annulus and provide a good seal against perivalvular leakage (PVLs). The cinching process pulls a proximal sidewall 519 inwards and reduces the circumference of the transannular region 512. This allows the oversized valve to drop into the native annulus during deployment of the valve. Then, once the valve is seated as desired, the transannular region 512 is pushed back out and/or otherwise allowed to expand to its full or nearly full, circumference, and thereby form a tight, sealed fit of the prosthetic valve in the native annulus. In some implementations, the proximal anchoring element 534 of the subannular member 530 can also be cinched inward and/or upward with the transannular region 512 and/or independent of the transannular region 512.

FIG. 26 is a schematic bottom view of the valve 500 and shows how the perimeter (circumference) of the transannular region 512 at or near a proximal end of the valve 500 can be cinched inward (as indicated by the arrow and dashed line). In some implementations, this can allow for an over-sized transannular circumference (e.g., between about 5-20% over-sizing), which can promote a tight fit of the valve 500 within the native annulus and provides a good seal against perivalvular leakage (PVLs).

FIG. 27 is a schematic cross-sectional side view of the valve 500 and shows how the perimeter (circumference) of the transannular region 512 of the valve 500 can be cinched inward. An actuator 570 such as, for example cinch tethers and/or the like is/are shown as a non-limiting mechanism for performing the cinching process. The actuator 570 (or a portion thereof) can travel from a delivery catheter (not shown), through a way-guide, waypoint, attachment point, through hole, eyelet, and/or any other suitable component (referred to herein as "waypoint 528"). In this embodiment, the actuator 570 (e.g., cinch tether(s)) travel through the supra-annular member 520 by way of the waypoint 528 to mount on the proximal sidewall 519 of the transannular region 512 and/or the proximal anchoring element 534 of the subannular member 530 at one or more attachment points 536. Actuating the actuator 570 (e.g., pulling the cinch tether(s) proximally, towards the operator) pulls the proximal sidewall 519 of the transannular region 512 inwards and reduces the circumference of the transannular region 512. In some implementations, this allows the oversized valve 500 to drop into the native annulus during deployment of the valve 500. Then, once the valve 500 is seated as desired, the actuator 570 can be actuated (e.g., the cinch tether(s) can be advanced or retracted/released) to push the proximal sidewall 519 of the transannular region 512 back out and/or to otherwise allow the transannular region 512 to expand to its full or nearly full, circumference, and thereby form a tight, sealed fit of the prosthetic valve 500 in the native annulus. Similarly, the proximal anchoring element 534 can be actuated (e.g., by the actuator 570) along with the transannular region 512 or independent of the transannular region 512.

Figure 28:
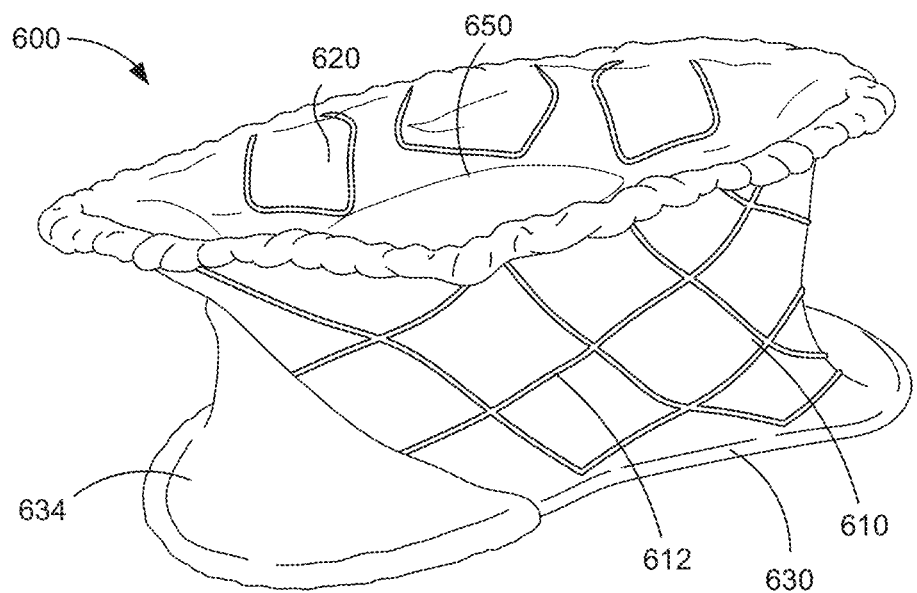
FIGS. 28 and 29 are illustrations of a side perspective view of a prosthetic valve, according to an embodiment, with a proximal subannular anchoring element in an extended configuration and a retracted configuration, respectively.
Figure 29:
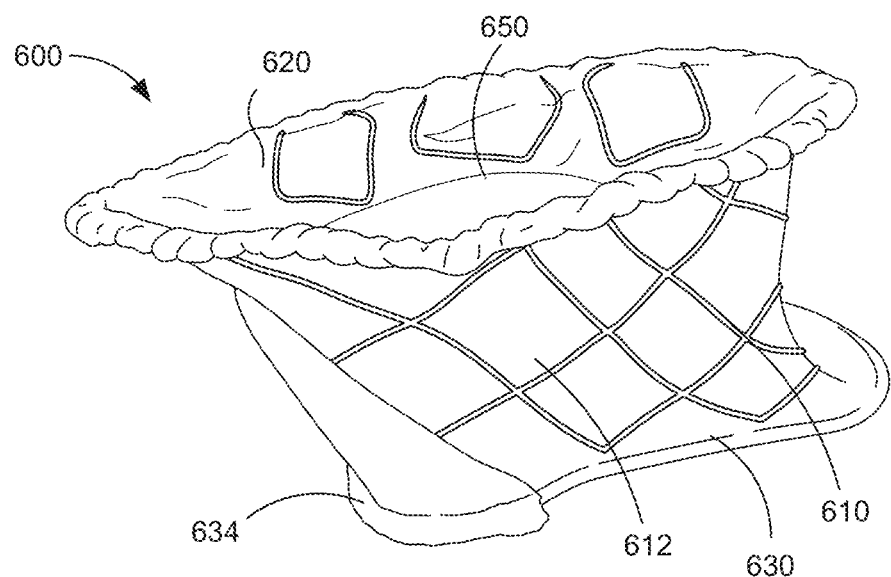

FIGS. 28 and 29 are illustrations of a side view of a side-deliverable prosthetic valve 600 with a lower proximal anchoring element 634 in an extended configuration and a retracted configuration, respectively, according to an embodiment. FIG. 28 illustrates the valve replacement 600 having an outer frame 610 with a flow control component 650 mounted therein. The outer frame 610 includes a supra-annular member 620, a subannular member 630, and a transannular member 612 coupled therebetween. In this embodiment, the subannular member 630 and the transannular member 612 can collectively for the lower proximal anchoring element 634. FIG. 28 shows the proximal anchoring element 634 in the extended configuration. FIG. 29 shows the proximal anchoring element 634 in a retracted configuration, in which the subannular member 630 and transannular member 612 have a reduced perimeter allowing the valve 600 to be deployed in the annulus of a native valve. After deploying and/or seating the valve 600 in the annulus, the proximal anchoring element 634 can be transitioned back to or toward the extended configuration. Although not shown, in some embodiments, the valve 600 can be removably coupled to a delivery system and/or an actuator that can be manipulated to transition the proximal anchoring element 634 between the extended and retracted configurations.

Figure 30:
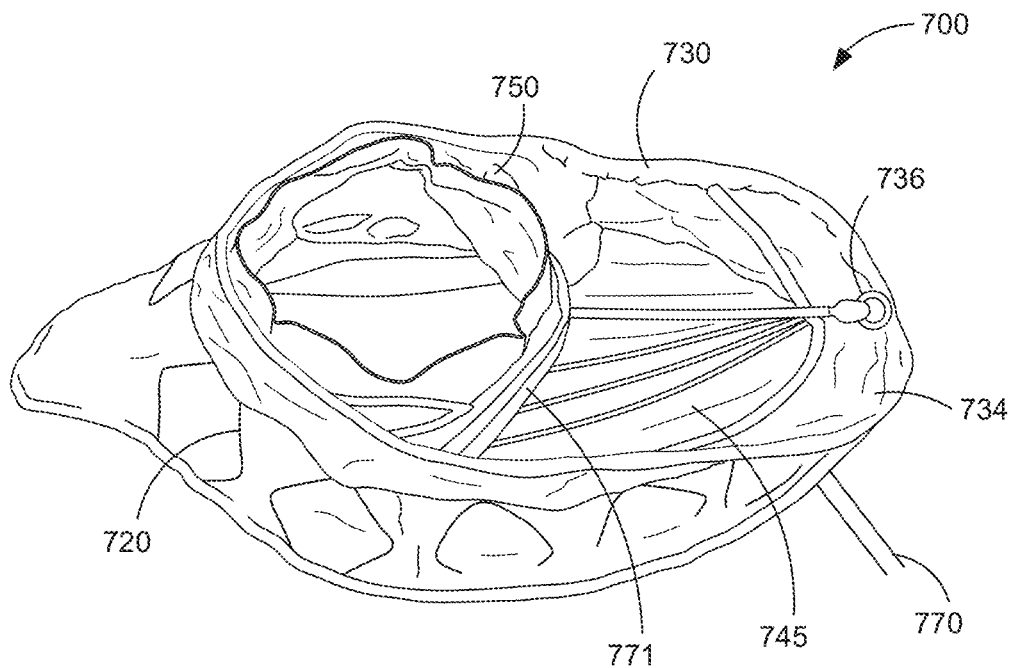
FIGS. 30 and 31 are illustrations of bottom perspective view of a prosthetic valve, according to and embodiment, with a proximal subannular anchoring element coupled to an actuator and/or cinching assembly and shown in an extended configuration and a retracted configuration, respectively.
Figure 31:
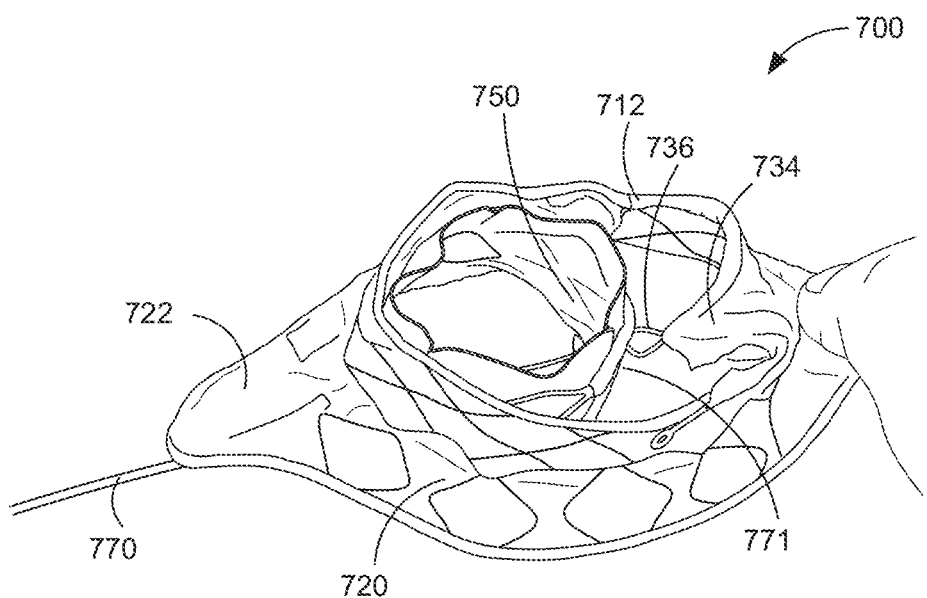
Figure 32A:
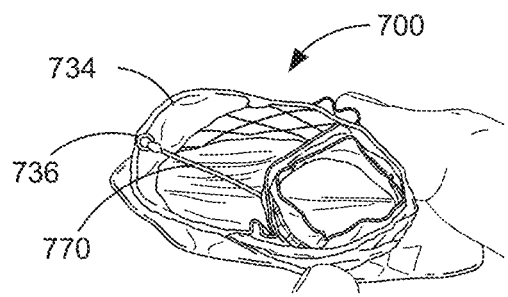
FIGS. 32A-32E are bottom perspective views of the prosthetic valve of FIG. 30 showing a sequence of transitioning the lower proximal anchoring element from the extended configuration to the retracted configuration.
Figure 32B:
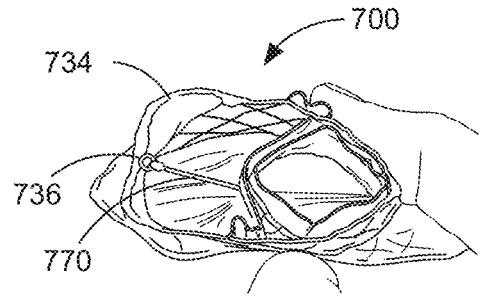
Figure 32C:
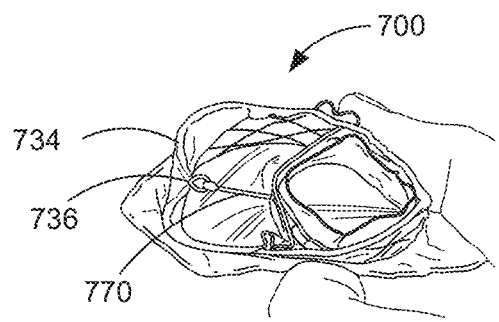
Figure 32D:
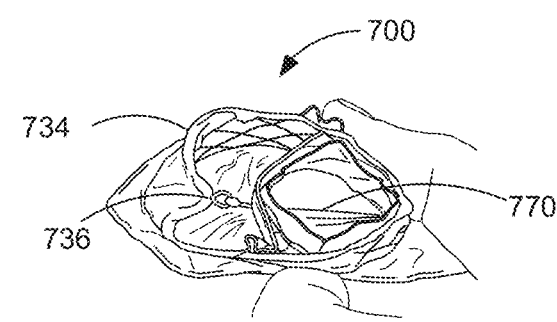
Figure 32E:
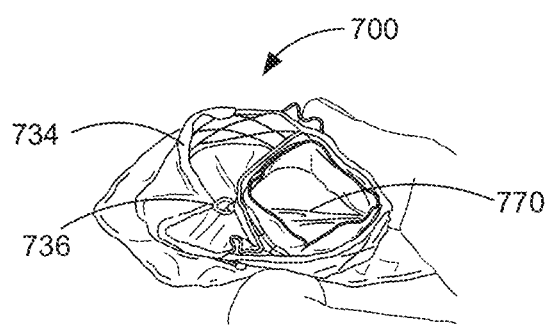

FIGS. 30, 31, and 32A-32E are bottom view illustrations of a side-delivered prosthetic valve 700, according to an embodiment, and showing a proximal anchoring element 734 in and/or transitioning between a first configuration and a second configuration. FIG. 30 illustrates the prosthetic valve 700 having an outer frame 710 and an inner flow control component 750 mounted therein. The frame 710 includes a supra-annular member 720 and a subannular member 730. The supra-annular member 720 includes a drum 745 extending across the supra-annular member 720. The subannular member 730 includes a proximal anchoring element 734. FIG. 30 shows the proximal anchoring element 734 in a first, unactuated, and/or expanded configuration. FIG. 31 shows the proximal anchoring element 734 in a second, actuated, and/or compressed configuration. The valve 700 is removably coupled to an actuator 770, which can be and/or can include one or more tethers that are attached to an attachment point 736 on the proximal anchoring element 734. In this embodiment, a portion of the actuator 770 can extend through a waypoint or other opening in the drum 745 to couple to the attachment point 736. Moreover, the actuator 770 can include a support member 771 or the like that is included in and/or coupled to the valve 700 adjacent to the inner flow control component 750. The support member 771 can support at least a portion of the actuator 770 (e.g., tether(s)) to limit an amount of force, for example, that is exerted on the drum 745 when the actuator 770 is actuated. FIGS. 32A-32E are a time series of illustrations of the prosthetic valve 700 showing the actuator 770 being actuated to transition the proximal anchoring element 736 from the first, unactuated, and/or expanded configuration to the second, actuated, and/or compressed configuration.

As described above, any of the prosthetic valves described herein can be delivered via a delivery system and can be configured to engage with the delivery system in any suitable manner. In some implementations, a prosthetic valve can be configured to engage a delivery system in a manner similar to those described in the '010 PCT incorporated by reference hereinabove.

Figure 33A:
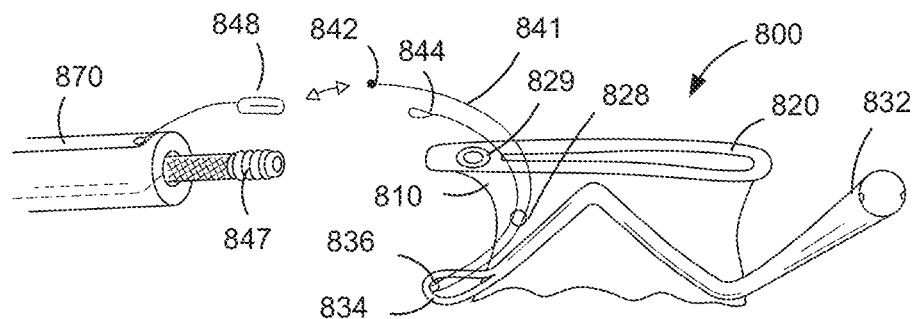
FIGS. 33A-33C are side perspective view illustrations of a portion of a proximal anchoring element of a prosthetic valve being coupled to and decoupled from an actuator or the like, according to an embodiment.
Figure 33B:
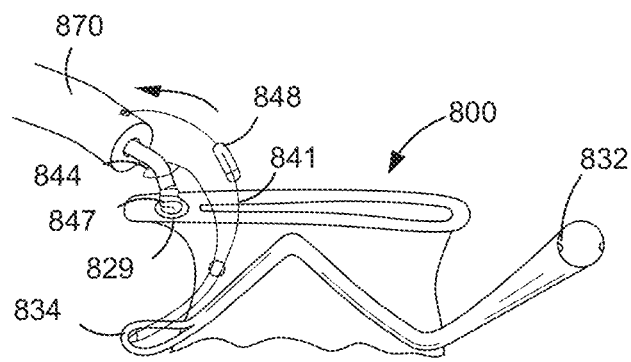
Figure 33C:
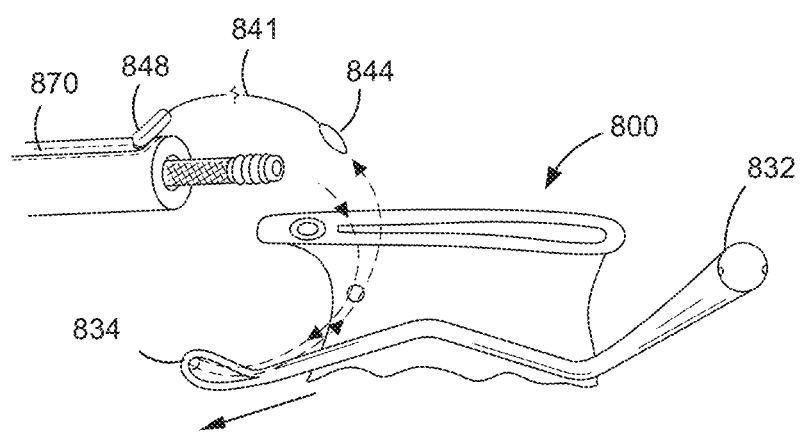

For example, FIGS. 33A-33C illustrate side perspective views of a side delivered transcatheter prosthetic heart valve 800 and an actuator 870 according to an embodiment. The valve 800 has a frame 810 with a collar 820 (e.g., a supra-annular member), a distal anchoring element 832, and a proximal anchoring element 834 (e.g., wire loop anchoring elements and/or any other suitable type of anchoring element). The frame 810 defines a waypoint 828. The collar 820 includes and/or forms an attachment point 829. While the waypoint 828 is shown along a body of the frame 810, in other embodiments, the collar 820 and/or any other suitable portion of the valve 800 can form and/or define the waypoint 828. Similarly, while the attachment point 829 is shown along the collar 820, in other embodiments, the body of the frame 810 and/or any other suitable portion of the valve 800 can include the attachment point 829.

In the embodiment shown in FIGS. 33A-33C, the actuator 870 is arranged as a tensile member and/or the like. The actuator 870 includes a lead 841 configured to be coupled to and/or threaded through an attachment point 836 of the proximal anchoring element 834. The lead 841 includes a first end that has and/or forms a first coupling feature 844 and a second end that has and/or forms a second coupling feature 844. The coupling features can be any suitable configuration. For example, in this embodiment, the first coupling feature 844 is and/or forms a loop, eyelet, opening, and/or the like, and the second coupling feature 842 is and/or forms a ball, protrusion, knob, knot, and/or the like. The actuator 870 can be and/or can include any suitable cable, tether, wire, catheter, conduit, etc. In some implementations, the actuator 870 can be used, for example, as a pusher or the like configured to push and/or otherwise advance the valve 800 through a delivery system.

In this embodiment, the actuator 870 includes a first cable 847 with an end portion that forms a threaded coupler configured to engage and/or couple to the attachment point 829 formed by the collar (e.g., a threaded nut or the like). The actuator 870 includes a second cable 848 with an end portion that forms a receiving member configured to receive and/or removably couple to the second end of the lead 841. For example, the receiving member of the second cable 848 and the coupling feature 842 formed by the second end of the lead 841 can be a ball and cup coupling mechanism. Moreover, the actuator 870 can include and/or can form an outer sheath or catheter configured to at least partially house the first cable 847 and the second cable 848.

FIG. 33A shows the actuator 870 prior to coupling to the valve 800 and/or the lead 841. The lead 841 is shown threaded through a portion of the valve 800 and the waypoint 828, looped around or through the attachment point 836 of the proximal anchoring element 834, and threaded back through the waypoint 828 and portion of the valve 800 such that the first end 844 and the second end 842 are each outside of the valve 800 and/or above or proximal to the collar 820.

FIG. 33B shows, the end portion of the first cable 847 of the actuator 870 coupled to the attachment point 829 of the collar 820, for example, via a threaded coupling. The first coupling feature 844 of the lead 841 is coupled to the first cable 847 (e.g., the first coupling feature 844 can be a loop that is disposed on or about the first cable 847). In some implementations, the actuator 870 can be used as a proximal pusher by virtue of the first cable 847 being coupled to the attachment point 829 formed by the collar 820. For example, a substantially fixed portion of the first cable 847 can extend from the actuator 870 (e.g., the outer sheath) such that a distal or pushing force applied to the actuator 870, via the first cable 847, pushes the valve 800. With the first coupling feature 844 coupled to the first cable 847, the first end of the lead 841 is maintained in a relatively fixed position relative to the valve 800. The second cable 848 of the actuator 870 is shown coupled to the second coupling feature 842 of the lead 841 (e.g., via a ball and cup coupling mechanism and/or the like). Thus, while the actuator 870 and/or the first cable 847 can be used to push the valve 800, a tensile or pulling force can be applied to the second cable 848, which can pull the second end of the lead 841 in a proximal direction, thereby placing the lead in tension. Accordingly, the lead 841 can maintain the proximal anchoring element 834 in its first configuration during deployment.

FIG. 33C shows the first cable 847 decoupled from the attachment point 829 of the collar 820 and the first coupling feature 844 at the first end of the lead 841. The second coupling feature 842 at the second end of the lead 841 can remain coupled to the second cable 848. After the valve has been deployed, the actuator 870 is pulled to remove the actuator 870 and the lead 841 from the valve 800 and the delivery system. With the actuator 870 removed, the proximal anchoring element 834 is allowed to transition to its second configuration.

As described above, any of the prosthetic valves described herein can include a proximal anchoring element or tab that can be transitioned between two or more configurations and/or that can include one or more engagement features configured to engage native tissue to secure the proximal anchoring element or tab thereto. In some implementations, a proximal anchoring element or tab can be similar to and/or can include engagement features similar to any of those described in the '059 Provisional and/or the '269 Provisional incorporated by reference hereinabove.

Figure 34:
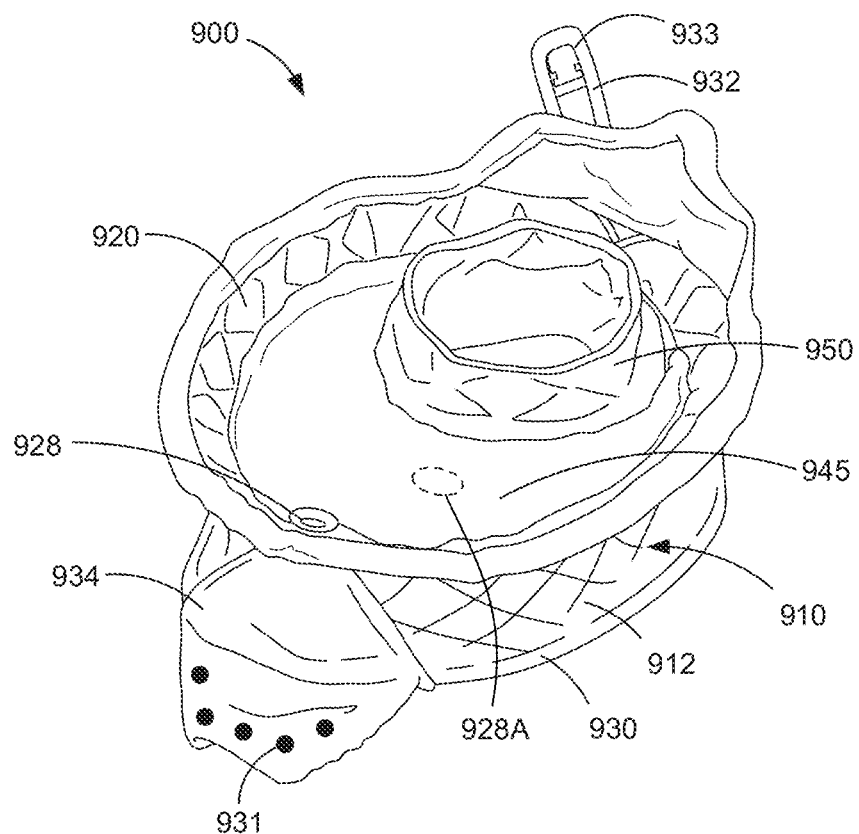
FIG. 34 is a proximal end perspective view illustration of a prosthetic valve, according to an embodiment, and shown having a set of projections affixed to a proximal anchoring element.

For example, FIG. 34 is a proximal end perspective view illustration of a side-delivered transcatheter prosthetic heart valve 900 (also referred to herein as "prosthetic valve 900") according to an embodiment. The prosthetic valve 900 includes a flow control component 950 mounted within a central aperture of an outer frame 910. The flow control component 950 is shown in this embodiment, in an offset position (e.g., distally located). In addition, the flow control component 950 is shown mounted to the outer frame 910 such that a portion of the flow control component 950 is above a drum 945 of the frame 910. In some embodiments, the flow control component 950 provides a normal flow volume (e.g. associated with and/or from a 29 mm valve), while filling an overstretched native annulus with the outer frame 910.

The outer frame 910 includes a supra-annular member 920 (e.g., an upper wire frame portion) and a subannular member 930 (e.g., a lower wire frame portion), as well as a transannular member 912 forming a set of perimeter walls spanning a transannular section of the prosthetic valve 900. The supra-annular member 920 and the subannular member 930 can also support a valve without a wire-cell sidewall and instead having pericardial tissue sidewalls strung between the supra-annular member 920 and the subannular member 930. The subannular member 930 includes and/or forms a distal anchoring element 932 and a proximal anchoring element 934. The distal anchor element 932 is shown having a guidewire coupler 933 at a terminal end portion thereof. The proximal anchor element 934 is shown with atraumatic round projections 931 affixed thereto. The projection(s) 931 on the proximal anchoring element 934 can engage native tissue to entrap or snare chordae, leaflet, trabeculae, papillary or annular tissue and, like a button in a button-hole, the projection(s) 931 will anchor and fasten the proximal anchoring element 934 to the native subannular tissue. The projection(s) 931 can be any suitable shape, size, and/or configuration. For example, in some embodiments, the projection(s) 931 are protrusions, beads, barbs, tabs, knobs, ribs, loops, hooks, bent or otherwise formed portions of the proximal anchoring element 934, and/or the like.

The supra-annular member 920 forms an atrial collar of the outer frame 910 and is shown having a distal atrial panel for matching native anatomy. The drum 945 is shown extending over or across the supra-annular member 920 and filling an area within the central aperture of the outer frame 910 that is not otherwise filled or occupied by the flow control component 950. The drum 945 can also be used to provide purposeful/intentional regurgitation if desirable to accommodate the functional needs of a given patient, and which can be sealed/stitched closed at a later time. The drum 945 can also provide a wire access location for a pacemaker device, which is commonly used in conjunction with prosthetic valves. For example, the drum 945 can optionally include an opening 928A, which can be used as a regurgitation opening and/or used to pass any suitable device, wire, lead, etc., from the atrium to the ventricle of the heart. In some embodiments, the drum 945 can include a pop off cover, flap, film, fabric, plug, etc. that can be at least temporarily attached to the drum 945 and removed if, based on the anatomy or need of a patient, the opening 928A needs to be utilized.

A waypoint 928 is shown along the drum 945 within an inner segment of the atrial collar 920. The waypoint 928 can provide an opening, port, etc., through which one or more component of a delivery system can extend. For example, a delivery system can include an actuator, a guidewire catheter, and/or any other suitable component that can be inserted into and extend through the waypoint 928. While not shown, the actuator can be coupled to the proximal anchoring element and configured to transition the proximal anchoring element between two or more positions, configuration, states, etc. The guidewire catheter can be threaded over a guidewire to provide sufficient rigidity to allow the valve 900 to be advanced along the guidewire. Moreover, the guidewire catheter can extend below the valve 900 (e.g., below the flow control component 950) and through the guidewire coupler 933 of the distal anchoring element 932.

In some embodiments, a pusher cable or the like can be passed through the waypoint 928 and can engage the guidewire coupler 933. In such embodiments, the pusher cable is used to expel the valve 900 from a delivery catheter and to direct delivery to a pre-determined location by riding on top of a pre-placed guidewire that runs down the lumen of the pusher cable. Although the guidewire can be threaded through the guidewire coupler 933, the pusher cable cannot fit through the opening in the guidewire coupler 933. This allows a practitioner to push on the pusher cable, while effecting a pulling of the valve 900 down along and from the delivery catheter, thus avoiding the problems associated with pushing a pliable item down a tube and causing undesired compression within the delivery catheter and attendant damage to the prosthetic valve 900.

Figure 35:
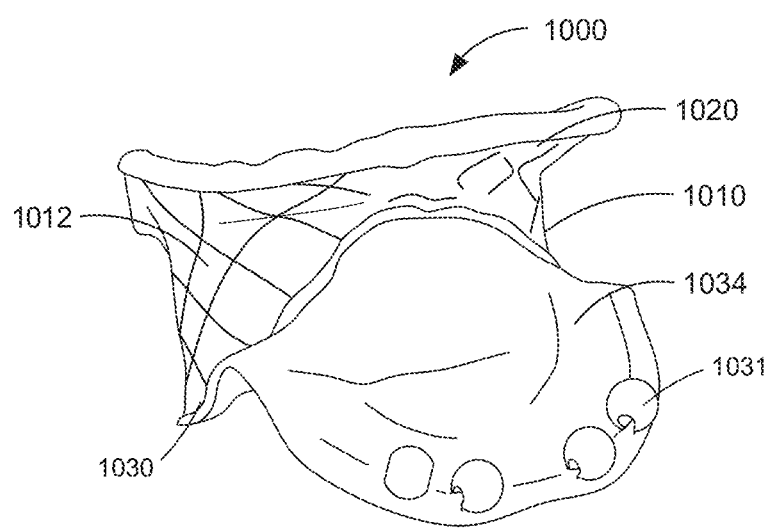
FIGS. 35 and 36 are a proximal end perspective view and a side view illustration of a prosthetic valve, according to an embodiment, and shown with a proximal anchoring element in a first or compressed configuration and having a set of projections affixed thereto.
Figure 36:
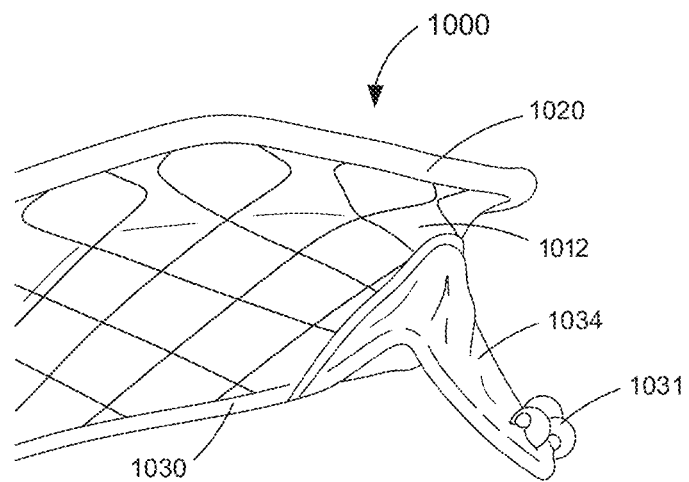
Figure 37:
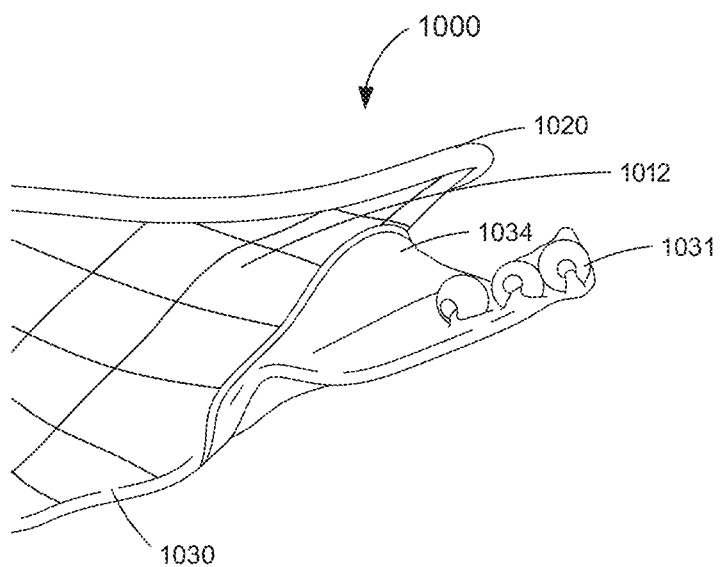
FIG. 37 is a side-view illustration of the prosthetic valve of FIG. 34 and shown with the proximal anchoring element in a second or extended configuration for engaging native tissue on a proximal subannular side of an annulus.

FIGS. 35-37 are various views of at least a portion of a side-delivered transcatheter prosthetic heart valve 1000 (also referred to herein as "prosthetic valve") according to an embodiment. An outer support frame 1010 of the valve 1000 includes a supra-annular member 1020 (e.g., an atrial collar), a transannular member 1012, and a subannular member 130. The supra-annular member or atrial collar 1020 forms the upper atrial anchoring structure and is connected to the transannular component frame 1012, which in turn is connected to the subannular member 1030. The frame 1010 may be any elliptical or cylindrical form. In some embodiments, at least a portion of the frame 1010 (e.g., the transannular component 1012) is composed of two wire mesh panels connected to form an elliptical or cylindrical form. Making at least a portion of the frame from two panels allows the structure to fold on itself, front to back, to provide the compression required to fit into a delivery catheter. Made from horizontal cells allows the panels to compress vertically. In some embodiments, the outer frame 1010 may comprise a cylindrical curtain of treated pericardium that is attached to upper and lower loops of metal wire. The outer frame 1010 is shown with supporting wire cell structure on anterior and septal sidewalls. In some embodiments, the outer frame 1010 is discontinuous and includes an open space section without supporting wire cell structure at the proximal end of the valve.

FIGS. 35-37 show the subannular member 1030 as having projections 1031 affixed to a foldable proximal tab or proximal anchoring element 1034. FIGS. 35 and 36 show the proximal anchoring element 1034 in a first configuration (e.g., a deployment configuration). The proximal anchoring element 1034 can be, for example, partially retracted to facilitate deployment and/or seating of the valve 1000 in a native annulus. FIG. 37 shows the proximal anchoring element in an extended configuration for compressing native tissue between the underside of the atrial collar 1020 and the proximal anchoring element 1034.

FIG. 38A-38F are illustrations of a subannular member 1130 of an outer support frame for a side deliverable transcatheter prosthetic heart valve, according to an embodiment. The subannular member 1130 is shown having a distal anchor element 1132 with a guidewire coupler 1133 attached thereto and a proximal anchor element 1134 with one or more projection 1131. In this embodiment, the subannular member 1130 can be unitary and made in a single laser cut of Nitinol.

The subannular member 1130 is heat shaped to bias the distal anchoring element 1132 upwards and to bias the proximal anchoring element 1134 downwards. Thus, when the valve is delivered over a guidewire, the guidewire can extend through the guidewire coupler 1133 and, in some instances, the distal anchoring element 1132 can be straightened along the guidewire during delivery. When the guidewire is removed, the bias of the distal anchoring element 1132 can result in the distal anchoring element 1132 bending, springing, and/or otherwise being biased upwards to clip or pinch native subannular tissue against the prosthetic valve.

The subannular member 1130 is also heat shaped to bias the proximal anchor. Thus, when the valve is deployed, the proximal anchoring element 1134 is folded-under and stowed in order to reduce the circumference of the prosthetic valve so it can be seated into the native annulus with the trans-annular section of the valve sealing against the inner surface of the native annulus. When the proximal anchoring element 1134 is released, the proximal anchoring element 1134 will spring outward and upward to resume the heat-set shape, which will cause the proximal anchoring element 1134 to engage and wedge against native subannular tissue. The projection(s) 1131 on the proximal anchoring element 1134 will then entrap or snare chordae, leaflet, trabeculae, papillary or annular tissue and, like a button in a button-hole, the projection(s) will anchor and fasten the proximal anchoring element 1134 to the native subannular tissue.

Figure 38A:
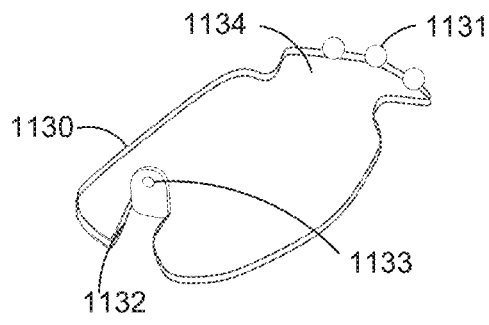
FIGS. 38A-38F are illustrations of a lower wire frame loop for a prosthetic valve with at least a distal anchoring element and a proximal anchoring element, each according to a different embodiment.
Figure 38B:
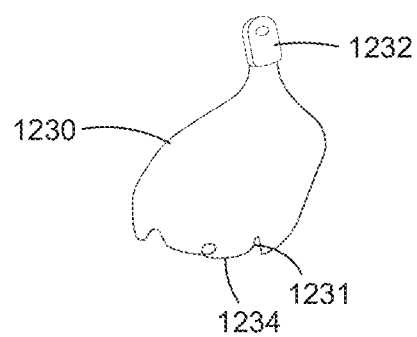
Figure 38C:
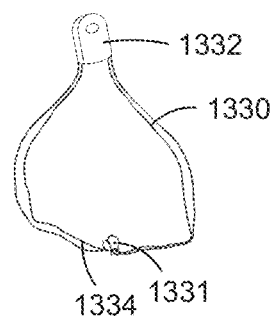
Figure 38D:
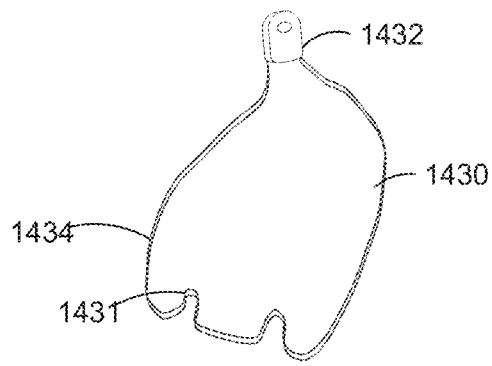
Figure 38E:
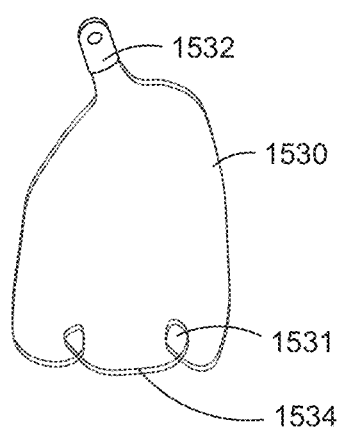
Figure 38F:
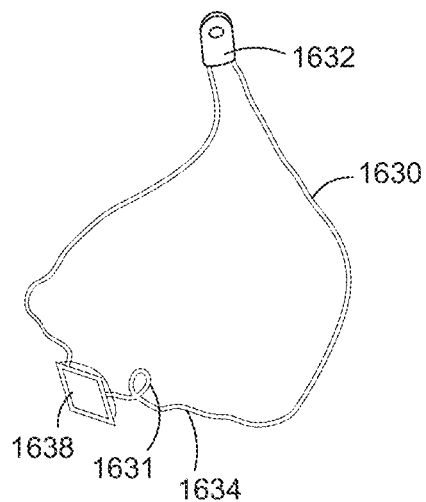

The subannular member 1130 shown in FIG. 38A has three (3) rounded projections. FIG. 38B shows a subannular member 1230 with three (3) loop projections, two (2) open loop and one (1) closed loop, according to an embodiment. FIG. 38C shows a subannular member 1330 with one (1) closed loop projection, centrally located, according to an embodiment. FIG. 38D shows a subannular member 1430 with two (2) open loop projections, according to an embodiment. FIG. 38E shows a subannular member 1530 with two (2) closed loop projections, according to an embodiment. FIG. 38F is an illustration of a subannular member 1630 having a pledget 1638 for a side deliverable transcatheter prosthetic heart valve with an extendable distal anchoring element, and a proximal anchoring element, according to an embodiment. FIG. 38F shows a closed loop projection 1631 located adjacent the tissue pledget 1638. The tissue pledget 1638 functions to provide an atraumatic surface to avoid tissue damage or the "cheese slicer" problem that can occur from tissue micro-motion against non in-grown prosthetic components.

Figure 39:
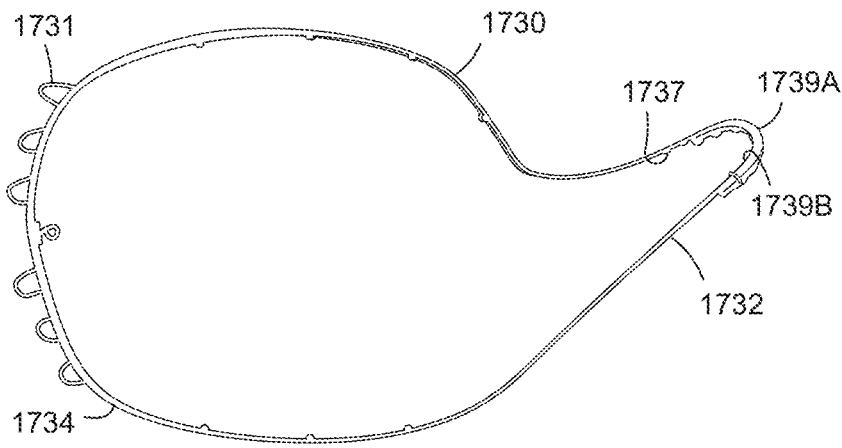
FIGS. 39 and 40 are a top view and a side perspective view, respectively, of a subannular member of an outer support frame of a prosthetic valve having a wire loop configuration with a distal anchoring element and a proximal anchoring element that each include tissue engaging features according to an embodiment.
Figure 40:
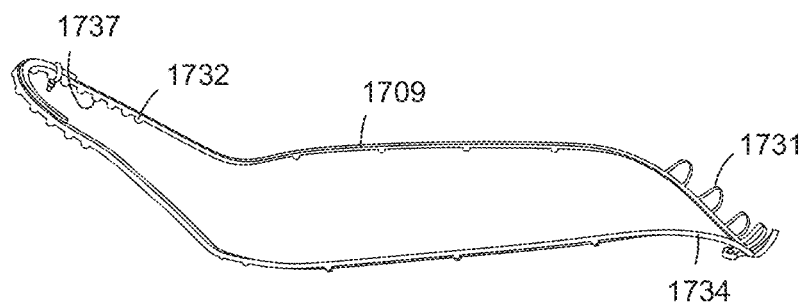

FIGS. 39 and 40 are a top view illustration and a side view illustration, respectively, of an integrated laser-cut subannular member 1730 having a distal anchoring element 1732 (e.g., an RVOT tab) and a proximal anchoring element 1734 (e.g., a proximal tab) combination. FIG. 39 shows the distal anchoring element 1732 in an offset position (11 o'clock) and the proximal anchoring element 1734 having six (6) loop-style projections 1731 for engaging native subannular tissue. A distal end of the distal anchoring element 1732 includes free ends 1739A, 1739B that can be clipped to a desired length and then coupled to use the same laser-cut pattern for various valve sizes. Wire beading or scalloping 1737 can be included and/or coupled to the distal anchoring element 1734. The wire beading or scalloping 1737 allows for a guidewire coupler (nosecone) (not shown) to be secured when the wire beading or scalloping 1737 engages with internal detents within the guidewire coupler. The wire beading or scalloping 1737 also provides suture anchor positions for future suture placement around and through the guidewire coupler. FIG. 40 shows that the subannular member 1730 can be configured to conform to native anatomy, such as a partial hyperbolic paraboloid shape.

Figure 41:
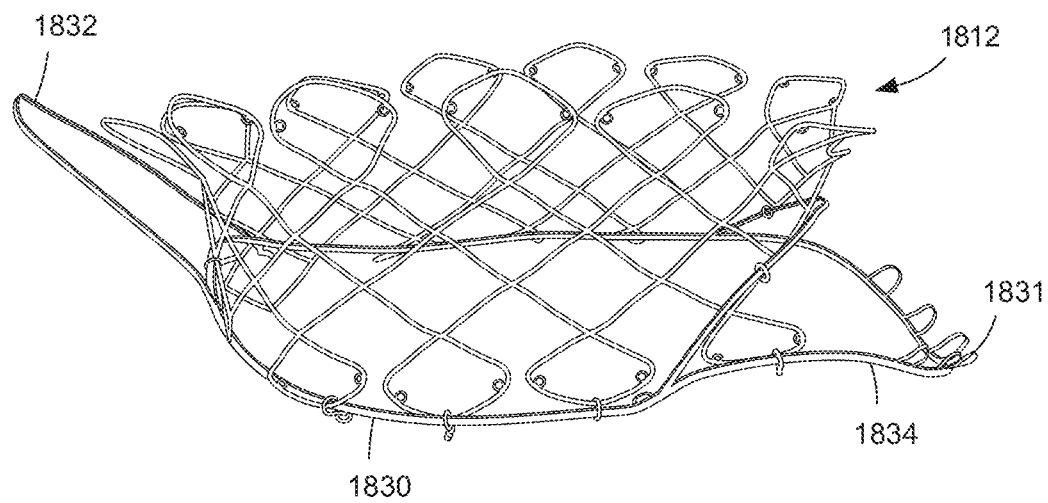
FIG. 41 is a side perspective view of a portion of an outer support frame, according to an embodiment, and showing a subannular member having a distal anchoring element and a proximal anchoring element with tissue engaging features and being coupled to a transannular member.

FIG. 41 is a side view illustration of an integrated laser-cut subannular member 1830 having a distal anchoring element 1832 (e.g., an RVOT tab) and a proximal anchoring element 1834 (e.g., a proximal tab) combination, and having a transannular member 1812 (e.g., a wire frame perimeter sidewall) mounted thereon. FIG. 41 shows that the transannular member 1812 or the subannular member 1830 can have an integrated inverted V-shape (caret) on a distal side thereof. FIG. 41 shows an embodiment with a distal end portion of the distal anchoring element 1832 forming a continuous loop. Projections 1831 are shown mounted on the proximal anchoring element 1834. FIG. 41 also shows that the transannular member 1812 can have a set of wire cells that is about 2 or 2½ diamonds in height and a supra-annular section that includes flared diamond-shaped wire cells that provides a section for coupling the transannular member 1812 to a supra-annular member (not shown) of the valve frame.

Figure 42A:
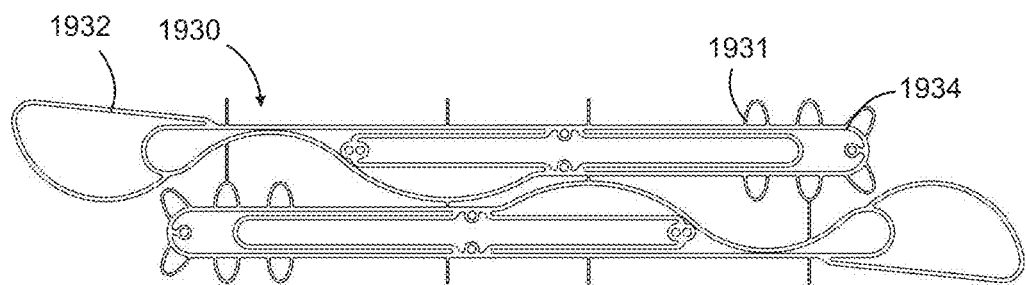
FIGS. 42A and 42B are a top view and a side view, respectively, of a laser-cut workpiece configured to form a subannular member of an outer support frame of a prosthetic valve according to an embodiment.
Figure 42B:
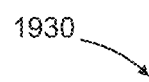

FIGS. 42A and 42B are a top view illustration and a side-profile view illustration, respectively, of a laser-cut work product of a subannular member 1930 having a continuous loop design with two joined pieces for forming a pair of integrated laser-cut subannular members 1930 having a distal anchoring element 1932 (e.g., an RVOT tab) and a proximal anchoring element 1934 (e.g., a proximal tab) combination. FIG. 42 shows that the subannular member 1930 can be manufactured (laser-cut) as a single continuous piece.

Figure 43A:
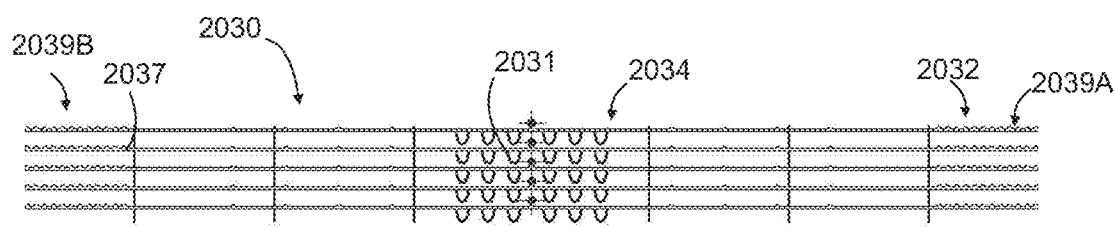
FIGS. 43A and 43B are a top view and a side view, respectively, of a laser-cut workpiece configured to form a subannular member of an outer support frame of a prosthetic valve according to an embodiment.
Figure 43B:
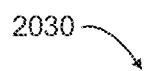

FIGS. 43A and 43B are a top view illustration and a side-profile view illustration, respectively, of a laser-cut work product for manufacturing an integrated laser-cut subannular member 2030 having free ends 2039A, 2039B, a distal anchoring element 2032 (e.g., an RVOT tab) and a proximal anchoring element 2034 (e.g., a proximal tab). Wire beading 2037 is shown on the subannular member 2030, along with projections 2031. In some implementations, the laser-cut subannular member 2030 provides additional opportunities to change cross-sectional widths and thicknesses to optimize stiffness along the flexible regions (as opposed to a wire with fixed cross-section). It also allows for integrated geometry for engagement tabs ("scallops") to provide additional securement forces by capturing the native leaflets. Moreover, one or more portions of the laser-cut work product can be twisted during heat setting to dictate and/or control a direction of flexibility of such portions. For example, the laser-cut work product can be twisted at or near the proximal anchoring element to set and/or control a direction of flexibility associated with moving the proximal anchoring element between two or more positions and/or configurations.

Figure 44:
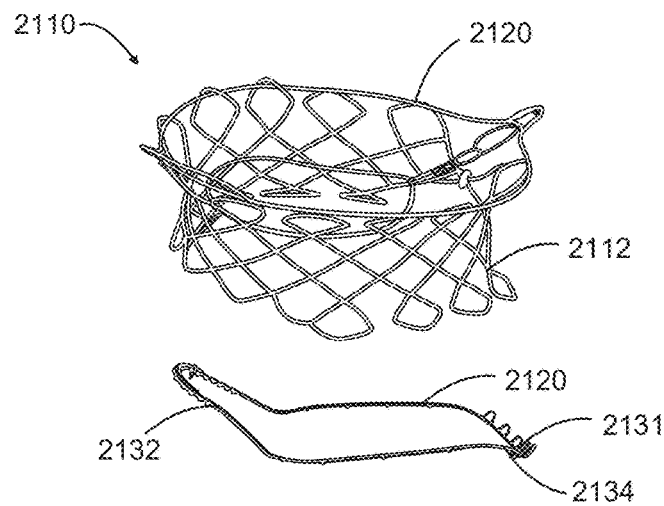
FIG. 44 is a side perspective view of a supra-annular member of an outer support frame having an outer support loop, an inner support loop, and a central spine extending between the outer support loop and the inner support loop, which is mounted to a supra-annular portion of a transannular member of the outer support frame (e.g., a cylindrical sidewall component), and shown above a subannular member of the outer support frame arranged as a wire loop with a shaped distal anchoring element and a proximal anchoring element with eyelets or the like mounted thereto for engaging native tissue.

FIG. 44 is a partially exploded side perspective view of an outer support frame 2110 according to an embodiment. The outer support frame 2110 includes a supra-annular member 2120 (e.g., an upper valve frame) configured as a wire loop with a central spine leading to an inner support loop, mounted on top of a transannular member 2112 (e.g., a cylindrical sidewall component), which is shown above a subannular member 2130 (e.g., a lower valve frame) configured as a wire loop with a shaped distal anchoring element 2132 and a proximal anchoring element 2134 with leaflet capturing features 2131 (e.g., eyelets) formed on the proximal end.

Figure 45A:
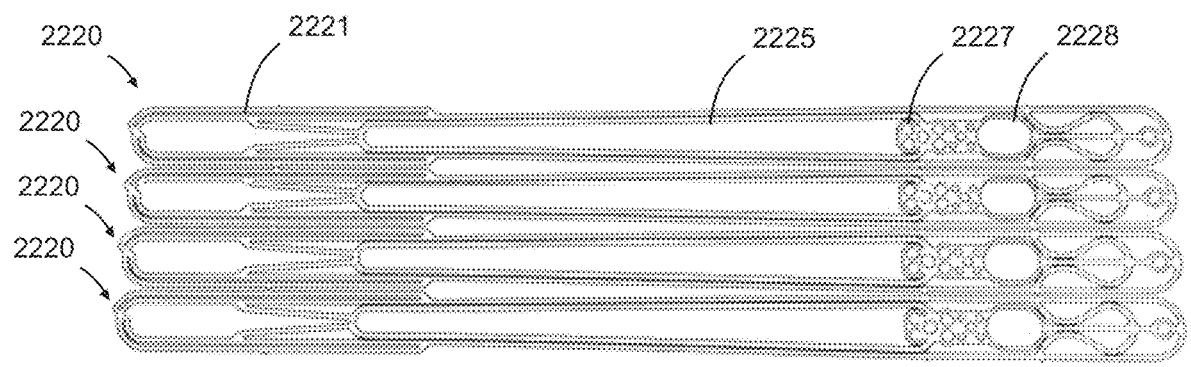
FIGS. 45A and 45B is a top view and a side view, respectively, of a laser-cut design workpiece for a supra-annular member of an outer support frame according to an embodiment.
Figure 45B:

FIGS. 45A and 45B are a top view illustration and a side view illustration, respectively, of a laser-cut design workpiece for one or more supra-annular member(s) 2220 of an outer support frame according to an embodiment. For example, FIG. 45A shows a laser-cut design workpiece including four (4) supra-annular members 220. After being laser-cut, the supra-annular members 2220 can be separated and heat-set into a supra-annular member having a desired shape, size, and/or configuration. In this embodiment, the supra-annular member 2220 can be set to include and/or form an outer loop 2221, an inner loop 2225, and at least one spline 2227. The spline 2227 can form and/or define a waypoint 2228 configured to couple to and/or receive a portion of a delivery system.

Figure 46A:
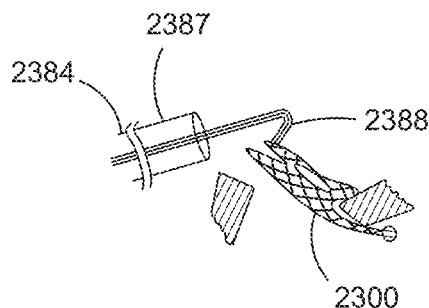
FIGS. 46A-46C are side view schematic illustrations of a prosthetic valve showing a sequence of retracting the valve into a portion of a delivery and/or retraction system according to an embodiment.
Figure 46B:
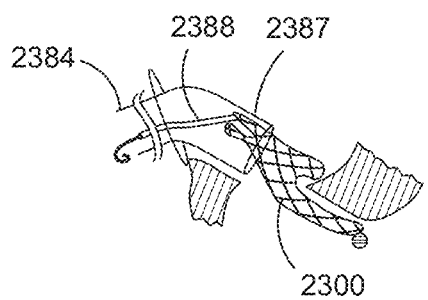
Figure 46C:
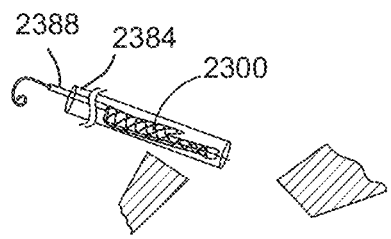

FIGS. 46A-46C are illustrations according to the invention of a series of three (3) images showing a prosthetic valve 2300 being retrieved into a delivery/retrieval catheter 2384 where the longitudinal axis of the catheter 2384 is not parallel to the central blood flow axis thru the valve 2300 like in traditional replacement valves, but instead approaches from the side (i.e., orthogonally) relative to the orientation of the blood flow through the valve 2300.

FIG. 46A shows a distal end portion 2387 of the delivery/retrieval catheter 2384 accessing an atrium of the heart (e.g., via the inferior vena cava using a transfemoral delivery and/or the like). FIG. 46B shows how an elongated connection member 2388 (e.g., a guidewire, a control push rod, a steerable catheter, a yoke, a tensile member, a suture, a tether, a retrieval tool, etc.) connects to a proximal side of the valve 2300 (e.g., to a delivery system-valve attachment point, waypoint, connector, and/or the like). In some implementations, the elongated connection member 2388 is already attached to the valve 2300 (e.g., for delivery of the valve 2300 to the annulus.

In some implementations, a retrieval process (or a portion thereof) may be performed during the initial valve deployment/delivery procedure and while the valve 2300 is still attached and/or connected to the elongated connection member 2388. For example, the retrieval process can be performed to at least partially withdraw the prosthetic valve 2300 due to a problem or medical issue identified by the interventionalist that calls for the valve 2300 that was being deployed, to be retrieved or at least partially retrieved. In other implementations, a retrieval process (or a portion thereof) may be performed after the valve 2300 has been deployed and disconnected from the elongated connection member 2388. In such implementations, the elongated connection member 2388 can be reconnected to the valve 2300 (or a new elongated connection member can be connected to the valve 2300). In some implementations, attachment and/or connection can be aided by the use of radio-markers on the elongated connection member 2388 and on a proximal portion of the valve 2300.

FIG. 46C shows the valve 2300 pulled into the delivery/retrieval catheter 2384. For example, the elongated connection member 2388 can be used to pull the proximal end of the valve 2300 into the distal end portion 2387 of the catheter 2384. In some implementations, the distal end portion 2387 of the catheter 2384 can be and/or can include a compression tip with one or more features to assist compression and retraction of the valve 2300, such as a surface coating, spiraled bead lines, spiraled channels, and/or the like on the inner surface of the distal end portion 2387 of the catheter 2384 to assist compression and retraction of the valve 2300 into the catheter 2300. As shown, the valve 2300 is folded and compressed into the catheter 2384 with the elongated connection member 2388 attached so that, in some instances, the delivery catheter 2384 can be withdrawn and the valve 2300 retrieved from the patient.

Figure 47:
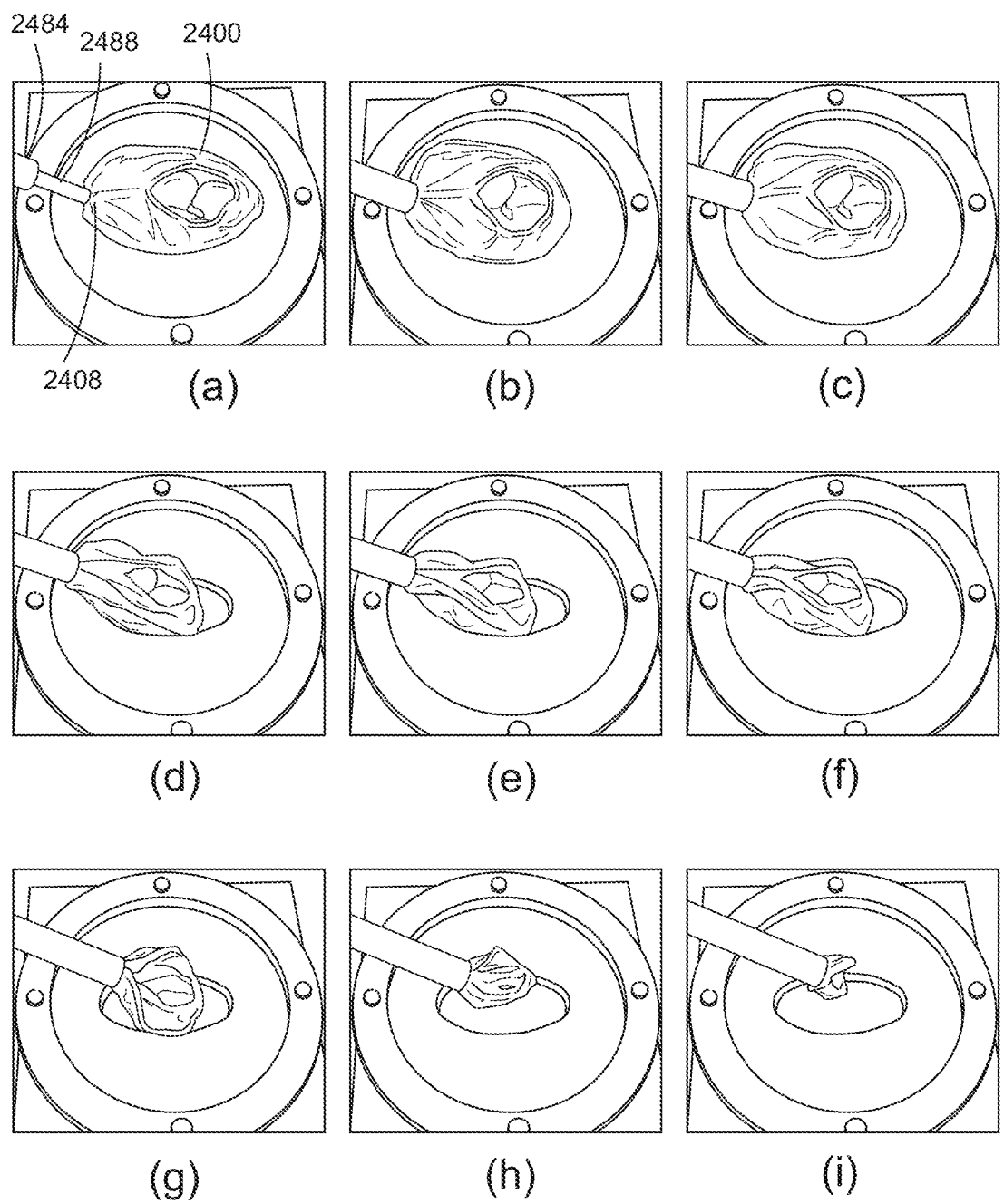
FIGS. 47(*a*)-47(*i*) are top perspective views of a valve sequence illustrations showing a sequence of retracting a prosthetic valve into a portion of a delivery and/or retraction system according to an embodiment.

FIG. 47 is an illustration according to the invention of a series of nine (9) images (a) thru (i) showing a valve 2400 being retrieved from a native annulus model and into a delivery/retrieval catheter 2484 where the longitudinal axis of the catheter 2484 is orthogonal to the orientation of the frame and flow control (valve leaflets) component of the valve 2400.

FIG. 47(*a*) shows a distal end portion of the delivery/retrieval catheter 2484 having an elongated connection member 2488 (e.g., a guidewire, a control push rod, a steerable catheter, a yoke, a tensile member, a suture, a tether, a retrieval tool, etc.) attached to a proximal portion 2408 of the prosthetic valve 2400. FIG. 47(*a*) shows a relatively large diameter valve (e.g., 65 mm×45 mm tubular frame (110 mm×72 mm including atrial collar), with a 29 mm flow control component mounted within the tubular frame of the valve 2400) at least partially disposed in an opening corresponding to and/or representing an annulus of a native heart valve.

FIG. 47(*b*) shows the prosthetic valve 2400 being drawn into the delivery/retrieval catheter 2484 with about 10-20% of the valve 2400 compressed within a lumen of the catheter 2484. FIG. 47(*b*) illustrates how the prosthetic valve 2400 is designed to fold, front side approaching back side, and is designed to vertically compress, so that the large valve becomes compressed within a standard sized transfemoral catheter (e.g., 24-32 Fr, or about a 28 Fr catheter). For sake of definition, French sizing can be converted to millimeter by dividing by 3, so that a 24 Fr catheter has about an 8 mm inner diameter, a 30 Fr catheter has about a 10 mm inner diameter, and so forth.

FIG. 47(*c*) shows the prosthetic valve 2400 being drawn into the delivery/retrieval catheter 2484 with about 20-30% of the valve 2400 compressed within the lumen of the catheter 2484. FIG. 47(*c*) shows, for example, a proximal anchoring location at least partially housed within the catheter 2484.

FIG. 47(*d*) shows the prosthetic valve 2400 being drawn into the delivery/retrieval catheter 2484 with about 30-40% of the valve 2400 compressed within the lumen of the catheter 2484. FIG. 47(*d*) shows, for example, an atrial collar and/or supra-annular member of the valve frame beginning to fold inward toward a longitudinal axis (not shown).

FIGS. 47(*e*) and 47(*f*) show the prosthetic valve 2400 being drawn into the delivery/retrieval catheter 2484 with about 50-60% of the valve 2400 compressed within the lumen of the catheter 2484. FIGS. 47(*e*) and 47(*f*) show how the valve 2400 has been at least partially withdrawn from the opening (annulus) and the valve 2400 has started to be vertically compressed.

FIGS. 47(*g*)-47(*i*) show the valve 2400 continuing to be drawn into the lumen of the delivery/retrieval catheter 2484 with about 70%, 80%, and over 90%, respectively, of the valve 2400 shown compressed within the lumen of the catheter 2484. FIGS. 47(*g*)-47(*i*) show how the valve 2400 continues to fold and/or compress and retract into the delivery/retrieval catheter 2484.

Figure 48A:
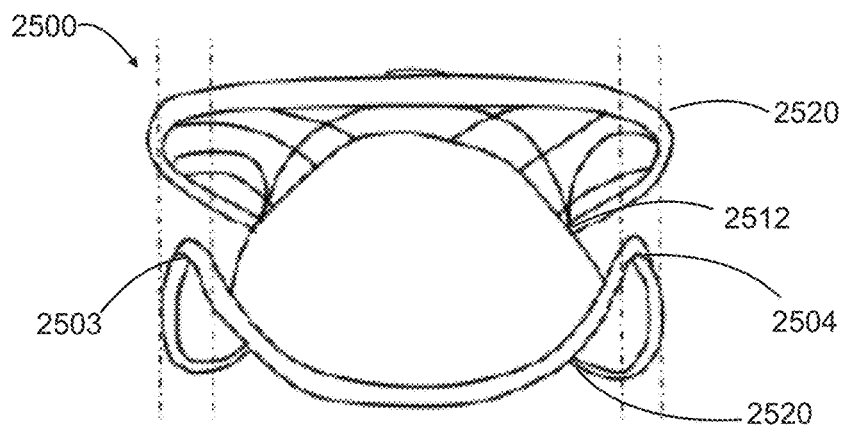
FIGS. 48A-48C are sequence illustrations showing the subannular flares on the freewall (left) and the septal (right) sides transitioning from extended configuration (FIG. 46A) after delivery to a retracted configuration (FIG. 46B) for seating into and/or through the native annulus, and substantially back to the extended configuration (FIG. 46C) to allow the valve to use the subannular flares as an anchoring mechanism.
Figure 48B:
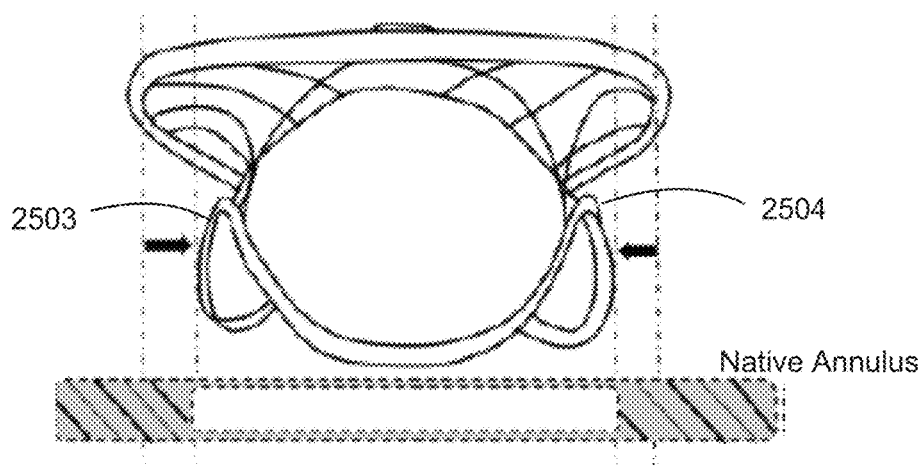
Figure 48C:
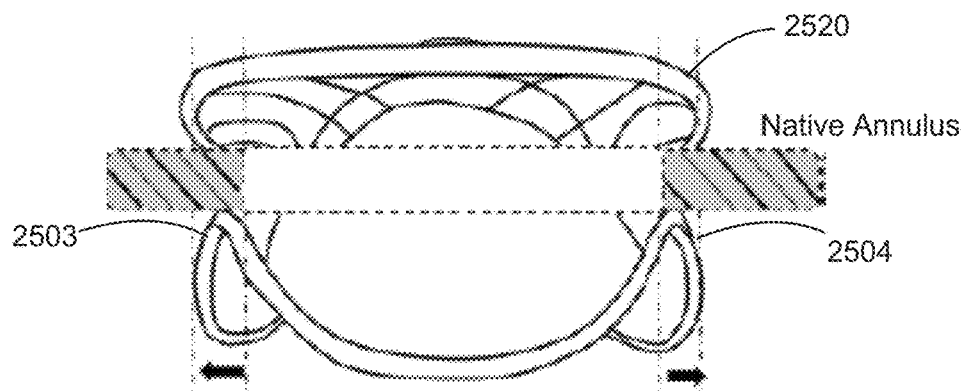

FIGS. 48A-48C illustrate at least a portion of a process for deploying a prosthetic valve 2500 according to an embodiment. FIGS. 48A and 48B show the prosthetic valve 2500 having an outer support frame that includes a supra-annular member 2520, a subannular member 2530, and a transannular member 2512. The subannular member 2520 can include subannular flares 2503 and 2504 on the freewall (left) and the septal (right) sides, respectively, that can transition between extended (FIG. 48A) and retracted positions (FIG. 48B) to allow the valve 2500 to slide through the native annulus. FIG. 48C shows the valve 2500 deployed, seated, and/or otherwise extending through the native annulus and the subannular flares 2503 and 2504 on the freewall (left) and the septal (right) sides, respectively, transitioned from the retracted positions (FIG. 48B) to or toward the extended positions. As such, the subannular flares 2503 and 2504 extend radially to allow the valve 2500 to use the subannular flares 2503 and 2504 as an anchoring mechanism (e.g., against native tissue that forms and/or defines the native annulus. The subannular flares 2503 and 2504 can be actuated using any of the actuation methods described herein.

Figure 49A:
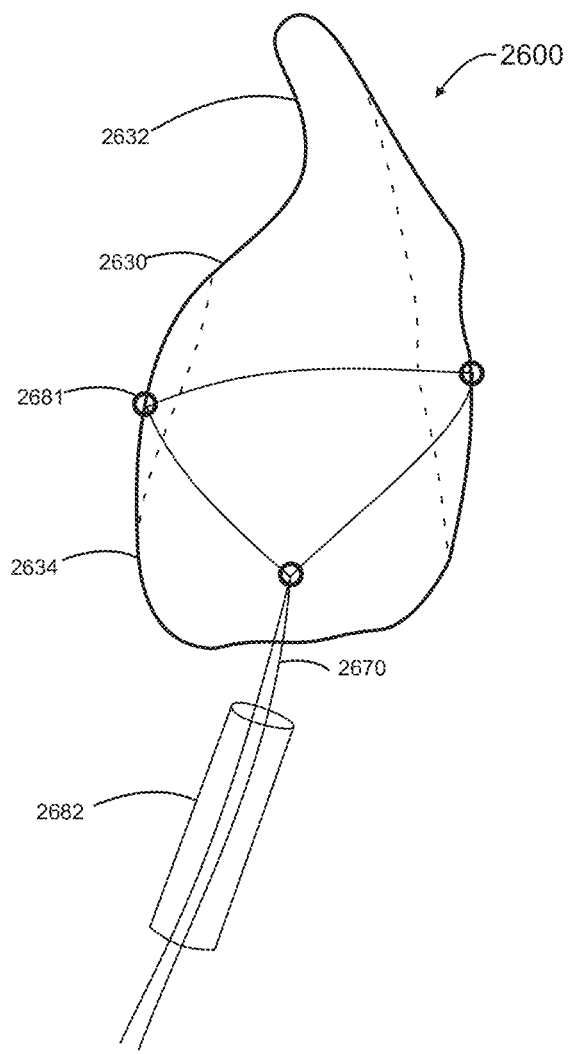
FIGS. 49A and 49B are sequence illustrations showing a top view of a portion of a prosthetic valve, according to an embodiment, and having a subannular member of an outer support frame removably coupled to an actuator and being drawn inward to reduce a perimeter or circumference of at least a portion of the prosthetic valve and/or outer support frame to facilitate deployment of the prosthetic valve in the native annulus.
Figure 49B:
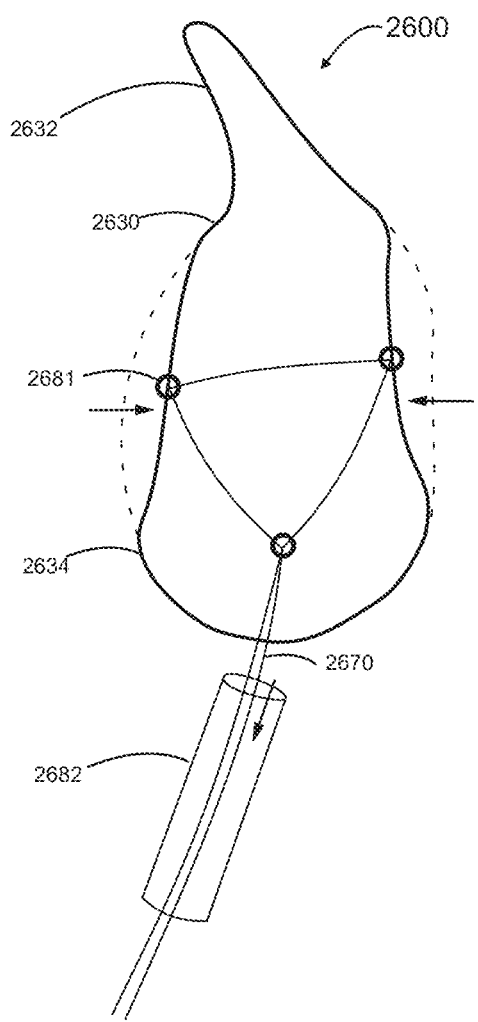

FIGS. 49A and 49B are sequence illustrations showing a top view of a portion of a prosthetic valve 2600 with a subannular member 2630 that can have and/or can form a wire loop (and attached sidewalls), which is/are drawn inward to reduce the perimeter or circumference of the valve body to facilitate deployment of the valve 2600 in the native annulus. FIGS. 49A and 49B show that the valve 2600 can be advanced through a delivery catheter 2682 and removably coupled to an actuator 2670 such as one or more tethers, sutures, tensile members, cords, etc. The actuator 2670 can be used to actuate the subannular member 2630 and/or any other suitable portion of the valve 2600 (e.g., by pulling the actuator 2670 in a proximal direction) and can be delivered with the prosthetic valve 2600 via the delivery catheter 2682. The actuator 2670 can couple to the subannular member 2630 via attachment points 2681. The subannular member 2630 is shown with a distal anchoring element 2632 and a proximal anchoring element 2634. In some implementations, the actuator 2670 may also be used to actuate the proximal anchoring element 2634 and/or the distal anchoring element 2632. In some implementations, once the valve 2600 is deployed in an annulus of a native valve, the actuator 2670 can be removed or decoupled from the valve 2600 and retracted through the delivery catheter 2682.

FIGS. 50A-50D are sequence illustrations showing a bottom view of a prosthetic valve 2700 removably coupled to an actuator 2770 used to actuator one or more portions of the valve 2700 according to an embodiment. The valve 2700 has a subannular member 2730 that can have and/or can form a wire loop (and attach to sidewalls), which is/are drawn inward to reduce the perimeter or circumference of the at least the subannular member 2730 to facilitate deployment of the valve 2700 in the native annulus. In this embodiment, the actuator 2770 can be and/or can include a set of tethers, tensile members, sutures, cables, and/or any other suitable connectors that can be attached to one or more attachment points along the subannular member 2730 (e.g., a proximal anchoring element of the subannular member 2730). The actuator 2770 can also include and/or can be at least partially disposed in a catheter that can be inserted through a dynamic waypoint, opening, attachment point, through hole, etc. formed by a supra-annular member of the valve frame. In some implementations, the actuator 2770 can be and/or can include separate tethers used to actuate (e.g., fold) the proximal anchoring element), to actuate (e.g., fold) the septal wall sidewall, and/or to actuate (e.g., fold) the freewall sidewall.

FIGS. 50A-50D show a set of tethers of the actuator 2770 extending from a catheter that extends through and/or is at least partially disposed below a supra-annular member of the valve frame. For example, the tethers can be run through a relatively small dynamic waypoint catheter and can be actuated outside of the patient to manipulate a shape of the proximal anchoring element, the subannular member 2730, and/or the valve 2700 to facilitate seating a proximal side of the valve 2700 into the native annulus. In some implementations, during delivery, the dynamic waypoint catheter can be proximal to the compressed valve 2700 in a delivery catheter to avoid having the dynamic waypoint catheter stacked on top of the compressed valve 2700 within the delivery catheter. An actuator with a single tether or multiple tethers is contemplated within the scope of the invention (e.g., one tether, two tethers, three tethers, four tethers, five tethers, six tethers, seven tethers, eight tethers, nine tethers, ten tethers, or more, each of which can be removably coupled to one or more attachment points on the valve 2700). The actuator 2770 and/or the tethers may be equipped with disconnection elements to allow the actuator 2770 and/or tethers to be withdrawn after the valve 2700 is deployed and secured in the native annulus. The dynamic waypoint catheter may also be included in and/or housed within a portion of a delivery system such as, for example, a pusher catheter and/or the like, whereby the dynamic waypoint catheter can drop through the waypoint, through hole, opening, etc. of the valve 2700 to a subannular position, while the pusher catheter or other portion of the delivery system is too large to pass through the waypoint. As such, the pusher catheter or other portion of the delivery system can be used to control a placement of at least a portion of the valve 2700. For example, the pusher catheter or other portion of the delivery system can be used to push down onto a surface of the supra-annular member to seat the proximal side of the valve 2700 in the native annulus while the subannular member 2730 is in an actuated configuration.

Figure 50A:
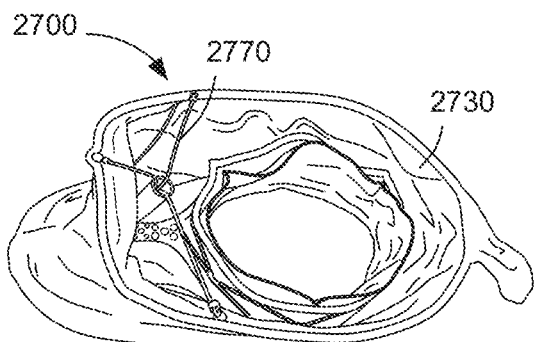
FIGS. 50A-50C are bottom perspective views and FIG. 50D is a bottom-side perspective view of a side-delivered transcatheter prosthetic heart valve, according to an embodiment, and showing a sequence of actuating one or more portions of the prosthetic valve to reduce a perimeter and/or circumference of a subannular member to facilitate deployment of the valve in the native annulus.
Figure 50B:
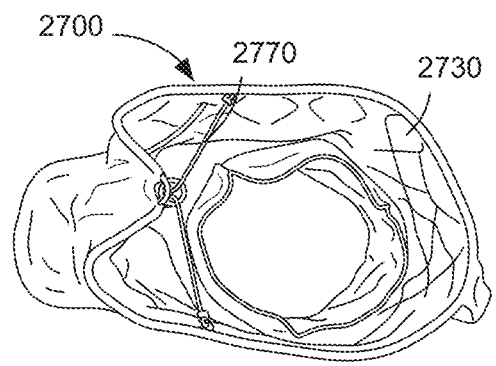
Figure 50C:
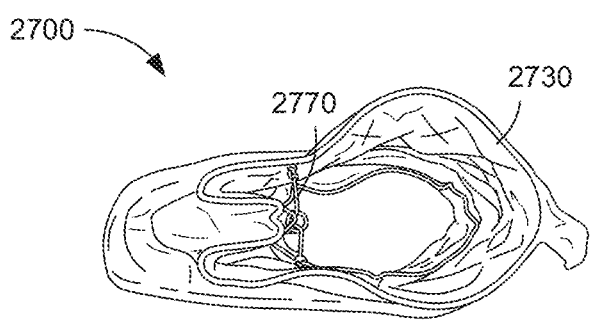
Figure 50D:
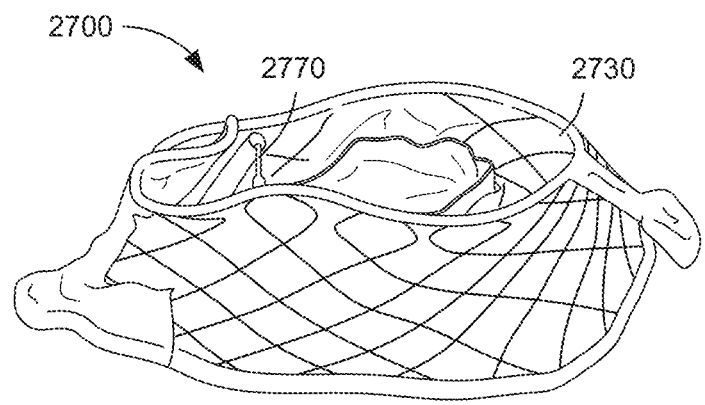

FIG. 50A is a bottom perspective view of the valve 2700 and the actuator 2770 and shows the subannular member 2730 in an at least partially extended or unactuated configuration. FIG. 50B is a bottom perspective view of the valve 2700 and the actuator 2770 and shows the subannular member 2730 partially actuated such that, for example, the proximal anchoring element of the subannular member 2730 is drawn toward the dynamic waypoint catheter and/or the flow control component of the valve 2700. FIG. 50C is a bottom perspective view of the valve 2700 and the actuator 2770 and shows the subannular member 2730 in a compressed, folded, and/or actuated configuration such that the proximal anchoring element and, for example, a proximal portion of a septal wall sidewall and a freewall sidewall of the valve 2700 are drawn toward the dynamic waypoint catheter and/or the flow control component of the valve 2700. FIG. 50D is a side perspective upside down view of the valve 2700 and the actuator 2770 and shows the subannular member 2730 in the actuated configuration, the dynamic waypoint catheter extending below the supra-annular member of the valve frame, and the tethers retracted or pulled toward and/or into the dynamic waypoint catheter. FIG. 50D shows that the dynamic waypoint catheter can also be used to pull the valve down into the ventricle (e.g., via the retracted tethers), avoiding the need to push a compressible valve into the native annulus.

Figure 51:
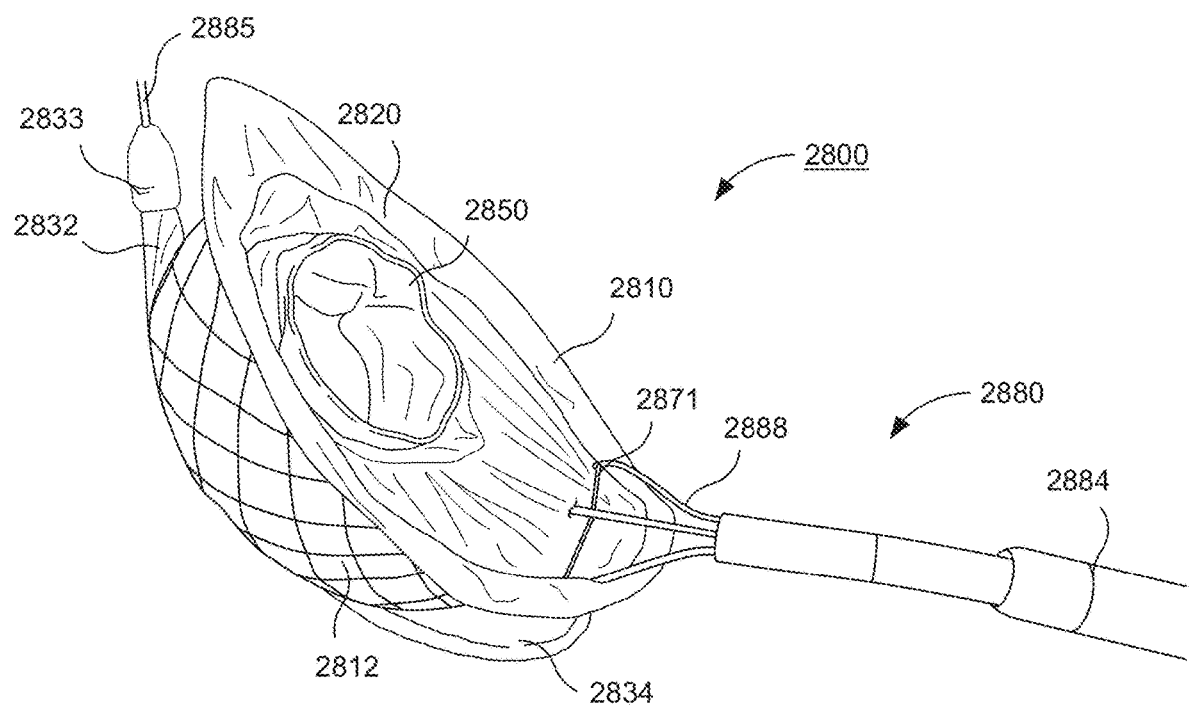
FIGS. 51-53 are a side perspective view, a top view, and a bottom perspective view, respectively, of a prosthetic valve removably coupled to at least a portion of a delivery and/or actuating system, according to an embodiment.
Figure 52:
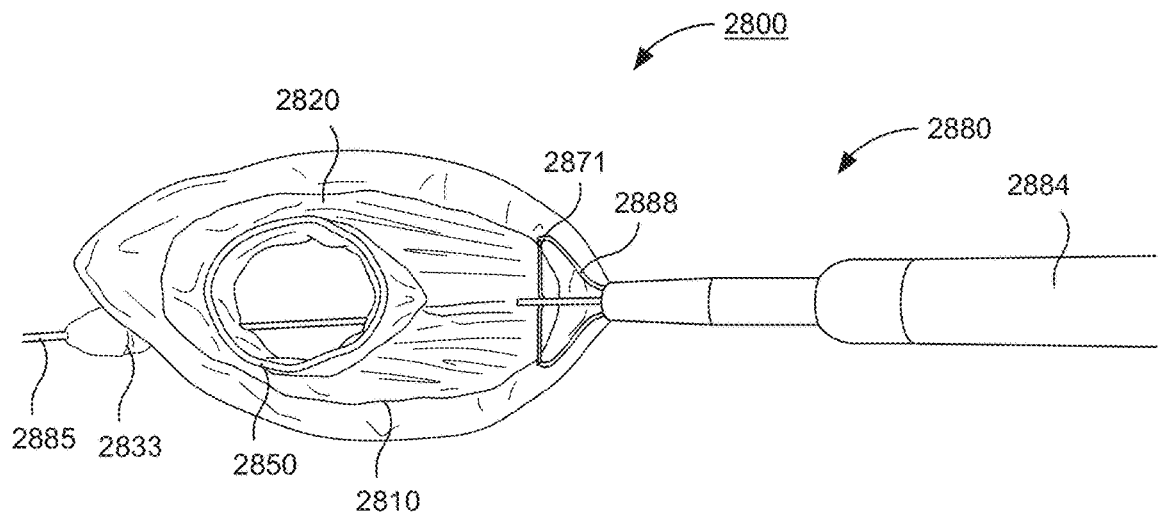
Figure 53:
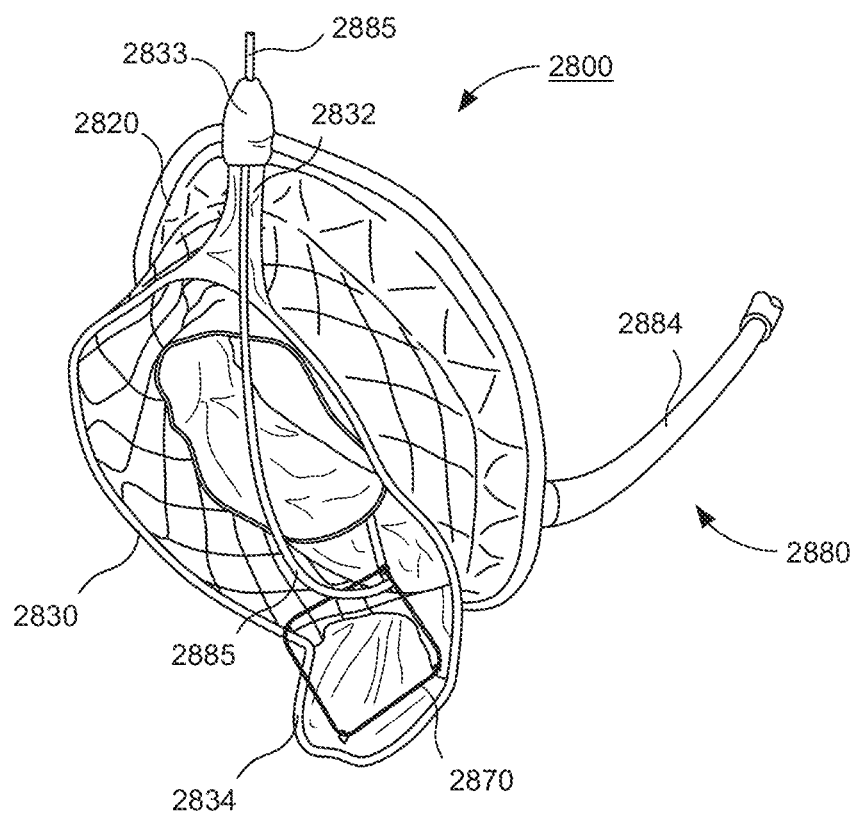

FIGS. 51-53 are a side perspective view, a top view, and a bottom perspective view, respectively, of a side-deliverable transcatheter prosthetic valve 2800 removably coupled to a delivery system 2880 according to an embodiment. The valve 2800 includes a valve frame 2810 and a flow control component 2850 mounted therein. The valve frame 2810 includes a supra-annular member 2820, a subannular member 2830, and a transannular member 2812 coupling the supra-annular member 2820 to the subannular member 2830. The delivery system 2880 and/or at least the portion of the delivery system 2880 includes a delivery catheter 2884 through which the valve 2800 is delivered into an atrium of a heart. The delivery system 2880 further includes an attachment member 2888 that is removably coupleable to the valve 2800. FIGS. 51-53 show the attachment member 2888 having a wishbone or yoke configuration, though other configurations are possible. The attachment member 2888 can be coupled to and/or included in a distal end portion of a multi-lumen steerable catheter, which can be used to deliver one or more components of the valve 2800 and/or the delivery system 2880.

FIGS. 51 and 52 show the attachment member 2888 (e.g., a yoke) in contact with the supra-annular member 2820 of the valve frame 2810. In some embodiments, the attachment member 2888 can be in contact with and/or removably coupled to a drum or the transannular member 2812 of the frame 2810. In other embodiments, the attachment member 2888 can be in contact with and/or coupled to any suitable portion of the valve 2800. The attachment member 2888 can removably couple to the valve 2800 via sutures, tethers, cables, clips, couplers, and/or any other removable coupling. For example, FIGS. 51 and 52 show an attachment member 2871 of the valve 2800 coupled to and/or extending from the supra-annular member 2820. In some embodiments, the attachment member 2871 of the valve 2800 can be a tether, suture, cable, frame structure, and/or the like that can be coupled to and/or extend from a wire frame portion of the supra-annular member 2820 or, for example, a drum or biocompatible covering. In such embodiments, the attachment member 2888 of the delivery system 2880 can be removably coupled (e.g., via a suture, tether, and/or any other removable coupling) to the attachment member 2871 of the valve 2800.

FIGS. 51 and 52 further show a guidewire catheter 2885 of the delivery system 2880 extending through, for example, a waypoint or opening in the supra-annular member 2830 and/or drum thereof and extending through a guidewire coupler 2833 of a distal anchoring element 2832 of the subannular member 2830. FIG. 53 shows the guidewire catheter 2885 extending below the flow control component 2850 of the valve 2800. During delivery, the guidewire catheter 2885 can be extend through the valve 2800 (as shown in FIG. 53) and advanced over a guidewire already placed in a desired position within the heart. As such, delivering the valve 2800 in a compressed configuration through the delivery catheter 2884 includes advancing the guidewire catheter 2885 along the guidewire. The guidewire catheter 2885 can extend through the guidewire coupler 2833 of the distal anchoring element 2832 (e.g., a distal end of the guidewire catheter 2885 can be distal to the guidewire coupler by about 0.1 cm to about 1.0 cm, or more).

The guidewire catheter 2885 can be sufficiently stiff to, for example, limit and/or define (at least in part) a range of motion of the valve 2800 during delivery. For example, the guidewire catheter 2885 can define an axis about which the valve 2800 can rotate during delivery but can substantially limit or oppose movement of the valve 2800 in other directions. In some implementations, the arrangement of the attachment member 2888 (e.g., yoke) and the guidewire catheter 2885 can allow for greater control of a position of the valve 2800 during delivery. The guidewire catheter 2885 and/or one or more portions of the valve 2800 can also include radiopaque markers allowing for enhanced visualization during image guided delivery.

FIG. 53 further shows an actuator 2870 (or at least a portion of the actuator 2870) included in the portion of the delivery system 2880. The actuator 2870 can be and/or can include, for example, one or more tethers, sutures, cables, tensile members, ties, etc. removably coupled to one or more attachment points on the valve 2800. For example, the tether(s) are shown removably coupled to a proximal anchoring element 2834 of the subannular member 2830. The actuator 2870 (e.g., tether(s)) can be used to actuate the proximal anchoring element 2834 between two or more configurations, positions, states, etc. FIG. 53 shows the proximal anchoring element 2834 in an expanded or unactuated configuration. During deployment, an operator can actuate a proximal end portion of the actuator 2870 (e.g., disposed outside of the body) to, for example, pull the tether(s) in a proximal direction, thereby folding or compressing the proximal anchoring element 2834 toward the flow control component 2850. The actuation of the actuator 2870 can also fold, compress, and/or draw a proximal portion of a posterior and anterior wall of the transannular member 2812 inward toward the flow control component 2850. After deploying the valve 2800 in the annulus of the native valve, the actuator 2870 can be removed or decoupled from the valve 2800, the guidewire catheter 2885 (and the guidewire extending therethrough) can be retracted through the waypoint or opening in the supra-annular member 2820, and the portion of the delivery system 2880 can be decoupled from the valve 2800 and withdrawn from the patient, leaving the deployed prosthetic valve 2800 in place in the annulus of the native heart valve.

Figure 54A:
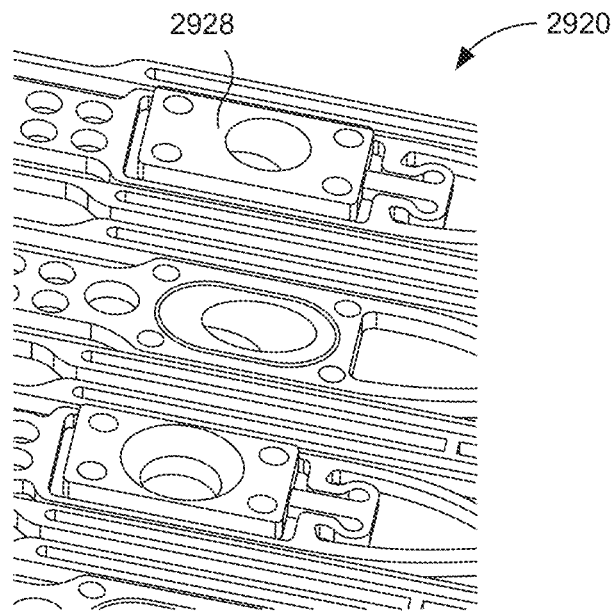
FIG. 54A is an illustration of a laser cut design for a portion of a prosthetic valve including delivery system-valve attachment point (e.g., a waypoint) according to an embodiment.
Figure 54B:
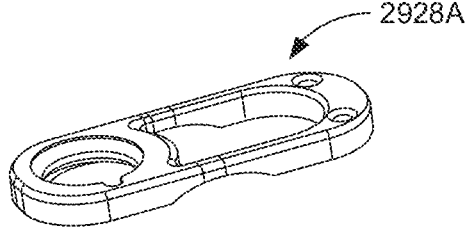
FIGS. 54B-54D are is a set of illustrations of the delivery system-valve attachment point of FIG. 54A, showing the waypoint having a flex design for removably coupling the prosthetic valve to a portion of a delivery system.
Figure 54C:
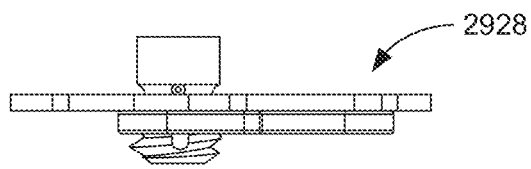
Figure 54D:
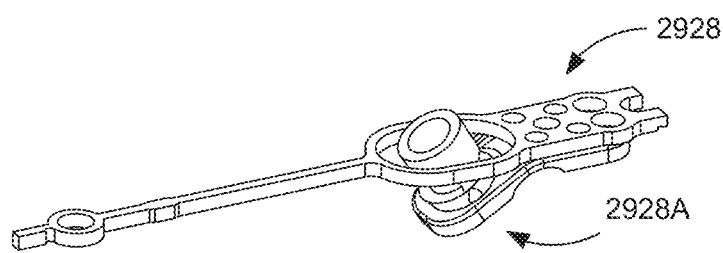

FIGS. 54A-54D are various views of a delivery system-valve attachment point 2928 according to an embodiment. FIG. 54A is a perspective view illustration of a portion of a laser cut design for a supra-annular member 2920 that shows at least a portion of the delivery system-valve attachment point 2928. The delivery system-valve attachment point 2928 can be, for example, a waypoint flex design that includes and/or couples to a flex component 2928A that removably couples to a portion of a delivery system (e.g., via a threaded coupling or any suitable form of coupling). The waypoint flex design of the delivery system-valve attachment point 2928 can achieve a relatively high pivot angle and can limit and/or reduce a loading angle/force. FIG. 54B shows the flex component 2928A that can be a laser cut component included in the laser cut design for the supra-annular member 2890 or can be separately laser cut. FIG. 54C shows the flex component 2928A coupled to the supra-annular member 2920 to form the delivery system-valve attachment point 2928 with threads that are perpendicular to a top surface of the flex component 2828A. The flex component 2928A can be coupled via sutures, rivets, screws, bolts, adhesive, and/or any other suitable coupling. FIG. 54D shows the flex component 2928A being flexed into the interior of the valve during loading. While the flex component 2928A is described as being separate from and coupled to the supra-annular member 2920, in other embodiments, the flex component 2928A (or at least a portion thereof) can be integrally formed with the supra-annular member 2920. For example, the flex component 2928A can be an inner and/or concentric portion of a spline included in the supra-annular member 2920.

FIGS. 55A and 55B are a perspective view and a top view, respectively, of a delivery system-valve attachment point 3028 according to an embodiment. The delivery system-valve attachment point 3028 can be, for example, a waypoint yoke design, which can achieve a relatively high pivot angle and limit and/or reduce a loading angle/force. The delivery system-valve attachment point 3028 can be a single component formed, for example, from Nitinol wire or laser cut from a Nitinol sheet and heat set to for a #4-40 screw thread for attachment to a portion of the delivery system. The delivery system-valve attachment point 3028 can be formed separately from a supra-annular member and coupled thereto after each component has been formed. The delivery system-valve attachment point 3028 can be movably coupled, for example, to a spline, an outer loop, and/or any other suitable portion of the supra-annular member.

FIGS. 56A-56C are various views of a delivery system-valve attachment point 3128 according to an embodiment. The delivery system-valve attachment point 3128 can be, for example, a waypoint hinged design, which can achieve a relatively high pivot angle (e.g., greater than 90 degrees) and limit and/or reduce a loading angle/force. The delivery system-valve attachment point 3128 includes multiple parts that can be press fit, welded, and/or otherwise coupled together and can have and/or can form threads for a #4-40 screw. In some instances, the delivery system-valve attachment point 3128 can include a coupler that has a minimum outside dimension of about 0.140". The delivery system-valve attachment point 3128 can be formed separately from a supra-annular member and coupled thereto after each component has been formed. The delivery system-valve attachment point 3128 can be movably coupled, for example, to a spline of the supra-annular member (or other suitable portion thereof).

FIGS. 57-60 are bottom perspective views of a prosthetic valve 3200 and illustrating a process of transitioning a proximal anchoring element 3234 of the prosthetic valve 3200 between a first configuration and a second configuration, according to an embodiment. The valve 3200 is shown as including an outer support frame 3210 and a flow control component 3250 mounted within a central region of the outer support frame 3210. The frame 3210 is shown having at least a supra-annular member 3220 and a subannular member 3230. The supra-annular member 3220 and the subannular member 3230 can be similar to any of those described above. Accordingly, certain aspects and/or features may not be described in further detail herein.

Figure 57:
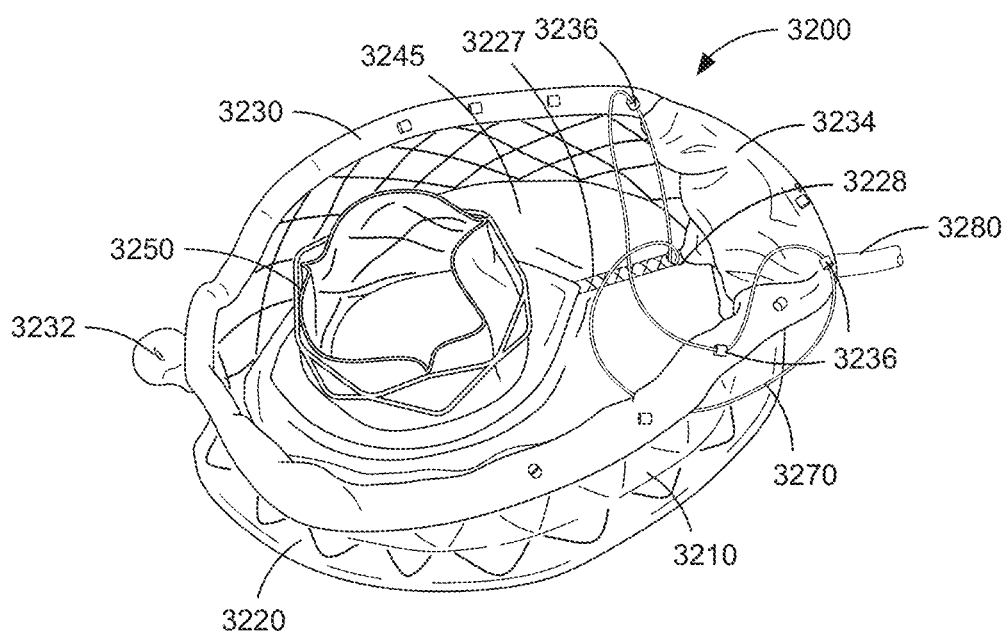
FIGS. 57-60 are bottom perspective views of a prosthetic valve and illustrating a process of transitioning a proximal anchoring element of the prosthetic valve between a first configuration and a second configuration, according to an embodiment.

FIG. 57 shows the subannular member 3230 having and/or forming a distal anchoring element 3232 and the proximal anchoring element 3234. The supra-annular member 3220 is shown including a spline 3227 (e.g., extending between an outer loop and an inner loop of the supra-annular member 3220 (not shown)) that defines a waypoint 3228 at or near a proximal end portion of the supra-annular member 3220. The supra-annular member 3220 is further shown as including a drum 3445 that extends between and/or is coupled to the inner and outer loops of the supra-annular member 3220 and covers a space not otherwise occupied by the flow control component 3250. The supra-annular member 3220 (or an inner loop thereof) is shown coupled to the flow control component 3250, which is distally offset relative to the valve 3200.

The valve 3200 is configured to engage or to be engaged by at least a portion of a delivery system 3280, or the like. The delivery system 3280 can include any suitable component for delivering, retrieving, deploying, moving, manipulating, actuating, and/or otherwise interacting with one or more portions of the valve 3200. In this embodiment, the delivery system 3280 can include, for example, one or more catheters. For example, the delivery system 3280 can include a delivery catheter through which the valve 3200 is delivered to an annulus of a native heart valve. The delivery system 3280 can also include one or more steerable catheters, control catheters, multi-lumen catheters, and/or the like, or combinations thereof. In some embodiments, the delivery system 3280 can include a multi-lumen control catheter that has a distal end portion configured to removably engage and/or couple to one or more portions of the valve 3200 to facilitate delivery, deployment, and/or retrieval of the valve 3200. Although not shown in FIGS. 57-60, the delivery system 3280 can also include a guidewire catheter that can be advanced over a guidewire during delivery and/or deployment. In such implementations, the guidewire catheter can pass through the waypoint 3228, below the flow control component 3250, and through a guidewire coupler of the distal anchoring element, as described above with reference to the valve 2800 shown in FIGS. 51-53.

FIG. 57 further shows the delivery system 3280 including an actuator 3270. The actuator 3270 can be similar to those described above with reference to, for example, 170, 270, and/or 370. For example, the actuator 3270 can be and/or can include a tether that extends through the waypoint 3228 of the spline 3227 and is threaded through one or more attachment point(s) 3236 coupled to and/or formed along the subannular member 3230. The tether loops through the attachment(s) 3236 and extends in a proximal direction back through the waypoint 3228. As such, both ends of the tether can be maintained outside of the body, allowing a user to manipulate the tether (actuator 3270). In this embodiment, the tether is shown threaded through multiple attachment points 3236 at or along the proximal anchoring element 3234 of the subannular member 3230 such that actuation of the actuator 3270 (e.g., tether(s)) transitions and/or moves at least the proximal anchoring element 3234 between the first configuration and the second configuration. The tether can be threaded through the attachment points 3236 in any suitable manner, which in turn, can control and/or determine a way that the proximal anchoring element 3234 is transitioned or moved. Moreover, the attachment points 3236 can be formed from any suitable material that can facilitate the passage or threading of the tether therethrough. For example, the attachment points 3236 can be included in and/or integrally formed with a laser-cut wire frame of the subannular member 3220 (e.g., like eyelets and/or the like). In other embodiments, the attachment points 3236 can be sutured loops and/or loops formed in or by a biocompatible fabric at least partially wrapping around the subannular member 3220. In still other embodiments, the attachment points 3236 can be formed from a biocompatible polymer such as, for example, polyethylene, and/or the like. In some such embodiments, the biocompatible material can be, for example, a self-lubricating polymer composite and/or the like that can facilitate the movement of the tether through the attachment point 3236.

Figure 58:
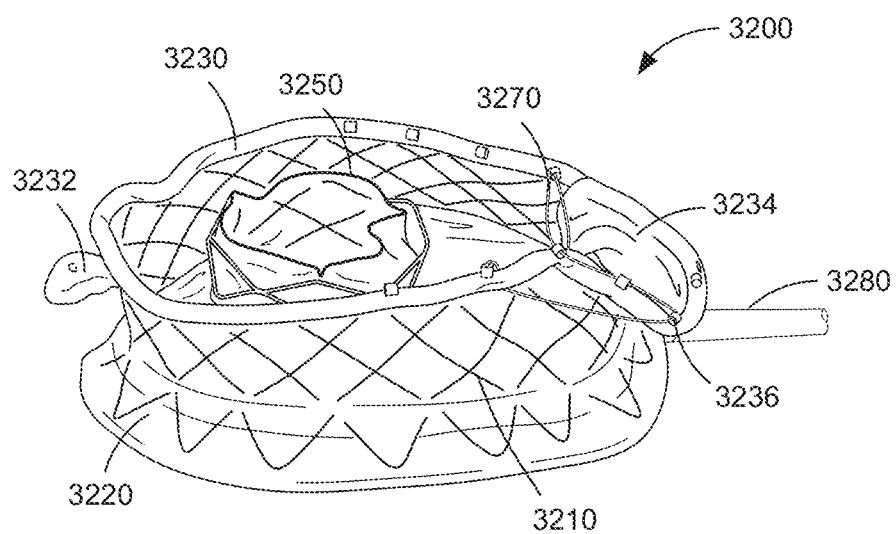
Figure 59:
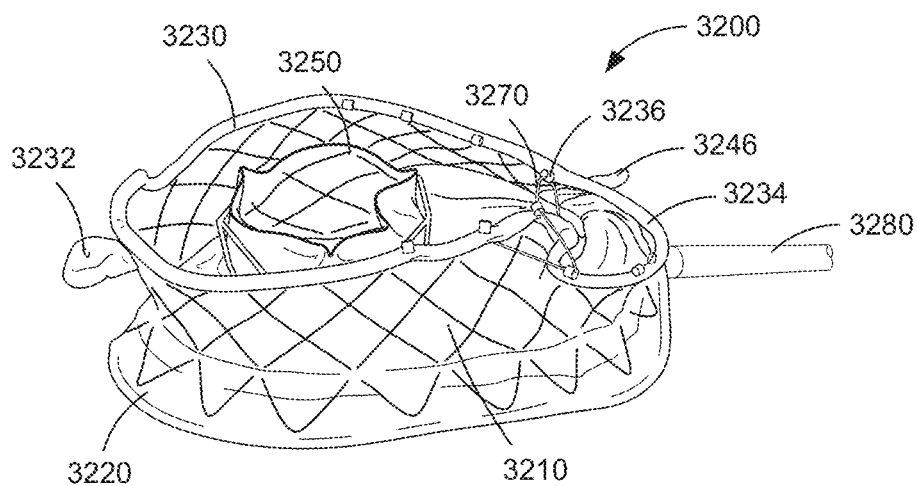
Figure 60:
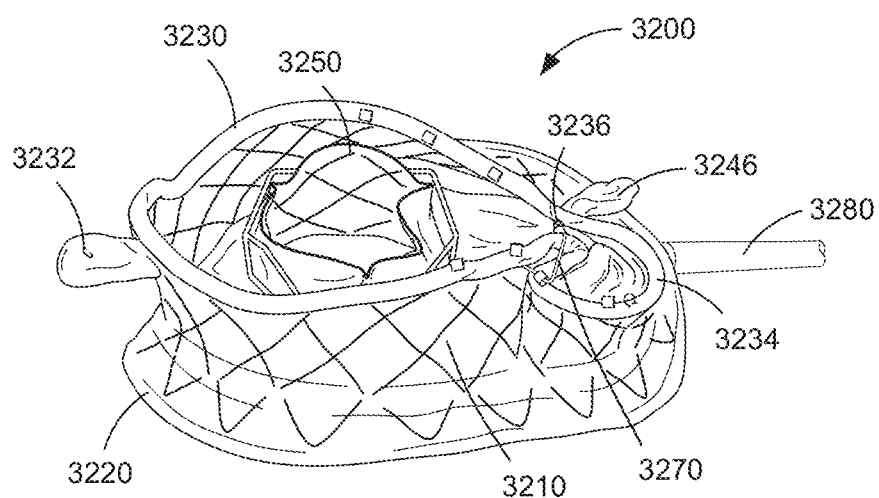

FIG. 57 shows the proximal anchoring element 3234 in a first or unactuated configuration with the tether (actuator 3270) looped through the attachment points 3236 in a serpentine manner. FIGS. 58 and 59 show the proximal anchoring element 3234 as it is transitioned from the first, unactuated configuration toward a second, actuated configuration in response to an actuation of the actuator 3270 (e.g., pulling on the tether in a proximal direction and/or in a direction that otherwise results in tension along a length of the tether). FIG. 60 shows the proximal anchoring element 3234 in the second, actuated configuration.

In the embodiment shown in FIGS. 57-60, the actuator 3270 engages the proximal anchoring element 3234 such that one of the attachment points 3236 on an anterior or freewall side of the subannular member 3230 acts as a pivot point about which the proximal anchoring element 3234 is at least partially rotated, folded, rolled, etc. In other embodiments, the actuator 3270 can engage the proximal anchoring element 3234 such that an attachment point 3236 on a posterior or septal side of the subannular member 3230 acts as the pivot point. In other words, the proximal anchoring element 3234 can be rotated, folded, rolled, pivoted, swung, and/or otherwise moved toward an anterior side of the valve 3200 or a posterior side of the valve 3200 depending on how the actuator 3270 engages the attachment points 3236 of the proximal anchoring element 3234.

FIGS. 59 and 60 also show a tab 3246 included on and/or formed by the proximal anchoring element 3234. In some implementations, the tab 3246 can contact native subannular tissue to facilitate securement of a proximal side of the valve 3200 in the annulus of the native valve. More specifically, the tab 3246 can be positioned along and/or adjacent to the proximal anchoring element 3234 and can rotate, swing, pivot, and/or otherwise move with the proximal anchoring element 3234 in response to actuation of the actuator 3270. In some implementations, the placement of the tab 3246 can be such that as the proximal anchoring element 3234 is moved (e.g., from the compressed configuration to the expanded configuration, after the valve 3200 is deployed and/or seated in the annulus), the tab 3246 moves or slides behind, for example, a commissure, posterior or septal leaflets, chordae, trabeculae, and/or any other desirable portion of native tissue. While one tab 3246 is shown in FIGS. 59 and 60, in other embodiments, the proximal anchoring element 3234 can include two or more tabs 3246 that can be arranged and/or otherwise act as hooks or the like to hook onto or behind native tissue, thereby securing the proximal anchoring element 3234 to native subannular tissue.

FIGS. 61-64 are bottom perspective views of a prosthetic valve 3300 and illustrating a process of transitioning a proximal anchoring element 3334 of the prosthetic valve 3300 between a first configuration and a second configuration, according to an embodiment. The valve 3300 is shown as including an outer support frame 3310 and a flow control component 3350 mounted within a central region of the outer support frame 3310. The frame 3310 is shown having at least a supra-annular member 3320 and a subannular member 3330. The supra-annular member 3320 and the subannular member 3330 can be similar to any of those described above. Accordingly, certain aspects and/or features may not be described in further detail herein.

Figure 61:
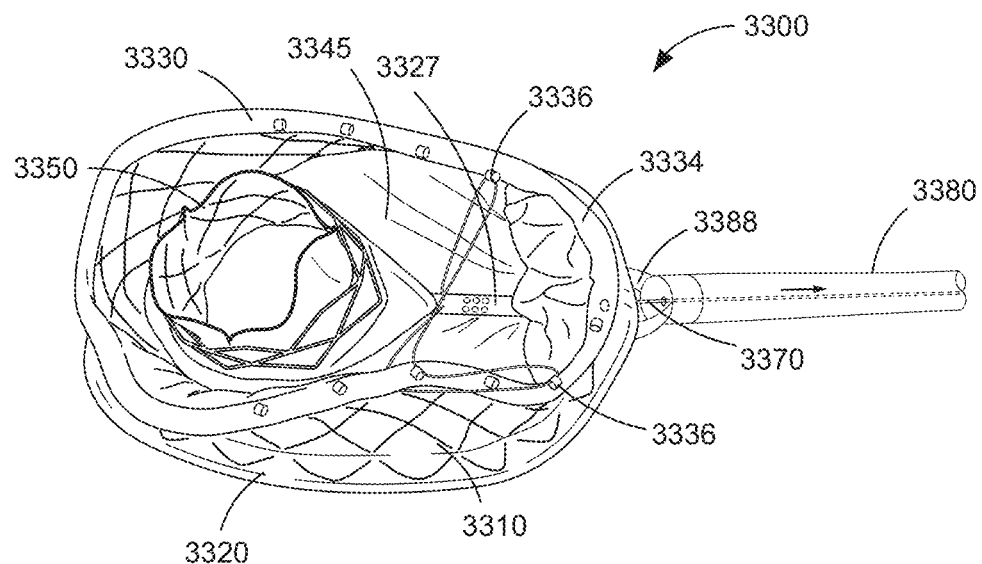
FIGS. 61-64 are bottom perspective views of a prosthetic valve and illustrating a process of transitioning a proximal anchoring element of the prosthetic valve between a first configuration and a second configuration, according to an embodiment.

FIG. 61 shows the supra-annular member 3320 including a spline 3327 (e.g., extending between an outer loop and an inner loop of the supra-annular member 3320 (not shown)) at or near the inner loop of the supra-annular member 3320. The supra-annular member 3320 is further shown as including a drum 3445 that extends between and/or is coupled to the inner and outer loops of the supra-annular member 3320 and covers a space not otherwise occupied by the flow control component 3350. The supra-annular member 3320 (or an inner loop thereof) is shown coupled to the flow control component 3350, which is distally offset relative to the valve 3300.

The valve 3300 is configured to engage or to be engaged by at least a portion of a delivery system 3380, or the like. The delivery system 3380 can include any suitable component for delivering, retrieving, deploying, moving, manipulating, actuating, and/or otherwise interacting with one or more portions of the valve 3300. In this embodiment, the delivery system 3380 can include, for example, one or more catheters. For example, the delivery system 3380 can include a delivery catheter through which the valve 3300 is delivered to an annulus of a native heart valve. The delivery system 3380 can also include one or more steerable catheters, control catheters, multi-lumen catheters, and/or the like, or combinations thereof. In some embodiments, the delivery system 3380 can include a multi-lumen control catheter that has a distal end portion configured to removably engage and/or couple to one or more portions of the valve 3300 (e.g., an outer or inner loop the supra-annular member 3320, the drum of the supra-annular member 3320, the spline 3327 of the supra-annular member 3320, one or more anchoring elements of the subannular member 3330, and/or any other portion of the valve 3300). For example, FIGS. 61-64 show an attachment member 3388 (e.g., a yoke, wishbone, and/or the like) coupled to and/or integrated into a distal end of a multi-lumen control catheter. The attachment member 3388 can be removably coupled to the supra-annular member 3320 (e.g., the drum 3445 and/or spline 3327). Although not shown in FIGS. 61-64, in some embodiments, the attachment member 3388 can be removably coupled to the drum 3345 of the supra-annular member 3320 via one or more tethers, sutures, and/or retractable/retrievable connectors.

FIG. 61 shows the actuator 3370 including and/or configured as a tether that extends, for example, through a distal portion of the spline 3327 and is threaded through one or more attachment point(s) 3336 coupled to and/or formed along the subannular member 3330. Although not shown, in some embodiments, the spline 3327 can form and/or define a waypoint at or near the flow control component 3350 through which the tether extends. The location of the waypoint can be based at least in part on a size of the valve 3300 with smaller valves having a waypoint in a distal position relative to the waypoint of larger valves. In some embodiments, a through hole, flap, opening, port, and/or the like can be formed in the drum 3445 to allow the tether to pass therethrough (e.g., the spline 3327 does not define a waypoint). The tether is shown looped through multiple attachment points(s) 3336 of the proximal anchoring element 3334 and extending in a proximal direction back through the drum 3345 and/or spline 3327 such that both ends of the tether are maintained outside of the body, allowing a user to manipulate the tether (actuator 3370). Thus, actuation of the actuator 3370 (e.g., tether(s)) transitions and/or moves at least the proximal anchoring element 3334 between the first configuration and the second configuration. The tether can be threaded through the attachment points 3336 in any suitable manner, which in turn, can control and/or determine a way that the proximal anchoring element 3334 is transitioned or moved.

Figure 62:
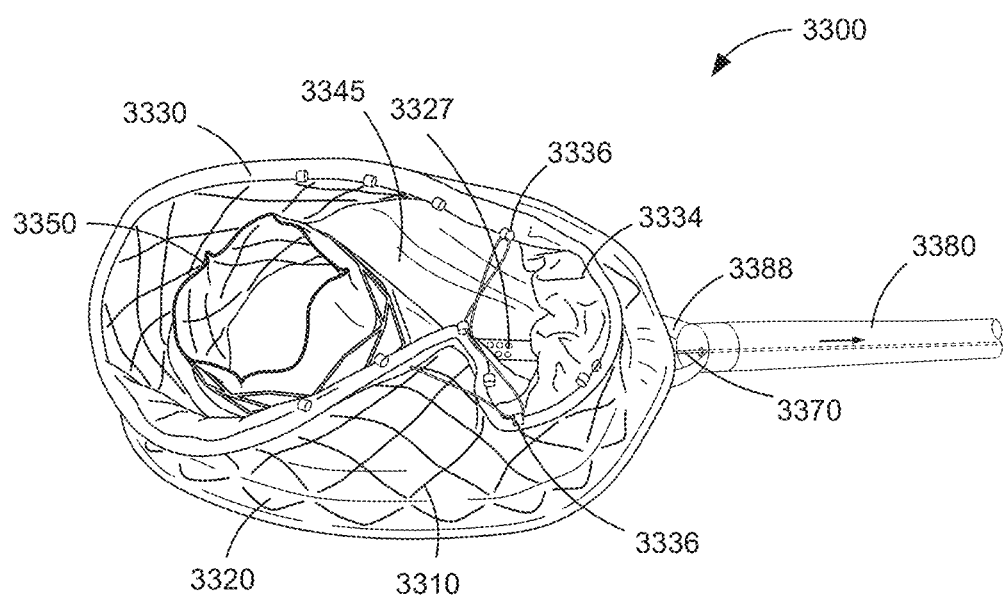
Figure 63:
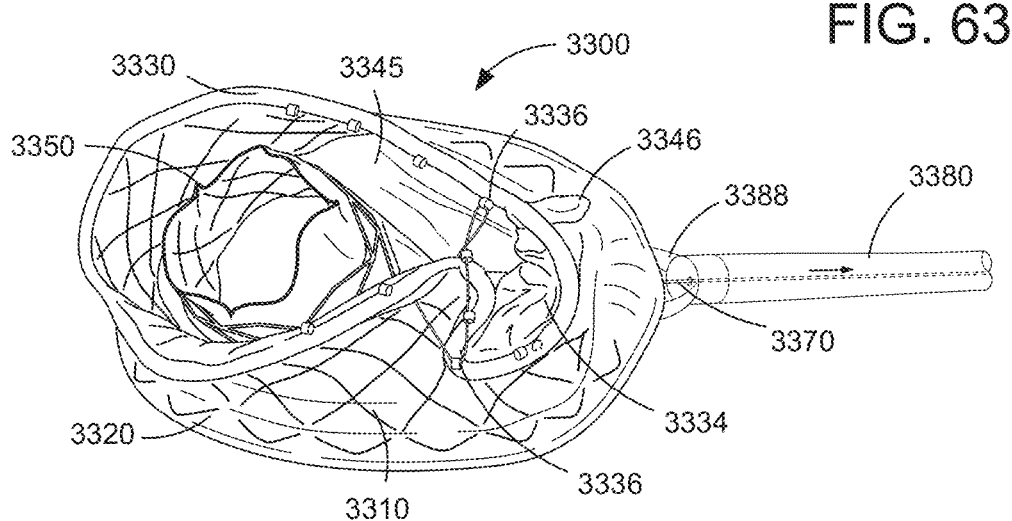
Figure 64:
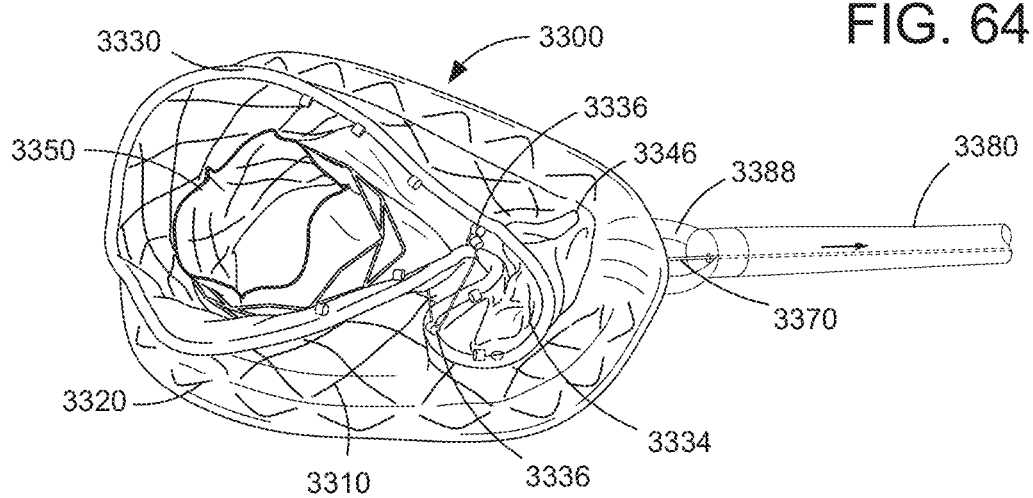

FIG. 61 shows the proximal anchoring element 3334 in a first or unactuated configuration with the tether (actuator 3370) looped through the attachment points 3336 in a serpentine manner. FIGS. 62 and 63 show the proximal anchoring element 3334 as it is transitioned from the first, unactuated configuration toward a second, actuated configuration in response to an actuation of the actuator 3370 (e.g., pulling on the tether in a proximal direction and/or in a direction that otherwise results in tension along a length of the tether). FIG. 64 shows the proximal anchoring element 3334 in the second, actuated configuration. In the embodiment shown in FIGS. 61-64, the actuator 3370 engages the proximal anchoring element 3334 such that one of the attachment points 3336 acts as a pivot point about which the proximal anchoring element 3334 is at least partially rotated, folded, rolled, etc. (e.g., an attachment point 3336 on an anterior side or a posterior side of the subannular member 3320, as described above with reference to the valve 3200).

FIGS. 63 and 64 also show a tab 3346 included on and/or formed by the proximal anchoring element 3334. In some implementations, the tab 3346 can contact native subannular tissue to facilitate securement of a proximal side of the valve 3300 in the annulus of the native valve. More specifically, the tab 3346 can be positioned along and/or adjacent to the proximal anchoring element 3334 and can rotate, swing, pivot, and/or otherwise move with the proximal anchoring element 3334 in response to actuation of the actuator 3370. In some implementations, the placement of the tab 3346 can be such that as the proximal anchoring element 3334 is moved (e.g., from the compressed configuration to the expanded configuration, after the valve 3300 is deployed and/or seated in the annulus), the tab 3346 moves or slides behind, for example, a commissure, posterior or septal leaflets, chordae, trabeculae, and/or any other desirable portion of native tissue. While one tab 3346 is shown in FIGS. 63 and 64, in other embodiments, the proximal anchoring element 3334 can include two or more tabs 3346 that can be arranged and/or otherwise act as hooks or the like to hook onto or behind native tissue, thereby securing the proximal anchoring element 3334 to native subannular tissue.

Figure 65:
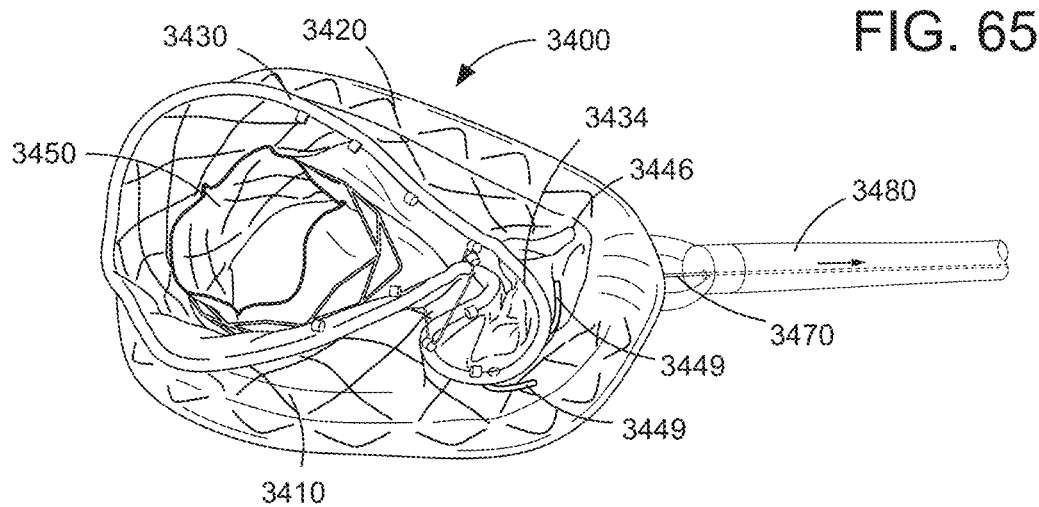
FIG. 65 is a bottom perspective view of a prosthetic valve showing a proximal anchoring element, in a compressed configuration, and having a set of tabs extending from the proximal anchoring element, according to an embodiment.

FIG. 65 is bottom perspective view of a prosthetic valve 3400 showing a proximal anchoring element 3434, in a compressed configuration, and having a set of tabs 3449 extending from the proximal anchoring element 3434, according to an embodiment. The valve 3400 is configured to engage or to be engaged by at least a portion of a delivery system 3480, or the like. The delivery system 3480 can include any suitable component for delivering, retrieving, deploying, moving, manipulating, actuating, and/or otherwise interacting with one or more portions of the valve 3400. In this embodiment, the delivery system 3480 can include, for example, one or more catheters and an actuator 3470 (as described above with reference to the delivery systems 3280 and 3380).

FIG. 65 shows the valve 3400 having an outer support frame 3410 and a flow control component 3450 mounted within a central region of the outer support frame 3410. The frame 3410 is shown having at least a supra-annular member 3420 and a subannular member 3430. The supra-annular member 3420 and the subannular member 3430 can be similar to any of those described above. Accordingly, certain aspects and/or features may not be described in further detail herein.

The subannular member 3430 includes and/or forms the proximal anchoring element 3434, which can be movable between at least a first, unactuated, and/or expanded configuration and a second, actuated, folded, and/or compressed configuration. FIG. 65 shows the proximal anchoring element 3434 in the second or actuated configuration. As described above with reference to the proximal anchoring elements 3234 and 3334, a tether included in and/or forming at least a portion of the actuator 3470 is looped through a set of attachment points 3436 of the proximal anchoring element 3434 in a serpentine manner. In the embodiment shown in FIG. 65, the actuator 3470 engages the proximal anchoring element 3434 such that one of the attachment points 3436 (e.g., an attachment point 3436 on a freewall side of the valve 3400) acts as a pivot point about which the proximal anchoring element 3434 is at least partially rotated, folded, rolled, etc. (e.g., an attachment point 3436 on an anterior side or a posterior side of the subannular member 3420, as described above with reference to the valve 3200).

FIG. 65 further shows a tab 3446 included on and/or formed by the proximal anchoring element 3434, which can be similar to the tabs 3246 and 3346 described above. The proximal anchoring element 3434 is also shown as including and/or forming a set of anchors, tabs, hooks, arms, extensions, etc. (referred to herein as "hooks 3449"). In some implementations, the hooks 3449 can extend from the proximal anchoring element 3434 and can be curved, angled, and/or oriented in such a way that when the proximal anchoring element 3434 rotates, swings, pivots, and/or otherwise moves in response to actuation of the actuator 3470 (e.g., moves from the second, folded, and/or compressed configuration toward the first, unfolded, and/or expanded configuration, after the valve 3400 is deployed and/or seated in the annulus), the hooks 3449 move or slide behind, for example, a commissure, posterior or septal leaflets, chordae, trabeculae, and/or any other desirable portion of native tissue.

While the proximal anchoring element 3434 is shown as including two hooks 3449, in other embodiments, the proximal anchoring element 3434 can include one hook 3449, two hooks 3449, or more than two hooks 3449 that can be arranged and/or otherwise act to hook onto or behind native tissue, thereby securing the proximal anchoring element 3434 to native subannular tissue. While the hooks 3449 are shown as extending, for example, in a direction associated with the proximal anchoring element 3434 moving from the compressed to the expanded configuration (e.g., toward a posterior or septal side of the valve 3400), in other embodiments, the hooks 3449 can be oriented in the opposite direction or any suitable combination of directions. Moreover, while the hooks 3449 are shown as being relatively elongate extensions, in other embodiments, a hook or set of hooks can have any suitable shape, size, and/or configuration. For example, in some embodiments, the proximal anchoring element 3434 can include an edge portion that is serrated with blunt serrations, teeth, hooks, ridges, protrusions, etc.

FIGS. 66-69 are various views of a side-deliverable prosthetic valve 3500 and illustrating a portion of a supra-annular member 3520 having a bowed configuration, according to an embodiment. The valve 3500 is shown as including an outer support frame 3510 and a flow control component 3550 mounted within a central region of the outer support frame 3510. The frame 3510 is shown having at least a supra-annular member 3520, a subannular member 3530, and a transannular member 3512 coupled therebetween. The frame 3510 and/or aspects thereof can be similar to any of those described above. Accordingly, certain aspects and/or features may not be described in further detail herein.

The valve 3500 is shown with the subannular member 3530 having and/or forming a distal anchoring element 3532 and a proximal anchoring element 3534. The distal anchoring element 3532 includes a guidewire coupler 3533 that can receive a guidewire and/or a guidewire catheter through an opening, hole, aperture, port, etc., defined by the guidewire coupler 3533. In some implementations, a guidewire catheter can extend beyond the distal anchoring element 3532 and can have and/or can provide sufficient stiffness to allow the valve 3500 be advanced along a guidewire that is threaded through a lumen of the guidewire catheter. The proximal anchoring element 3534 can be, for example, a movable anchoring element configured to be moved and/or otherwise transitioned (e.g., by an actuator) between a first configuration and a second configuration to reduce a perimeter of the subannular member 3520 during delivery and/or deployment.

The proximal anchoring element 3534 can be configured to move in any suitable direction from the first, extended configuration (FIG. 66) to the second, compressed configuration based at least in part on how the proximal anchoring element 3534 is coupled to an actuator. For example, the proximal anchoring element 3534 can be moved inward toward the flow control component 3550, moved upward toward the supra-annular member 3520 and/or portion thereof, and/or moved toward an anterior side or a posterior side of the valve 3500. Moreover, with the transannular member 3512 of the frame 3510 coupled to the subannular member 3530, actuation of an actuator can, in some implementations, move one or more portions of the transannular member 3512.

The supra-annular member 3520 is shown having laser cut frame (e.g., formed of a shape-memory material such as Nitinol) that is wrapped or covered in a biocompatible material. The supra-annular member 3520 includes a distal portion 3522, a proximal portion 3524, an outer loop 3521, an inner loop 3525, and at least one spline 3527. In some embodiments, the outer loop 3521 can be shaped and/or sized to engage native tissue. For example, the distal portion 3522 of the supra-annular member 3520 (formed at least in part by the outer loop 3521) is configured to engage distal supra-annular tissue and the proximal portion 3524 (formed at least in part by the outer loop 3521) is configured to engage proximal supra-annular tissue. The distal and proximal portions 3522 and 3524 can have a rounded and/or curved shape, wherein a radius of curvature of the proximal portion 3524 is larger than a radius of curvature of the distal portion 3522. The distal portion 3522 and/or the proximal portion 3524 can form, for example, a distal supra-annular anchoring element and/or a proximal supra-annular anchoring element, respectively, each of which can engage supra-annular tissue to at least partially stabilize and/or secure the frame 3510 in the native annulus.

The inner loop 3525 of the supra-annular member 3520 can have an oblong or teardrop-shape can be coupled to and/or suspended from the outer loop 3521 by the one or more splines 3527. The inner loop 3525 can be coupled to the flow control component 3550 via, for example, biocompatible material 3526. The inner loop 3525 is shown as being coupled to the flow control component 3550 such that the flow control component 3550 is distally offset relative to the valve 3500. In some implementations, suspending the inner loop 3525 from the outer loop 3521 can, for example, at least partially isolate the inner loop 3525 (and the flow control component 3550 coupled to the inner loop 3525) from at least a portion of the force associated with transitioning the frame 3510 between the expanded configuration and the compressed configuration (e.g., during delivery and/or deployment).

The one or more splines 3527 of the supra-annular member 3520 can be any suitable shape, size, and/or configuration. For example, in some embodiments, the supra-annular member 3520 can include a proximal spline 3527 that defines a waypoint 3528. The waypoint 3528 can be, for example, an opening, a hole, an aperture, a port, a coupler, a sealable/resealable access point, and/or the like configured to at least temporarily couple to and/or receive a portion of a delivery system. For example, in some implementations, the portion of the delivery system can include at least an actuator and a guidewire catheter.

Figure 66:
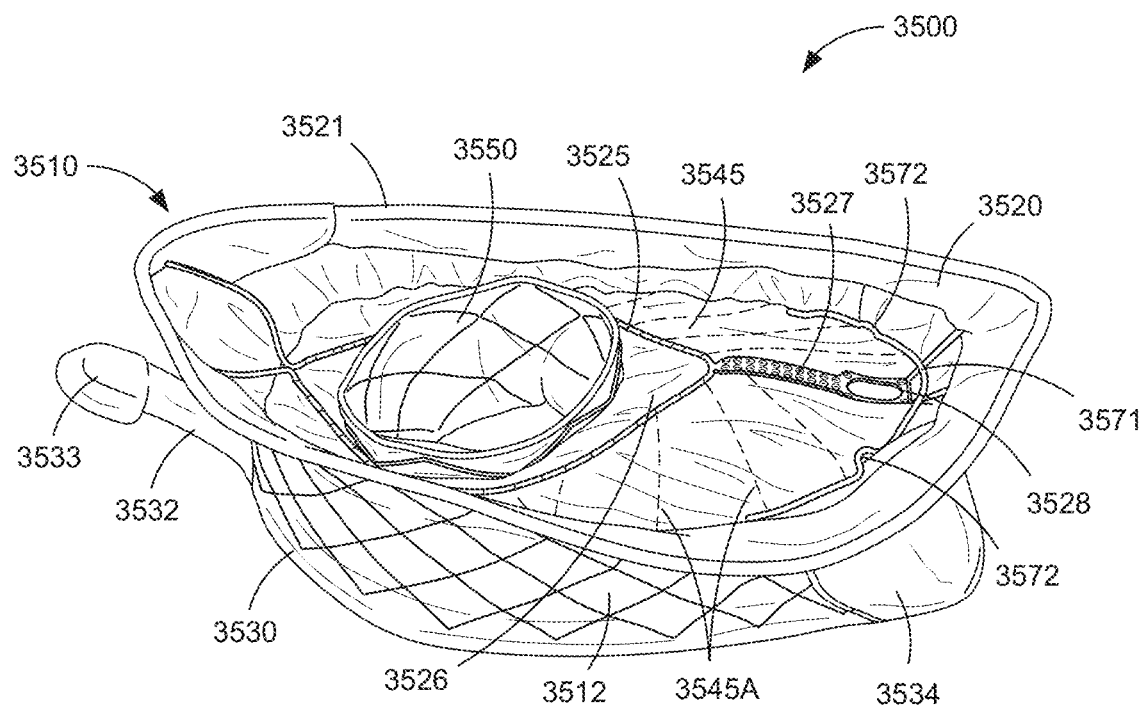
FIGS. 66-68 are a top perspective view, a side perspective view, and a bottom view, respectively, of a prosthetic valve and illustrating a supra-annular member having a bowed configuration, according to an embodiment.

The supra-annular member 3520 is further shown as including a drum 3545 that extends between and/or is coupled to the outer loop 3521 and the inner loop 3525 and covers a space not otherwise occupied by the flow control component 3550. FIG. 66 shows the drum 3545 having and/or forming a set of spokes 3545A that can be used to increase a stiffness of the drum 3545. The spokes 3545A can be, for example, sutures that are sewn into the drum 3545 to increase the stiffness of the drum 3545 and/or to otherwise modify a deformation mode of the drum 3545 during, for example, systole, which in turn, can enhance performance of the valve 3500 and/or reduce fatigue in or along the drum 3545. While particularly shown in FIG. 66, the spokes 3545A can be arranged in any suitable manner that results in an increase in drum stiffness. For example, the spokes 3545A can be arranged longitudinally, laterally, and/or at angles relative to a longitudinal or lateral direction. In other embodiments, the spokes 3545A can be arranged in a cross-hatch pattern and/or any other suitable pattern.

FIG. 66 further shows the drum 3545 including an attachment member 3571 that can facilitate a temporary attachment to a portion of the delivery system. The attachment member 3571 can be, for example, a braided thread, a suture, a tether, a cable, and/or the like. As described above, in some implementations, a delivery system can include a control or steerable catheter that can include an integrated yoke or other suitable removable coupler. More particularly, the attachment member 3571 can include a set of loops 3572 through which a set of tethers can be threaded to removably couple the yoke of the delivery system to the valve 3500. The tethers can be passed through the loops 3572 such that each end of the tethers is maintained outside the patient allowing an operator to manipulate the tethers to control a contact between the yoke and the drum 3545.

While the attachment member 3571 is shown coupled to the drum 3545 at or near a proximal edge of the drum 3545, in other embodiments, the attachment member 3571 can be coupled to the drum 3545 in any suitable location (e.g., a proximal position adjacent to the flow control component 3550, a distal position as shown in FIG. 66, or any suitable position therebetween). Although the attachment member 3571 is described above as being coupled to the drum 3545, in other embodiments, any portion of the valve 3500 can include an attachment member 3571. In some embodiments, for example, the supra-annular member 3520 can include a laser cut portion of the wire frame that extends across a portion of the outer loop 3525 (e.g., perpendicular to the spline 3527).

Figure 67:
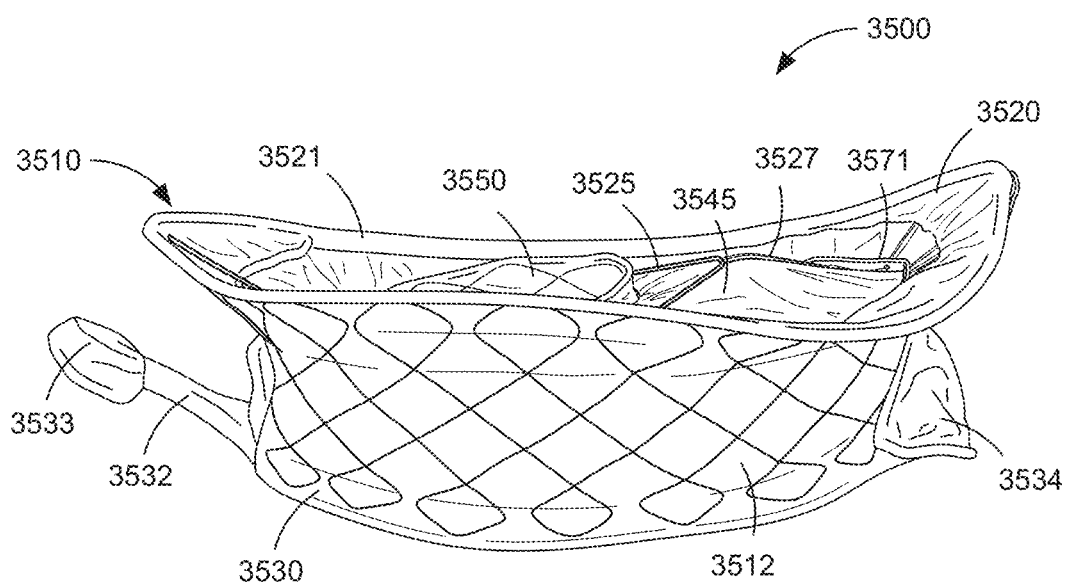
Figure 68:
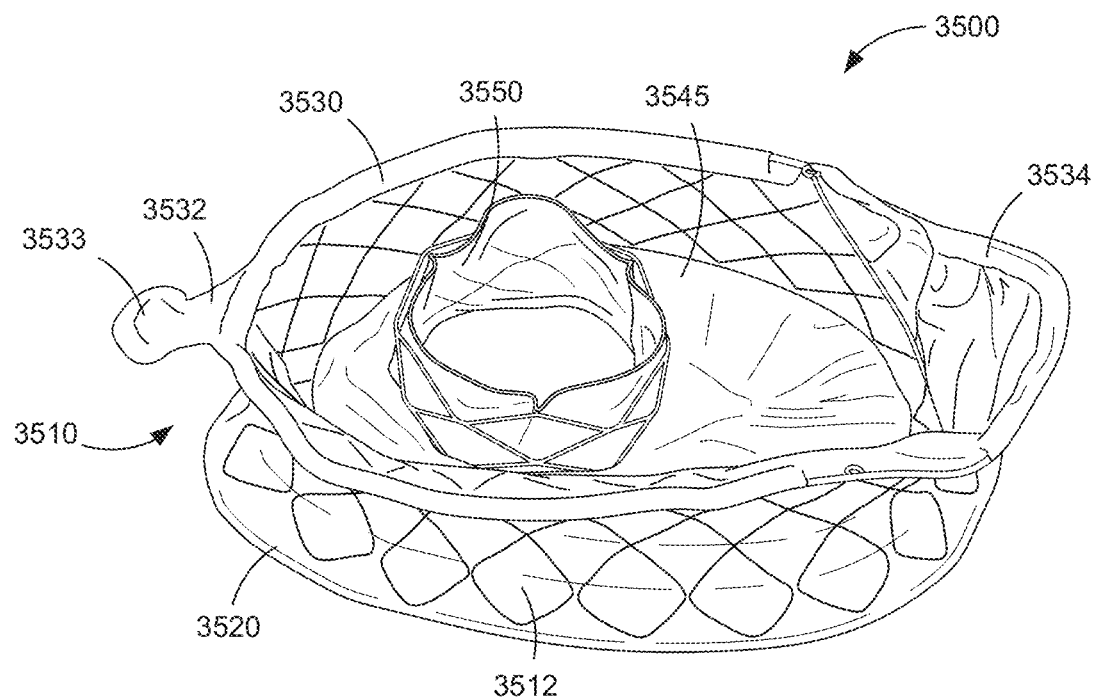
Figure 69:
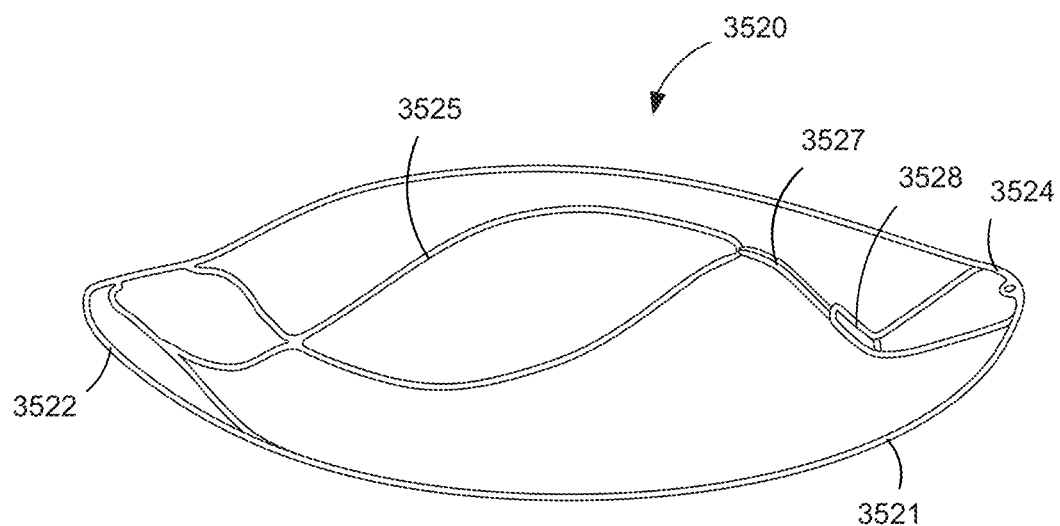
FIG. 69 is a perspective view of the supra-annular member included in the prosthetic valve of FIGS. 66-68.

FIGS. 66-69 further show the spline 3527 of the supra-annular member 3520 having a bowed shape and/or configuration. FIGS. 67 and 68 are a side view and a bottom view, respectively, of the valve 3500 showing the spline 3527 protruding away from the subannular member 3520 and FIG. 69 is a top perspective view showing the laser cut frame of the supra-annular member 3520 with the spline 3527 having the bowed configuration. In some implementations, bowed spline 3527 can exert a force on the drum 3545 that bows the drum 3545 and increases a tension across the area of the drum 3545. The increase in tension, in turn, increases a relative stiffness of the drum 3545, which can reduce and/or limit an amount of drum deformation during, for example, diastole or systole, thereby enhancing performance of the valve 3500 and/or reduce fatigue in or along the drum 3545. Said another way, the pressure produced on the atrial side of the drum 3545 during contraction of the atrium (diastole) is not sufficient to invert the bowed configuration of the drum 3545 (i.e., will not produce an oil-can like deflection) due to the bowed spline 3527. The bowed configuration of the drum 3545 can also withstand the greater pressure produced on the ventricle side of the drum 3545 during contraction of the ventricle (systole) without substantial deflection. Moreover, the bow in the spline 3527 can be such that the waypoint 3528 is positioned at a desired angle and/or orientation to facilitate the insertion or retrieval of one or more portions of the delivery system through the waypoint 3528.

Figure 70:
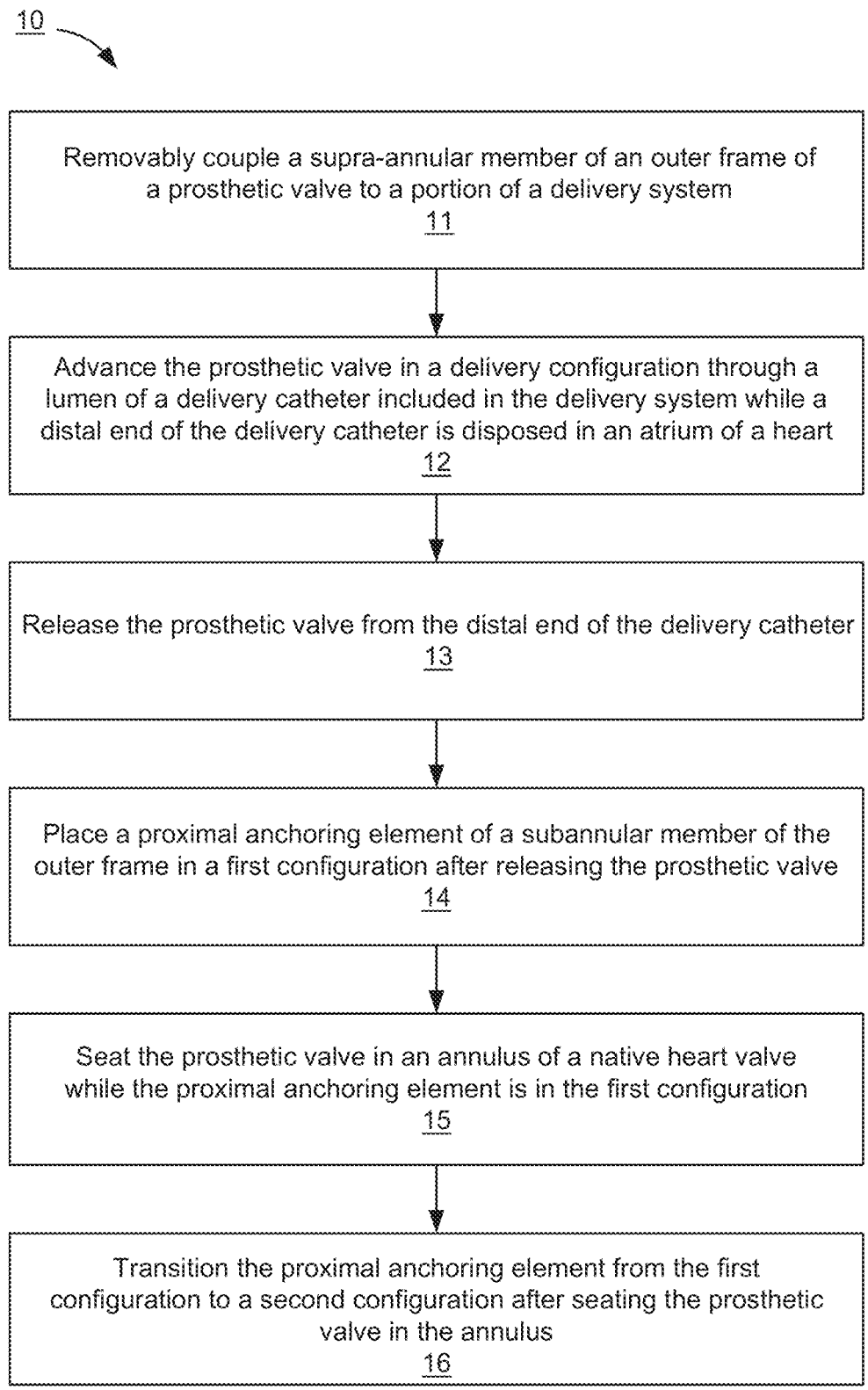
FIG. 70 is a flowchart illustrating a method of deploying a side-deliverable transcatheter prosthetic valve according to an embodiment.

FIG. 70 is a flowchart illustrating a method 10 of deploying a side-deliverable transcatheter prosthetic valve according to an embodiment. The side-deliverable transcatheter prosthetic valve can be similar to and/or substantially the same as any of the prosthetic valves described herein. For example, the prosthetic valve can include an outer support frame and an (inner) flow control component that is mounted in and/or to the outer support frame. The outer support frame can include, for example, a supra-annular member or region, a subannular member or region, and a transannular member or region coupled therebetween. The flow control component is mounted to the outer support frame such that is extends through a portion of the transannular member or region, as described above.

The method 10 includes removably coupling the supra-annular member of the outer frame to a portion of a delivery system, at 11. For example, in some embodiments, the supra-annular member can include an attachment member or the like that can be used to temporarily couple the delivery system to the valve, as described above with reference to the valve 3500 shown in FIGS. 66-69. In other embodiments, the supra-annular member can form and/or define an attachment point, waypoint, and/or any other suitable coupler that can removably couple to the portion of the delivery system.

The prosthetic valve in a delivery configuration is advanced through a lumen of a delivery catheter included in the delivery system while a distal end of the delivery catheter is disposed in an atrium of a heart, at 12. As described above with reference to the valve 100, the prosthetic valve can be placed into the delivery configuration and loaded into the lumen of the delivery catheter. In some instances, placing the valve into the delivery configuration can include, for example, folding the valve in a lateral direction or along a lateral axis and compressing the valve in an axial or blood flow direction or along a central axis of the valve. In some instances, the supra-annular member of the outer frame is removably coupled to the portion of the delivery system prior to being advanced through the lumen of the delivery catheter. In some such instances, for example, the portion of the delivery system can be used to advance the prosthetic valve in the delivery configuration through the lumen of the delivery catheter.

The prosthetic valve is released from the distal end of the delivery catheter, at 13. In some instances, the prosthetic valve can be partially released from the delivery catheter to allow a distal end portion of the valve (e.g., a distal anchoring element of the subannular member) to be inserted into the annulus of the native valve prior to fully releasing the valve. In other instances, the prosthetic valve can be fully released from the delivery catheter prior to inserting a portion of the prosthetic valve into the annulus. Moreover, the releasing of the prosthetic valve allows the released portion (or the valve in its entirety) to transition from the delivery configuration to an expanded or deployment configuration.

A proximal anchoring element of the subannular member of the outer frame is placed in a first configuration after releasing the prosthetic valve, at 14. As described above with reference to at least the frames 210 and 310, the proximal anchoring element can be placed in a first configuration in response to an actuation of an actuator removably coupled thereto. For example, the actuator can be one or more tethers that can be placed in tension to actuate, move, and/or otherwise place the proximal anchoring element in the first configuration. Moreover, when the proximal anchoring element is in the first configuration, a perimeter and/or circumference of at least the subannular member is reduced to a size similar to or smaller than a perimeter and/or circumference of the annulus. Thus, the prosthetic valve is seated in the annulus of the native heart valve while the proximal anchoring element is in the first configuration, at 15.

After seating the prosthetic valve in the annulus, the proximal anchoring element is transitioned from the first configuration to a second configuration, at 16. For example, in some implementations, the actuator can be actuated to move the proximal anchoring element from the first configuration to the second configuration. In some implementations, a user or operator can reduce an amount of tension in one or more tethers allowing the proximal anchoring element to return to a biased or expanded state or configuration. In some implementations, the actuator can be actuated such that the proximal anchoring element is moved from the first (compressed) configuration, through an extended configuration, and to a cinched configuration, in which native tissue on a proximal side of the annulus is compressed or sandwiched between the proximal anchoring element of the subannular member and a proximal portion of the supra-annular member, thereby securing the valve in the annulus. In some implementations, once the valve is seated and/or secured in the annulus of the native valve, the portion of the delivery system can be decoupled and/or removed from the valve and withdrawn from the body of the patient.

FIG. 71 is a flowchart illustrating a method of 20 manufacturing at least a portion of a side-deliverable transcatheter prosthetic valve according to an embodiment. The prosthetic valve can be similar to any of the prosthetic valves (or portions thereof) described herein. For example, the prosthetic valve can be similar to the valve 3400 described above with reference to FIGS. 66-69.

The method 20 includes forming, from a single workpiece, a supra-annular member of a valve frame having an outer loop, an inner loop, and a spline suspending the inner loop from the outer loop, at 21. As described above, the supra-annular member can be and/or can include a wire frame that is laser-cut from a single workpiece (e.g., a Nitinol sheet or tube) and then heat-set into a desired shape. In some embodiments, the outer loop can have a size, shape, and/or configuration that is based at least in part on the anatomy of an atrium in which it will be disposed. The inner loop can be suspended from the outer loop and can have a size and/or shape that is at least partially based on a size or configuration of an (inner) flow control component configured to be mounted thereto. In some embodiments, for example, the inner loop can be oblong or teardrop-shaped that is sufficiently wide to receive the flow control component therethrough. The spline is configured to at least partially suspend the inner loop from the outer loop. In some embodiments, the spline can be form and/or define a waypoint that is configured to engage and/or receive a portion of a delivery system during delivery and/or deployment.

A subannular member of the valve frame is formed from a single workpiece and has a distal anchoring element and a proximal anchoring element, at 22. As described above, the subannular member can be and/or can include a wire frame that is laser-cut from a single workpiece (e.g., a Nitinol sheet or tube) and then heat-set into a desired shape. For example, the subannular member can be formed (heat-set) into a closed loop such that the distal anchoring element extends from a distal end portion of the subannular member and the proximal anchoring element extends from a proximal end portion of the subannular member. As described above, in some instances, the distal anchoring element can include and/or can form one or more features, protrusions, eyelets, etc., that can facilitate engagement with native tissue during deployment. In some instances, the proximal anchoring element is formed to be movable and/or transitionable between two or more configurations, as described in detail above. In some instances, forming the subannular member optionally can include forming one or more twists along one or more portions of the subannular member, which can control and/or determine a direction and/or range of motion associated with the proximal anchoring element.

Each of a first sidewall and a second sidewall are formed from a single workpiece, at 23. In some embodiments, the first sidewall and the second sidewall can be a first half and a second half of the transannular member of the outer frame. As described above, the sidewalls can be and/or can include a wire frame that is laser-cut from a single workpiece (e.g., a Nitinol sheet or tube) and then heat-set into a desired shape (e.g., an arcuate shape, a semi-cylindrical shape, a curved hyperbolic or parabolic shape (or cross-sectional shape), and/or the like). The sidewalls can include any number of rows of wire cells oriented in a direction parallel to a blood flow direction through the valve (e.g., parallel to a central axis). In some embodiments, such an orientation can allow the sidewalls to compress when the frame is placed in a delivery configuration.

The first sidewall and the second sidewall are coupled to form the transannular member of the valve frame, at 24. As described above, the coupling of the sidewalls can form one or more hinge points between the first and second sidewalls. In some embodiments, the sidewalls can be sutured and/or otherwise coupled along distal and proximal wire cells. In some embodiments, the shape of the sidewalls is such that two hinge points are formed on a distal side of the transannular member and one hinge point is formed on a proximal side of the transannular member. Moreover, the shape and/or configuration of the transannular member is such that a longitudinal axis of the valve passes through the hinge points, thereby allowing the transannular member to fold in the direction of and/or otherwise along a lateral axis (orthogonal to the longitudinal axis), as described above with reference to the valve 100.

The supra-annular member is coupled to a supra-annular portion of the transannular member, at 25. In some embodiments, the transannular member has an hourglass-like shape with the supra-annular portion flaring outward (e.g., to or toward the outer loop of the supra-annular member). In some embodiments, the coupling of the supra-annular member to the transannular member includes suturing an upper or supra-annular row of wire cells to the outer loop of the supra-annular member.

The subannular member is coupled to a subannular portion of the transannular member, at 26. In some embodiments, the transannular member has an hourglass-like shape with the subannular portion flaring outward (e.g., to or toward the subannular member). In some embodiments, the coupling of the subannular member to the transannular member includes suturing a lower or subannular row of wire cells to the subannular member.

In some embodiments, the method 20 can also include wrapping and/or covering the wire frame subannular, supra-annular, and transannular members in a biocompatible material such as biocompatible fabric, pericardium, and/or the like. In some instances, the subannular, supra-annular, and/or transannular members can be wrapped and/or covered prior to or after the coupling steps at 25 and 26.

Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the disclosure. It is to be understood that this disclosure is not limited to particular methods, reagents, compounds, compositions or biological systems, which can, of course, vary. It is also to be understood that the terminology used herein is for the purpose of describing particular embodiments and is not intended to be limiting.

While various embodiments have been described above, it should be understood that they have been presented by way of example only, and not limitation. Various changes in form and/or detail may be made without departing from the scope of the disclosure and/or without altering the function and/or advantages thereof unless expressly stated otherwise. Where schematics and/or embodiments described above indicate certain components arranged in certain orientations or positions, the arrangement of components may be modified.

Although various embodiments have been described as having particular features and/or combinations of components, other embodiments are possible having a combination of any features and/or components from any of embodiments described herein, except mutually exclusive combinations. The embodiments described herein can include various combinations and/or sub-combinations of the functions, components, and/or features of the different embodiments described.

Where methods described above indicate certain events occurring in certain order, the ordering of certain events may be modified. Additionally, certain of the events may be performed concurrently in a parallel process when possible, as well as performed sequentially as described above.

What is claimed:

1. A side-deliverable prosthetic heart valve, the prosthetic valve comprising:
   an outer frame having a supra-annular region, a subannular region, and a transannular region therebetween, the transannular region circumscribing a central channel extending along a central axis; and
   a flow control component mounted to the outer frame such that at least a portion of the flow control component is disposed in the central channel of the transannular region,
   the prosthetic valve having a delivery configuration in which the prosthetic valve is compressed along the central axis and folded along a lateral axis orthogonal to the central axis for side-delivery via a delivery catheter such that a longitudinal axis orthogonal to each of the central axis and the lateral axis of the prosthetic valve in the delivery configuration is parallel to an axis extending through a lumen of the delivery catheter, the prosthetic valve having a deployment configuration in which the prosthetic valve is expanded along each of the central axis and the lateral axis from the delivery configuration when the prosthetic valve is released from the delivery catheter,
   the subannular region of the outer frame in a first configuration as the prosthetic valve is seated in an annulus of a native heart valve and in a second configuration after the prosthetic valve is seated in the annulus of the native heart valve.

2. The prosthetic valve of claim 1, wherein a perimeter of the subannular region in the first configuration is smaller than a perimeter of the subannular region in the second configuration.

3. The prosthetic valve of claim 1, wherein the subannular region forms a distal anchoring element and a proximal anchoring element, the proximal anchoring element being movable between a first position and a second position to transition the subannular region between the first configuration and the second configuration, a perimeter of the subannular region in the first configuration being smaller than a perimeter of the subannular region in the second configuration.

4. The prosthetic valve of claim 3, wherein the proximal anchoring element is movable between the first position, the second position, and a third position to transition the subannular region between the first configuration, the second configuration, and a third configuration, respectively, the subannular region being in the third configuration when the prosthetic valve is in the delivery configuration.

5. The prosthetic valve of claim 3, wherein the supra-annular region forms a spline configured to removably engage a portion of a delivery system.

6. The prosthetic valve of claim 5, wherein the spline defines a waypoint configured to receive an actuator included in the portion of the delivery system, the proximal anchoring element removably coupled to the actuator during delivery and configured to be moved between the first position and the second position in response to actuation of the actuator.

7. The prosthetic valve of claim 1, wherein the transannular region couples the supra-annular region to the subannular region, the transannular region includes a wireframe that forms a plurality of cells oriented in the direction of the central axis allowing the prosthetic valve to be compressed along the central axis, the wireframe of the transannular region has a first half and a second half coupled to the first half and forms a proximal hinge and a distal hinge therebetween allowing the prosthetic valve to be folded along the lateral axis, the longitudinal axis extending through the proximal hinge and the distal hinge.

8. The prosthetic valve of claim 7, wherein a perimeter of the subannular region in the first configuration is smaller than a perimeter of the subannular region in the second configuration.

9. The prosthetic valve of claim 7, wherein the subannular region forms a distal anchoring element and a proximal anchoring element, the proximal anchoring element being movable between a first position and a second position to transition the subannular region between the first configuration and the second configuration, a perimeter of the subannular region in the first configuration being smaller than a perimeter of the subannular region in the second configuration.

10. The prosthetic valve of claim 9, wherein the proximal anchoring element is movable between the first position, the second position, and a third position to transition the subannular region between the first configuration, the second configuration, and a third configuration, respectively, the subannular region being in the third configuration when the prosthetic valve is in the delivery configuration.

11. The prosthetic valve of claim 9, wherein the supra-annular region forms a spline configured to removably engage a portion of a delivery system.

12. The prosthetic valve of claim 11, wherein the spline defines a waypoint configured to receive an actuator included in the portion of the delivery system, the proximal anchoring element removably coupled to the actuator during delivery and configured to be moved between the first position and the second position in response to actuation of the actuator.

13. A side-deliverable prosthetic heart valve, the prosthetic valve comprising:

an outer frame having a single-piece supra-annular member forming an outer loop, an inner loop, and a spline extending between the outer loop and the inner loop; and a flow control component having an inner frame and a plurality of leaflets mounted within the inner frame, the inner frame of the flow control component mounted to the inner loop of the supra-annular member and extending along a central axis, the prosthetic valve in a delivery configuration being compressed along the central axis and folded along a lateral axis orthogonal to the central axis for side-delivery via a delivery catheter, the prosthetic valve when released from the delivery catheter expanding along each of the central axis and the lateral axis from the delivery configuration to a deployment configuration for deployment in an annulus of a native heart valve, the spline suspending the inner loop from the outer loop to limit an amount of stress transferred to the flow control component when the prosthetic valve is seated into the an annulus of the native heart valve.

14. The prosthetic valve of claim 13, wherein suspending the inner loop from the outer loop via the spline limits an amount of stress transferred to the flow control component when the prosthetic valve is placed in the delivery configuration.

15. The prosthetic valve of claim 13, wherein the outer loop has a first shape based at least in part on a shape of an atrial floor of a heart and the inner loop has a second shape different from the first shape and based at least in part on a shape of the inner frame of the flow control component.

16. The prosthetic valve of claim 13, wherein the outer frame includes a subannular member and a transannular member. the transannular member coupled to the outer loop of the supra-annular member and the subannular member to form the outer frame, the transannular member forming a set of wire cells with an orientation and cell geometry that allows compression of the prosthetic valve along the central axis and forming a proximal hinge and a distal hinge that allow folding of the prosthetic valve along the lateral axis to place the prosthetic valve in the delivery configuration, and wherein side-delivery of the prosthetic valve in the delivery configuration being such that the central axis and the lateral axis are orthogonal to an axis extending through a lumen of the delivery catheter when the prosthetic valve is in the delivery catheter.

17. The prosthetic valve of claim 16, wherein the delivery catheter is included in a delivery system, the supra-annular member forms at least a portion of a supra-annular region of the prosthetic valve that is removably coupleable to a yoke included in a portion of the delivery system via a tether when the prosthetic valve is in the delivery configuration and in the lumen of the delivery catheter.

18. The prosthetic valve of claim 17, wherein the prosthetic valve in the delivery configuration removably couples to the yoke such that the prosthetic valve is advanceable through the lumen of the delivery catheter in response to a force exerted on the supra-annular member by the yoke.

19. The prosthetic valve of claim 17, wherein the subannular member forms a distal anchoring element and a proximal anchoring element.

20. The prosthetic valve of claim 19, wherein the supra-annular region of the prosthetic valve defines a waypoint that removably receives a guidewire catheter and a guidewire extending through a lumen of the guidewire catheter, the distal anchoring element removably coupling to a portion of the guidewire catheter extending through the waypoint and below the flow control component.

21. The prosthetic valve of claim 19, wherein the proximal anchoring element is in a first position when the prosthetic valve is in the delivery configuration, the proximal anchoring element is transitionable to a second position after releasing the prosthetic valve from the delivery catheter and as the prosthetic valve is seated in an annulus of a native heart valve, and the proximal anchoring element is transitionable to a third position after the prosthetic valve is seated in the annulus of the native heart valve.

22. A side-deliverable prosthetic heart valve, the prosthetic valve comprising:

an outer frame having a supra-annular member, a subannular member, and a transannular member coupling the supra-annular member to the subannular member, the supra-annular member being a single-piece member forming an outer loop, an inner loop, and a spline extending between the outer loop and the inner loop, the supra-annular member forming at least a portion of a supra-annular region of the prosthetic valve that is removably coupleable to a delivery system, the transannular region circumscribing a central channel extending along a central axis; and a flow control component having an inner frame and a plurality of leaflets mounted within the inner frame, the flow control component mounted to the inner loop of the supra-annular member such that a portion of the flow control component is disposed in the central channel of the transannular member, the prosthetic valve having a delivery configuration in which the prosthetic valve is compressed along the central axis and folded along a lateral axis orthogonal to the central axis for side-delivery via a delivery catheter of the delivery system, the prosthetic valve having a deployment configuration in which the prosthetic valve is expanded along each of the central axis and the lateral axis from the delivery configuration when the prosthetic valve is released from the delivery catheter.

23. The prosthetic valve of claim 22, wherein the transannular member forms a set of wire cells with an orientation and cell geometry that allows compression of the prosthetic valve along the central axis and a proximal hinge and a distal hinge that collectively allow folding of the prosthetic valve along the lateral axis to place the prosthetic valve in the delivery configuration, wherein the side-delivery of the prosthetic valve in the delivery configuration being such that the central first axis and the lateral axis are orthogonal to an axis extending through a lumen of the delivery catheter when the prosthetic valve is in the delivery catheter.

24. The prosthetic valve of claim 22, wherein the supra-annular region of the prosthetic valve is removably coupleable to a yoke included the in delivery system.

25. The prosthetic valve of claim 24, wherein the supra-annular member includes a drum extending between the inner loop and the outer loop, the drum being formed from a biocompatible material, the drum of the supra-annular member being removably coupleable to the yoke via a set of tethers.

26. The prosthetic valve of claim 25, wherein the spline is bowed in a direction along the central axis such that the spline exerts a force on the drum to limit an amount of flex in the drum during at least one of diastole or systole of the heart when the prosthetic valve is seated in the annulus of the native heart valve.

27. The prosthetic valve of claim 26, wherein the subannular member forms a proximal anchoring element configured to removably couple to an actuator of the delivery system extending through the drum when the supra-annular member is removably coupled to the yoke of the delivery system, and the proximal anchoring element is configured to be moved in response to actuation of the actuator between a first position when the prosthetic valve is in the delivery configuration, a second position after releasing the prosthetic valve from the delivery catheter and as the prosthetic valve is seated in an annulus of a native heart valve, and a third position after the prosthetic valve is seated in the annulus of the native heart valve.

28. The prosthetic valve of claim 27, wherein the proximal anchoring element is moved toward the drum from the first position to the second position in response to a first actuation of the actuator, and wherein the proximal anchoring element is moved away from the drum from the second position to the third position in response to a second actuation of the actuator.

29. A side-deliverable prosthetic heart valve, the prosthetic valve comprising:

an outer frame having a supra-annular region, a subannular region, and a transannular region therebetween, the supra-annular region having a spline configured to engage a portion of a delivery system, the subannular region forming a distal anchoring element and a proximal anchoring element, the transannular region circumscribing a central channel extending along a central axis; and a flow control component mounted to the outer frame such that at least a portion of the flow control component is disposed in the central channel of the transannular region, the prosthetic valve having a delivery configuration in which the prosthetic valve is compressed along the central axis and folded along a lateral axis orthogonal to the central axis for side-delivery via a delivery catheter, the prosthetic valve having a deployment configuration in which the prosthetic valve is expanded along each of the central axis and the lateral axis from the delivery configuration when the prosthetic valve is released from the delivery catheter, the proximal anchoring element being movable between a first position and a second position to transition the subannular region of the outer frame between a first configuration and a second configuration, a perimeter of the subannular region in the first configuration being smaller than a perimeter of the subannular region in the second configuration, the subannular region being in the first configuration as the prosthetic valve is seated in an annulus of a native heart valve and being transitioned to the second configuration after the prosthetic valve is seated in the annulus of the native heart valve.

30. The prosthetic valve of claim 29, wherein the proximal anchoring element is movable between the first position, the second position, and a third position to transition the subannular region between the first configuration, the second configuration, and a third configuration, respectively, the subannular region being in the third configuration when the prosthetic valve is in the delivery configuration.

31. The prosthetic valve of claim 29, wherein the spline defines a waypoint configured to receive an actuator included in the portion of the delivery system, the proximal anchoring element removably coupled to the actuator during delivery and configured to be moved between the first position and the second position in response to actuation of the actuator.

32. The prosthetic valve of claim 29, wherein the spline defines a waypoint configured to receive an actuator included in the portion of the delivery system, the proximal anchoring element removably coupled to the actuator during delivery and configured to be moved between the first position and the second position in response to actuation of the actuator, the proximal anchoring element is movable between the first position, the second position, and a third position to transition the subannular region between the first configuration, the second configuration, and a third configuration, respectively, the subannular region being in the third configuration when the prosthetic valve is in the delivery configuration.

33. The prosthetic valve of claim 29, wherein the prosthetic valve has a longitudinal axis orthogonal to each of the central axis and the lateral axis, the side-delivery of the prosthetic valve in the delivery configuration being such that the longitudinal axis is parallel to an axis extending through a lumen of the delivery catheter when the prosthetic valve is in the delivery catheter.

34. The prosthetic valve of claim 33, wherein the transannular region couples the supra-annular region to the subannular region, the transannular region includes a wireframe that forms a plurality of cells oriented in the direction of the central axis allowing the prosthetic valve to be compressed along the central axis, the wireframe of the transannular region has a first half and a second half coupled to the first half and forms a proximal hinge and a distal hinge therebetween allowing the prosthetic valve to be folded along the lateral axis, the longitudinal axis extending through the proximal hinge and the distal hinge.

\* \* \* \* \*